(12) United States Patent
Sarkorov et al.

(10) Patent No.: US 10,850,036 B2
(45) Date of Patent: Dec. 1, 2020

(54) REUSABLE AUTOMATIC INJECTION DEVICE

(71) Applicant: E3D AGRICULTURAL COOPERATIVE ASSOCIATION LTD., Merom Hagalil (IL)

(72) Inventors: Dmitri Sarkorov, Ramat Gan (IL); Lior Raday, MP Hof Ashkelon (IL); David Daily, Herzliya (IL); Menachem Zucker, Haifa (IL)

(73) Assignee: E3D AGRICULTURAL COOPERATIVE ASSOCIATION, Merom Hagalil (IL)

( * ) Notice: Subject to any disclaimer, the term of this patent is extended or adjusted under 35 U.S.C. 154(b) by 181 days.

(21) Appl. No.: 15/754,825

(22) PCT Filed: Aug. 25, 2016

(86) PCT No.: PCT/IL2016/050929
§ 371 (c)(1),
(2) Date: Feb. 23, 2018

(87) PCT Pub. No.: WO2017/033193
PCT Pub. Date: Mar. 2, 2017

(65) Prior Publication Data
US 2019/0351139 A1  Nov. 21, 2019

Related U.S. Application Data

(60) Provisional application No. 62/210,962, filed on Aug. 27, 2015.

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3158* (2013.01); *A61M 5/31581* (2013.01);
(Continued)

(58) Field of Classification Search
CPC ................ A61M 5/2033; A61M 5/315; A61M 5/31581; A61M 5/3204; A61M 5/46;
(Continued)

(56) References Cited

U.S. PATENT DOCUMENTS 5,478,316 A   12/1995   Bitdinger
5,540,664 A   7/1996    Wyrick
(Continued)

FOREIGN PATENT DOCUMENTS

EP   0824922 B1   4/2002
EP   1317296 A1   6/2003
(Continued)

OTHER PUBLICATIONS

International Search Report of PCT/IL2016/050929 dated Feb. 23, 2017 [PCT/ISA/210].
(Continued)

*Primary Examiner* — Tiffany Legette
(74) *Attorney, Agent, or Firm* — Sughrue Mion, PLLC

(57) ABSTRACT

A user-powered medicament injector including a reusable, user-powered automatic injection assembly including a user energizable medicament injection subassembly and a medicament module removably insertable into the reusable, user-powered automatic injection assembly and including a module housing adapted to receive a syringe having a barrel, a needle engaged to said barrel, and a removable needle cap covering the needle; a needle shield configured to be moveable with respect to the module housing and a needle cap remover associated with the needle shield. The medicament module is configured for energizing the user energizable
(Continued)

medicament injection subassembly by insertion of the medicament module into the reusable, user powered automatic injection assembly.

19 Claims, 159 Drawing Sheets

(51) Int. Cl.
   *A61M 5/32* (2006.01)
   *A61M 5/46* (2006.01)

(52) U.S. Cl.
   CPC ............ *A61M 5/3204* (2013.01); *A61M 5/46* (2013.01); *A61M 2005/202* (2013.01); *A61M 2005/2073* (2013.01); *A61M 2005/2086* (2013.01); *A61M 2205/583* (2013.01)

(58) Field of Classification Search
   CPC .... A61M 2005/202; A61M 2005/2073; A61M 2005/2086; A61M 2205/583; A61M 5/24; A61M 5/283; A61M 5/3158; A61M 2005/2403; A61M 2005/2411; A61M 2005/2433; A61M 2005/2485; A61M 2005/2026; A61M 2005/208; A61M 5/31; A61M 5/3202; A61M 5/3275; A61M 2005/2407; A61M 2205/42; A61M 2005/583
   See application file for complete search history.

(56) References Cited

U.S. PATENT DOCUMENTS

| | | | |
|---|---|---|---|
| 5,558,648 A | 9/1996 | Shield | |
| 5,599,309 A | 2/1997 | Marshall | |
| 5,709,662 A | 1/1998 | Olive | |
| 5,788,671 A | 8/1998 | Johnson | |
| 5,843,036 A | 12/1998 | Olive | |
| 6,045,537 A | 4/2000 | Klitmose | |
| 6,056,522 A | 5/2000 | Johnson | |
| 6,059,753 A | 5/2000 | Faust | |
| 6,482,186 B1 | 11/2002 | Douglas | |
| 6,547,764 B2 | 4/2003 | Larsen | |
| 6,629,949 B1 | 10/2003 | Douglas | |
| 6,641,566 B2 | 11/2003 | Douglas | |
| 6,692,469 B1 | 2/2004 | Weekes | |
| 6,752,798 B2 | 6/2004 | McWethy | |
| 7,033,343 B2 | 4/2006 | McWethy | |
| 7,097,634 B2 | 8/2006 | Gilbert | |
| 7,150,735 B2 | 12/2006 | Hickle | |
| 7,195,616 B2 | 3/2007 | Diller | |
| 7,381,201 B2 | 6/2008 | Gilbert | |
| 7,449,012 B2 | 11/2008 | Young | |
| 7,458,962 B2 | 12/2008 | Mcwethy | |
| 7,500,963 B2 | 3/2009 | Westbye | |
| 7,563,252 B2 | 7/2009 | Marshall | |
| 7,635,356 B2 | 12/2009 | Stamp | |
| 7,645,265 B2 | 1/2010 | Stamp | |
| 7,674,246 B2 | 3/2010 | Gillespie | |
| 7,704,238 B2 | 4/2010 | Diller | |
| 7,717,877 B2 | 5/2010 | Lavi | |
| 7,811,254 B2 | 10/2010 | Wilmot | |
| 7,988,675 B2 | 8/2011 | Gillespie, III | |
| 8,048,035 B2 | 11/2011 | Mesa | |
| 8,052,645 B2 | 11/2011 | Slate | |
| 8,057,434 B2 | 11/2011 | Burroughs | |
| 8,075,522 B2 | 12/2011 | Larsen | |
| 8,177,749 B2 | 5/2012 | Slate | |
| 8,574,214 B2 | 11/2013 | Kuehn | |
| 8,647,306 B2 | 2/2014 | Schwirtz | |
| 8,672,899 B2 | 3/2014 | Diller | |
| 8,679,070 B2 | 3/2014 | Clavadetscher | |
| 8,808,244 B2 | 8/2014 | Adlon | |
| 8,870,827 B2 | 10/2014 | Young | |
| 8,900,197 B2 | 12/2014 | Crow | |
| 8,932,254 B2 | 1/2015 | Eaton | |
| 8,932,266 B2 | 1/2015 | Eaton | |
| 8,945,067 B2 | 2/2015 | McLoughlin et al. | |
| 9,022,988 B1 | 5/2015 | Shaban | |
| 9,028,453 B2 | 5/2015 | Jennings | |
| 9,095,660 B2 | 8/2015 | Larsen | |
| 9,168,339 B2 | 10/2015 | Cowe | |
| 9,186,459 B2 | 11/2015 | Bechmann | |
| 9,220,845 B2 | 12/2015 | Atterbury | |
| 9,884,159 B2 | 2/2018 | Daly | |
| 9,999,734 B2 | 6/2018 | Cowe | |
| 2002/0004648 A1 | 1/2002 | Larsen | |
| 2002/0068921 A1 | 6/2002 | McWethy | |
| 2002/0151855 A1 | 10/2002 | Douglas | |
| 2002/0169421 A1 | 11/2002 | Mcwethy | |
| 2003/0105430 A1 | 6/2003 | Lavi | |
| 2003/0139705 A1 | 7/2003 | Larsen | |
| 2004/0210199 A1 | 10/2004 | Atterbury | |
| 2004/0225262 A1 | 11/2004 | Fathallah | |
| 2004/0249358 A1 | 12/2004 | McWethy | |
| 2005/0165360 A1 | 7/2005 | Stamp | |
| 2005/0171485 A1 | 8/2005 | Larsen | |
| 2006/0030819 A1 | 2/2006 | Young | |
| 2006/0167413 A1 | 7/2006 | Marshall | |
| 2006/0229570 A1 | 10/2006 | Lovell | |
| 2007/0123829 A1 | 5/2007 | Atterbury | |
| 2007/0233001 A1 | 10/2007 | Burroughs | |
| 2007/0265568 A1 | 11/2007 | Tsals | |
| 2008/0097312 A1 | 4/2008 | Wilmot | |
| 2008/0228143 A1 | 9/2008 | Stamp | |
| 2009/0270804 A1 | 10/2009 | Mesa | |
| 2009/0292246 A1 | 11/2009 | Slate | |
| 2010/0004597 A1 | 1/2010 | Gyrn | |
| 2010/0022955 A1 | 1/2010 | Slate | |
| 2010/0069846 A1 | 3/2010 | Stamp | |
| 2010/0106098 A1 | 4/2010 | Atterbury | |
| 2010/0292643 A1 | 11/2010 | Wilmot | |
| 2010/0318037 A1 | 12/2010 | Young | |
| 2011/0098657 A1 | 4/2011 | Jennings | |
| 2011/0137247 A1 | 6/2011 | Mesa | |
| 2011/0144584 A1 | 6/2011 | Wozencroft | |
| 2011/0172602 A1 | 7/2011 | Eaton | |
| 2011/0202011 A1 | 8/2011 | Wozencroft | |
| 2011/0224640 A1 | 9/2011 | Kuehn | |
| 2012/0046609 A1 | 2/2012 | Mesa | |
| 2012/0095408 A1 | 4/2012 | Eaton | |
| 2012/0101439 A9 | 4/2012 | Slate | |
| 2012/0123346 A1 | 5/2012 | Davies | |
| 2012/0191047 A1 | 7/2012 | Raday et al. | |
| 2012/0233834 A1* | 9/2012 | Szechinski | B23P 19/04 29/407.01 |
| 2012/0277724 A1 | 11/2012 | Larsen | |
| 2013/0018323 A1 | 1/2013 | Boyd et al. | |
| 2013/0138049 A1 | 5/2013 | Kemp | |
| 2013/0218128 A1 | 8/2013 | Cowe | |
| 2013/0231614 A1 | 9/2013 | Cross | |
| 2013/0245553 A1 | 9/2013 | Mesa | |
| 2013/0281936 A1 | 10/2013 | Kemp | |
| 2013/0296807 A1 | 11/2013 | Lintern | |
| 2013/0338601 A1 | 12/2013 | Cowe | |
| 2013/0345642 A1 | 12/2013 | Cowe | |
| 2014/0046269 A1 | 2/2014 | Eaton | |
| 2014/0094776 A1 | 4/2014 | Cronenberg | |
| 2014/0207106 A1 | 7/2014 | Bechmann | |
| 2014/0221974 A1 | 8/2014 | Bechmann | |
| 2014/0257185 A1 | 9/2014 | Bechmann | |
| 2014/0276413 A1 | 9/2014 | Baker | |
| 2014/0276414 A1 | 9/2014 | Baker | |
| 2014/0330203 A1 | 11/2014 | McLoughlin | |
| 2014/0330207 A1 | 11/2014 | McLoughlin | |
| 2014/0330216 A1 | 11/2014 | Weaver | |
| 2014/0336587 A1 | 11/2014 | McLoughlin | |
| 2014/0336588 A1 | 11/2014 | McLoughlin | |
| 2014/0358072 A1 | 12/2014 | McLoughlin | |
| 2014/0358083 A1 | 12/2014 | McLoughlin | |
| 2014/0358084 A1 | 12/2014 | McLoughlin | |

(56) References Cited

U.S. PATENT DOCUMENTS

| | | |
|---|---|---|
| 2014/0358085 A1 | 12/2014 | McLoughlin |
| 2015/0011944 A1 | 1/2015 | Young |
| 2015/0045734 A1 | 2/2015 | McLoughlin |

FOREIGN PATENT DOCUMENTS

| | | |
|---|---|---|
| EP | 0824923 B1 | 7/2003 |
| EP | 0999864 B1 | 2/2004 |
| EP | 1285674 B1 | 8/2005 |
| EP | 1289587 B1 | 8/2005 |
| EP | 1646414 | 4/2006 |
| EP | 1644061 B1 | 1/2007 |
| EP | 1392377 B1 | 2/2007 |
| EP | 1715903 B1 | 10/2007 |
| EP | 1334739 B1 | 3/2008 |
| EP | 1528942 B1 | 9/2008 |
| EP | 2073866 A2 | 7/2009 |
| EP | 1732627 B1 | 5/2010 |
| EP | 2204201 | 7/2010 |
| EP | 2223714 | 9/2010 |
| EP | 2331171 | 6/2011 |
| EP | 2331174 | 6/2011 |
| EP | 2331175 A1 | 6/2011 |
| EP | 2344222 | 7/2011 |
| EP | 2346551 | 7/2011 |
| EP | 2437814 | 4/2012 |
| EP | 2258424 B1 | 1/2013 |
| EP | 2258425 B1 | 1/2013 |
| EP | 2275158 B1 | 1/2013 |
| EP | 2552521 | 2/2013 |
| EP | 2603255 | 6/2013 |
| EP | 2618870 | 7/2013 |
| EP | 2680905 | 1/2014 |
| EP | 2311510 B1 | 5/2014 |
| EP | 2753383 | 7/2014 |
| EP | 2753384 | 7/2014 |
| EP | 2753385 | 7/2014 |
| EP | 2429614 B1 | 4/2015 |
| EP | 2714145 B1 | 5/2015 |
| EP | 2179759 B1 | 11/2015 |
| EP | 2968769 A2 | 1/2016 |
| EP | 2968775 A2 | 1/2016 |
| EP | 1786491 B1 | 2/2016 |
| EP | 1907033 B1 | 8/2016 |
| EP | 2714142 B1 | 8/2016 |
| EP | 2714144 B1 | 8/2016 |
| EP | 2714157 B1 | 8/2016 |
| EP | 2714155 B1 | 9/2016 |
| EP | 2714151 B1 | 5/2017 |
| EP | 2680906 B1 | 8/2017 |
| EP | 2907537 B1 | 8/2017 |
| EP | 2714143 B1 | 9/2017 |
| EP | 2895220 B1 | 1/2018 |
| EP | 2276527 A1 | 2/2018 |
| JP | 7222799 | 8/1995 |
| JP | 10113387 | 5/1998 |
| JP | 10113388 | 5/1998 |
| JP | 2009022768 | 2/2009 |
| JP | 2014111177 | 6/2014 |
| JP | 2014147795 | 8/2014 |
| JP | 2014221407 | 11/2014 |
| JP | 2015061664 | 4/2015 |
| JP | 2015077461 | 4/2015 |
| JP | 2015097911 | 5/2015 |
| JP | 5735424 | 6/2015 |
| JP | 5836120 | 12/2015 |
| JP | 6085607 | 2/2017 |
| JP | 6141932 | 6/2017 |
| WO | 1995031235 | 3/1995 |
| WO | 1996038190 | 12/1996 |
| WO | 2001091837 | 12/2001 |
| WO | 2004000395 | 12/2003 |
| WO | 2004011065 | 2/2004 |
| WO | 2005002653 | 1/2005 |
| WO | 2005097237 | 10/2005 |
| WO | 2008014792 | 2/2008 |
| WO | 2009143255 | 11/2009 |
| WO | 2009153543 | 12/2009 |
| WO | 2010018411 | 2/2010 |
| WO | 2010023481 | 3/2010 |
| WO | 2010026414 | 3/2010 |
| WO | 2010139675 | 12/2010 |
| WO | 2011117282 | 9/2011 |
| WO | 2012019641 | 2/2012 |
| WO | 2012118687 | 9/2012 |
| WO | 2012127249 | 9/2012 |
| WO | 2012158137 | 11/2012 |
| WO | 2012164397 A1 | 12/2012 |
| WO | 2012164394 A3 | 1/2013 |
| WO | 2012164402 A3 | 1/2013 |
| WO | 2012164403 A3 | 1/2013 |
| WO | 2012164406 A3 | 1/2013 |
| WO | 2012164389 A3 | 4/2013 |
| WO | 2013001378 A3 | 4/2013 |
| WO | 2013034986 A3 | 7/2013 |
| WO | 2013034985 A3 | 12/2013 |
| WO | 2013178501 | 12/2013 |
| WO | 2012164404 A8 | 1/2014 |
| WO | WO-2014037946 A1 * | 3/2014 .......... A61M 5/3202 |
| WO | 2014080020 | 5/2014 |
| WO | 2014166900 | 10/2014 |
| WO | 2014166918 | 10/2014 |
| WO | 2014145535 A3 | 11/2014 |
| WO | 2014179117 | 11/2014 |
| WO | 2014166922 A3 | 12/2014 |
| WO | 2015010215 | 1/2015 |
| WO | 2015036345 | 3/2015 |
| WO | 2015036346 | 3/2015 |
| WO | 2015/055641 A1 | 4/2015 |
| WO | 2015074984 | 5/2015 |
| WO | 2015079219 | 6/2015 |
| WO | 2015117854 | 8/2015 |
| WO | 2015090320 A3 | 9/2015 |
| WO | 2016001307 | 1/2016 |

OTHER PUBLICATIONS

Written Opinion of PCT/IL2016/050929 dated Feb. 23, 2017 [PCT/ISA/237].

* cited by examiner

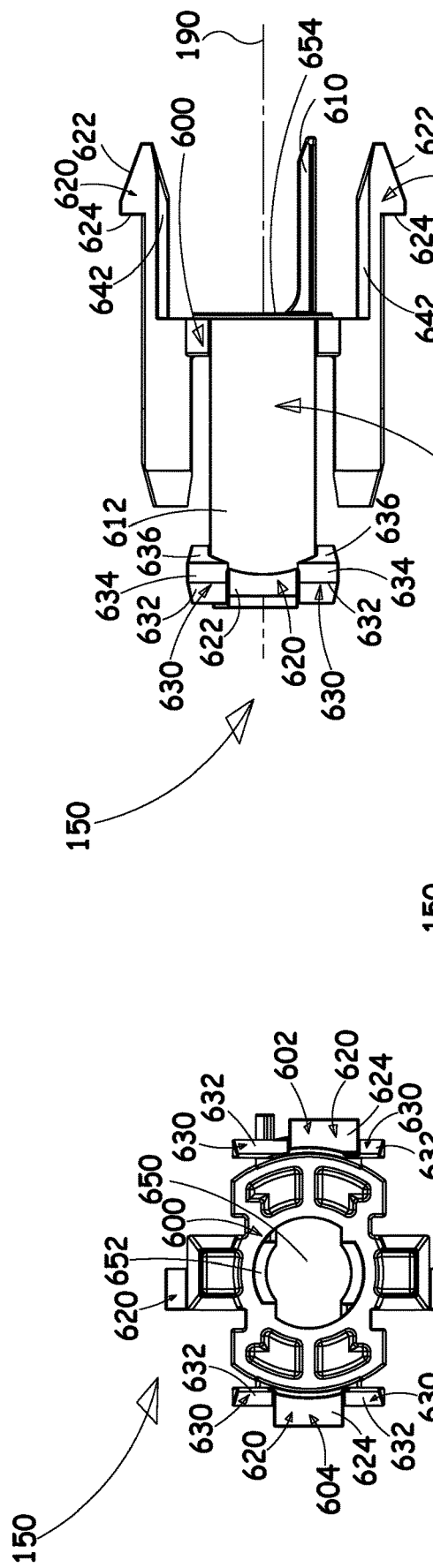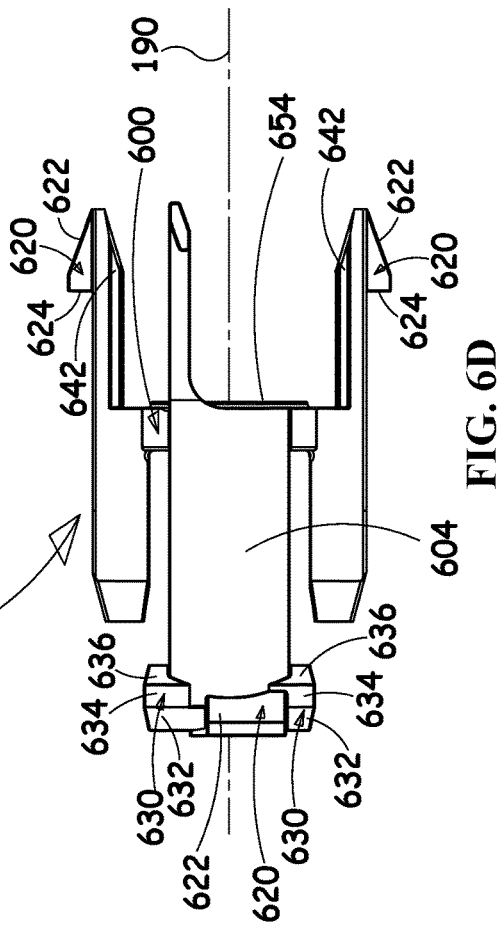

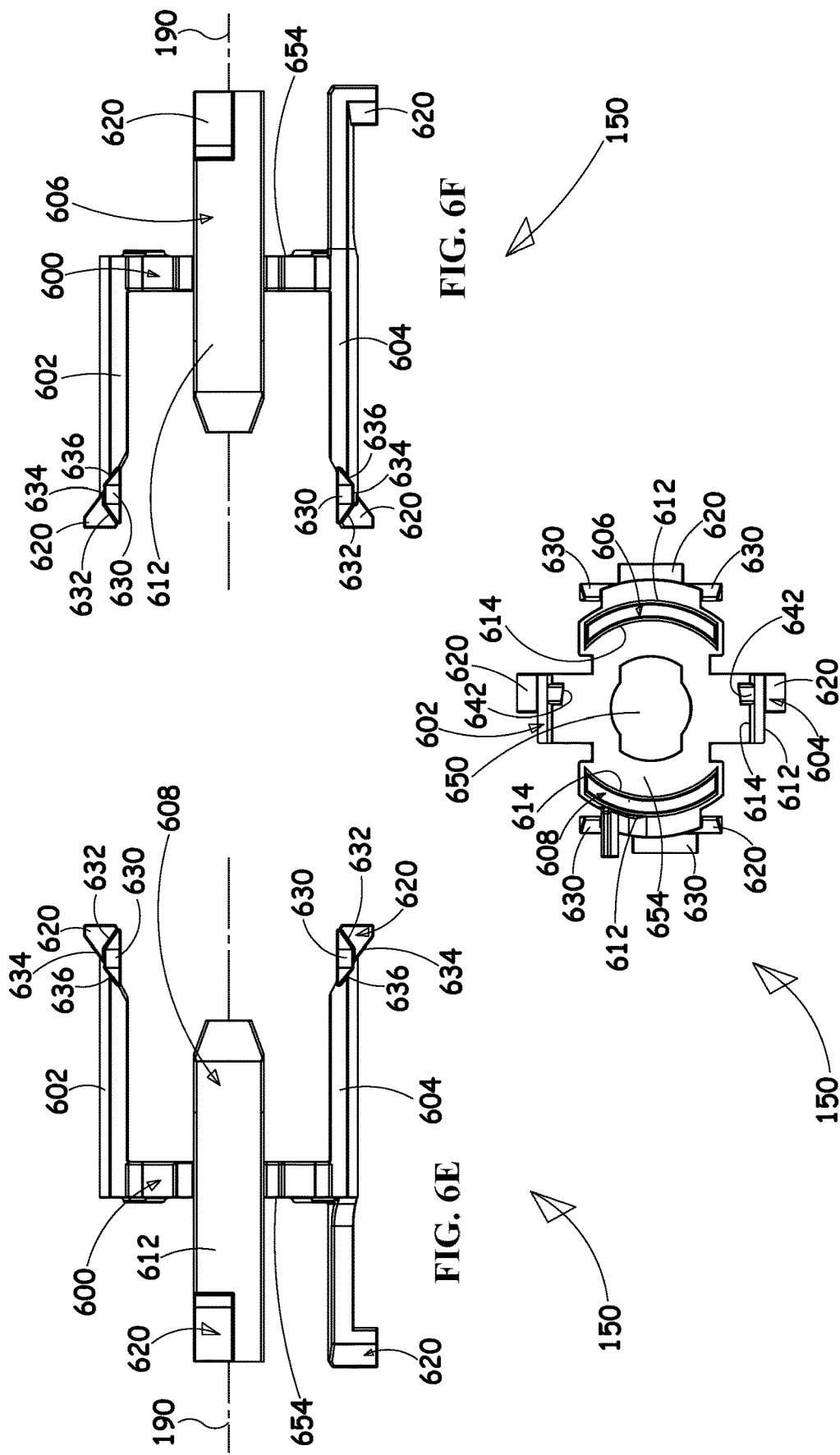

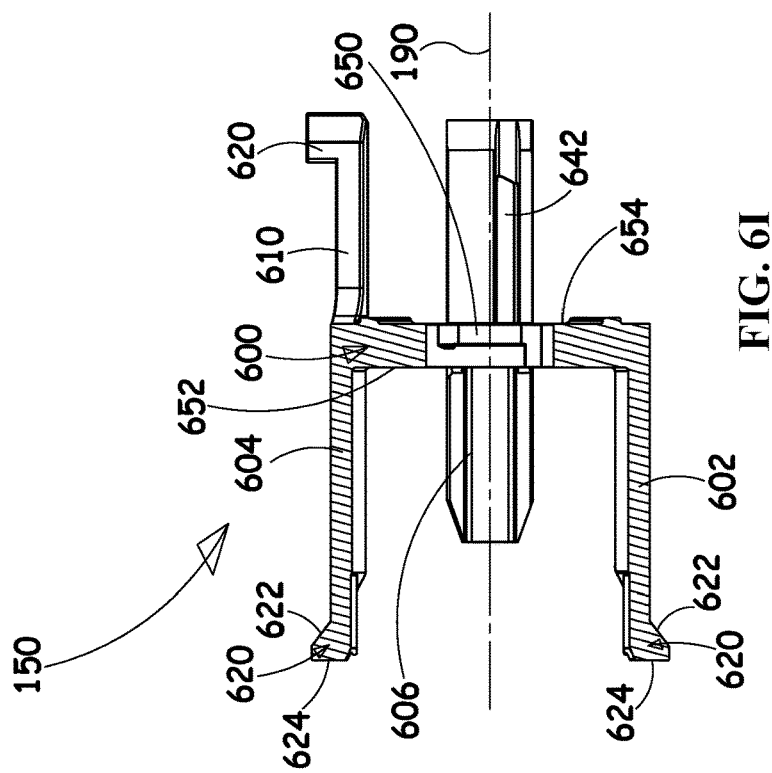
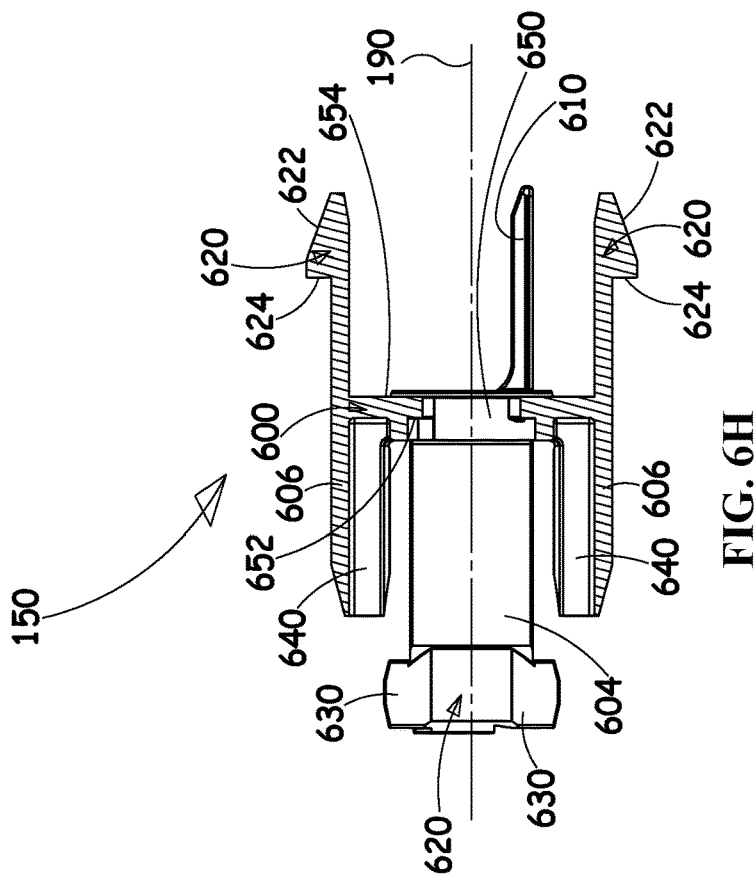
FIG. 6I
FIG. 6H

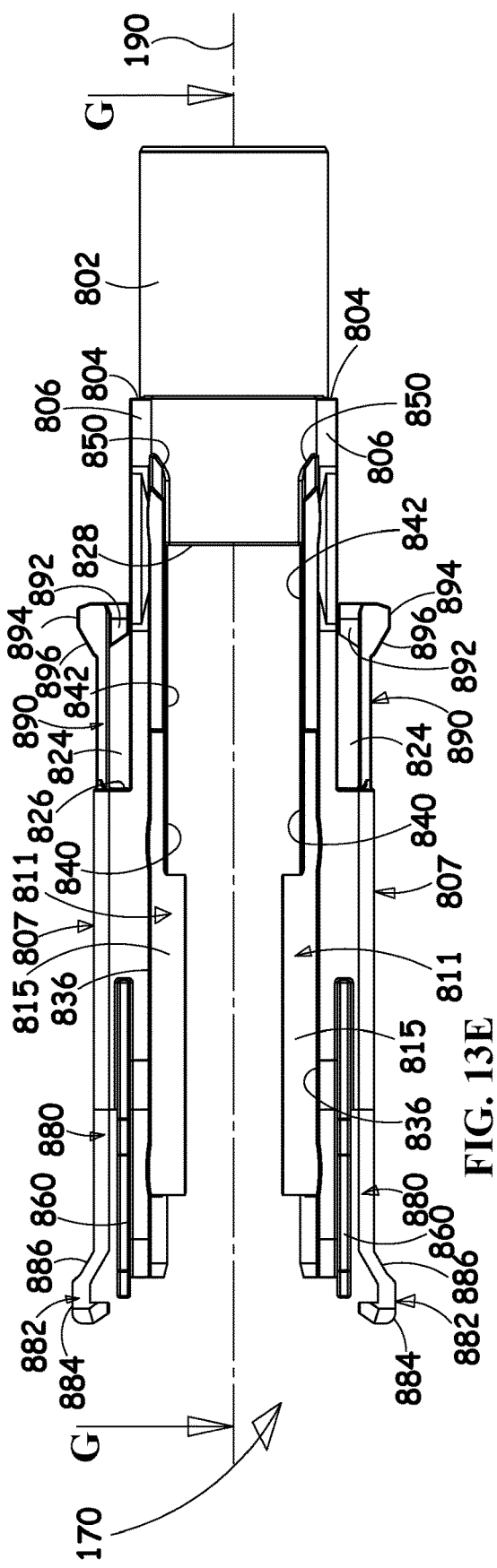
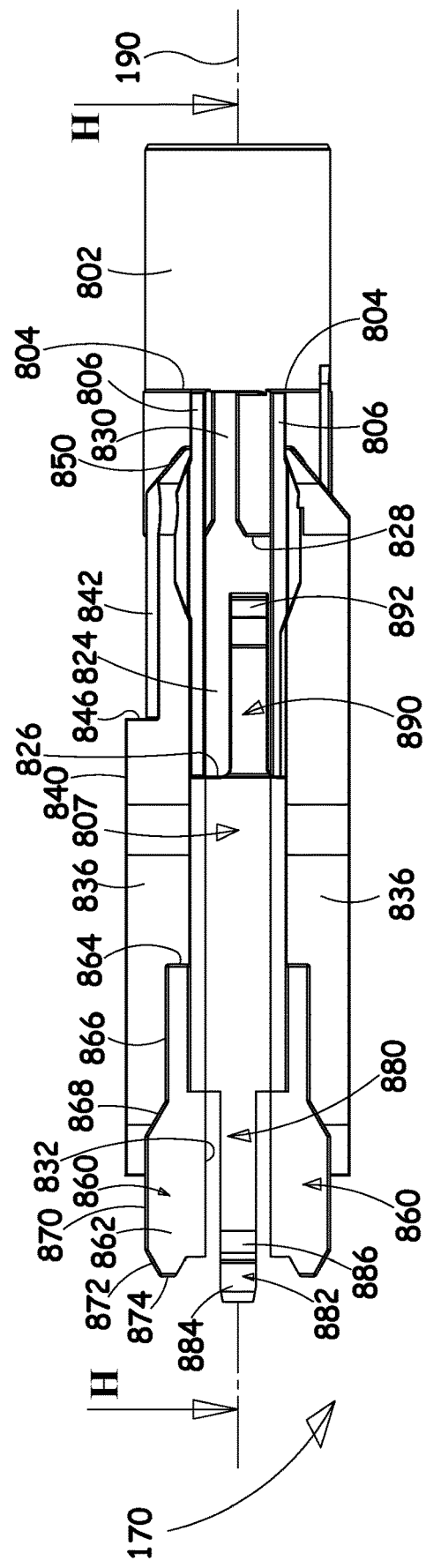

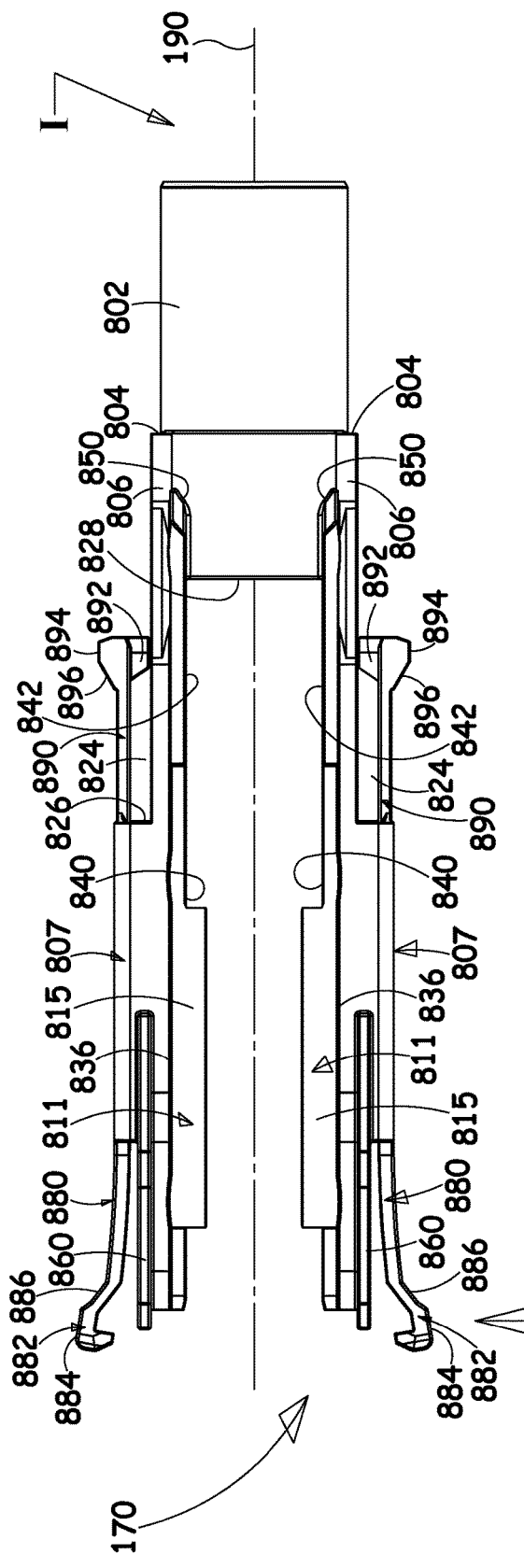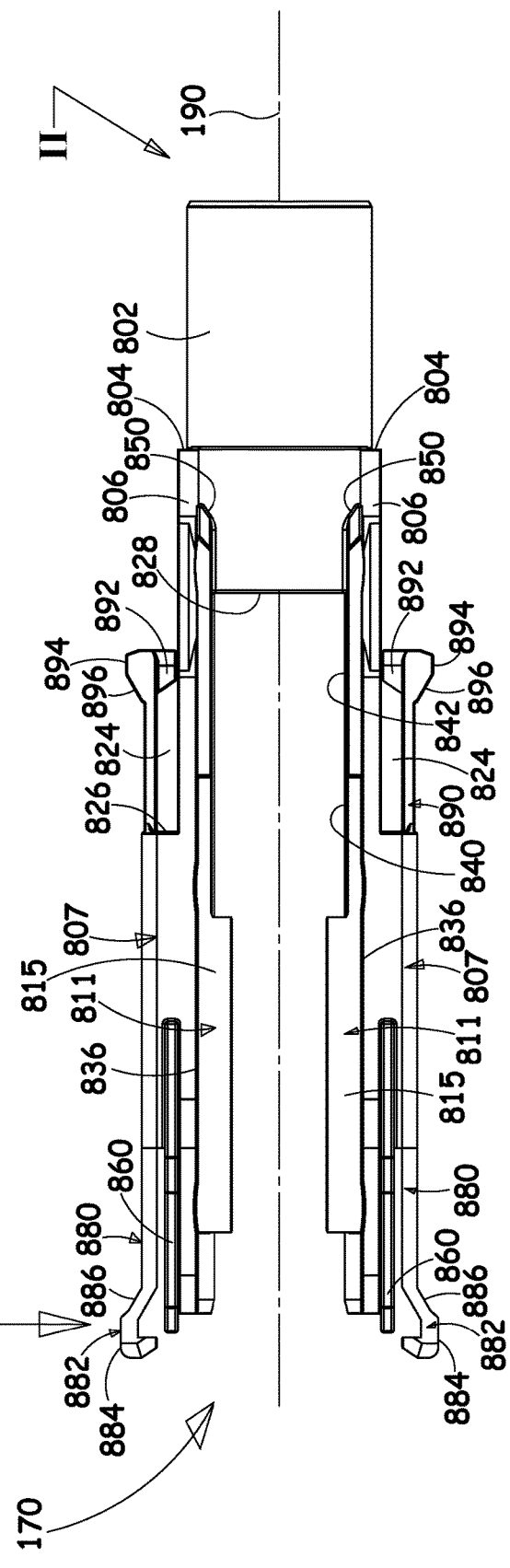
FIG. 14

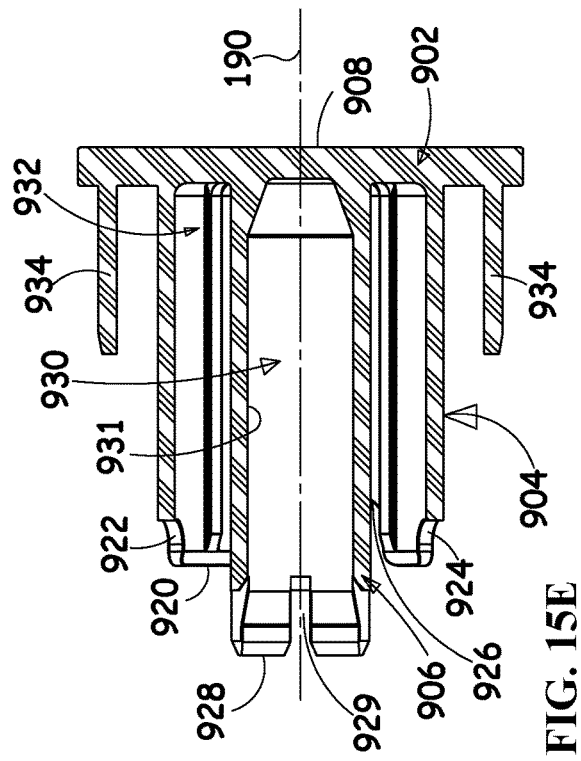
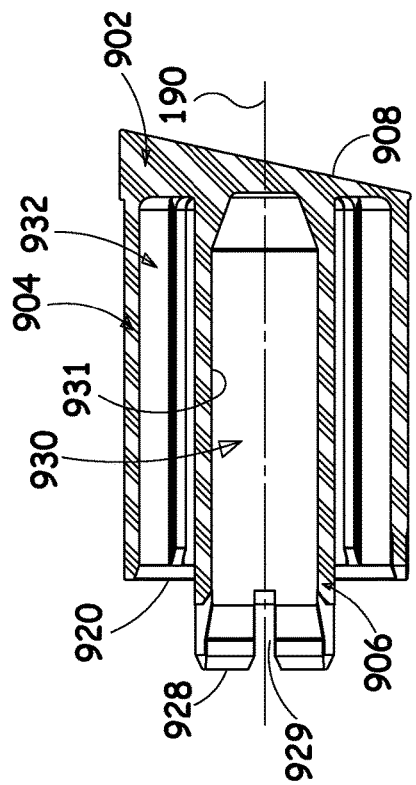
FIG. 15E
FIG. 15F

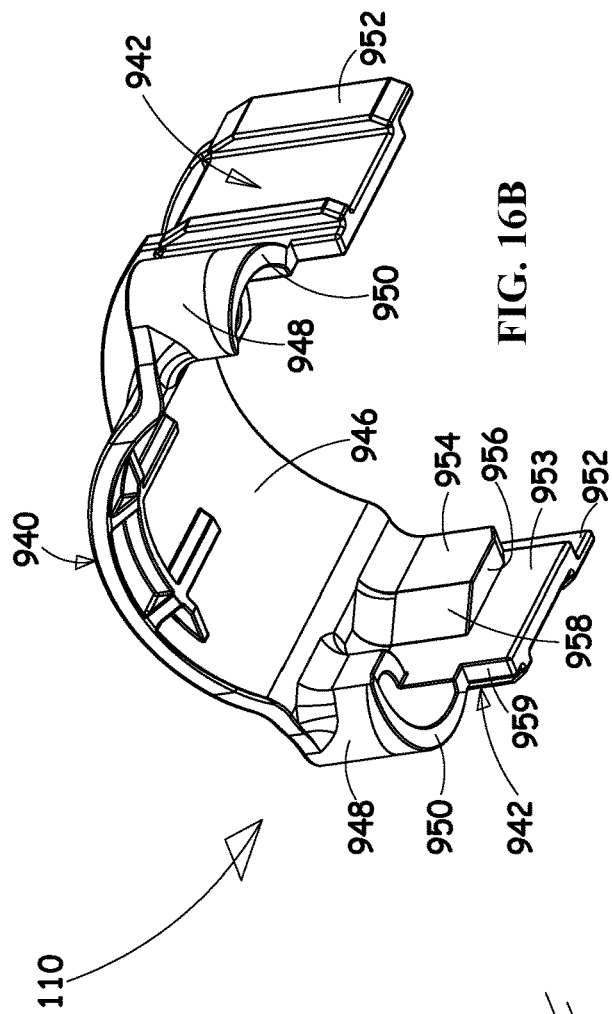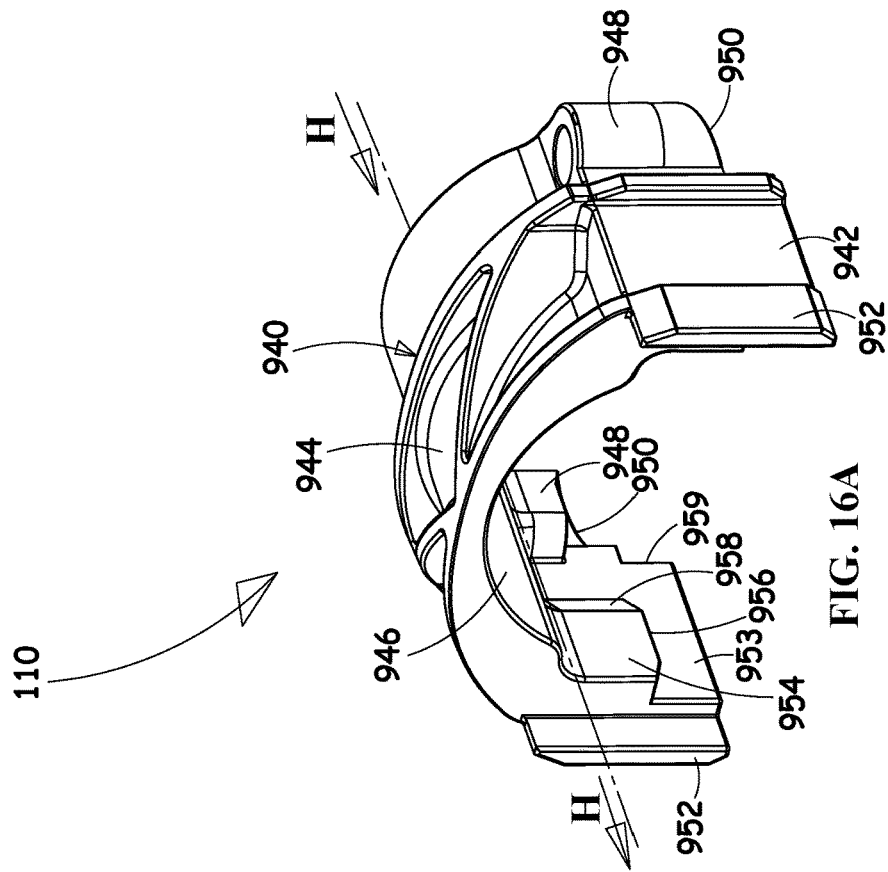

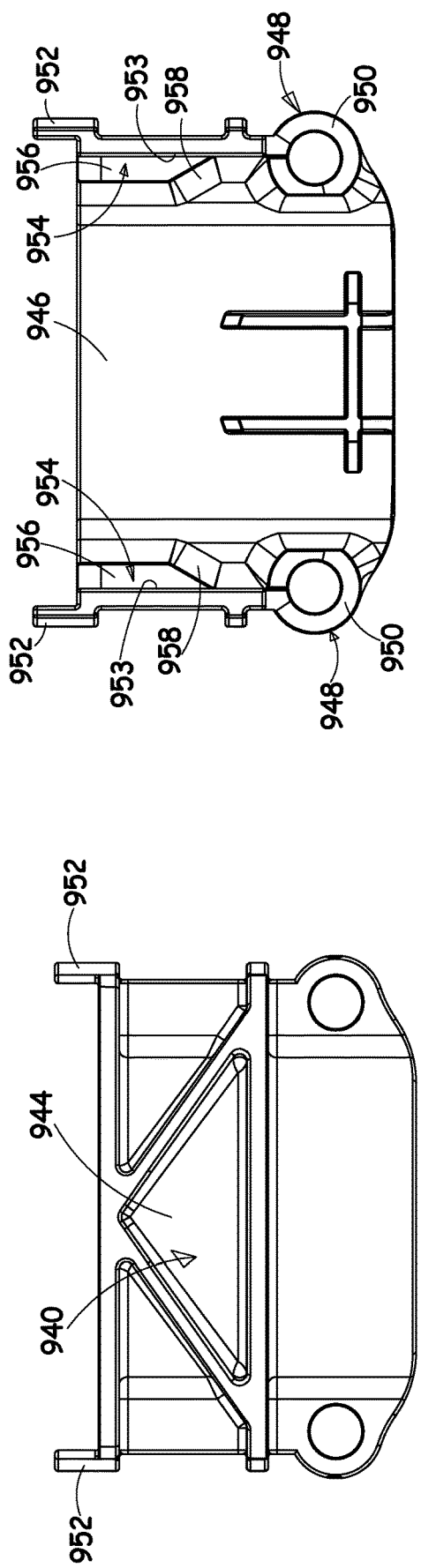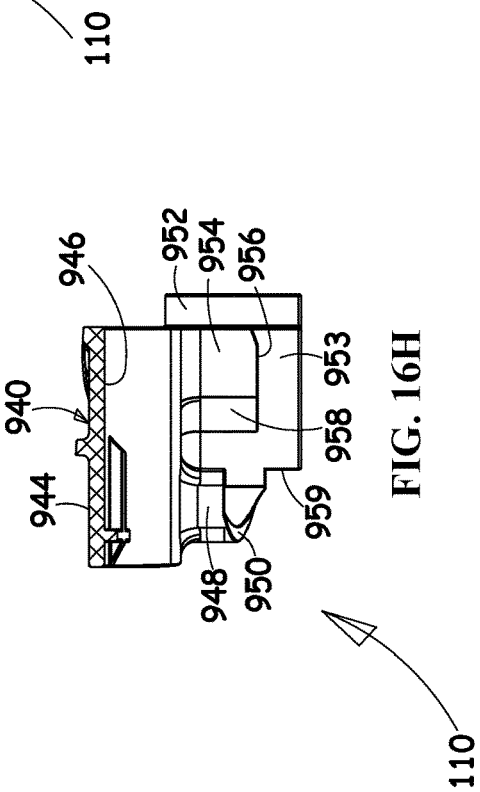
FIG. 16G
FIG. 16H
FIG. 16F

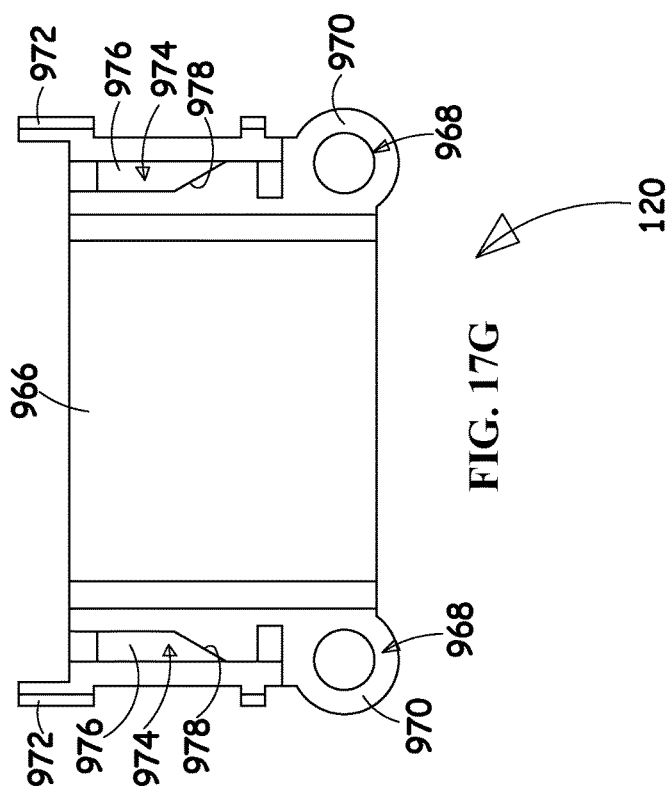
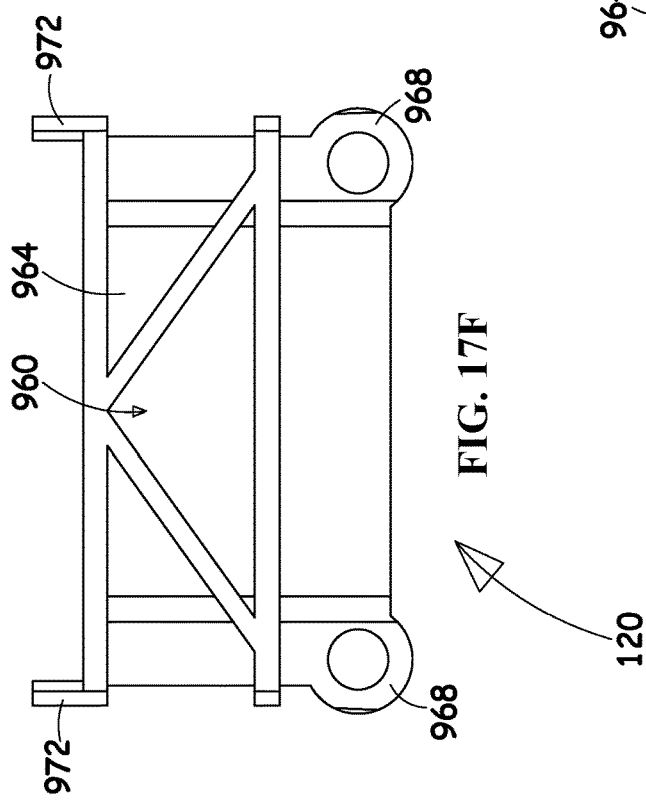
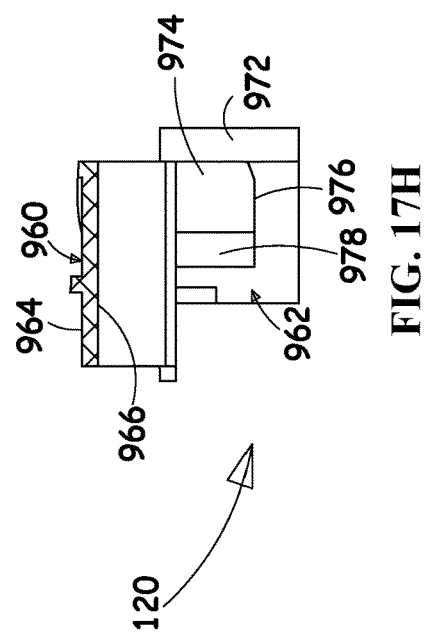
FIG. 17G
FIG. 17H
FIG. 17F

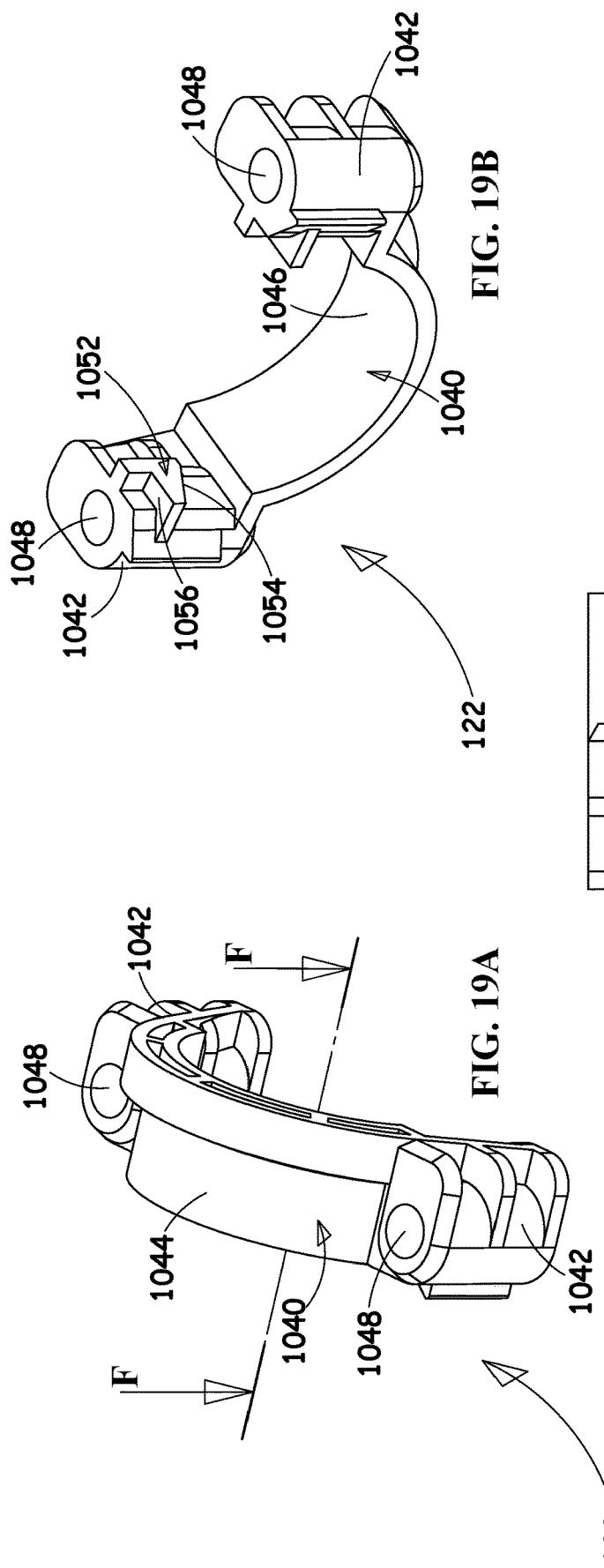

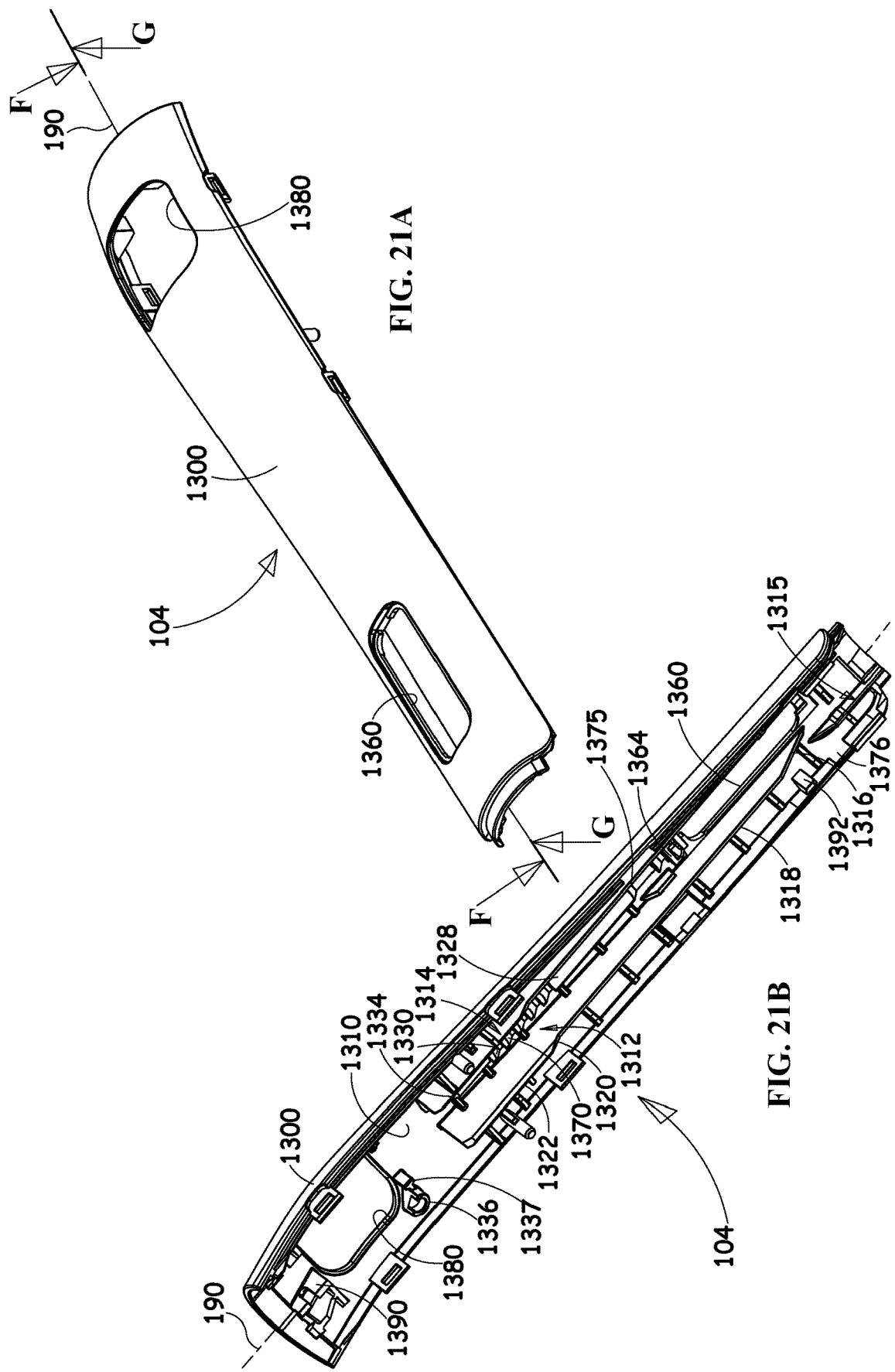

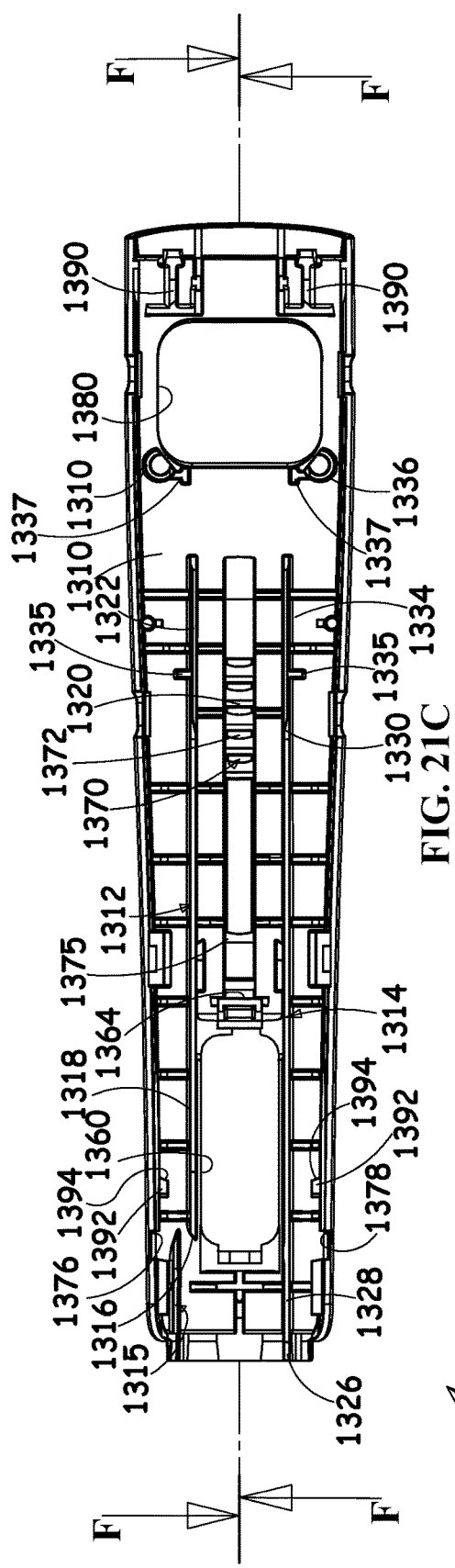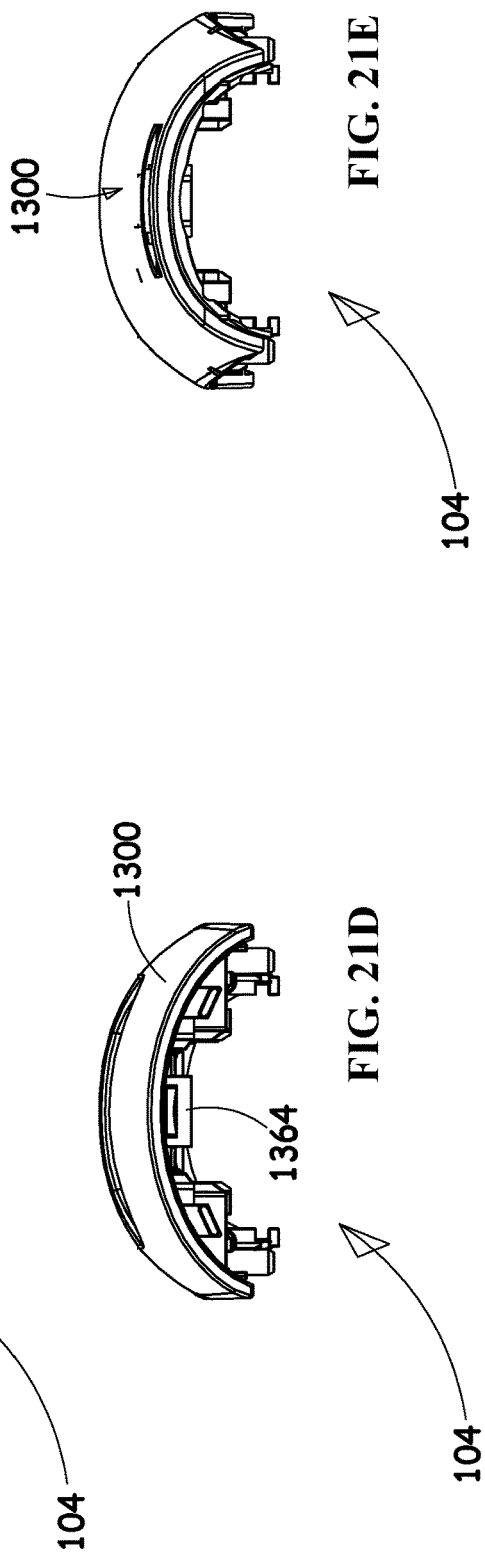

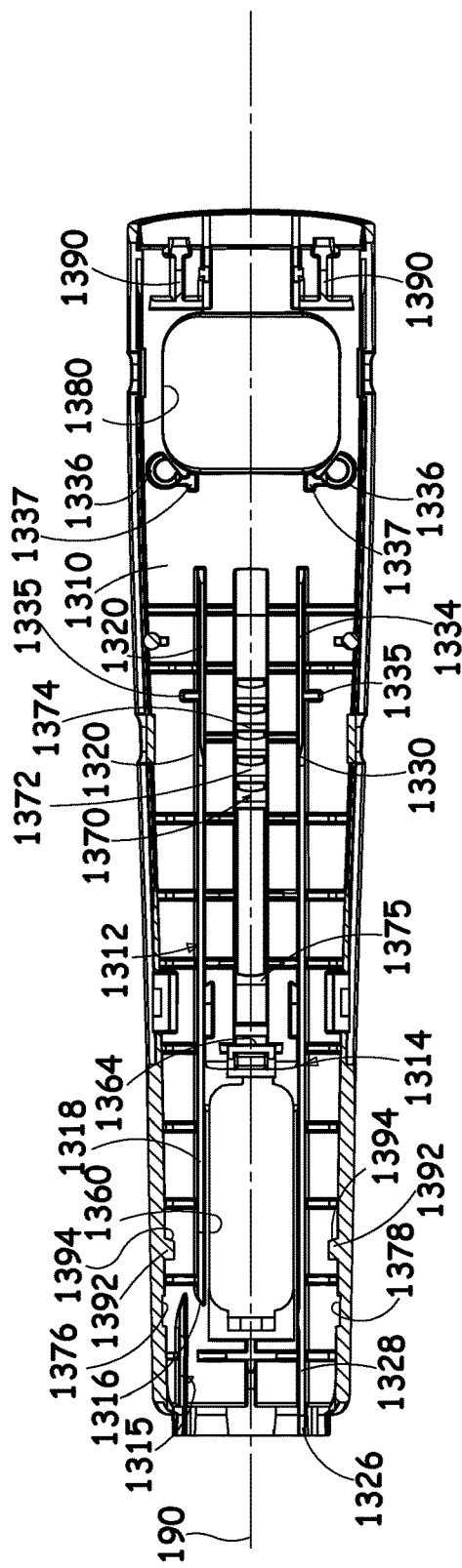
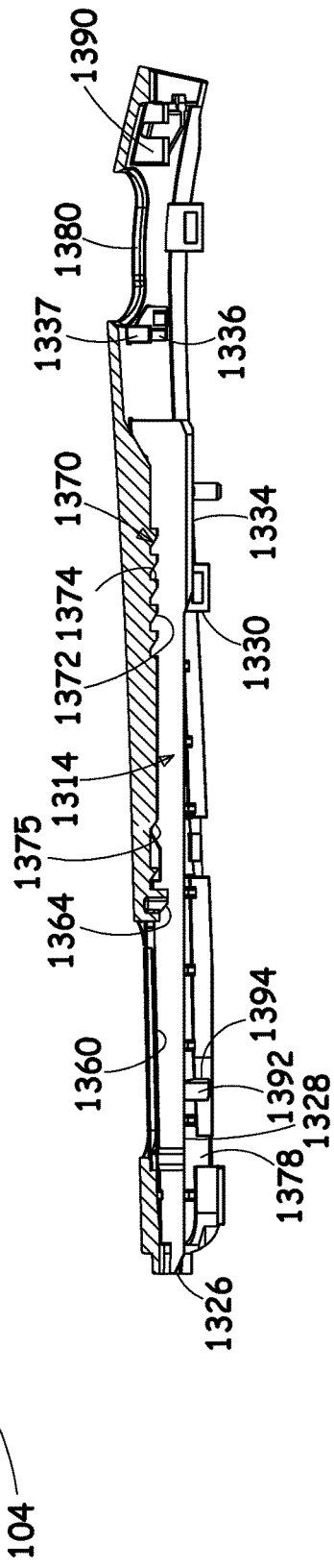
FIG. 21F
FIG. 21G

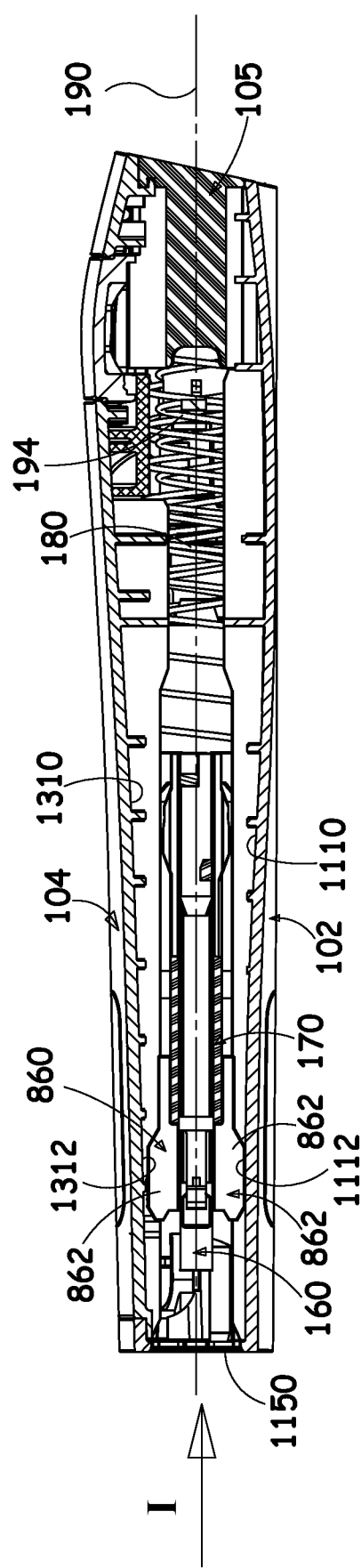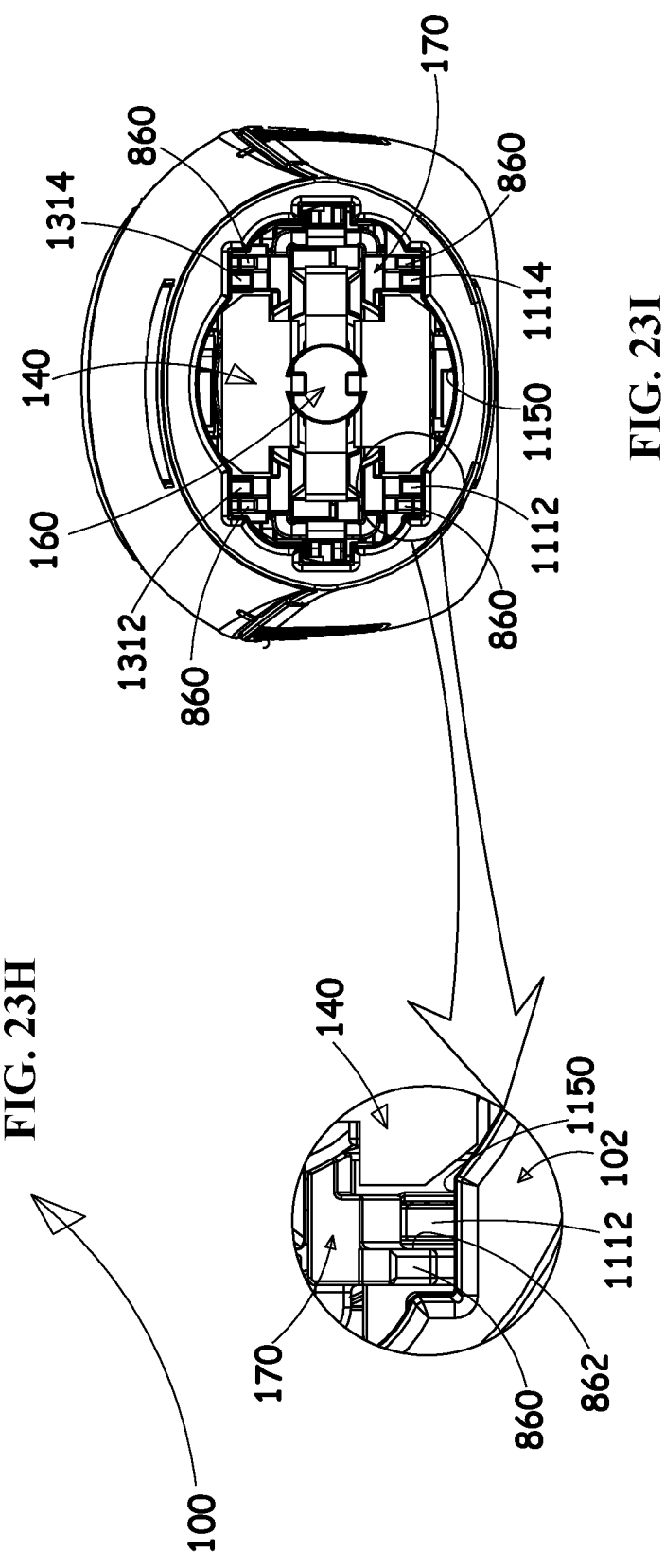
FIG. 23H
FIG. 23I

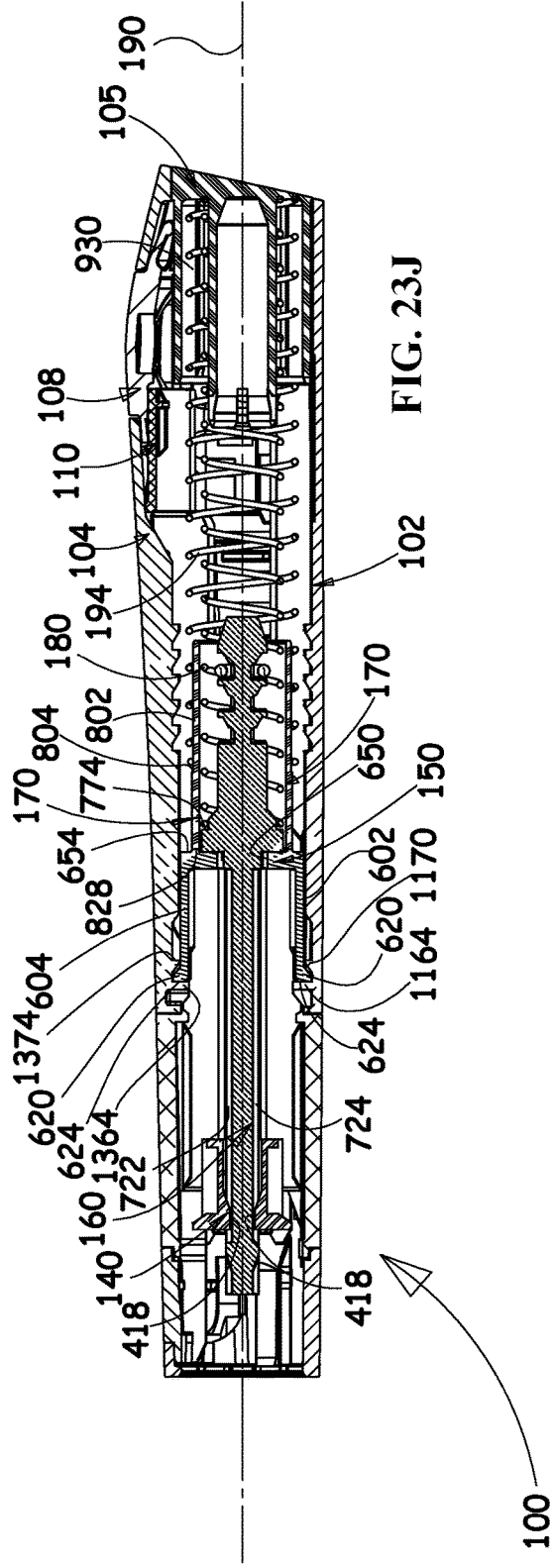
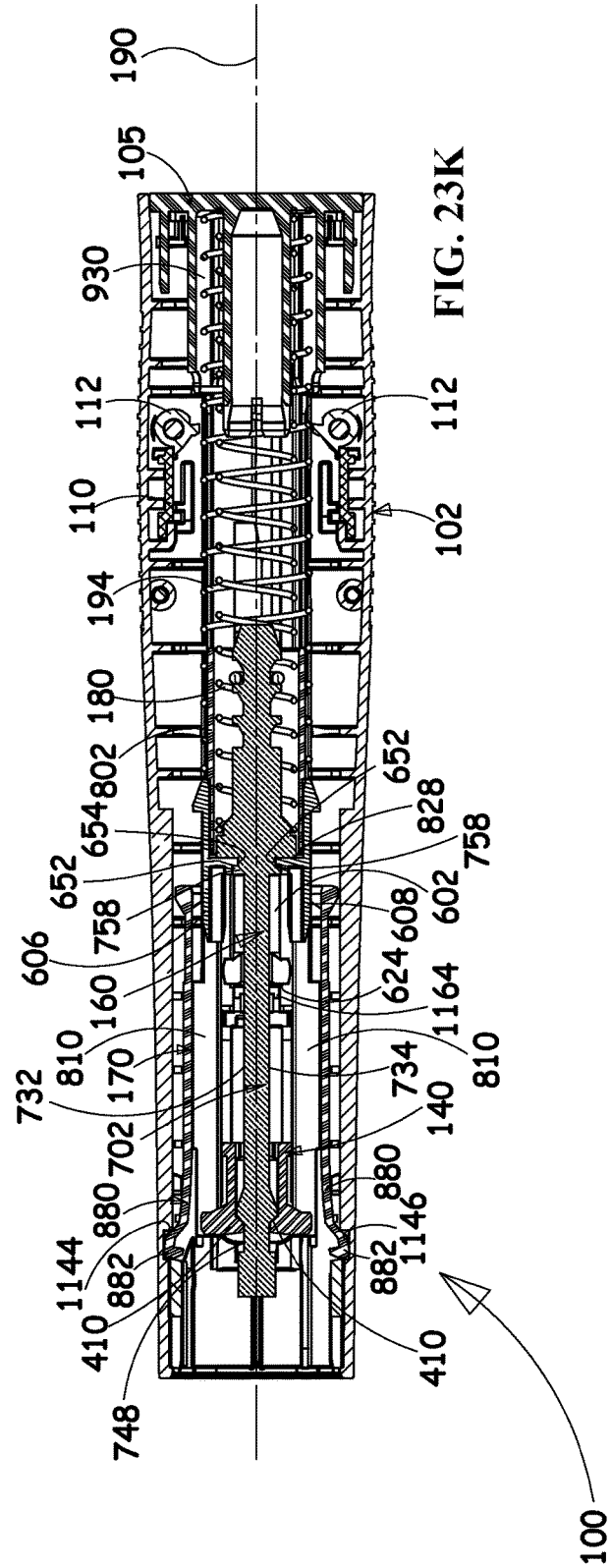
FIG. 23J
FIG. 23K

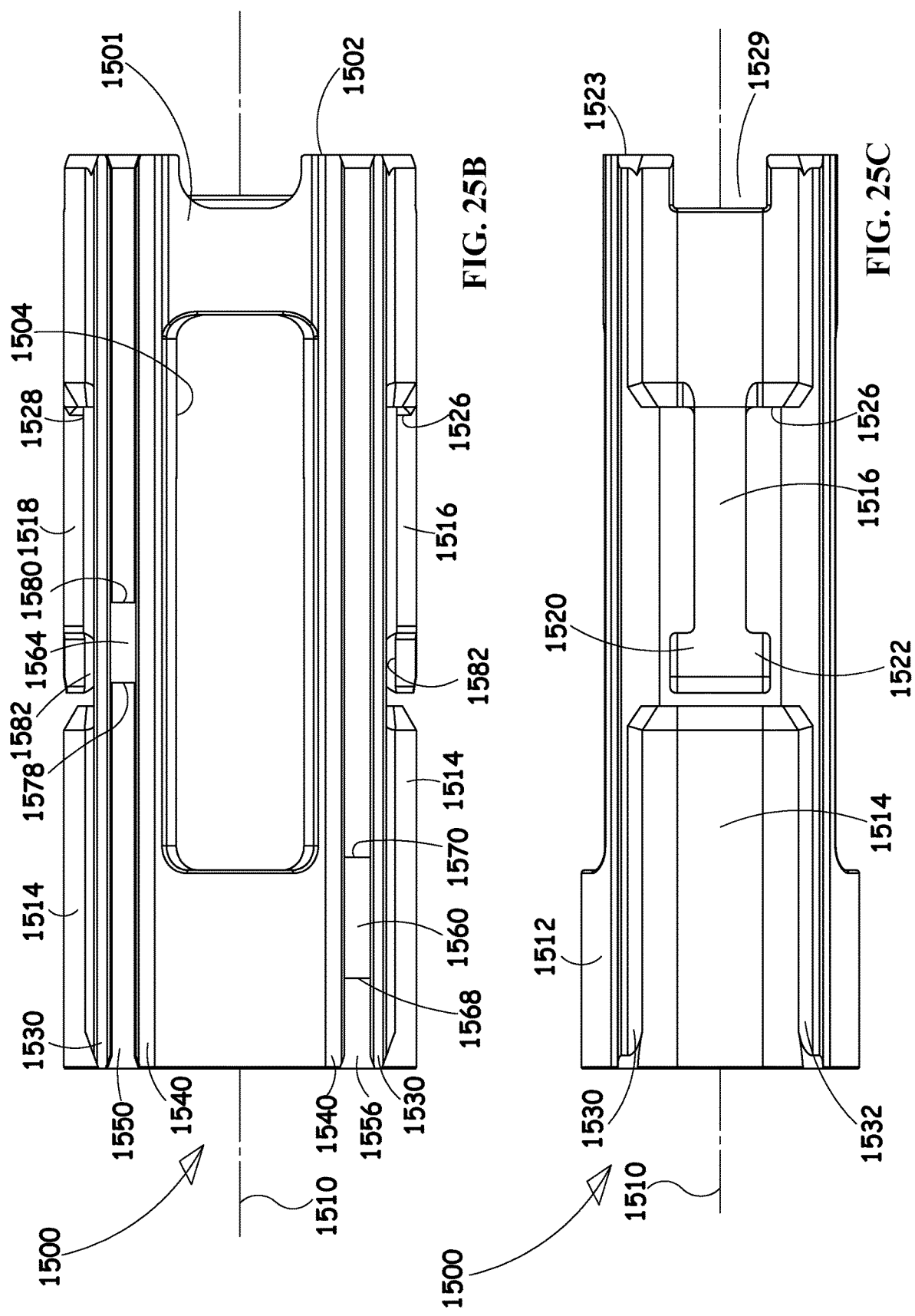

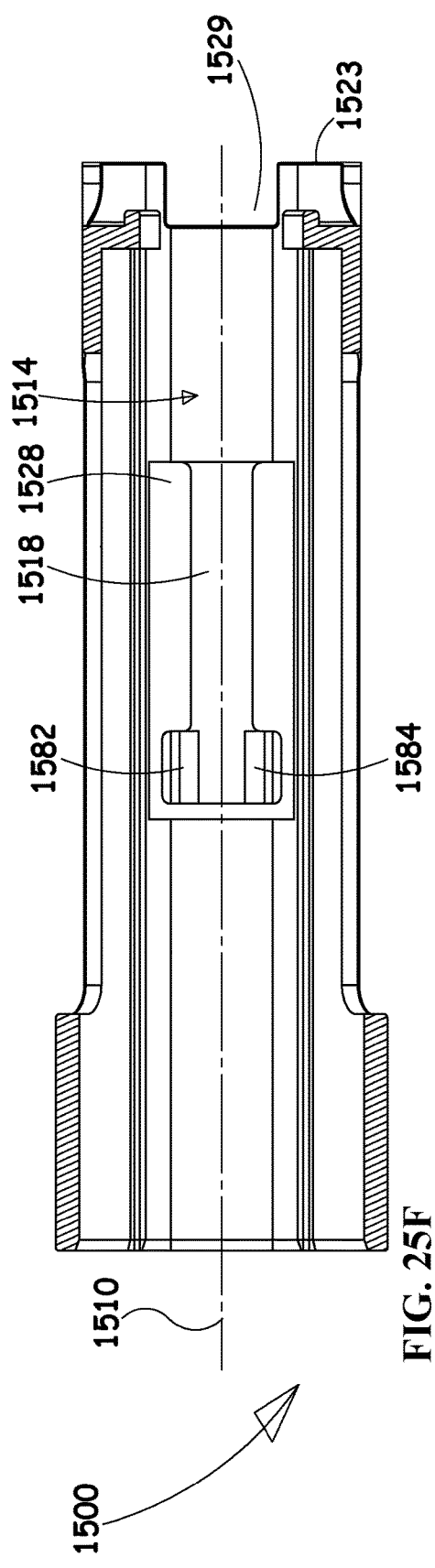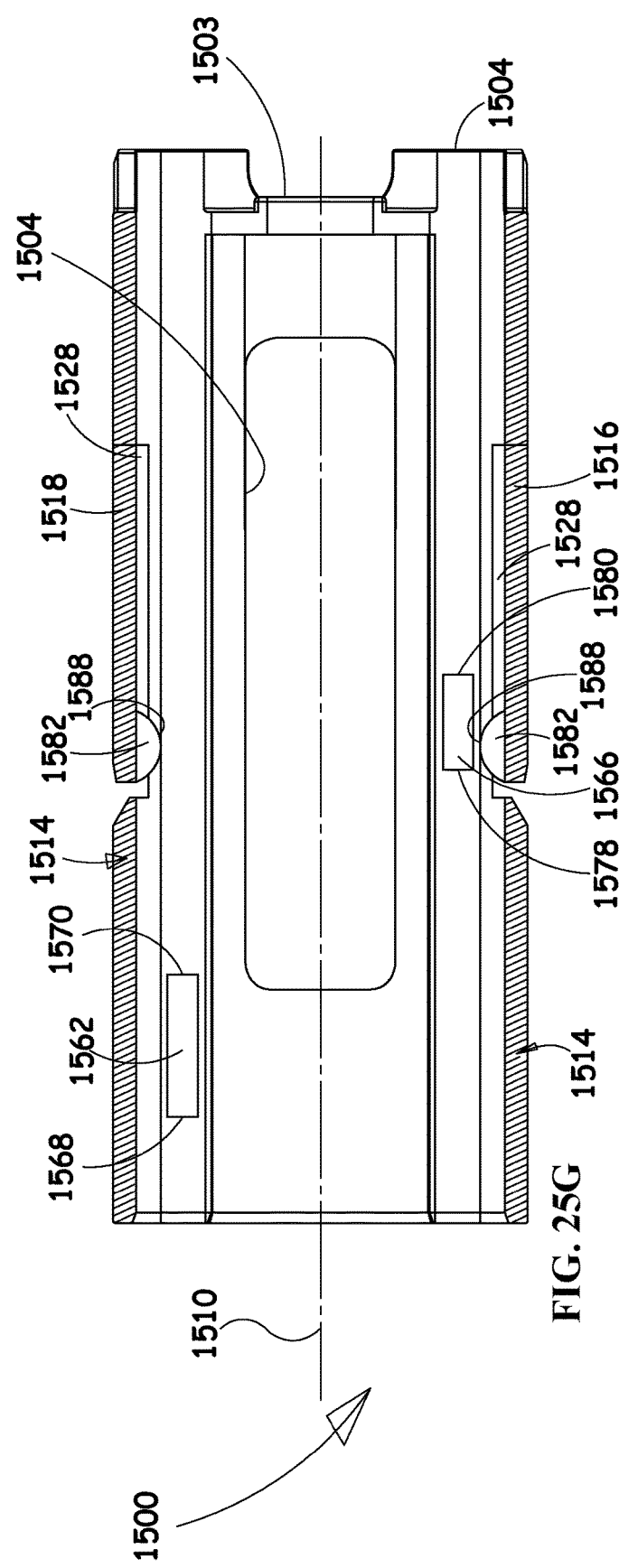
FIG. 25F
FIG. 25G

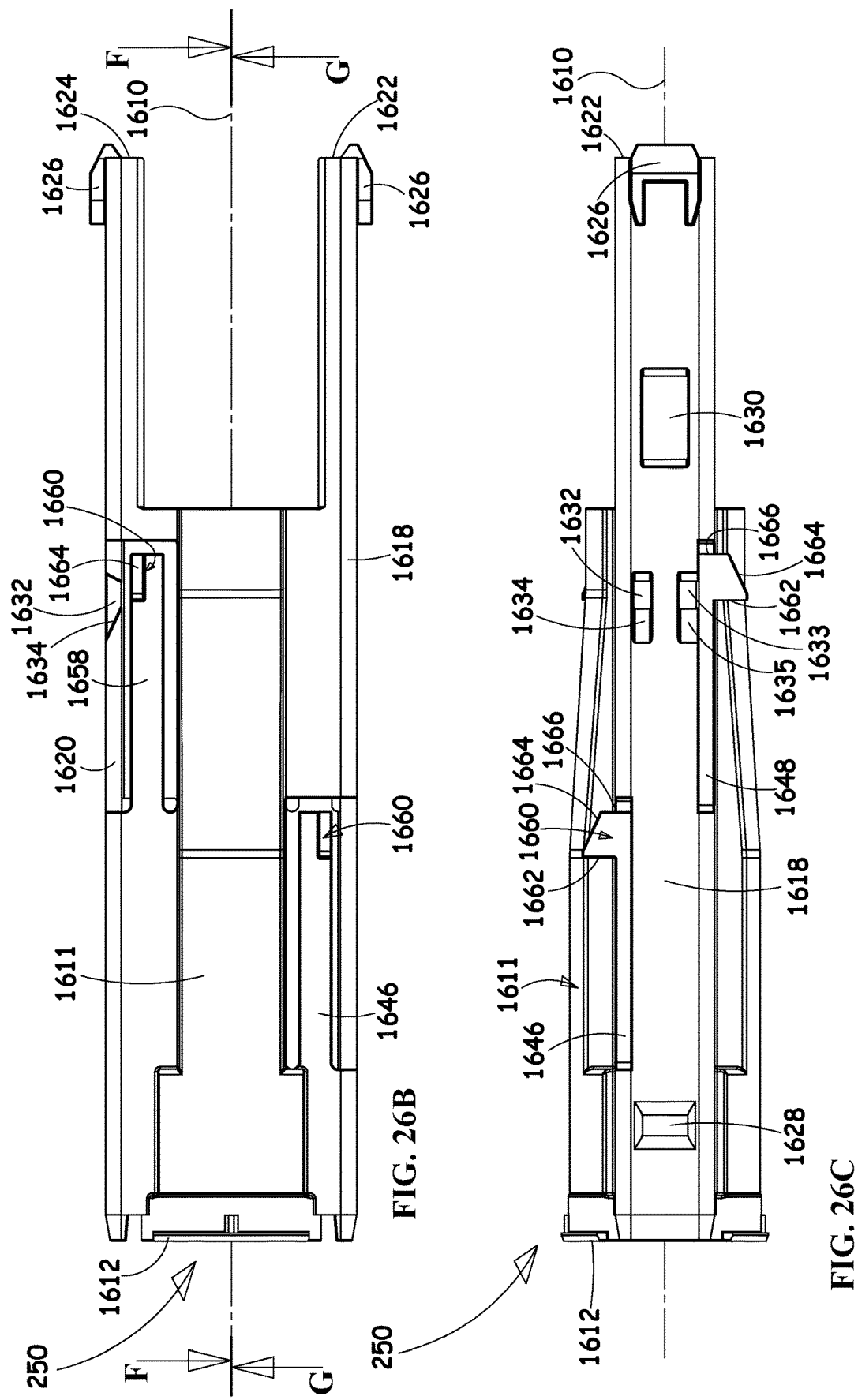

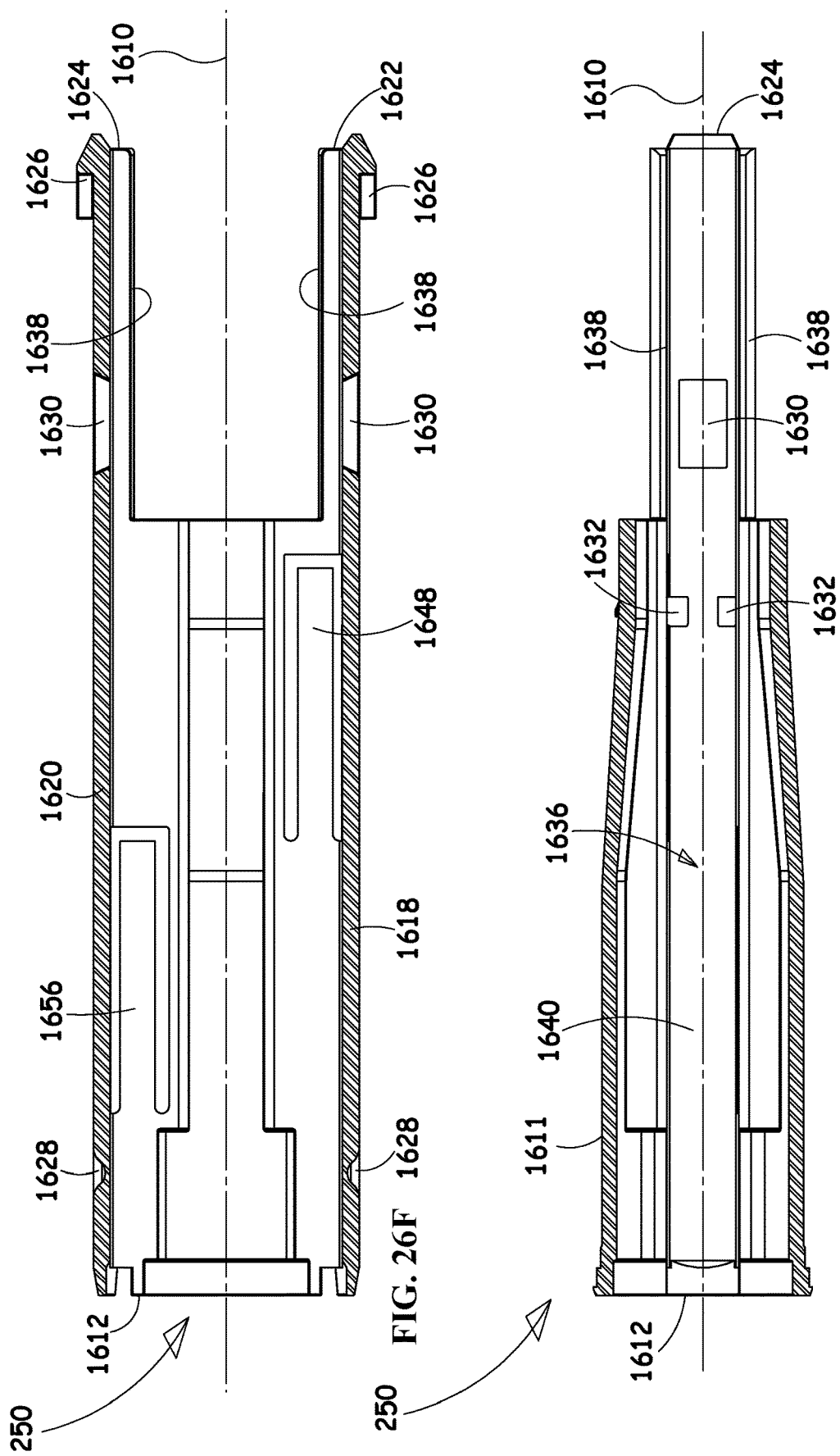

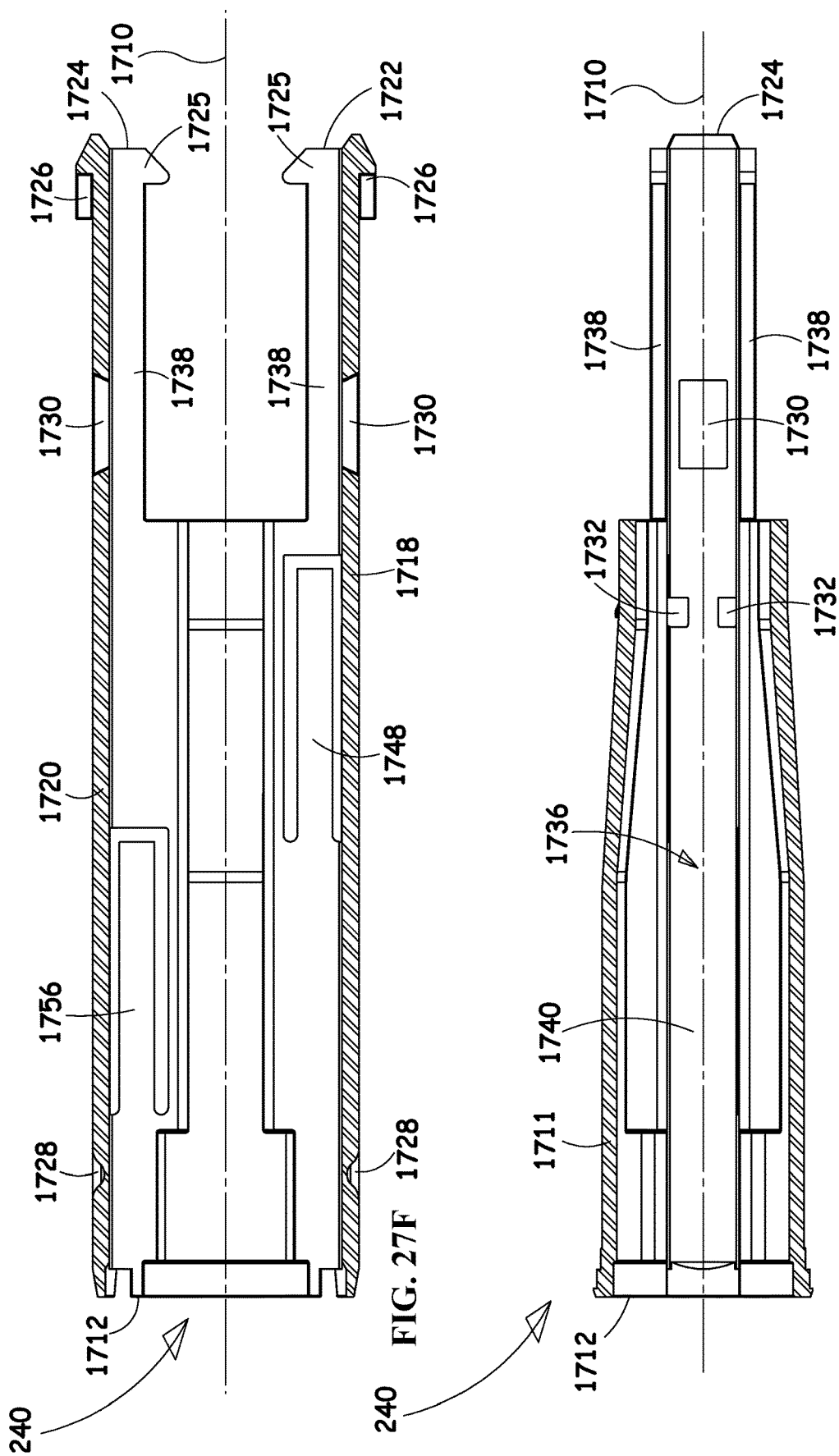

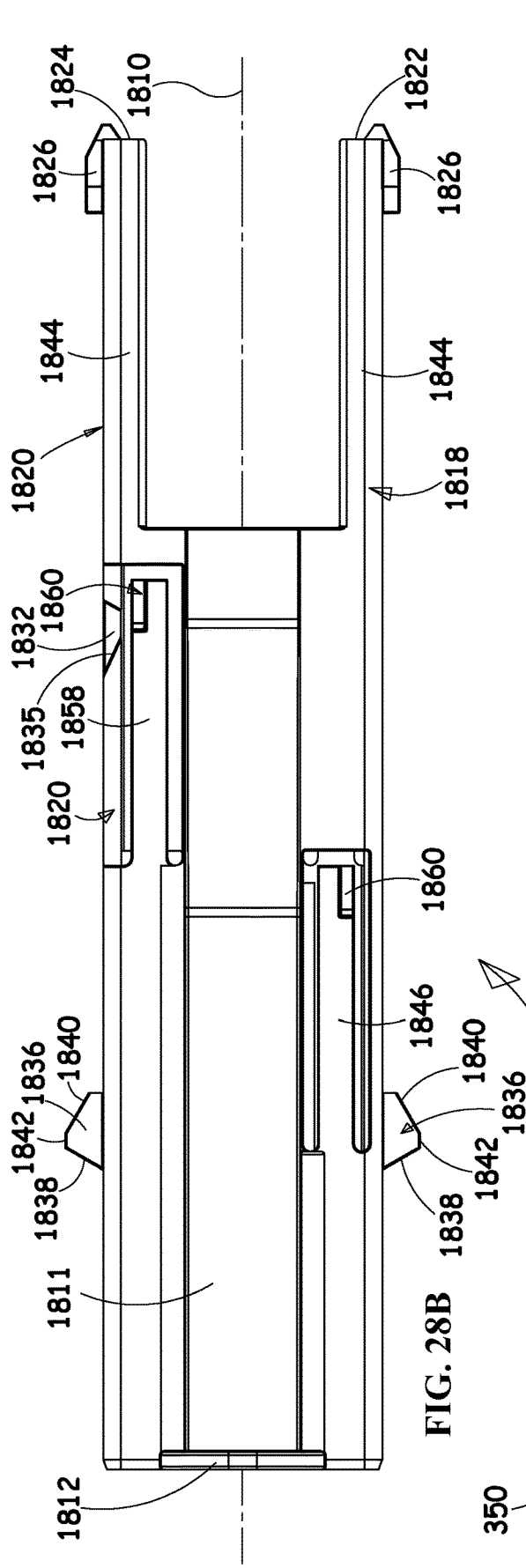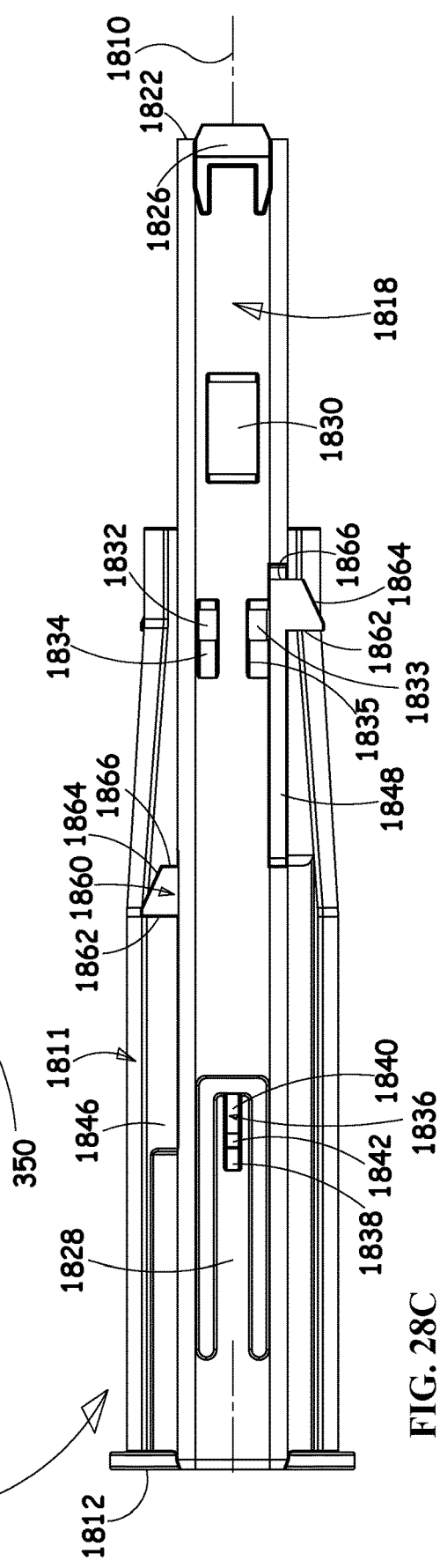
FIG. 28B
FIG. 28C

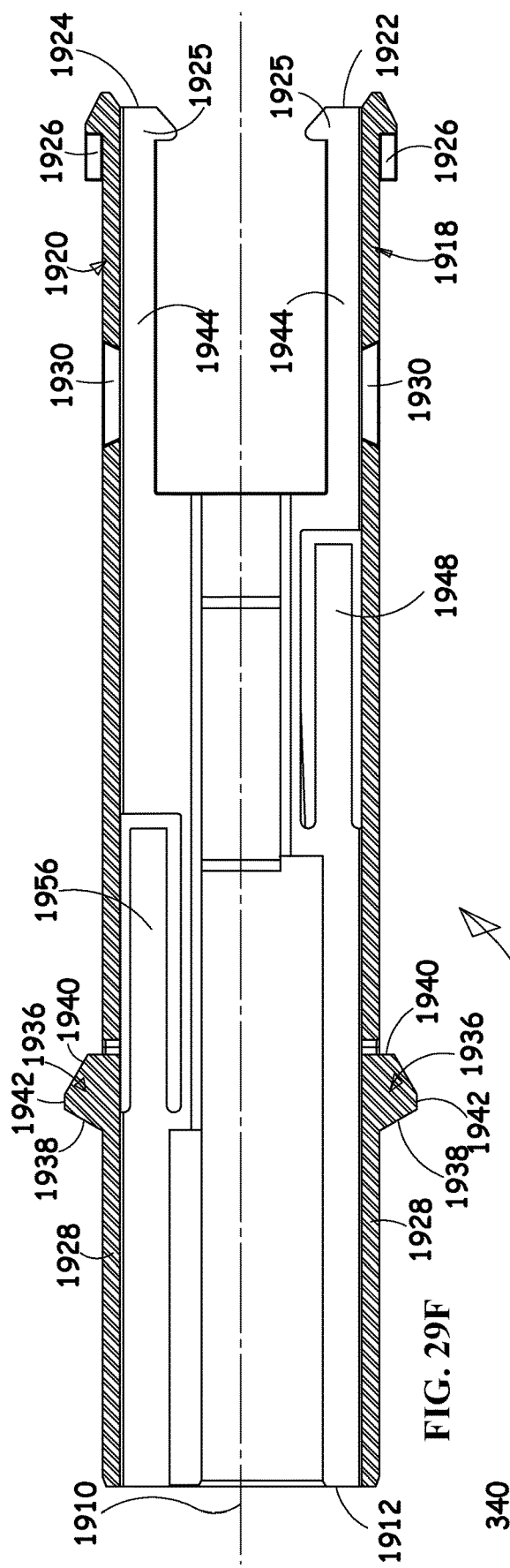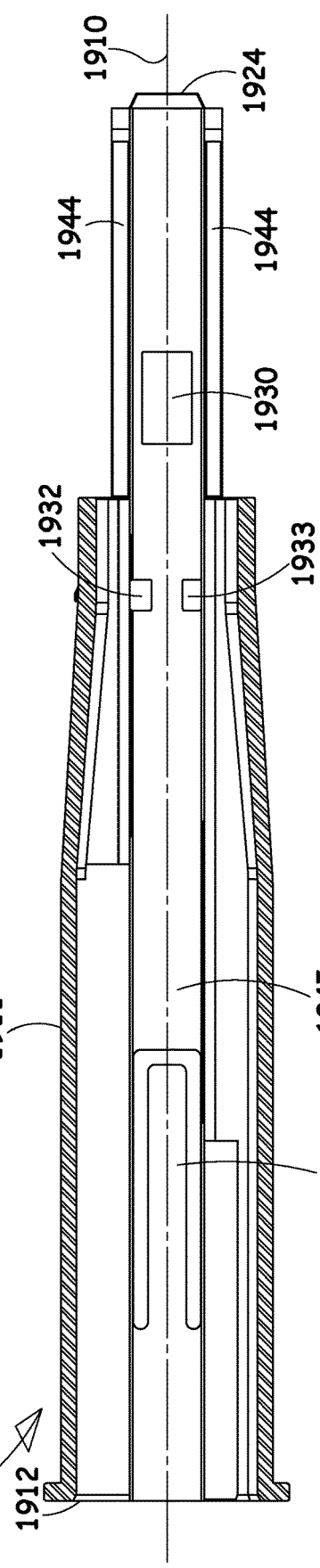
FIG. 29F
FIG. 29G

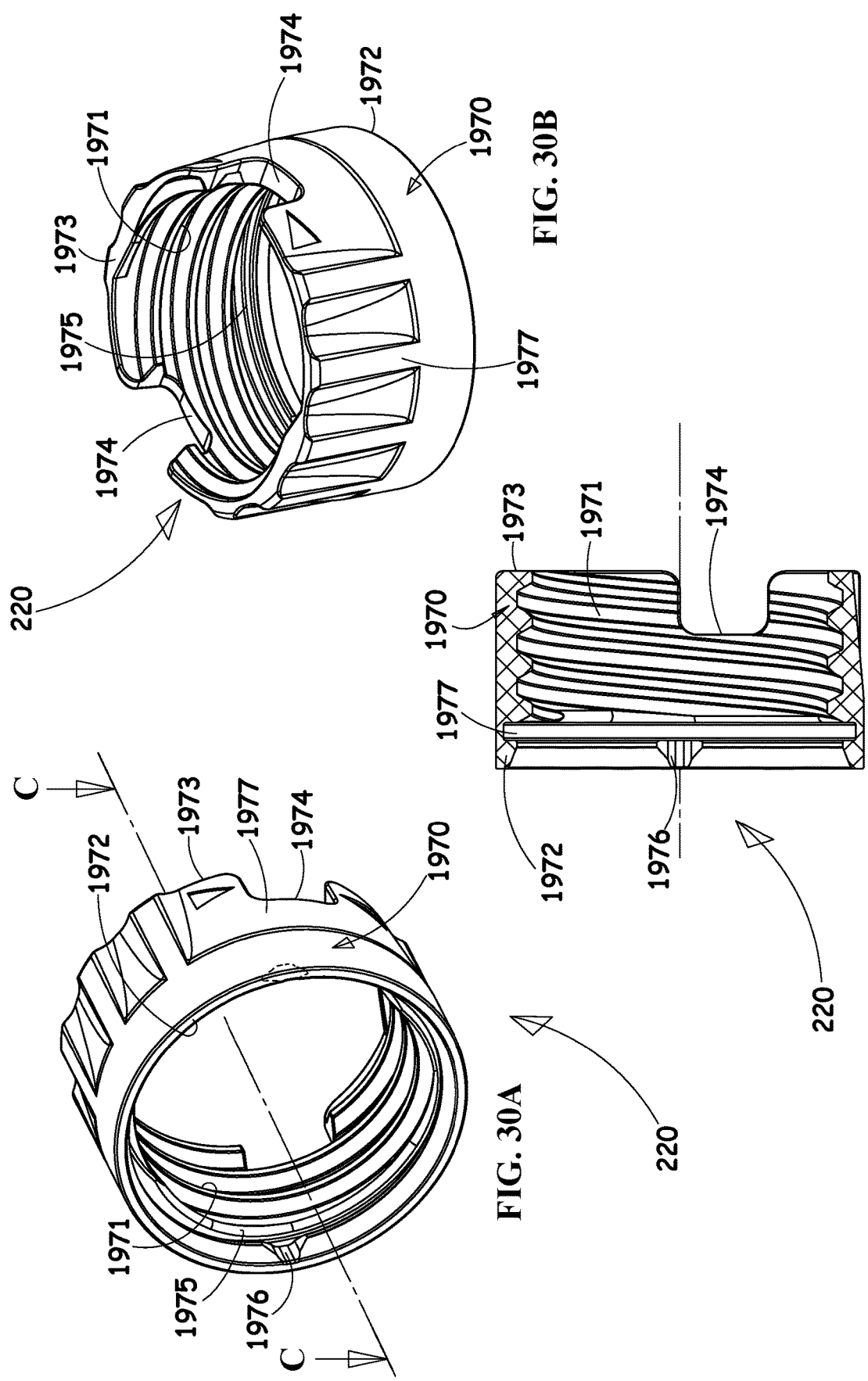

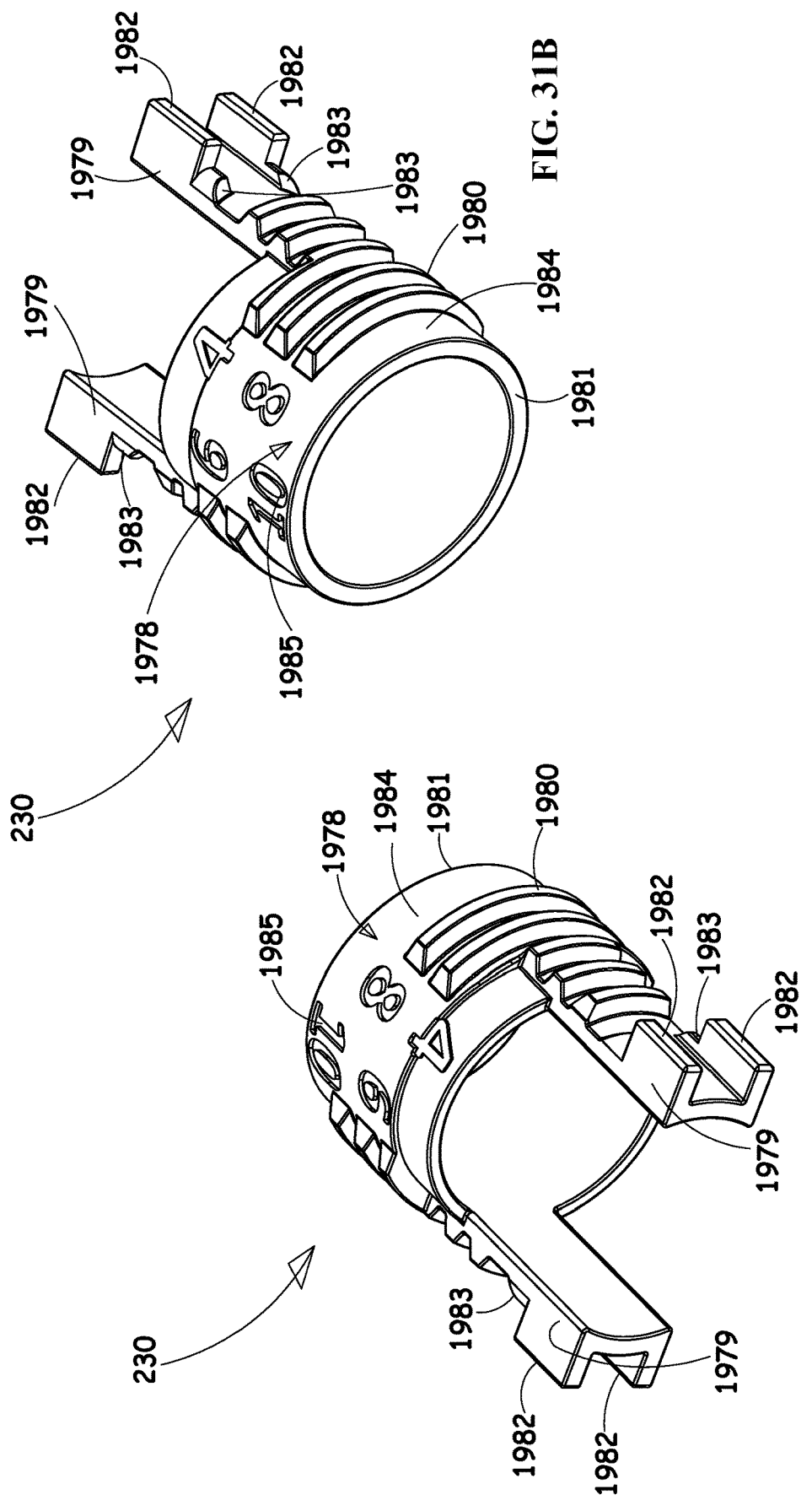

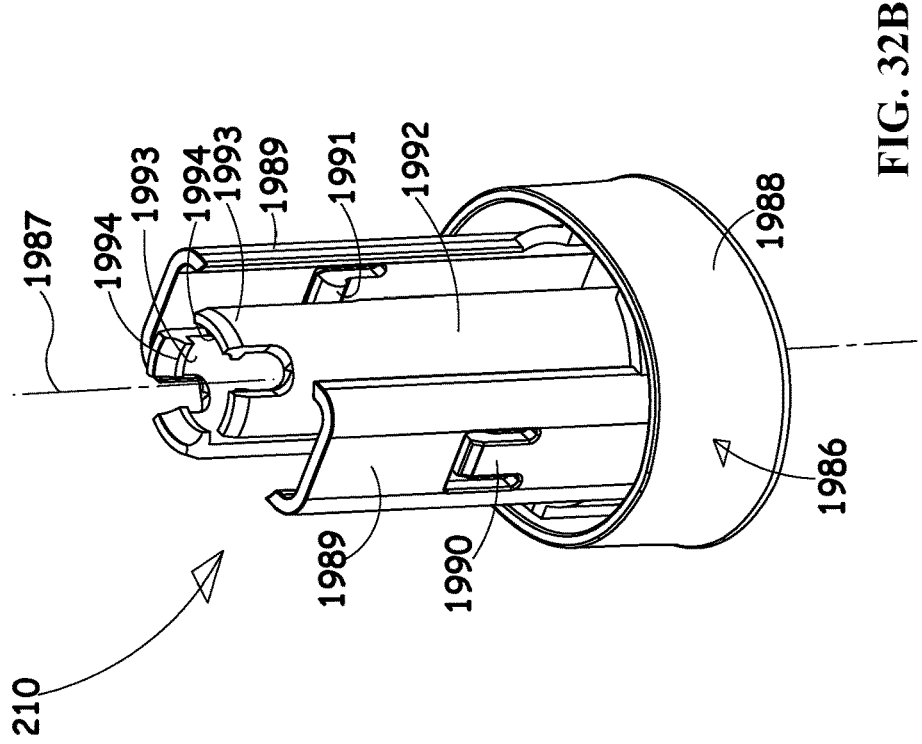
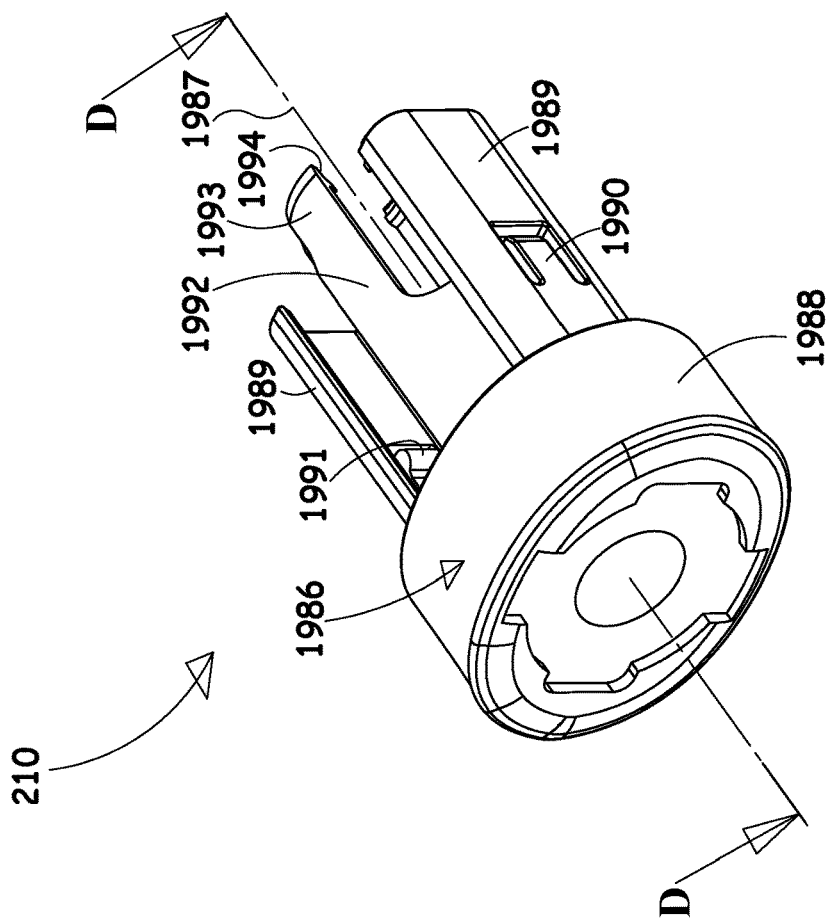
FIG. 32B
FIG. 32A

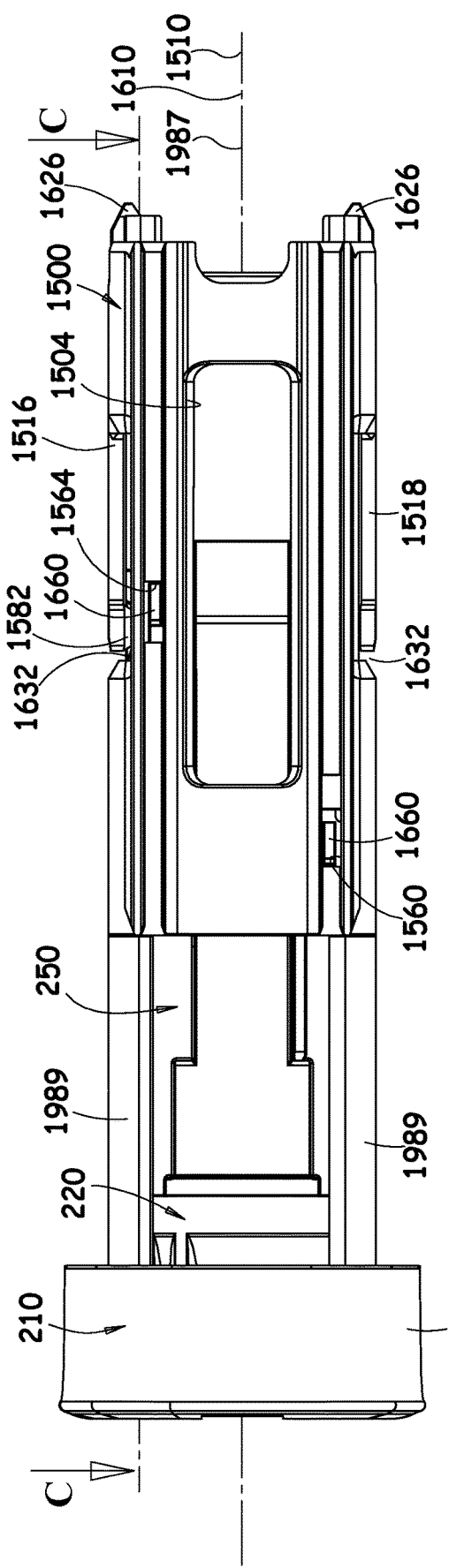
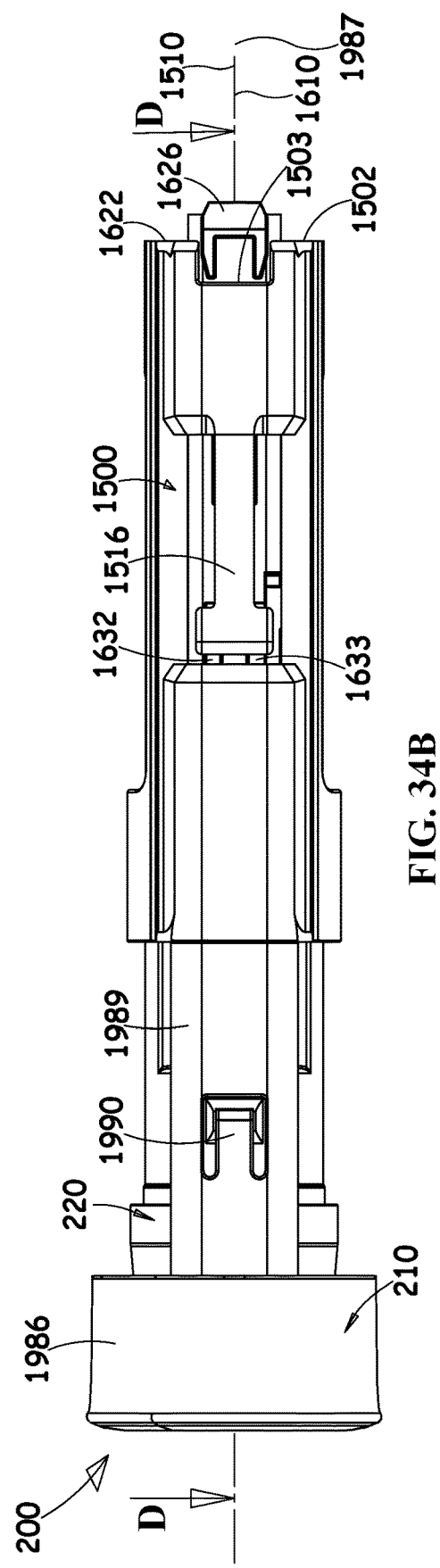

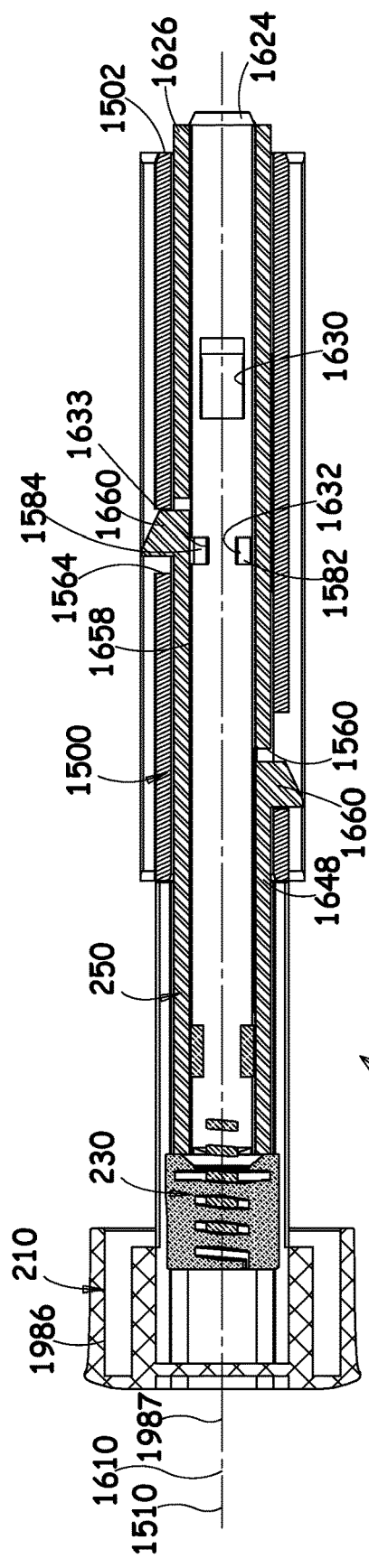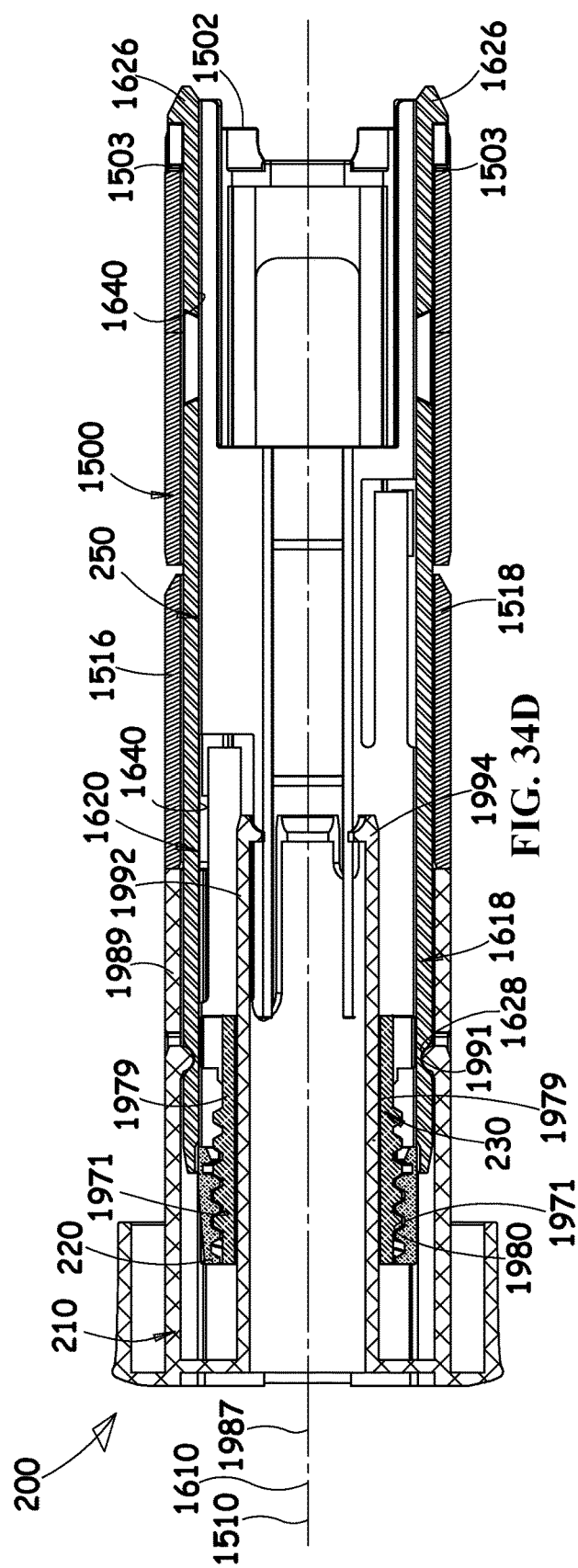
FIG. 34C
FIG. 34D

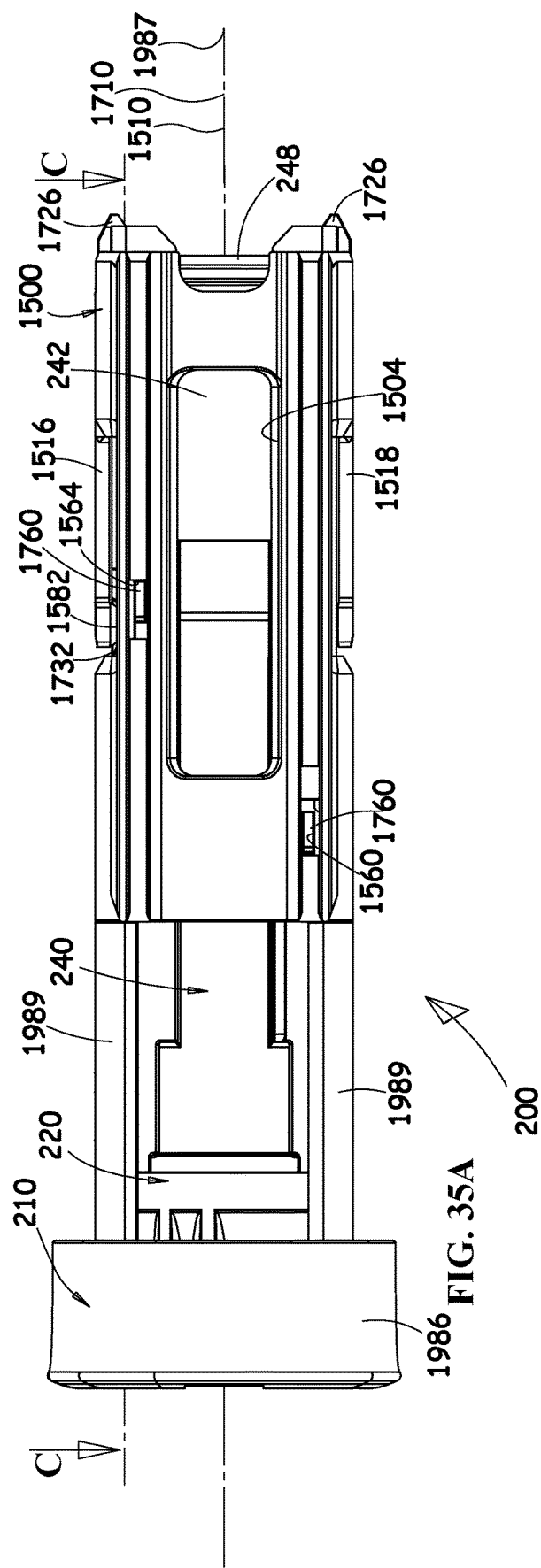
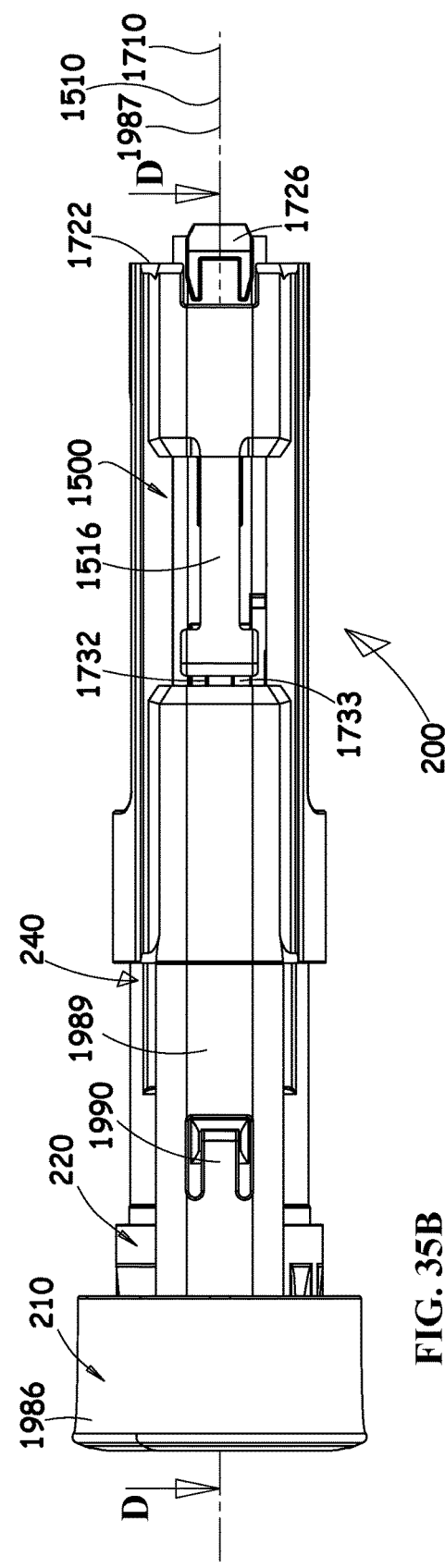
FIG. 35A
FIG. 35B

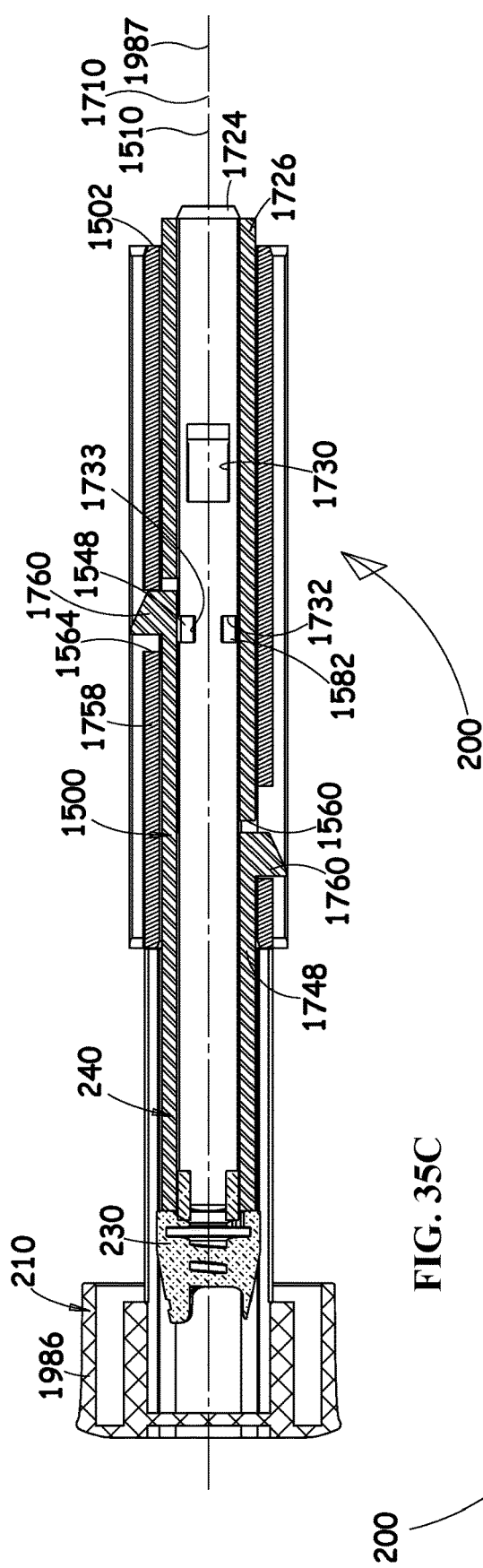
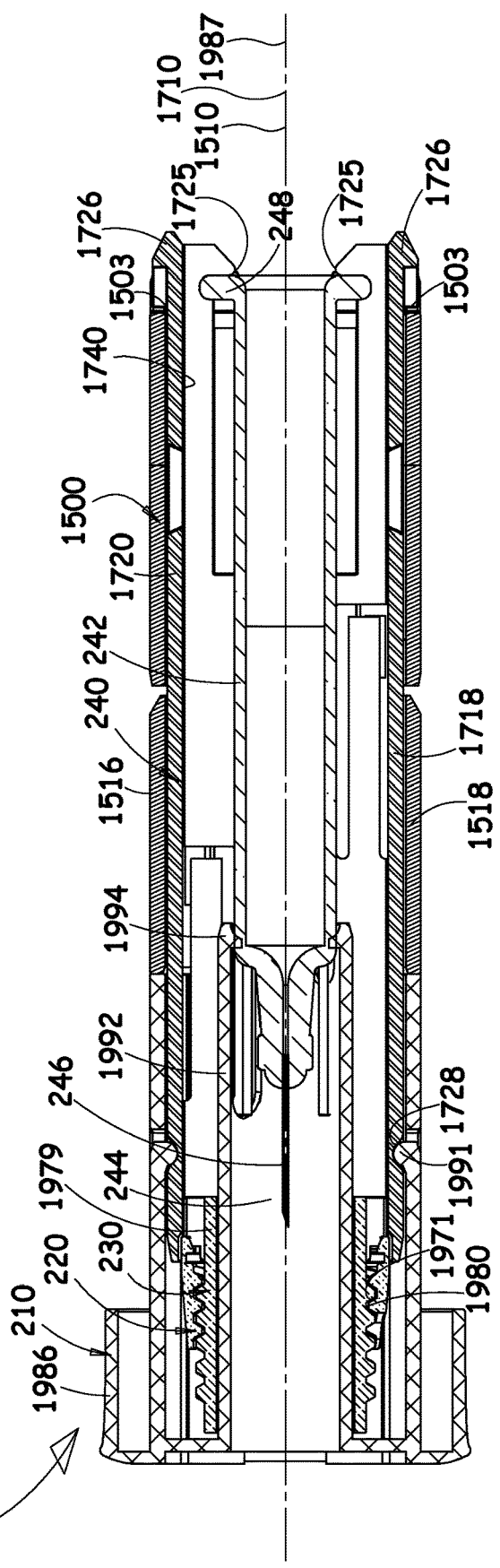
FIG. 35C
FIG. 35D

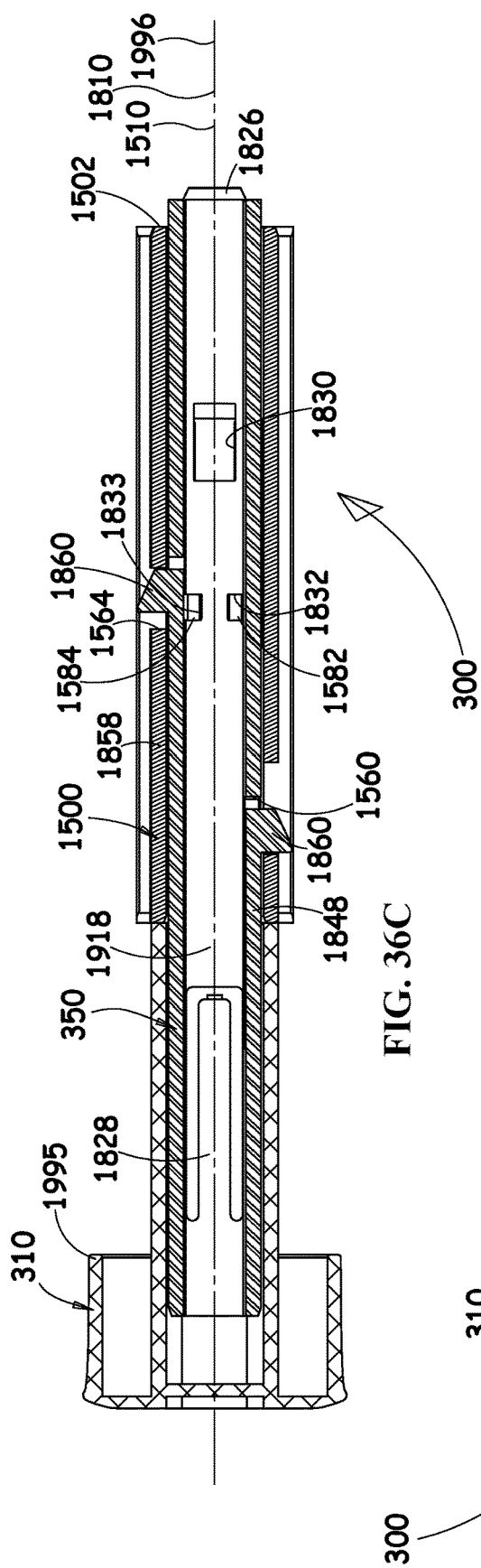
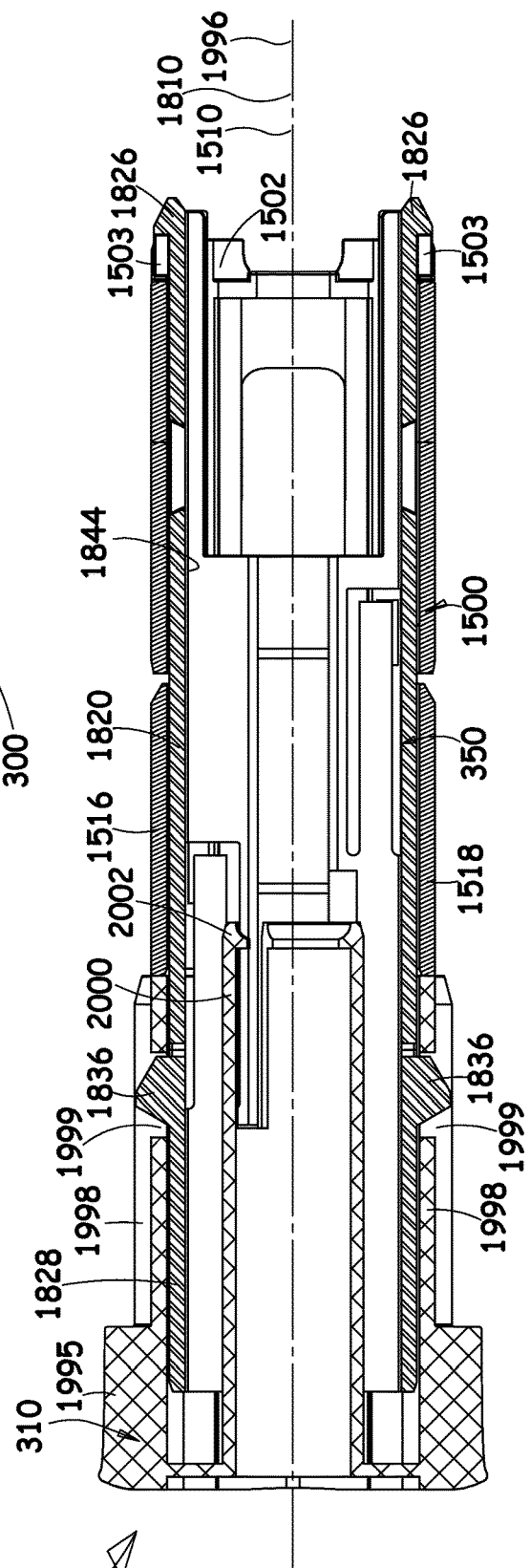
FIG. 36C
FIG. 36D

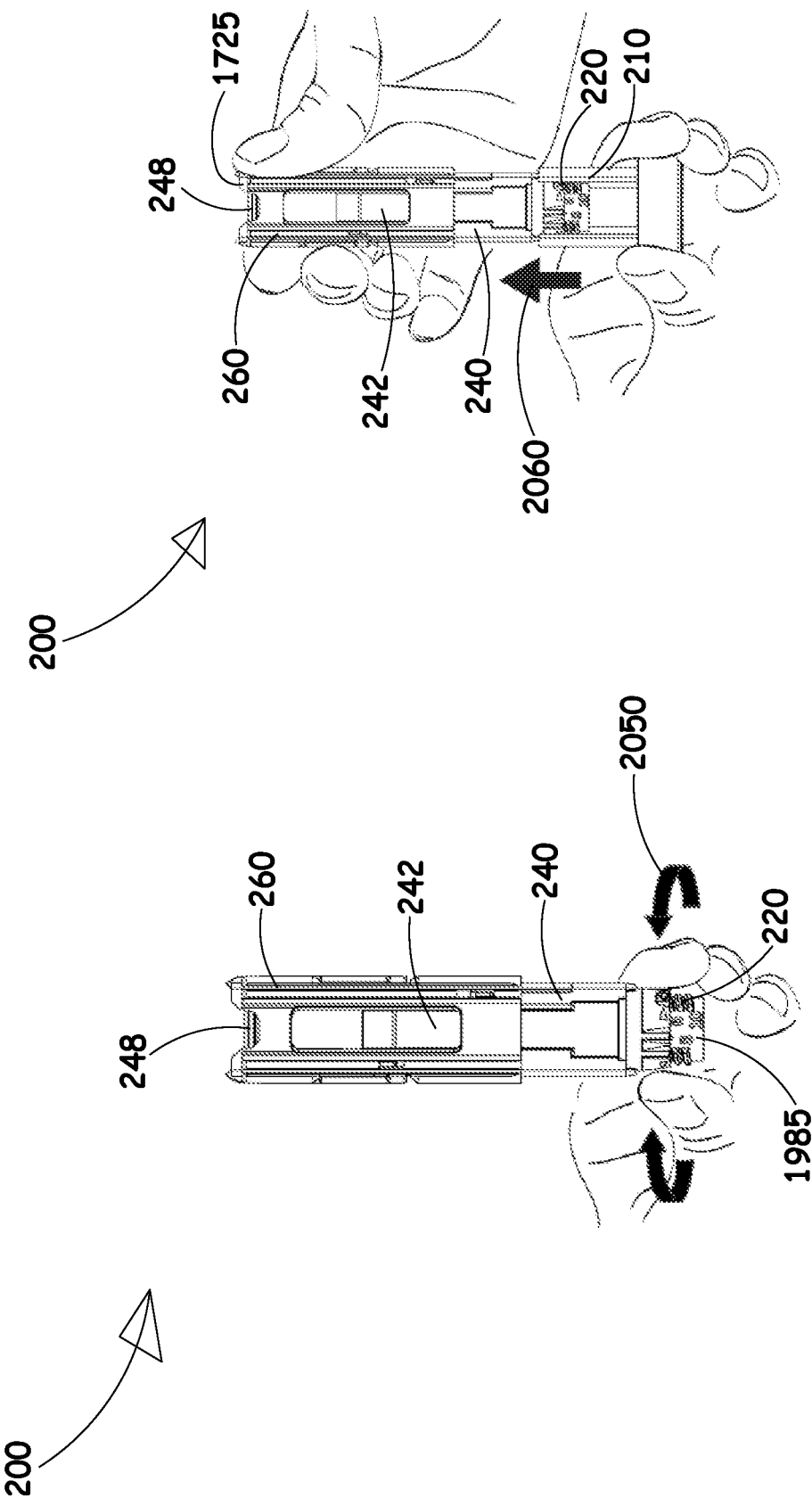

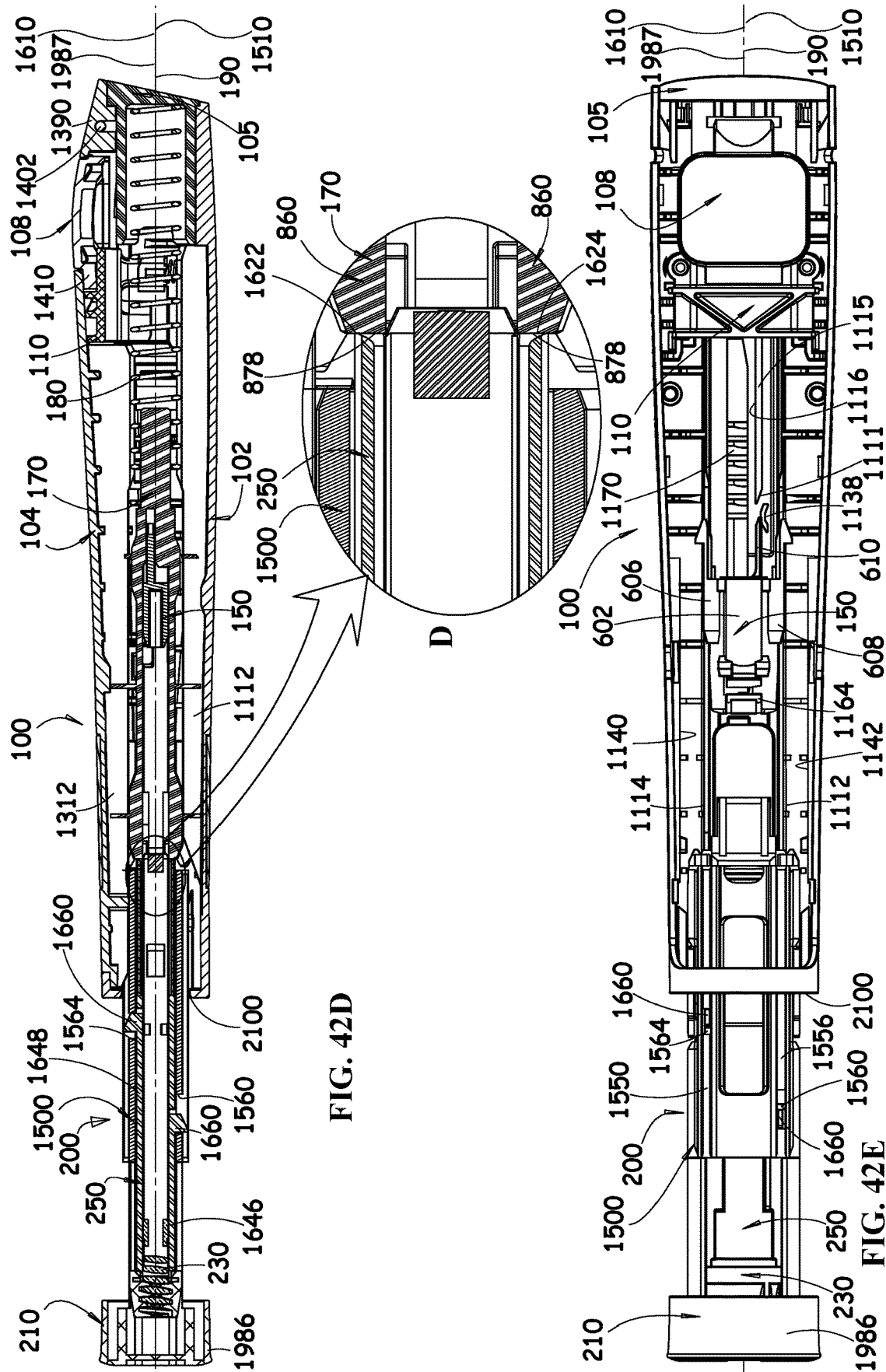

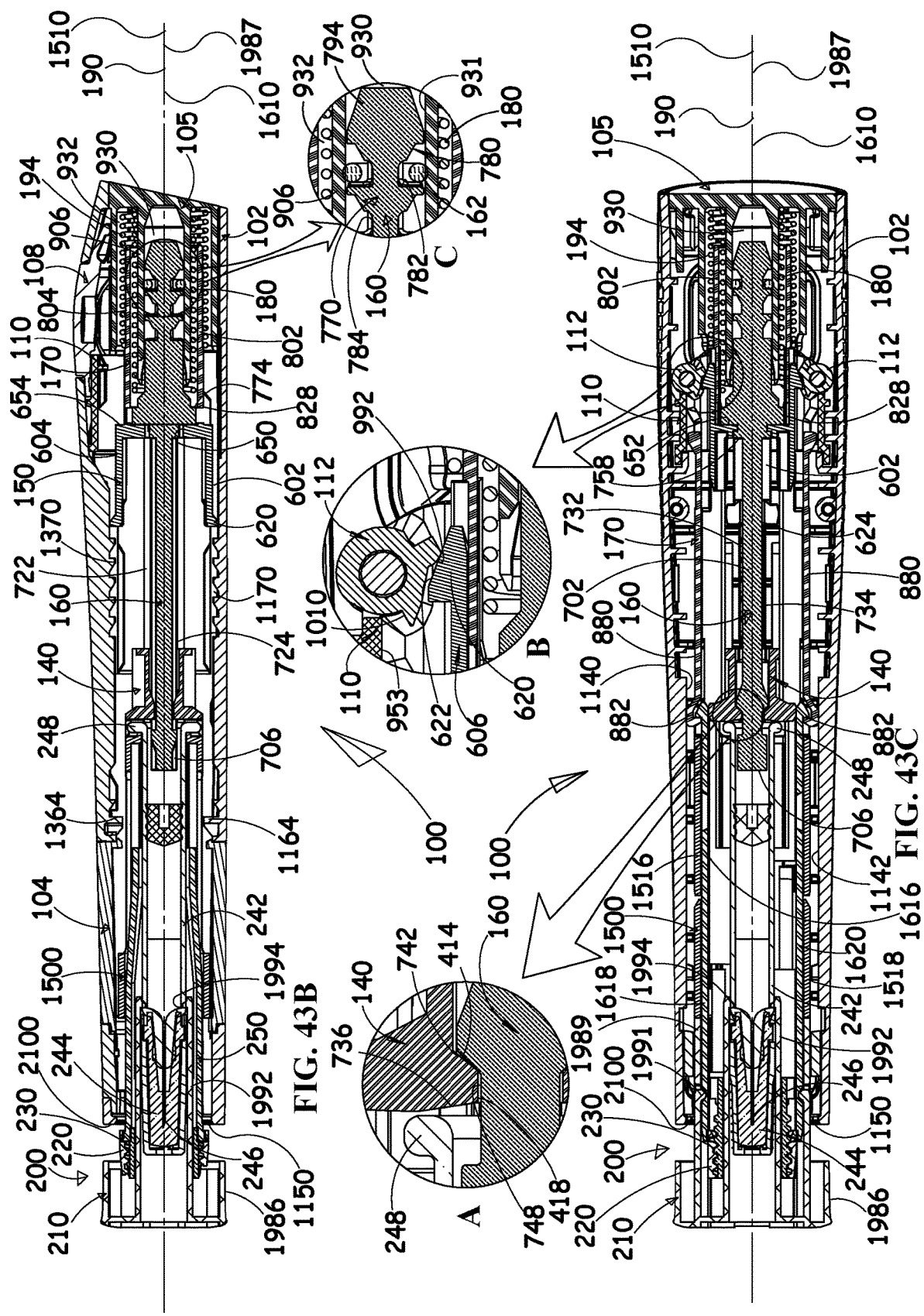

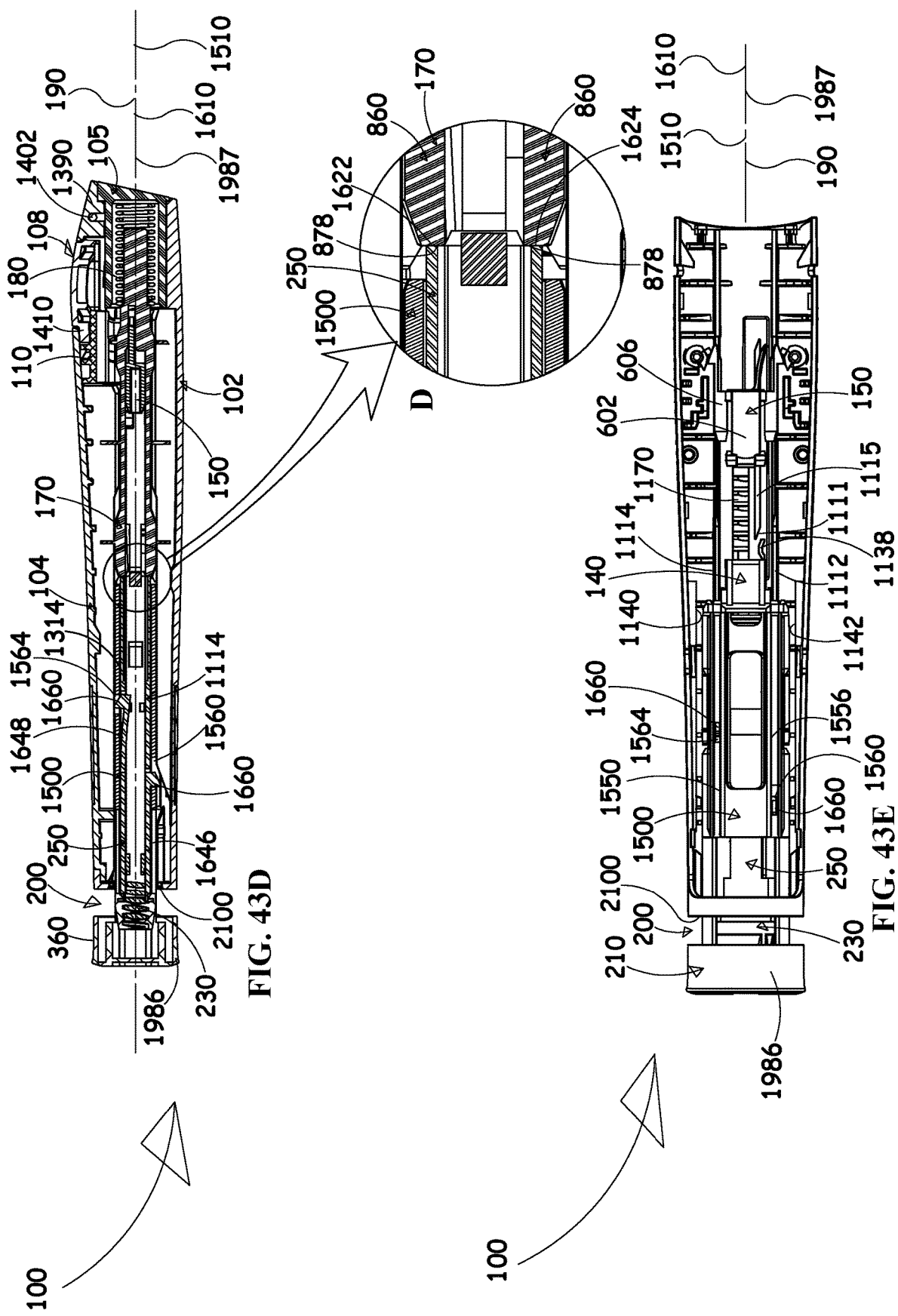

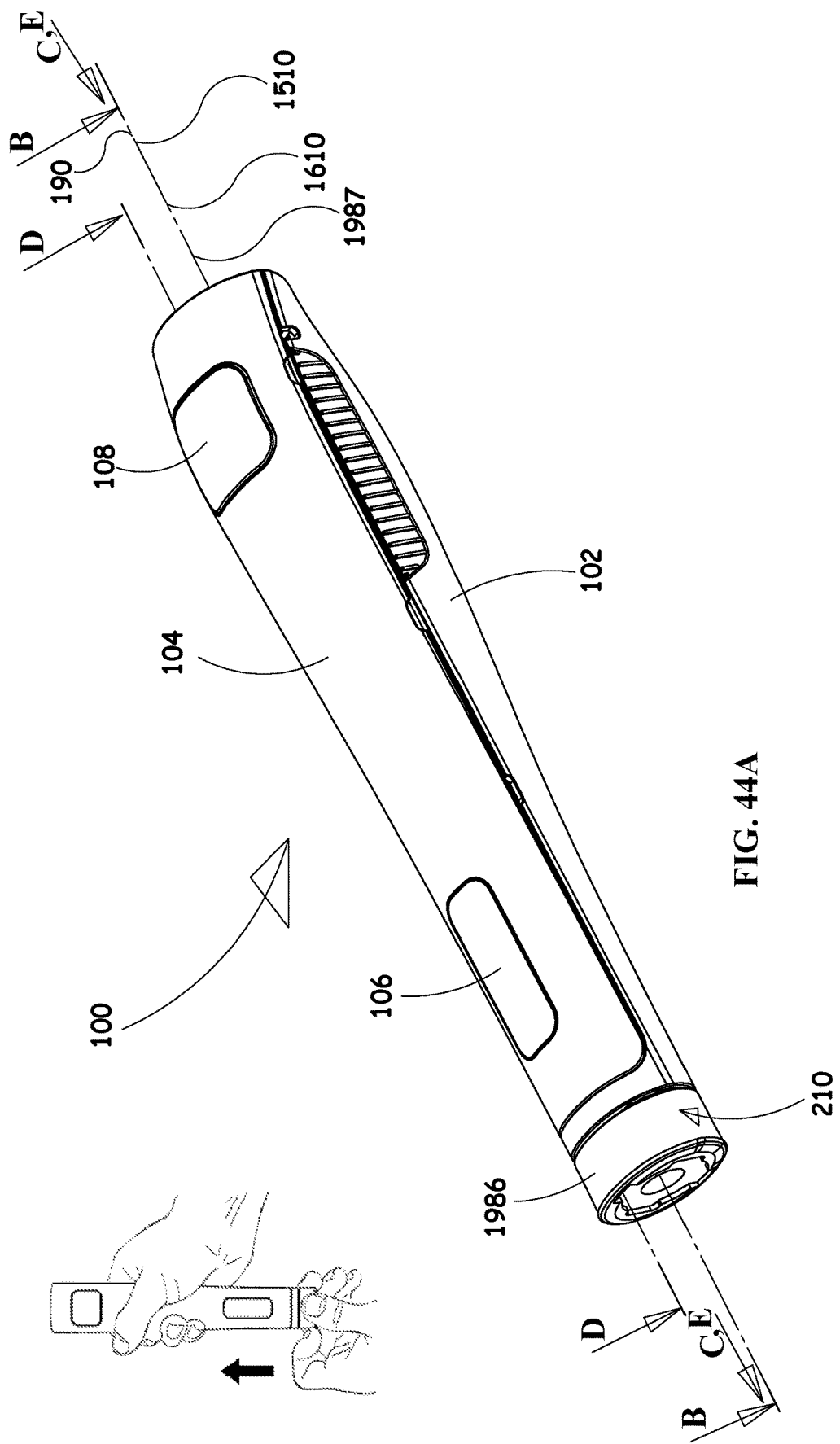

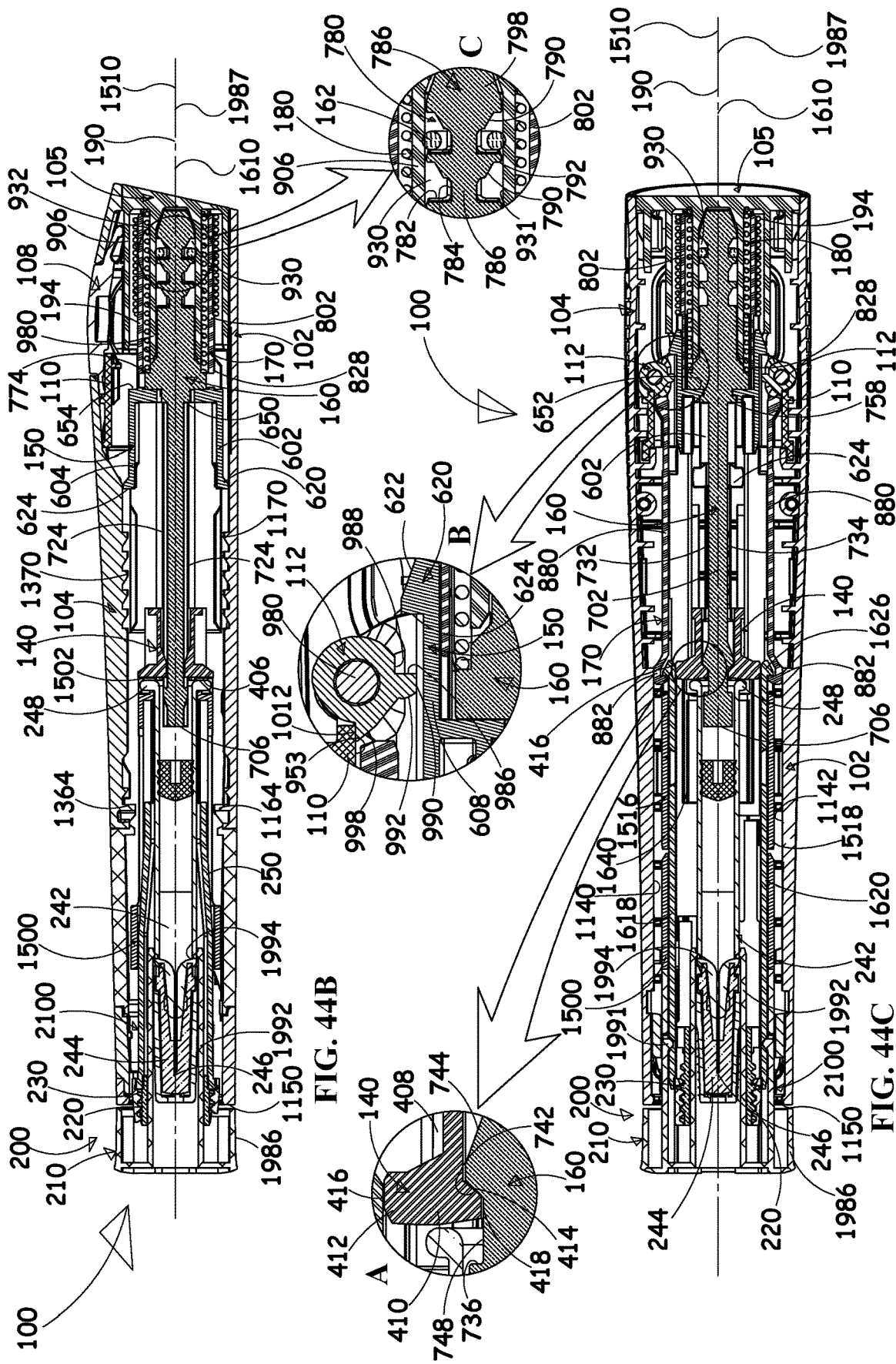

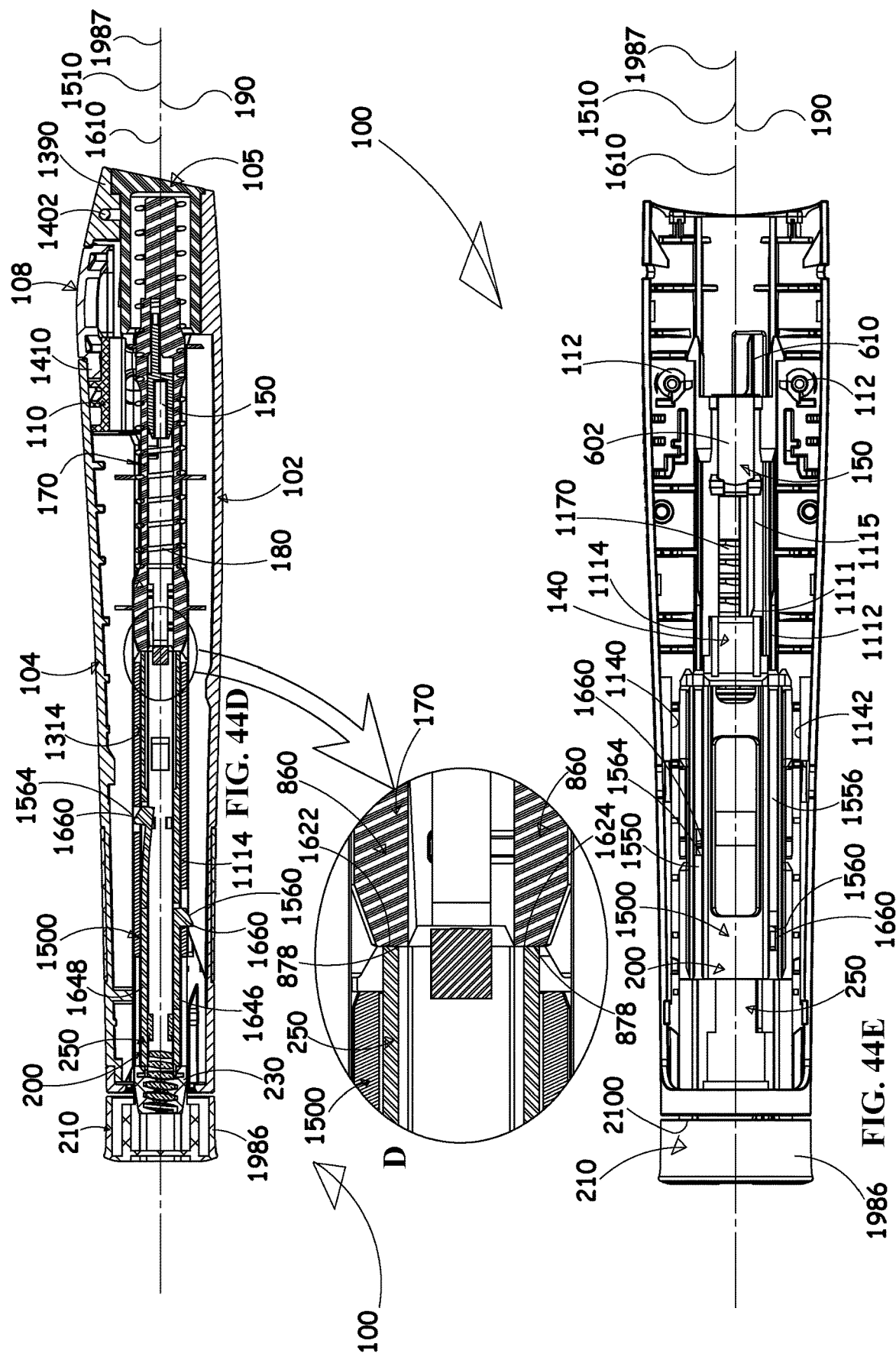

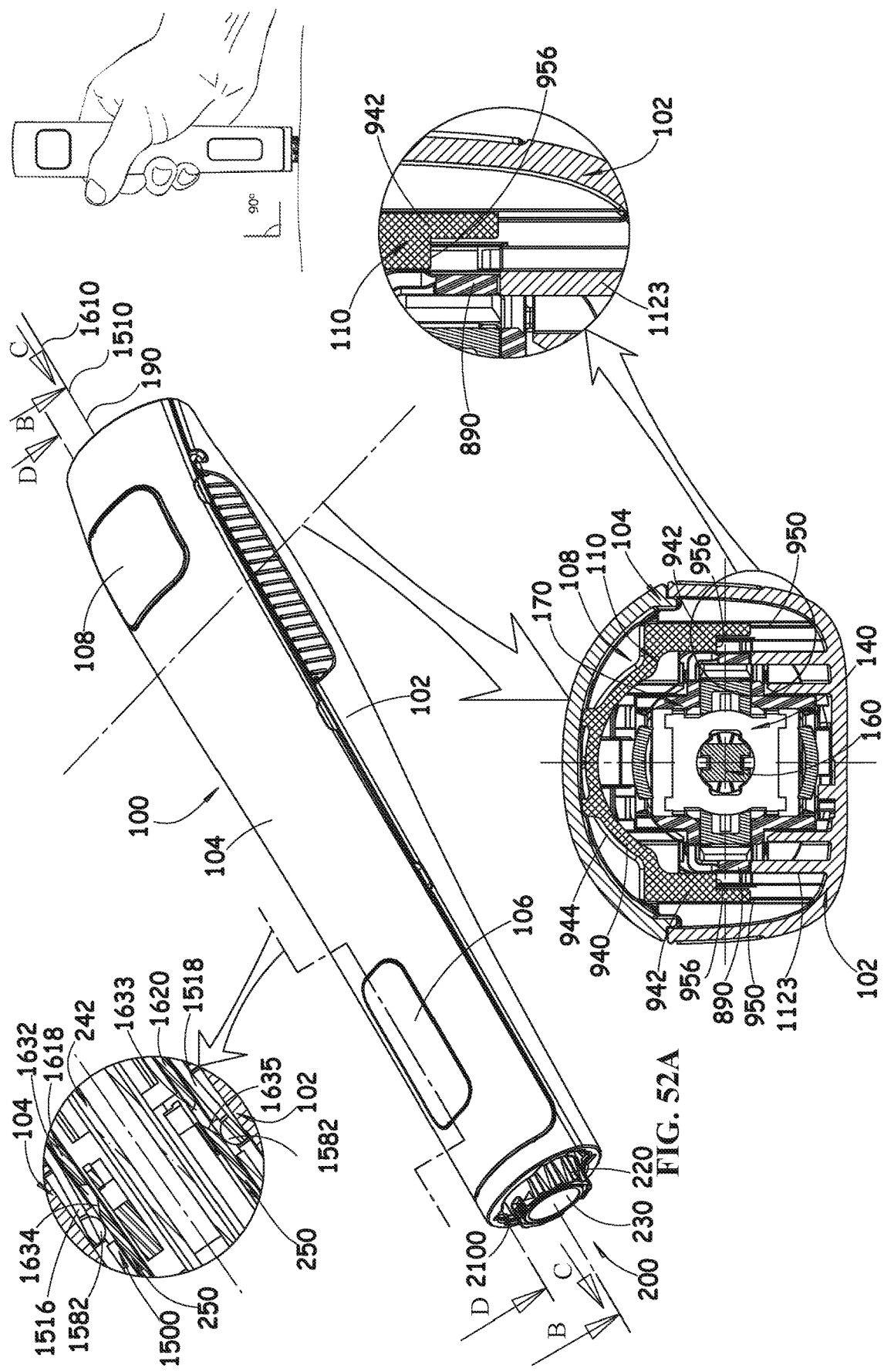

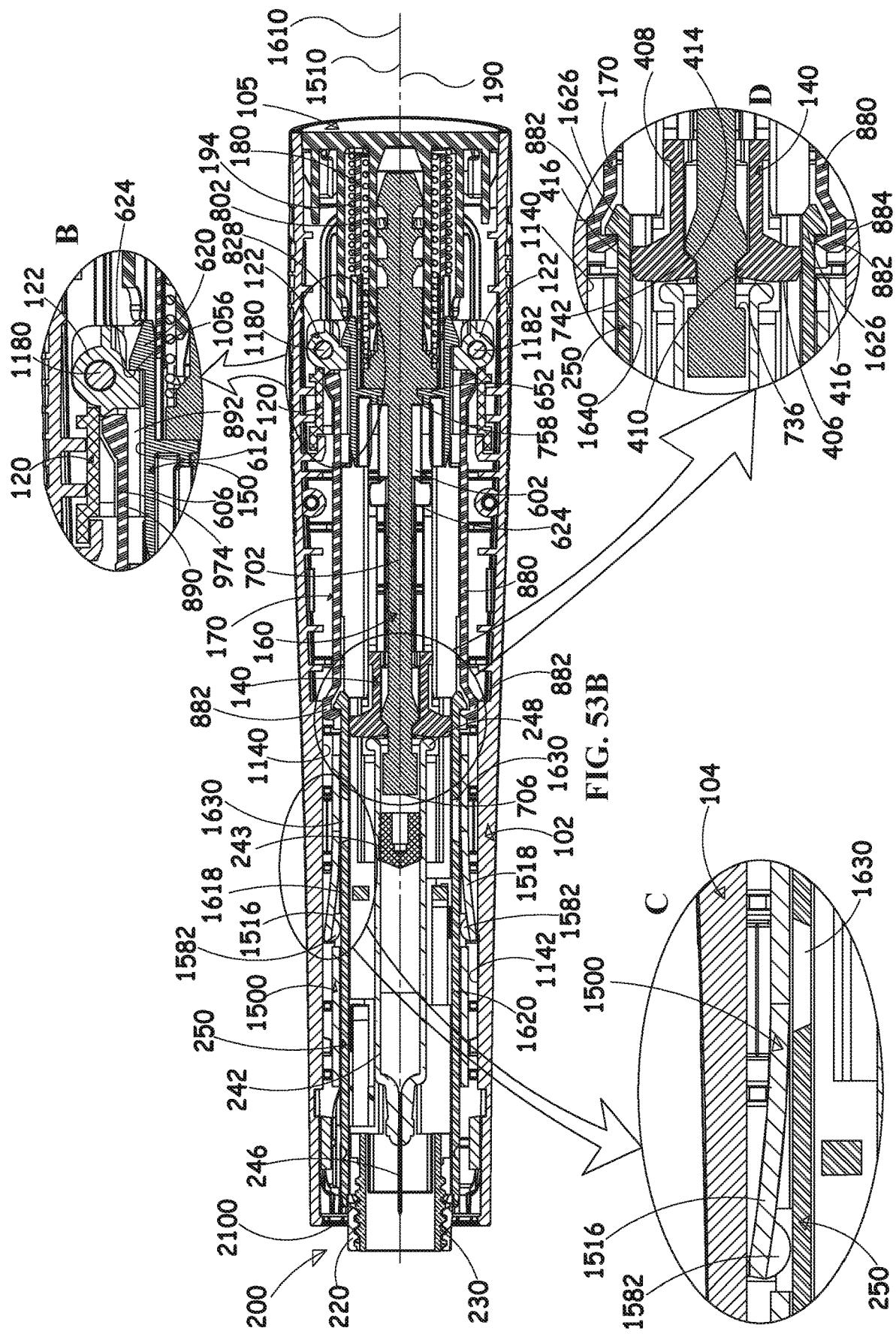

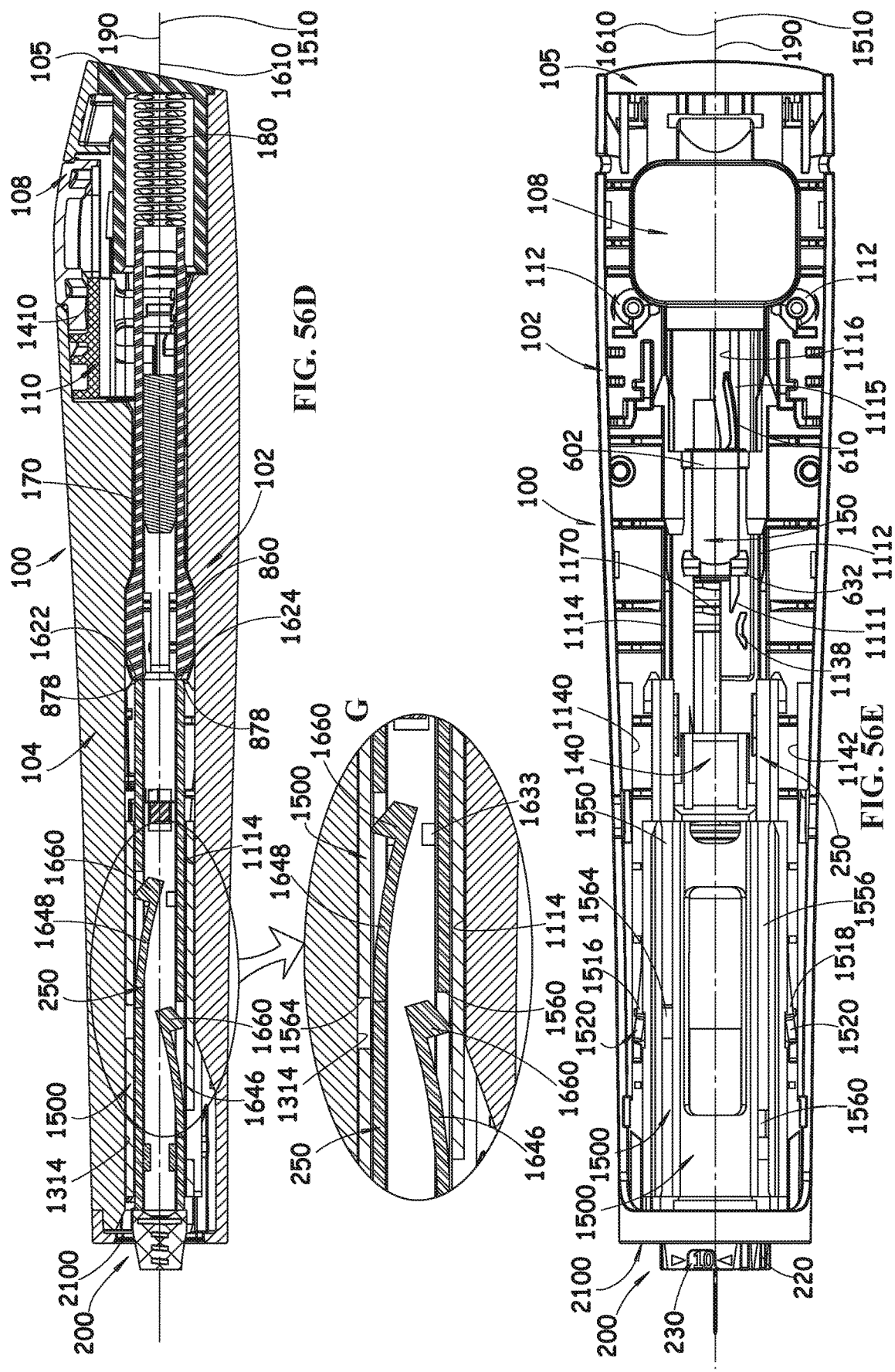

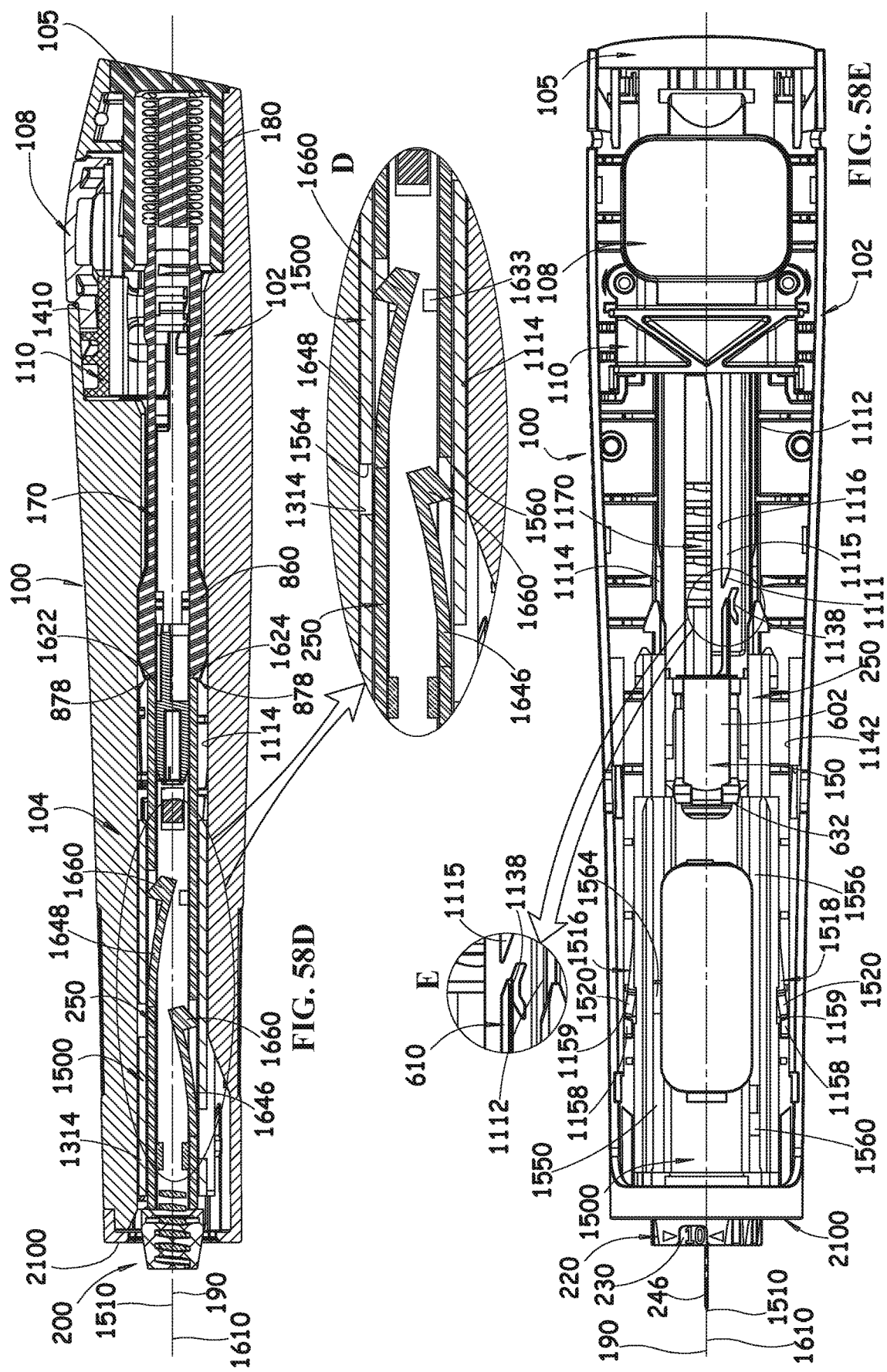

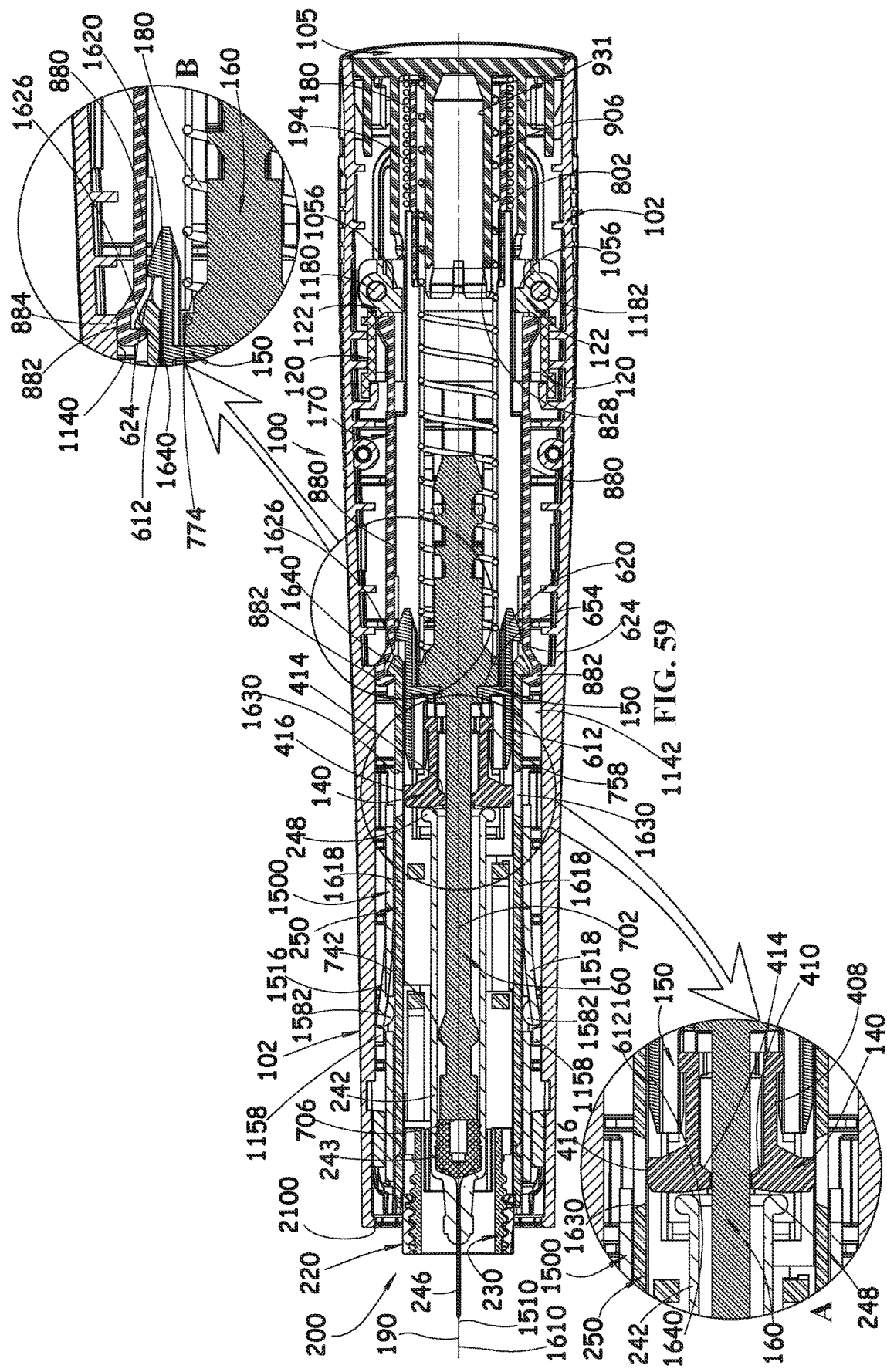

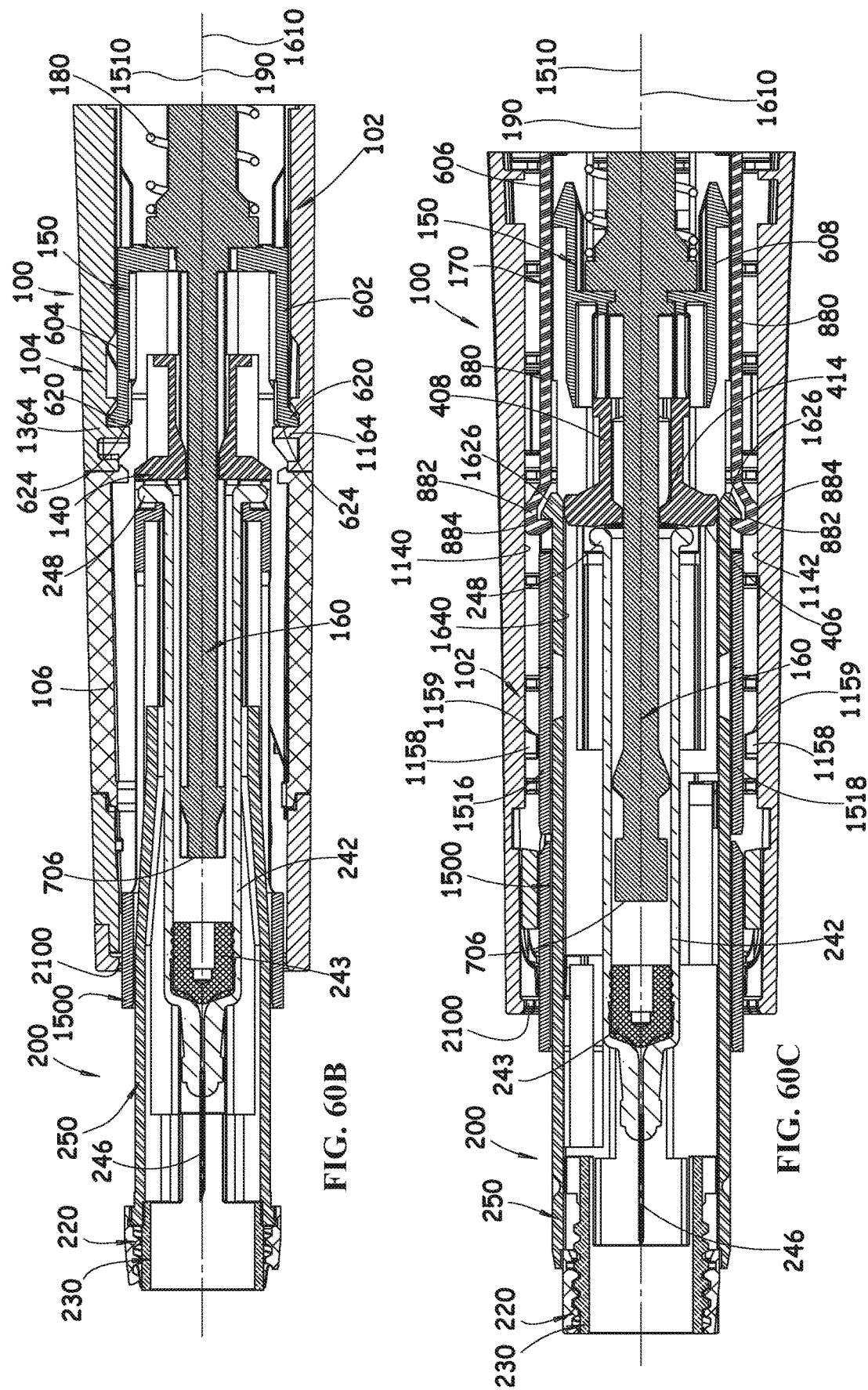

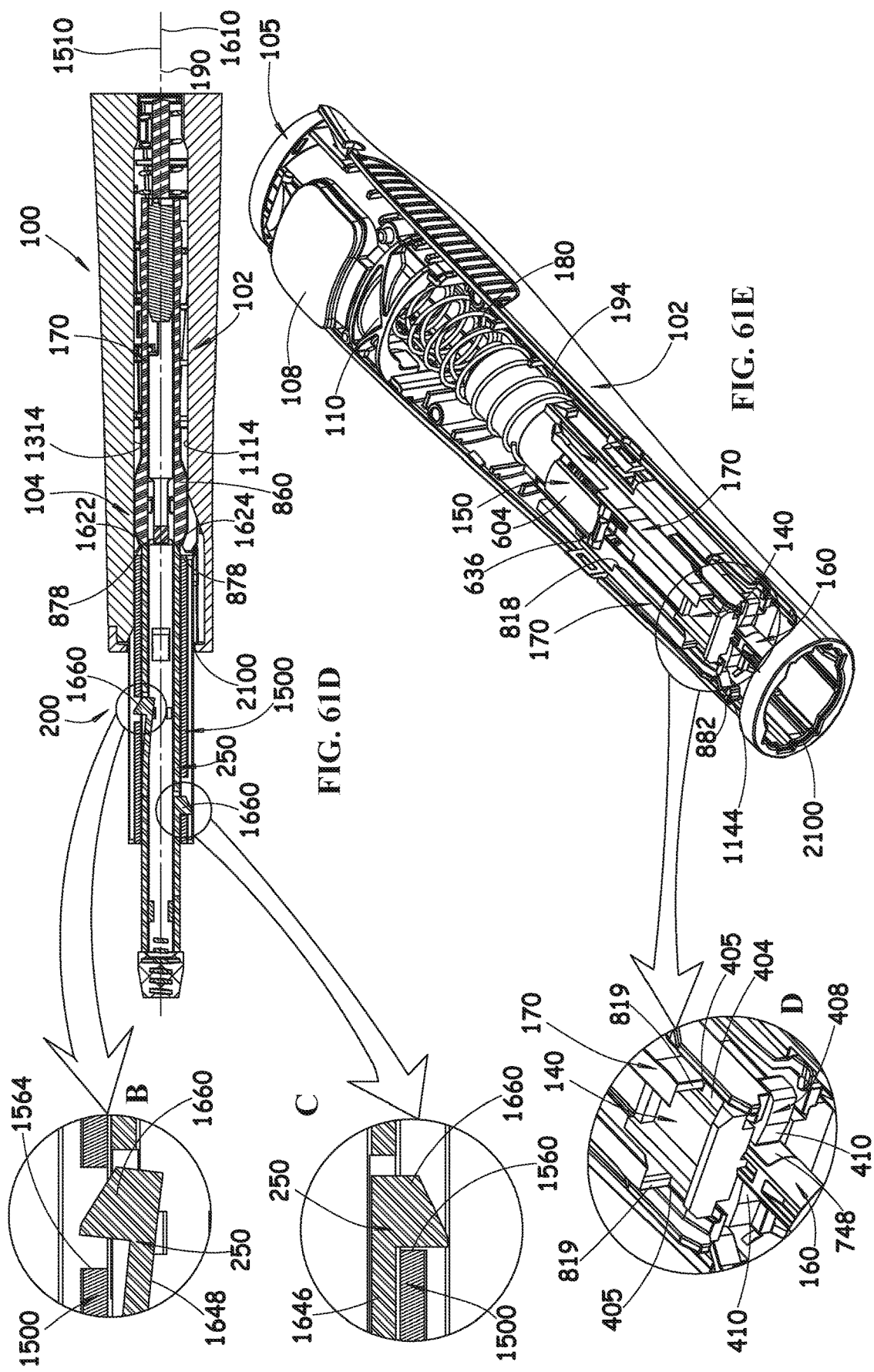

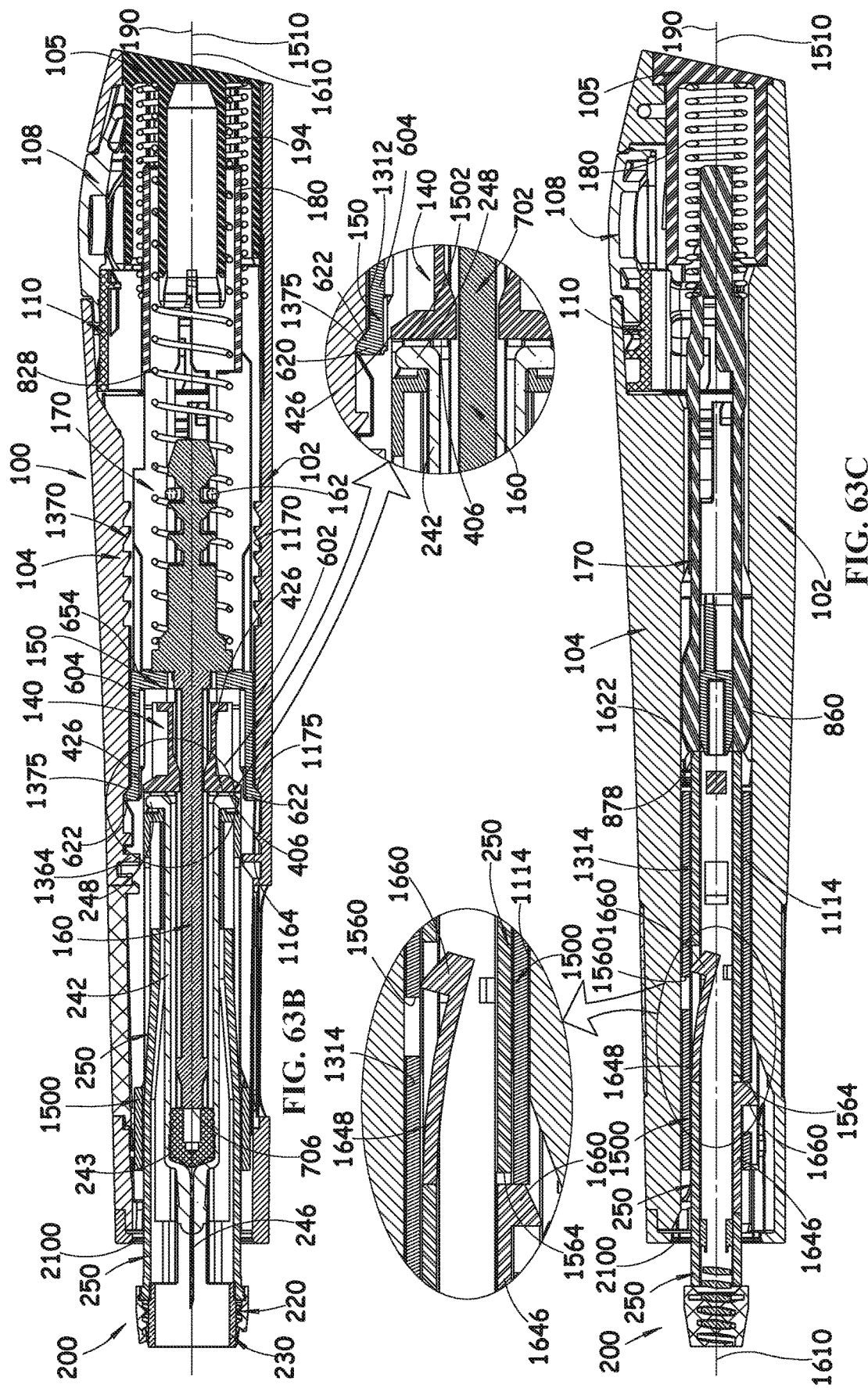

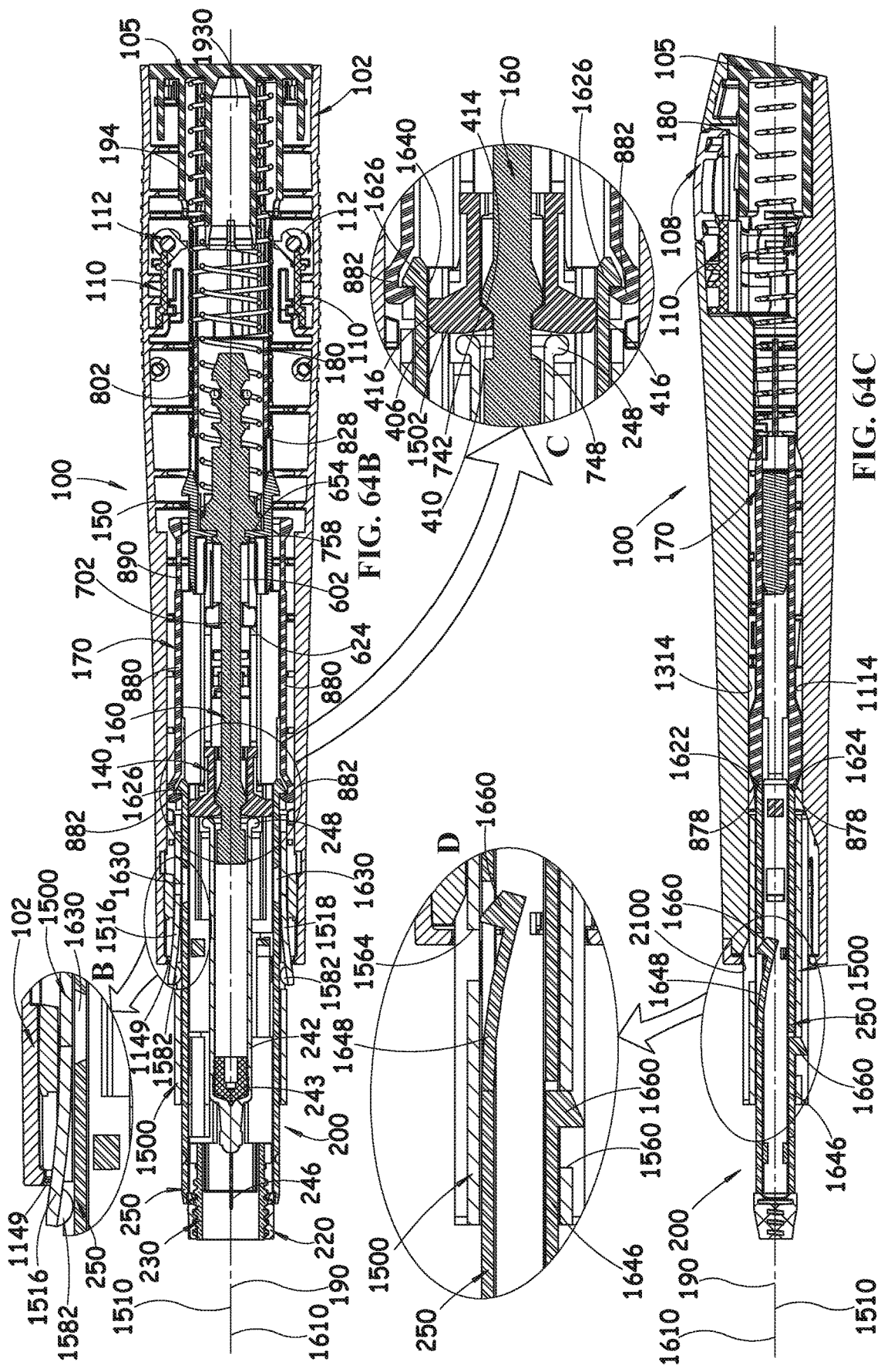

REUSABLE AUTOMATIC INJECTION DEVICE

CROSS REFERENCE TO RELATED APPLICATIONS

This application is a National Stage of International Application No. PCT/IL2016/050929, filed Aug. 25, 2016, claiming priority based on U.S. Provisional Patent Application No. 62/210,962, filed Aug. 27, 2015, the contents of all of which are incorporated herein by reference in their entirety.

Reference is also hereby made to PCT Publication No. WO 2015/118550, published Aug. 13, 2015 and entitled "SEMI DISPOSABLE AUTO INJECTOR", U.S. Patent Publication No. US20120191047 published Jul. 26, 2012 and entitled "Injector" and U.S. Pat. No. 8,708,968, issued Apr. 29, 2014 and entitled "Removal of needle shields from syringes and automatic injection devices", the disclosures of which are hereby incorporated by reference in their entirety.

FIELD OF THE INVENTION

The present invention generally relates to an auto injector, and more specifically to a semi disposable and safe auto-injector adapted for parenteral administration of substances (e.g., a medication) to a living organism (human or animal).

BACKGROUND OF THE INVENTION

As many as ten percent of patients may experience needle phobia, a condition recognized by the American Psychiatric Association, and may be hesitant to inject themselves (J. Hamilton, "Needle Phobia: a Neglected Diagnosis." *Journal of Family Practice,* 1995; 41:169-175).

Moreover, in the U.S., a recent law requires health care employers to implement "safer medical devices" to minimize needle sticks that could result in serious infections (such as HIV and Hepatitis) from viruses or bacteria in the blood. Interest in safety-needle protective devices is now increasing in all areas of healthcare. A particular drug may be used in various care settings.

SUMMARY OF THE INVENTION

The present invention seeks to provide a reusable automatic injection device.

There is thus provided in accordance with an embodiment of the present invention or a combination of embodiments thereof, a user-powered medicament injector including a reusable, user-powered automatic injection assembly including a user energizable medicament injection subassembly and a medicament module removably insertable into the reusable, user-powered automatic injection assembly and including: a module housing adapted to receive a syringe having a barrel, a needle engaged to the barrel, and a removeable needle cap covering the needle, a needle shield configured to be moveable with respect to the module housing and a needle cap remover associated with the needle shield and wherein the medicament module is configured for energizing the user energizable medicament injection subassembly by insertion of the medicament module into the reusable, user powered automatic injection assembly.

Preferably, the user energizable medicament injection assembly includes at least one mechanical energy storage element. Further preferably, the at least one mechanical energy storage element includes at least one resilient element and wherein the insertion of the medicament module into the reusable, user powered automatic injection assembly comprises relative displacement of the medicament module relative to the user powered automatic injection assembly, which causes the mechanical energy storage element to store energy.

Still preferably, the reusable, user-powered automatic injection assembly includes a driving assembly, which is comprised of a control element, a multifunctional retaining element and a damping driver element, which are adapted to operatively engage each other. Preferably, at least one sealing element is adapted to be operatively engaged with the damping driver element.

In accordance with an embodiment of the present invention or a combination of embodiments thereof, the reusable, user-powered automatic injection assembly includes a triggering subassembly comprised of a trigger element, actuation button and at least one spring loaded latch element.

Preferably, the triggering subassembly is adapted to be operatively engaged with the driving assembly such that the actuation button is locked in pre-injection site engagement operative orientation. Further preferably, the multifunctional retaining element is configured to displace the latch element during insertion of the medicament module into the reusable, user-powered automatic injection assembly. Preferably, the latch element is displaced axially. Alternatively or additionally, the latch element is displaced rotationally.

In accordance with an embodiment of the present invention or a combination of embodiments thereof, a medicament injector including a reusable, user-powered automatic injection assembly including a medicament injection subassembly; and a medicament module removably insertable into the reusable, user-powered automatic injection assembly; the medicament injection subassembly including a sealing element and a sealing element seating assembly which provides damping of forward motion of the medicament injection subassembly along a longitudinal axis which is greater than damping of rearward motion of the medicament injection subassembly along the longitudinal axis.

Preferably, the sealing element and the sealing element seating assembly are configured to provide vacuum damping of the forward motion of the medicament injection subassembly along the longitudinal axis. Further preferably, the reusable, user-powered automatic injection assembly also includes an end cover and the sealing element seating assembly with the sealing element mounted thereon is operatively and frictionally engaged with the end cover.

Still preferably, when the sealing element seating assembly is in rearward motion, the frictional engagement with the end cover is decreased and when the sealing element seating assembly is in forward motion, the frictional engagement with the end cover is increased. Yet preferably, at least one slot is formed in the sealing element seating assembly in order to provide air passage of air trapped between the end cover and the sealing element during the rearward motion.

In accordance with an embodiment of the present invention or a combination of embodiments thereof, vacuum is created between the end cover and the sealing element during the forward motion.

Preferably, the sealing element seating assembly includes a seating area at a rearward end thereof, the seating area includes a planar surface and a tapered surface. Further preferably, the sealing element is configured to engage the planar surface during the rearward motion and is further configured to engage the tapered surface during the forward motion.

Further preferably, the greater friction engagement and the partial vacuum are configured for preventing damage to at least part of the medicament injector during the forward motion of the sealing element seating assembly. Yet preferably, the sealing element seating assembly has a forward end configured to engage a piston of a syringe.

In accordance with an embodiment of the present invention or a combination of embodiments thereof, a user-powered medicament injector including a reusable automatic injection assembly including a medicament injection subassembly having injection ready and a non-injection ready operative states; and a medicament module removably axially insertable into the reusable automatic injection assembly. The medicament injection subassembly including at least one rotatable latch element operative to selectably retain the medicament injection subassembly in the injection ready operative state in response to axial insertion of the medicament module into the reusable automatic injection assembly.

Preferably, the medicament injection subassembly is comprised of a control element, a multifunctional retaining element and a damping driver element, which are adapted to operatively engage each other. Further preferably, the medicament injection subassembly also includes a trigger element and actuation button.

Still preferably, the latch element is spring loaded. Further preferably, the actuation button is locked in the injection ready operative state.

Yet preferably, the multifunctional retaining element is configured to displace the latch element during insertion of the medicament module into the reusable, user-powered automatic injection assembly.

In accordance with an embodiment of the present invention or a combination of embodiments thereof, the reusable user-powered automatic injection assembly is arranged along a longitudinal axis and the latch element is configured to be displaced both rotationally and axially along an axis that extends transversely to the longitudinal axis.

Preferably, the latch element is displaced rotationally during rearward displacement of the multifunctional retaining element. Further preferably, the latch element is displaced axially against urging force of a spring in response to pressing of the actuation button by a user. Still preferably, the medicament injection subassembly including two latch elements, each being rotatable in an opposite rotational direction during engagement of the medicament injection subassembly therewith.

In accordance with an embodiment of the present invention or a combination of embodiments thereof, a user-powered medicament injector including a reusable automatic injection assembly including a medicament injection subassembly; and a medicament module removably axially insertable into the reusable automatic injection assembly, the medicament module and the reusable automatic injection assembly being configured to prevent inadvertent axial release of the medicament module from the reusable automatic injection assembly following incomplete axial insertion thereof into the reusable automatic injection assembly.

Preferably, the medicament injection subassembly is comprised of a control element, a multifunctional retaining element and a damping driver element, which are adapted to operatively engage each other. Further preferably, the reusable automatic injection assembly also includes a multifunctional engagement element operatively engaged with medicament injection subassembly and configured to retain the medicament module within the reusable automatic injection assembly following insertion of the medicament module thereinto.

Further preferably, the reusable automatic injection assembly includes a main housing portion and a cover portion enclosing the medicament injection subassembly and arranged along a longitudinal axis. Still preferably, at least one of the main housing portion and the cover portion include an array of mutually spaced ratchet teeth. Preferably, the ratchet teeth are spaced axially along the longitudinal axis.

In accordance with an embodiment of the present invention or a combination of embodiments thereof, the multifunctional retaining element has at least one protrusion, which is configured to engage the array of mutually spaced ratchet teeth and thereby prevent forward displacement of the medicament injection subassembly.

Preferably, the medicament injection subassembly is energized due to force transfer thereto from the medicament module and through the control element. Further preferably, the damping driver element has a protrusion formed thereon and the control element is positioned forwardly to the protrusion and engaged therewith. Still preferably, the control element is retained from rearward displacement relative to the damping driver element due to the engagement with the protrusion, thus provides for rearward displacement of the medicament injection assembly.

In accordance with an embodiment of the present invention or a combination of embodiments thereof, a medicament module which is removably axially insertable into a reusable injection assembly, the medicament module including a syringe mount which is axially displaceable along a longitudinal axis; and a needle penetration depth assembly operatively associated with the needle mount for governing penetration depth of the needle at an injection site, the needle penetration depth assembly comprising: a manually rotatable dial; and an injection site engagement element bearing indicia enabling a person to select a desired needle penetration depth, which is axially displaceable along the longitudinal axis in accordance with a rotational orientation of the manually rotatable dial.

Preferably, the medicament module also includes a module housing operatively engageable with the syringe mount. Further preferably, the syringe mount is disposed within the module housing and arranged along a mutual longitudinal axis. Still preferably, the module housing includes a flange configured for holding a syringe and retaining forward displacement thereof with respect to the module housing.

Yet preferably, the syringe mount includes at least one inwardly directed protrusion, adapted to be axially rearwardly positioned with respect to the flange and configured to retain the syringe from rearward displacement relative to the syringe mount.

In accordance with an embodiment of the present invention or a combination of embodiments thereof, the manually rotatable dial is disposed at snap-fit engagement with the syringe mount.

Preferably, the manually rotatable dial has an inner threading and the injection site engagement element has an outer corresponding threading. Further preferably, the module housing includes at least one slot and the syringe mount includes at least one partially flexible arm, configured to be operative engaged with the at least one slot, thereby preventing relative displacement between the needle mount and the module housing. Yet preferably, the syringe mount includes at least one protrusion, which is configured to be engaged with the reusable injection assembly during insertion of the medicament module into the reusable injection assembly.

In accordance with an embodiment of the present invention or a combination of embodiments thereof, a medicament module which is removably axially insertable into a reusable injection assembly, the medicament module including a syringe mount which is axially displaceable along a longitudinal axis; and a needle cap remover which is removably mounted in the medicament module. The needle cap remover being configured to be removable from the medicament module only when the medicament module is inserted into the reusable injection assembly.

Preferably, the medicament module also including a needle shield configured to be moveable with respect to the syringe mount. Further preferably, the needle cap remover is associated with the needle shield. Still preferably, the syringe mount is adapted to receive a syringe. Yet further preferably, the syringe mount is adapted to retain the syringe.

Further preferably, the needle cap remover is removeable from the medicament module upon engagement with a protrusion formed within a receiving cavity of the reusable injection assembly.

In accordance with an embodiment of the present invention or a combination of embodiments thereof, a user-powered medicament injector including a reusable, user-powered automatic injection assembly including a user energizable medicament injection subassembly including a control element; a medicament module removably insertable into the reusable, user-powered automatic injection assembly. The medicament module is being configured to displace the control element and thereby energizing the user energizable medicament injection subassembly by insertion of the medicament module into the reusable, user powered automatic injection assembly and wherein injection is enabled upon deflection of the control element.

Preferably, the medicament injection subassembly further includes a multifunctional retaining element and a damping driver element, which are adapted to operatively engage each other. Further preferably, the medicament injection subassembly also includes a trigger element and actuation button.

In accordance with an embodiment of the present invention or a combination of embodiments thereof, a medicament injector including a reusable, user-powered automatic injection assembly including a medicament injection subassembly; and a medicament module removably insertable into the reusable, user-powered automatic injection assembly. The medicament injection subassembly including a plurality of sealing elements and a sealing element seating assembly which provides for varying damping of forward motion of the medicament injection subassembly along a longitudinal axis.

Preferably, the plurality of sealing elements and the sealing element seating assembly are configured to provide vacuum damping of the forward motion of the medicament injection subassembly along the longitudinal axis. Further preferably, the reusable, user-powered automatic injection assembly also includes an end cover and the sealing element seating assembly with the plurality of sealing elements mounted thereon is operatively and frictionally engaged with the end cover.

Still preferably, when the sealing element seating assembly is in rearward motion, the frictional engagement with the end cover is decreased and when the sealing element seating assembly is in forward motion, the frictional engagement with the end cover is increased.

Further preferably, the at least one slot is formed in the sealing element seating assembly in order to provide air passage of air trapped between the end cover and the plurality of sealing elements during the rearward motion. Still preferably, vacuum is created between the end cover and the plurality of sealing elements during the forward motion.

In accordance with an embodiment of the present invention or a combination of embodiments thereof, the sealing element seating assembly includes a plurality of seating areas at a rearward end thereof, the seating areas each include a planar surface and a tapered surface.

Preferably, the plurality of sealing elements is configured to engage the planar surfaces during the rearward motion and is further configured to engage the tapered surfaces during the forward motion. Further preferably, the greater friction engagement and the partial vacuum are configured for preventing damage to at least part of the medicament injector during the forward motion of the sealing element seating assembly.

In accordance with an embodiment of the present invention or a combination of embodiments thereof, a user-powered medicament injector including a reusable automatic injection assembly including a medicament injection subassembly enclosed in at least one housing element; and a medicament module removably axially insertable into the reusable automatic injection assembly. The medicament module includes a module housing and a needle shield, adapted to be moveable with respect to the module housing; and wherein in an injection operative state the module housing is selectably retained from forward displacement by engagement with the housing element.

Preferably, the reusable automatic injection assembly further including a multifunctional engagement element operative in a post-injection operative stage to displace the needle shield forwardly. Further preferably, during medicament module removal from the reusable automatic injection assembly, the multifunctional engagement element is displaced forwardly along with the medicament module until further forward displacement of the multifunctional engagement element is restricted by the housing element.

In accordance with an embodiment of the present invention or a combination of embodiments thereof, a user-powered medicament injector including a reusable automatic injection assembly including a medicament injection subassembly enclosed in at least one housing element; and a medicament module removably axially insertable into the reusable automatic injection assembly. The reusable automatic injection assembly includes an indication element, which is operative to provide an audible indication to the user at the end of insertion of the medicament module into the reusable automatic injection assembly and at the end of an injection operative stage, by means of selectable engagement of the indication element with the housing element.

BRIEF DESCRIPTION OF THE DRAWINGS

The present invention will be understood and appreciated more fully from the following detailed description, taken in conjunction with the drawings in which:

FIGS. 6A, 6B, 6C, 6D, 6E, 6F, 6G, 6H and 6I are respectively a simplified perspective view of a forward-facing portion, a simplified plan view of the forward-facing portion, a simplified top plan view, a simplified bottom plan view, a simplified first side plan view, a simplified second side plan view, a simplified plan view of a rearward-facing portion, a simplified sectional view taken along lines H-H in FIG. 6A and a simplified sectional view taken along lines I-I in FIG. 6A of a multifunctional retaining element forming part of the reusable automatic injection assembly of FIGS. 1A & 1B;

FIGS. 13A, 13B, 13C, 13D, 13E, 13F, 13G and 13H are respectively a simplified perspective view of a forward-facing portion, a simplified perspective view of a rearward-facing portion, a simplified plan view of the rearward-facing portion, a simplified plan view of the forward-facing portion, a simplified top/bottom plan view, a simplified side plan view, a simplified sectional view taken along lines G-G in FIG. 13A and a simplified sectional view taken along lines H-H in FIG. 13A of a multifunctional engagement element forming part of the reusable automatic injection assembly of FIGS. 1A & 1B;

FIG. 14 is a simplified plan view illustration of a transition between disengaged and engaged operative orientations of a first portion of the multifunctional engagement element of FIGS. 13A-13H;

FIGS. 15A, 15B, 15C, 15D, 15E and 15F are simplified respective perspective, first and second side view, planar forward facing end view and first and second sectional illustrations taken along lines E-E and F-F in FIG. 15A of an end cover forming part of the reusable automatic injection assembly of FIGS. 1A & 1B;

FIGS. 16A, 16B, 16C, 16D, 16E, 16F, 16G and 16H are simplified respective top and bottom perspective, first and second end view, side view, top and bottom view and a sectional illustration taken along lines H-H in FIG. 16A of one embodiment of a trigger element, forming part of the reusable automatic injection assembly of FIGS. 1A & 1B;

FIGS. 17A, 17B, 17C, 17D, 17E, 17F, 17G and 17H are simplified respective top and bottom perspective, first and second end view, side view, top and bottom view and a sectional illustration taken along lines H-H in FIG. 17A of another embodiment of a trigger element, forming part of the reusable automatic injection assembly of FIGS. 1A & 1B;

FIGS. 19A, 19B, 19C, 19D, 19E and 19F are simplified respective top and bottom perspective, side view, first and second end view and a sectional illustration taken along lines F-F in FIG. 19A of a unitary latch element, forming part of another embodiment of the reusable automatic injection assembly of FIGS. 1A & 1B;

FIGS. 21A, 21B, 21C, 21D, 21E, 21F and 21G are simplified respective top and bottom perspective view, bottom plan view, first and second end view and sectional illustrations taken along lines F-F and G-G in FIG. 21A of a cover portion forming part of the reusable automatic injection assembly of FIGS. 1A & 1B;

FIGS. 23A, 23B, 23C, 23D,23E, 23F, 23G, 23H, 23I, 23J, 23K and 23L are simplified drawings of the reusable automatic injection assembly of FIGS. 1A, 1B and 4A-22D in a "storage" operative orientation;

FIGS. 25A, 25B, 25C, 25D, 25E, 25F and 25G are simplified respective perspective, top and bottom view, side view, first and second end view and sectional illustrations taken along lines F-F and G-G in FIG. 25A of a module housing, forming part of the medicament module of FIGS. 2A & 2B and 3A & 3B;

FIGS. 26A, 26B, 26C, 26D, 26E, 26F and 26G are simplified respective perspective, top and bottom view, side view, first and second end view and sectional illustrations taken along lines F-F and G-G in FIG. 26A of one embodiment of a needle shield, forming part of the medicament module as seen in FIG. 2B;

FIGS. 27A, 27B, 27C, 27D, 27E, 27F and 27G are simplified respective perspective, top and bottom view, side view, first and second end view and sectional illustrations taken along lines F-F and G-G in FIG. 27A of another embodiment of a needle shield, forming part of the medicament module as seen in FIG. 2B;

FIGS. 28A, 28B, 28C, 28D, 28E, 28F and 28G are simplified respective perspective, top and bottom view, side view, first and second end view and sectional illustrations taken along lines F-F and G-G in FIG. 28A of one embodiment of a needle shield, forming part of the medicament module as seen in FIG. 3B;

FIGS. 29A, 29B, 29C, 29D, 29E, 29F and 29G are simplified respective perspective, top and bottom view, side view, first and second end view and sectional illustrations taken along lines F-F and G-G in FIG. 29A of another embodiment of a needle shield, forming part of the medicament module as seen in FIG. 3B;

FIGS. 30A and 30B are simplified pictorial illustrations of a forward needle depth adjustment element forming part of the medicament module as seen in FIG. 2B;

FIG. 30C is a simplified sectional illustration of forward needle depth adjustment element of FIGS. 30A and 30B, section line being taken along lines C-C in FIG. 30A;

FIGS. 31A and 31B are simplified pictorial illustrations of a rearward needle depth adjustment element forming part of the medicament module as seen in FIG. 2B;

FIGS. 32A, 32B, 32C and 32D are simplified respective first and second perspective views, end view and a sectional view taken along lines D-D in FIG. 32A showing a RNS remover, preferably forming part of a medicament module as in FIGS. 2A & 2B;

FIGS. 34A, 34B, 34C and 34D are simplified drawings of one embodiment of a medicament module of FIGS. 2A & 2B in a "storage" operative orientation;

FIGS. 35A, 35B, 35C and 35D are simplified drawings of another embodiment of a medicament module of FIGS. 2A & 2B in a "storage" operative orientation;

FIGS. 36A, 36B, 36C and 36D are simplified drawings of one embodiment of a medicament module of FIGS. 3A & 3B in a "storage" operative orientation;

FIGS. 39A and 39B are simplified illustrations of preparatory steps required prior insertion of the medicament module of FIGS. 35A-35D into operative engagement with the reusable injection assembly of FIGS. 1A-24C;

FIGS. 42A, 42B, 42C, 42D and 42E are simplified illustrations of a first stage in the insertion of the medicament module of FIGS. 34A-34D, following the preparatory steps shown in FIGS. 38A-38E, into the reusable automatic injection assembly of FIGS. 1A-16H, 18A-18F and 20A-24C;

FIGS. 43A, 43B, 43C, 43D and 43E are simplified illustrations of a second stage in the insertion of the medicament module of FIGS. 34A-34D, following the preparatory steps shown in FIGS. 38A-38E, into the reusable automatic injection assembly of FIGS. 1A-16H, 18A-18F and 20A-24C;

FIGS. 44A, 44B, 44C, 44D and 44E are simplified illustrations of a third stage in the insertion of the medicament module of FIGS. 34A-34D, following the preparatory steps shown in FIGS. 38A-38E, into the reusable automatic injection assembly of FIGS. 1A-16H, 18A-18F and 20A-24C;

FIGS. 47A and 47B are simplified illustrations of a second stage in the insertion of the medicament module of FIGS. 34A-34D, following the preparatory steps shown in FIGS. 38A-38E, into the reusable automatic injection assembly of FIGS. 1A-15F, 17A-17H and 19A-24C;

FIGS. 52A, 52B, 52C and 52D are simplified illustrations of an injection site engagement stage of the reusable automatic injection assembly of FIGS. 1A-16H, 18A-18F and 20A-24C following the RNS removal stage;

FIGS. 53A and 53B are simplified illustrations of an injection site engagement stage of the reusable automatic injection assembly of FIGS. 1A-15F, 17A-17H and 19A-24C following the RNS removal stage;

FIGS. 56A, 56B, 56C, 56D and 56E are simplified illustrations of an injection site needle penetration stage of the reusable automatic injection assembly of FIGS. 1A-16H, 18A-18F and 20A-24C following the user-engageable actuation button press stage;

FIGS. 58A, 58B, 58C, 58D and 58E are simplified illustrations of an injection stage of the reusable automatic injection assembly of FIGS. 1A-16H, 18A-18F and 20A-24C following the injection site needle penetration stage;

FIG. 59 is a simplified illustration of an injection stage of the reusable automatic injection assembly of FIGS. 1A-15F, 17A-17H and 19A-24C following the injection site needle penetration stage;

FIGS. 60A, 60B, 60C and 60D are simplified illustrations of an injection site disengagement stage of the reusable automatic injection assembly of FIGS. 1A-23L following the injection stage;

FIGS. 61A, 61B, 61C, 61D and 61E are simplified illustrations of a medication module removal from the reusable automatic injection assembly of FIGS. 1A-23L;

FIGS. 63A, 63B and 63C are simplified illustrations of a first mis-use orientation of the medicament module associated with the reusable automatic injection assembly of FIGS. 1A-23L;

FIGS. 64A, 64B and 64C are simplified illustrations of a second mis-use orientation of the medicament module associated with the reusable automatic injection assembly of FIGS. 1A-23L.

DESCRIPTION OF PREFERRED EMBODIMENTS

Figure 1A:
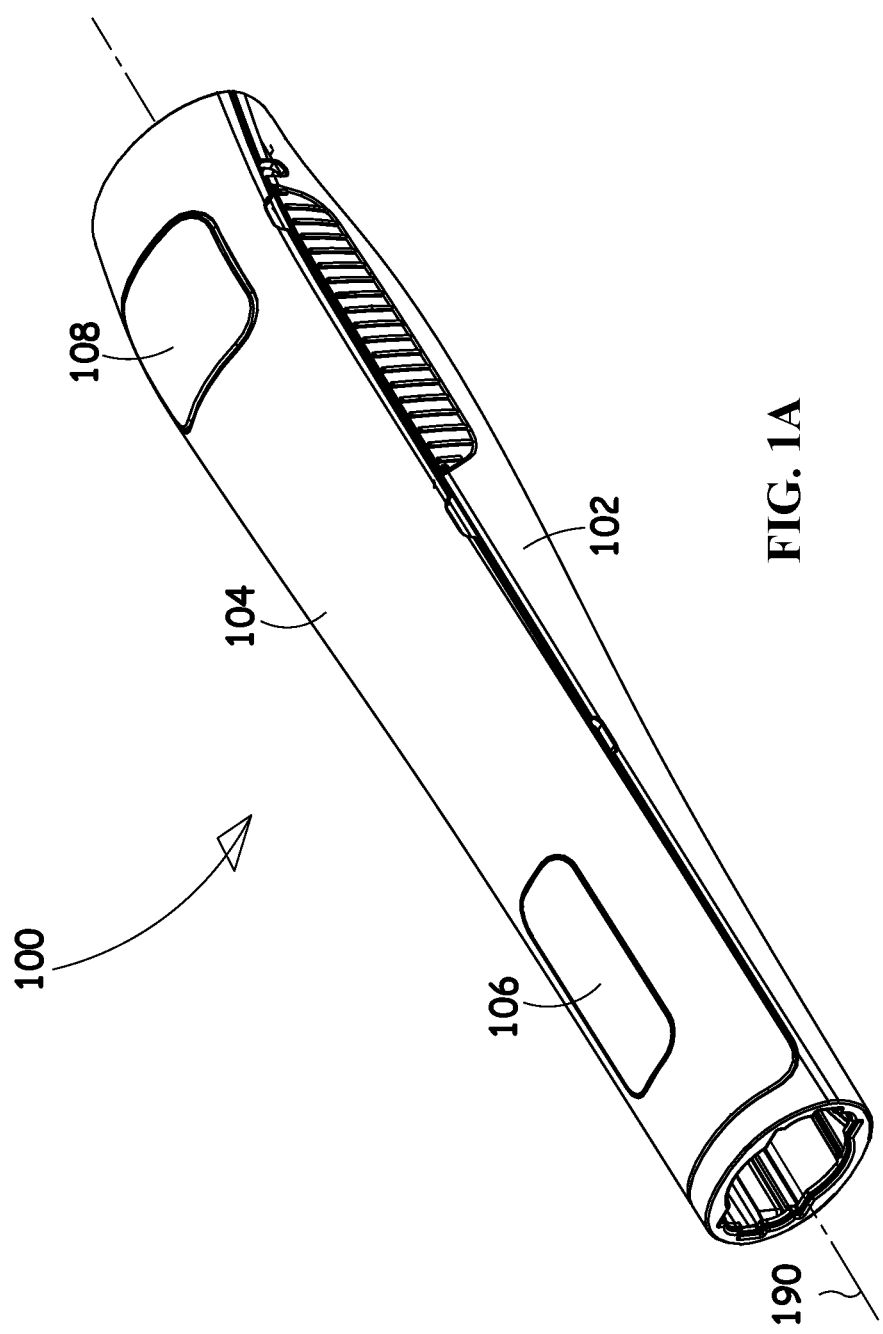
FIGS. 1A and 1B are respectively simplified assembled view and exploded view pictorial illustrations of a reusable automatic injection assembly constructed and operative in accordance with an embodiment of the present invention in conjunction with a medicament module.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

Figure 1B:
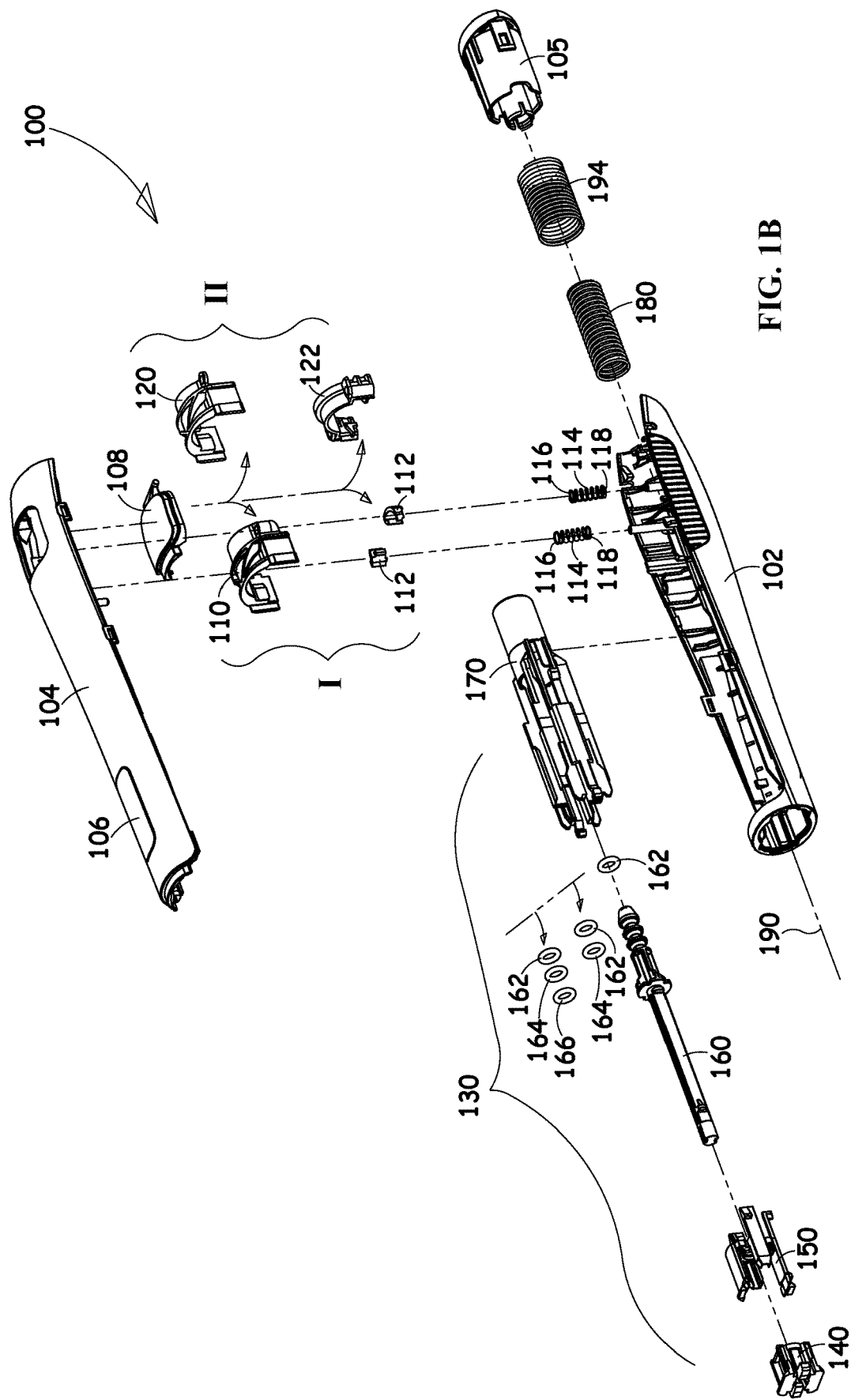

Reference is now made FIGS. 1A and 1B, which are respectively simplified assembled view and exploded view pictorial illustrations of a reusable automatic injection assembly 100 constructed and operative in accordance with an embodiment of the present invention in conjunction with a medicament module.

As seen in FIGS. 1A and 1B, the reusable automatic injection assembly comprises a main housing portion 102, a cover portion 104 and an end portion 105, both of which are preferably in fixed snap fit engagement with main housing portion 102.

Cover portion 104 is preferably formed with a transparent window portion 106, which is preferably in fixed snap fit engagement with cover portion 104 and with a user-engageable actuation button 108 which is pivotably mounted at one side thereof onto cover portion 104.

In accordance with one embodiment of the invention, shown at I in FIG. 1B, a trigger element 110 is operatively engaged by actuation button 108 and, in turn, operatively engages a pair of latches 112, which are spring loaded by a pair of compression coil springs 114, each having respective top and bottom coil ends 116 and 118.

In accordance with an alternative embodiment of the invention, shown at II in FIG. 1B, a slightly differently configured trigger element 120 is operative engaged by actuation button 108 and, in turn, engages a unitary latch element 122.

The pair of springs 114 are seated in main housing portion 102 and operatively engage either latches 112 or unitary latch element 122.

Disposed within main housing portion 102 there is provided a driving assembly 130, which includes a control element 140, which operatively engages a multifunctional retaining element 150, which, in turn operative engages an elongate damping driver element 160.

In accordance with three alternative embodiments of the invention, one, two or three sealing rings 162, 164 and 166 may be operatively engaged with elongate damping driver element 160.

A multifunctional engagement element 170 operatively engages elongate damping driver element 160 and multifunctional retaining element 150 and is operatively engaged by either latches 112 or unitary latch element 122.

A first compression spring 180 operatively engages multifunctional retaining element 150 and with elongate damping drive element 160 for driving them forwardly along a longitudinal axis 190 in a direction indicated by an arrow 192. A second compression spring 194 is arranged in coaxial relationship with first compression spring 180 and operatively engages multifunctional engagement element 170 for driving it forwardly along longitudinal axis 190 in a direction indicated by arrow 192.

Figure 2A:
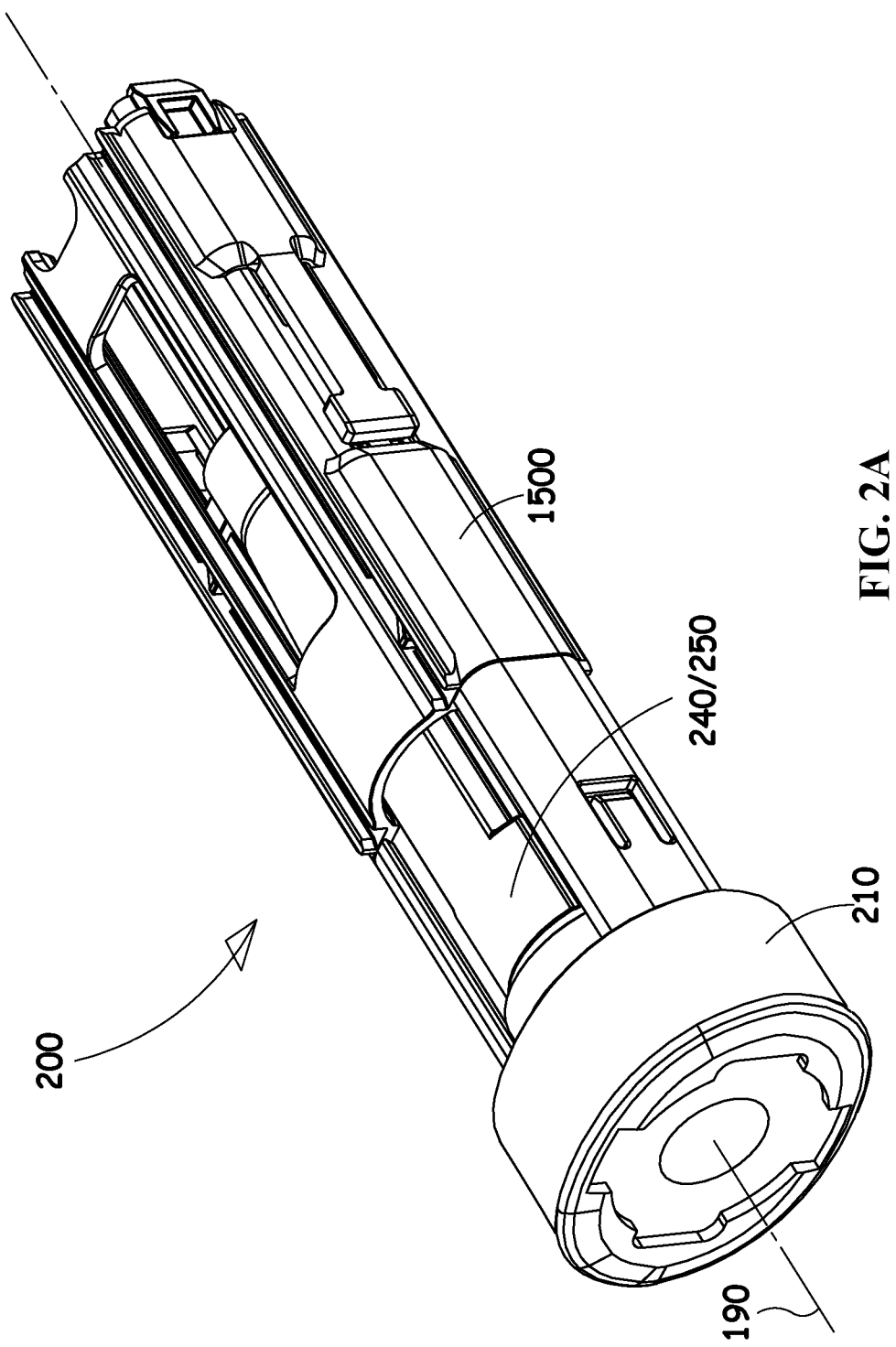
FIGS. 2A and 2B are respectively simplified assembled view and exploded view pictorial illustrations of one embodiment of a medicament module constructed and operative in accordance with an embodiment of the present invention and usable in conjunction with a reusable automatic injection assembly such as that illustrated in FIGS. 1A & 1B.
Figure 2B:
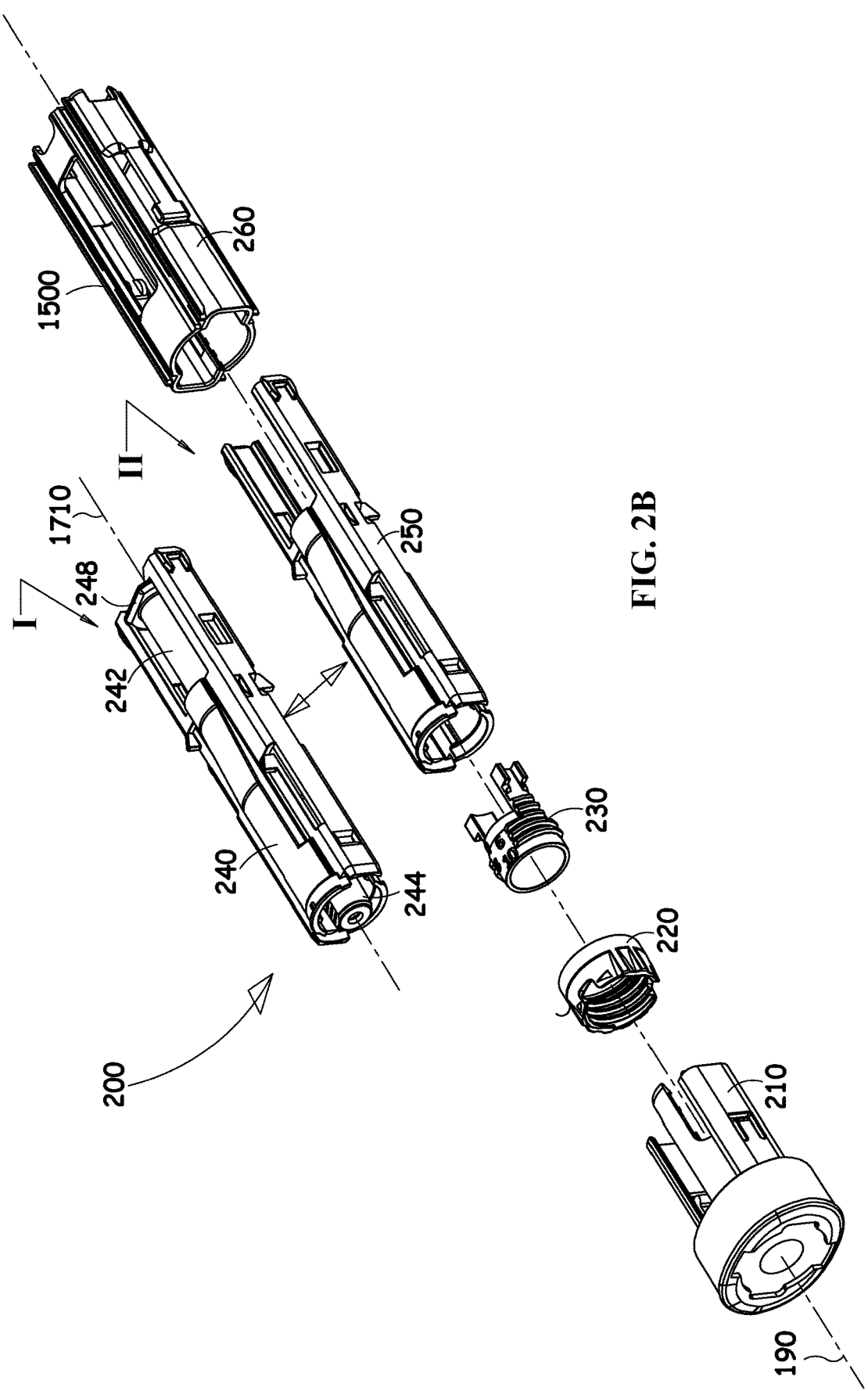

Reference is now made to FIGS. 2A and 2B, which are respectively simplified assembled view and exploded view pictorial illustrations of one embodiment of a medicament module 200 constructed and operative in accordance with an embodiment of the present invention and usable in conjunction with a reusable automatic injection assembly such as that illustrated in FIGS. 1A & 1B.

As seen in FIGS. 2A and 2B, medicament module 200 comprises an RNS remover 210, a forward needle depth adjustment element 220 and a rearward needle depth adjustment element 230.

In accordance with one embodiment of the invention, shown at I in FIG. 2B, there is provided a needle shield 240, suitable for single use and including a syringe 242 having a piston 243 contained therein and removable needle shield 244 surrounding a needle 246, which extends forwardly of a syringe flange 248.

In accordance with a second embodiment of the invention, shown at II in FIG. 2B, there is provided a needle shield 250, suitable for multiple use and not including a syringe or a removable needle shield, both of which are insertable thereinto.

A module housing 260 partially encloses either of needle shields 240 and 250.

It is appreciated that syringe 242 can be any type of medicament containers, such as pre-filled syringe, cartridge.

Figure 3A:
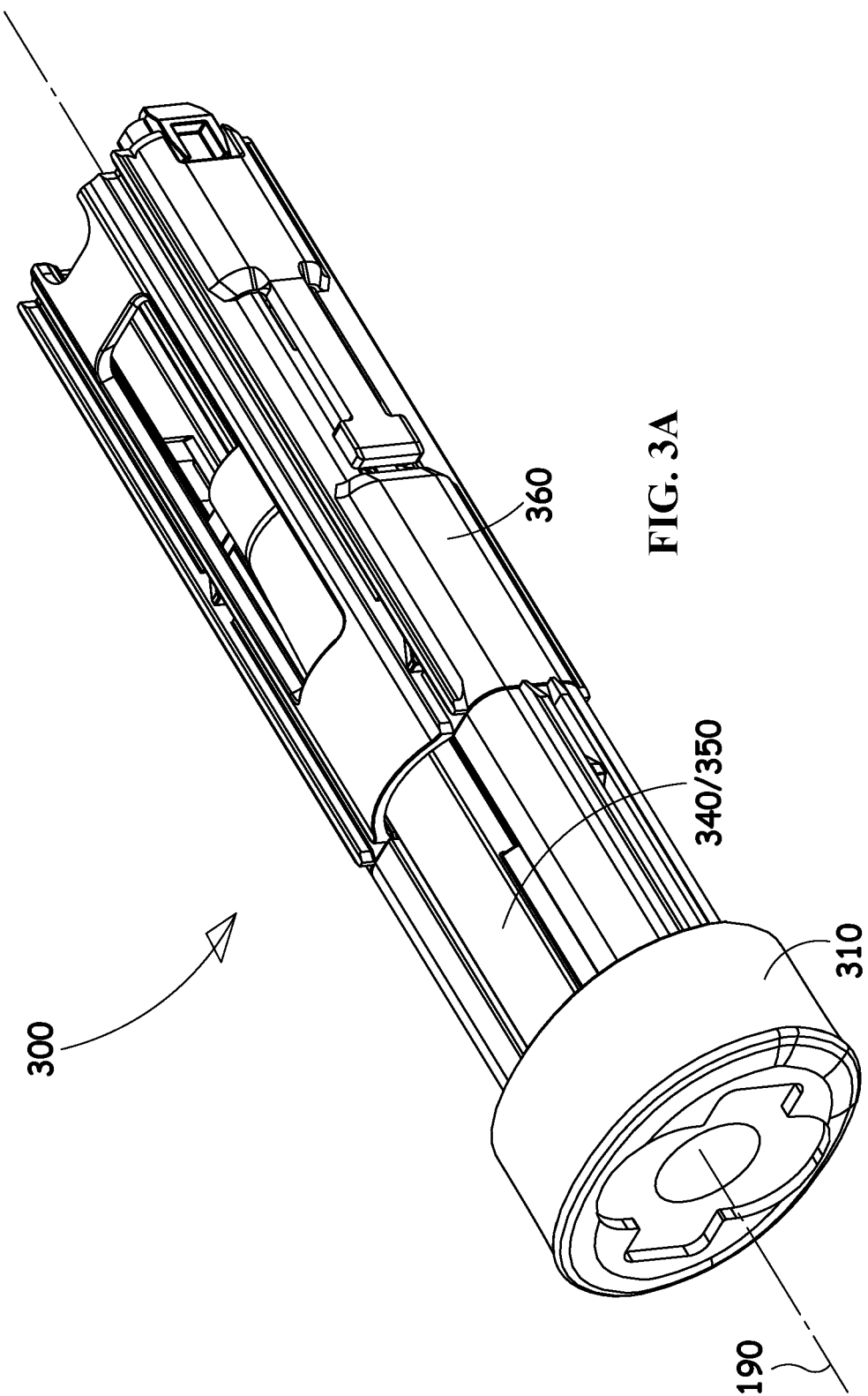
FIGS. 3A and 3B are respectively simplified assembled view and exploded view pictorial illustrations of another embodiment of a medicament module constructed and operative in accordance with an embodiment of the present invention and usable in conjunction with a reusable automatic injection assembly such as that illustrated in FIGS. 1A & 1B.
Figure 3B:
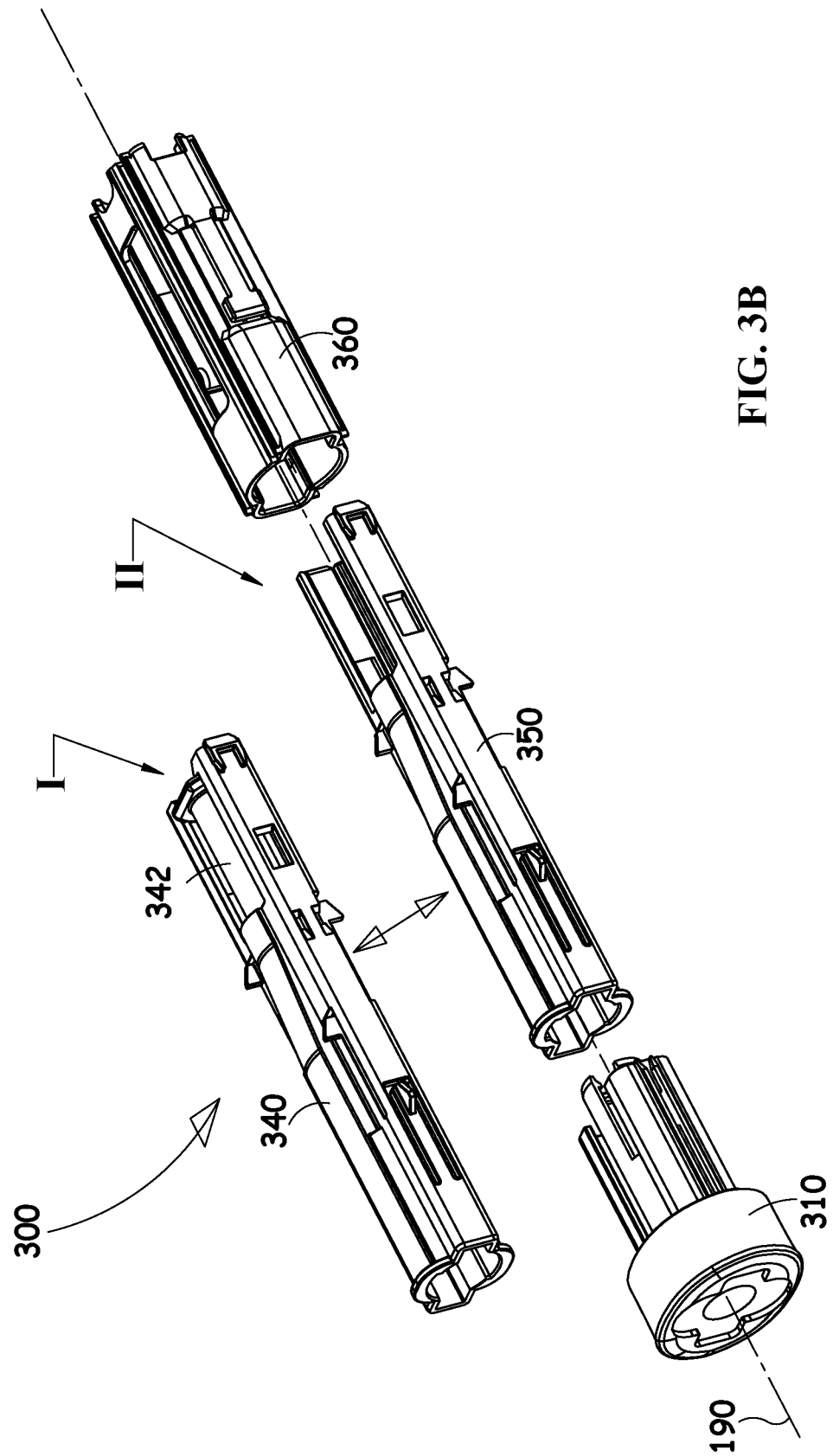
Figure 4A:
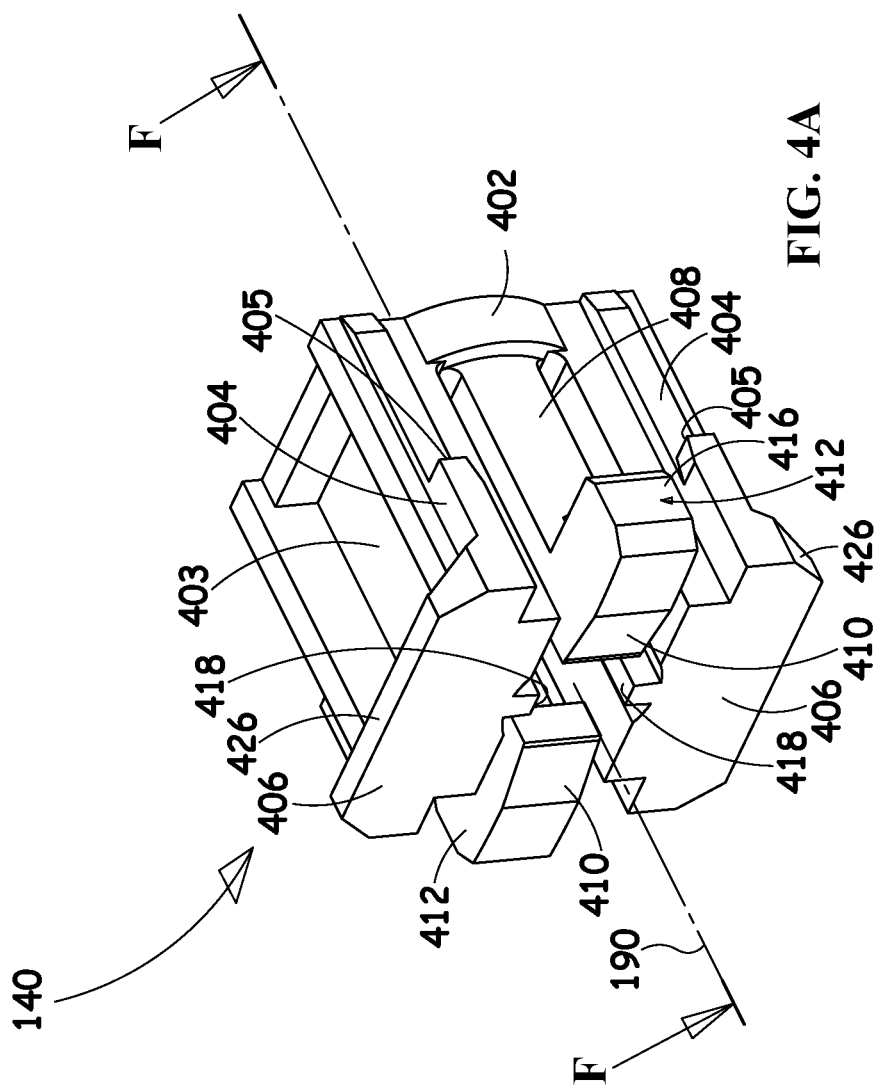
FIGS. 4A, 4B, 4C, 4D, 4E, 4F & 4G are respectively a simplified perspective view of a forward-facing portion, a simplified plan view of the forward-facing portion, a simplified top/bottom plan view, a simplified side plan view and a simplified plan view of a rearward-facing portion, a simplified sectional view taken along lines F-F in FIG. 4A and a simplified sectional view taken along lines G-G in FIG. 4A of a control element forming part of the reusable automatic injection assembly of FIGS. 1A & 1B.
Figure 4C:
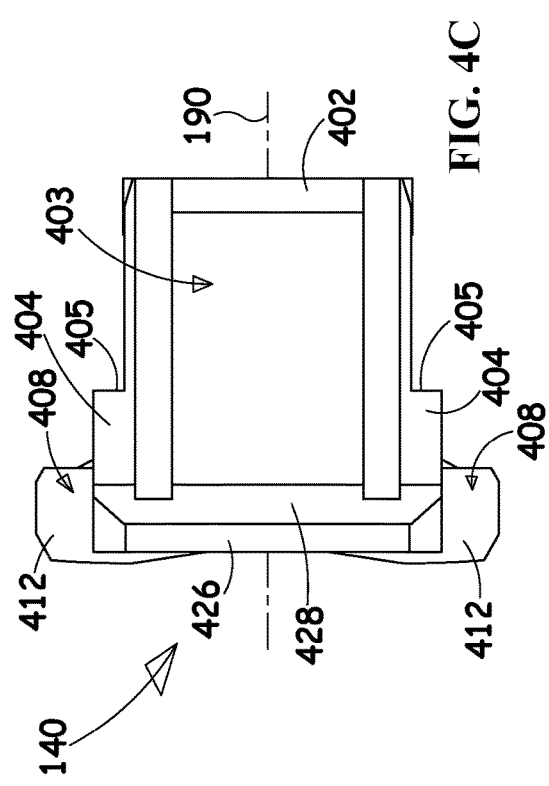
Figure 4E:
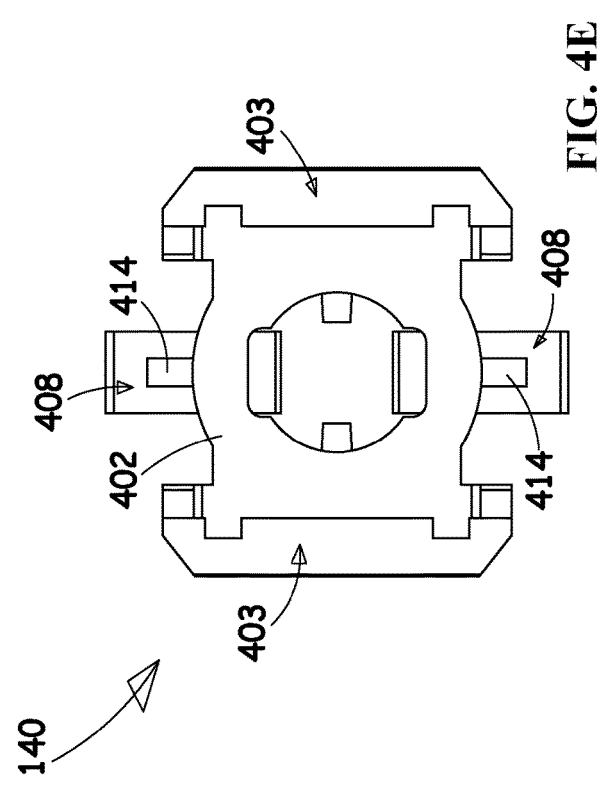
Figure 4B:
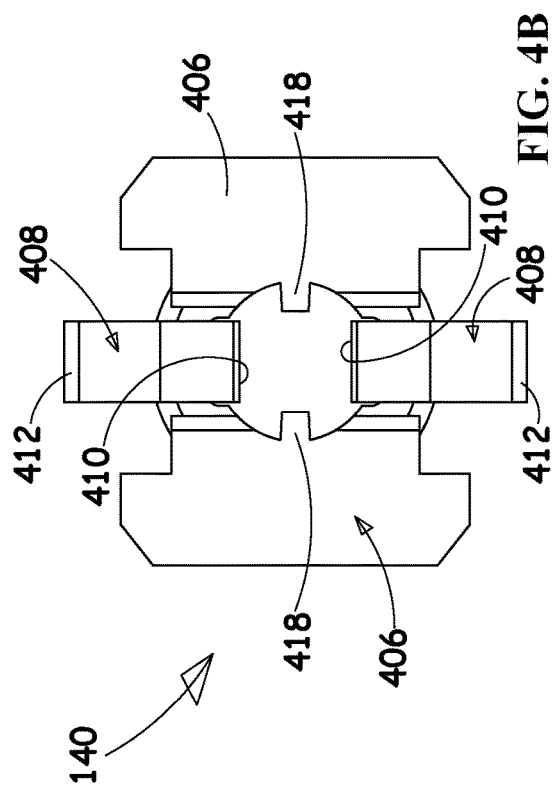
Figure 4D:
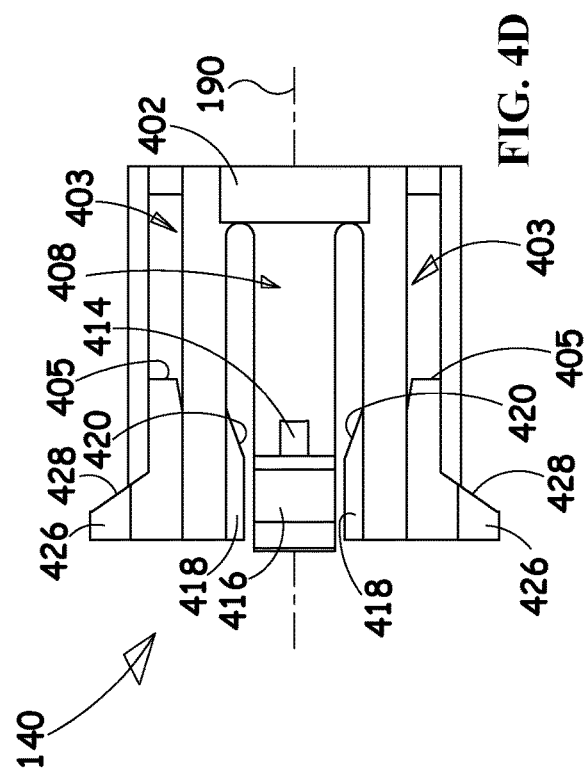
Figure 4G:
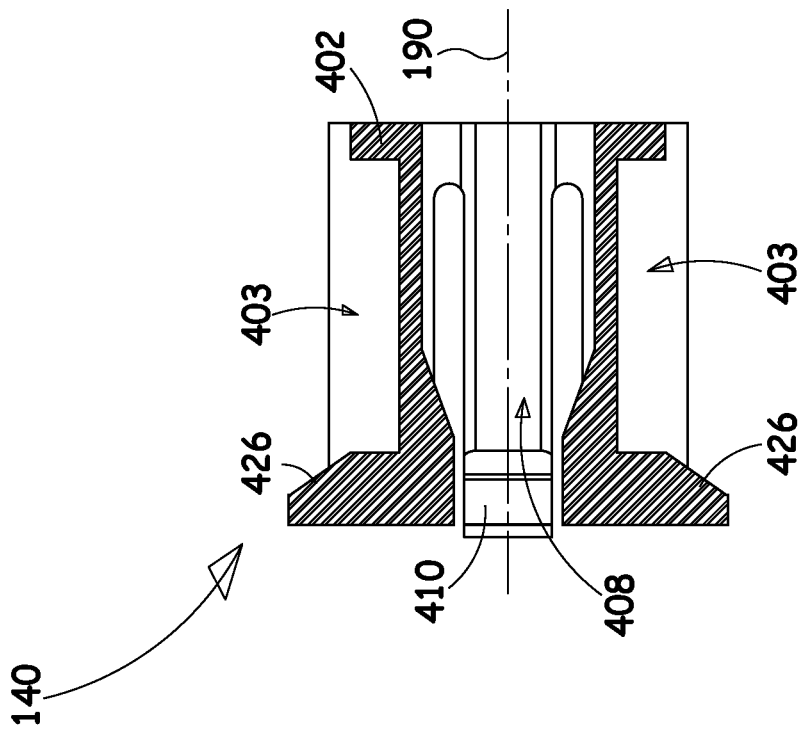
Figure 4F:
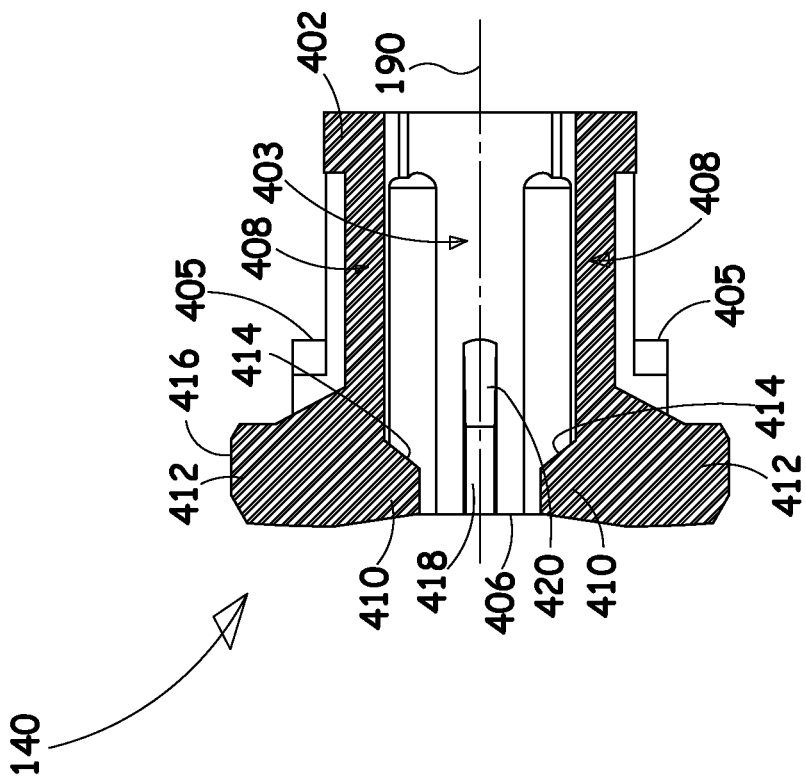

Reference is now made to FIGS. 3A and 3B, which are respectively simplified assembled view and exploded view pictorial illustrations of another embodiment of a medicament module, here designated by reference numeral 300, constructed and operative in accordance with another embodiment of the present invention and usable in conjunction with a reusable automatic injection assembly such as that illustrated in FIGS. 1A & 1B.

As seen in FIGS. 3A and 3B, medicament module 300 comprises an RNS remover 310.

In accordance with one embodiment of the invention, shown at I in FIG. 3B, there is provided a needle shield 340, suitable for single use and including a syringe 342, which may have a removable needle shield (not shown).

In accordance with a second embodiment of the invention, shown at II in FIG. 2B, there is provided a needle shield 350, suitable for multiple use and not including a syringe or a removable needle shield, both of which are insertable thereinto.

A module housing 360 partially encloses either of needle shields 340 and 350.

Reference is now made to FIGS. 4A-4G, 5A and 5B, which illustrate the structure and operation of the control element 140. As seen in FIGS. 4A-4G, the control element 140 preferably is an integrally formed element, preferably injection molded of plastic and is arranged along longitudinal axis of symmetry 190 and generally has side-to-side and top-bottom symmetry with respect to axis 190.

Control element 140 preferably includes a generally rearward-facing base portion 402, a pair of generally symmetric forwardly-extending portions 403 each having two laterally extending protrusions 404 defining a rearwardly facing surface 405. Forwardly extending portion 403 both terminate at forward facing surfaces 406 and a pair of forwardly-extending engagement fingers 408 generally located between respective generally symmetric forwardly-extending portions 403. Each of the fingers 408 is formed with respective inwardly and outwardly directed protrusions 410 and 412. Inwardly directed protrusions 410 are each formed with a rearward-facing tapered surface 414. Outwardly directed protrusions 412 are each formed with an outwardly-facing surface 416.

Each of the forwardly-extending portions 403 is preferably formed with an inwardly-facing protrusion 418 preferably including a rearwardly tapered surface 420. In addition, each of the forwardly extending portions 403 is formed with a pair of outwardly facing protrusions 426, each having a rearward facing end surface 428.

Figure 5A:
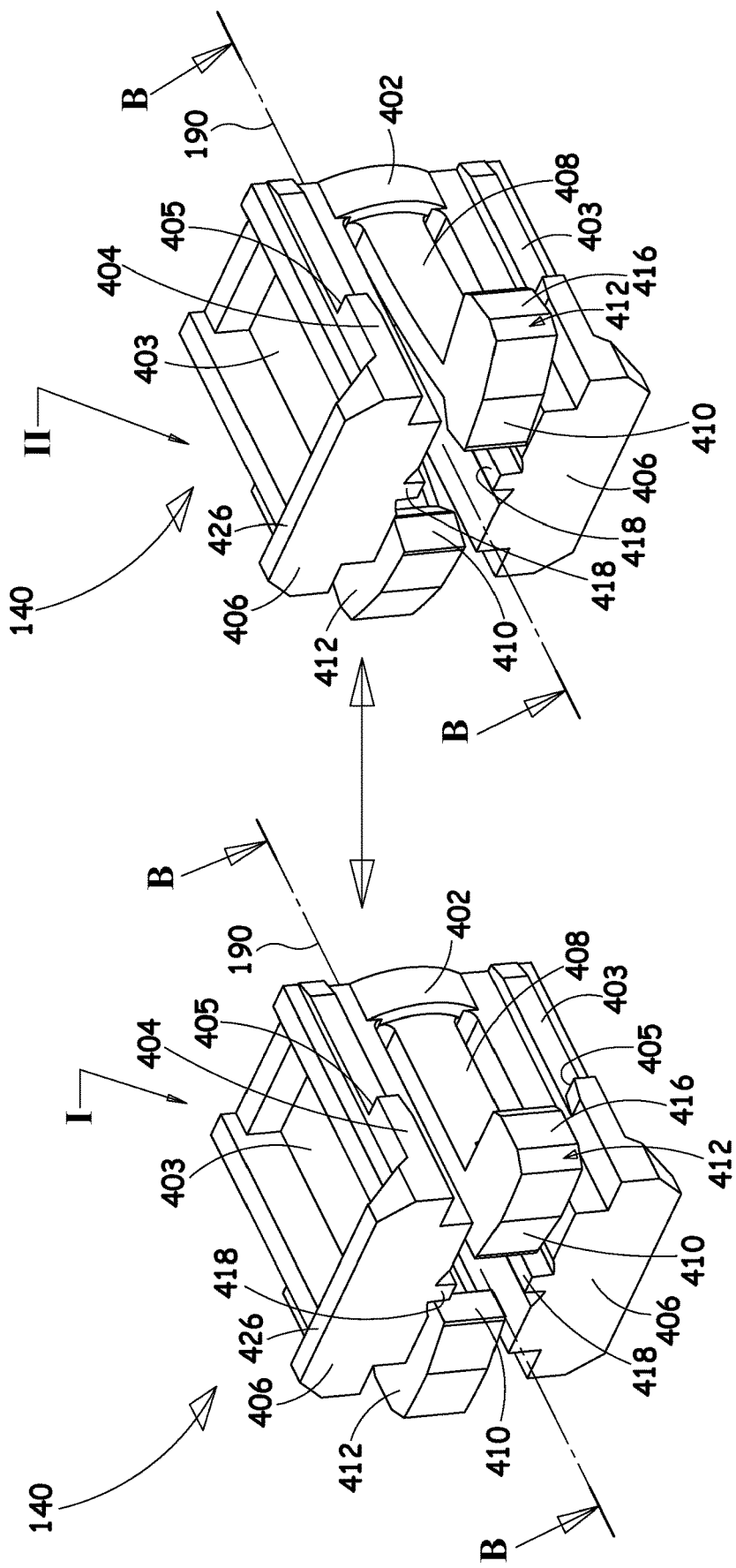
FIGS. 5A and 5B are respectively a simplified plan view illustration and a simplified sectional illustration taken along lines F-F in FIG. 4A of a transition between open and closed operative orientations of the control element of FIGS. 4A-4G.
Figure 5B:
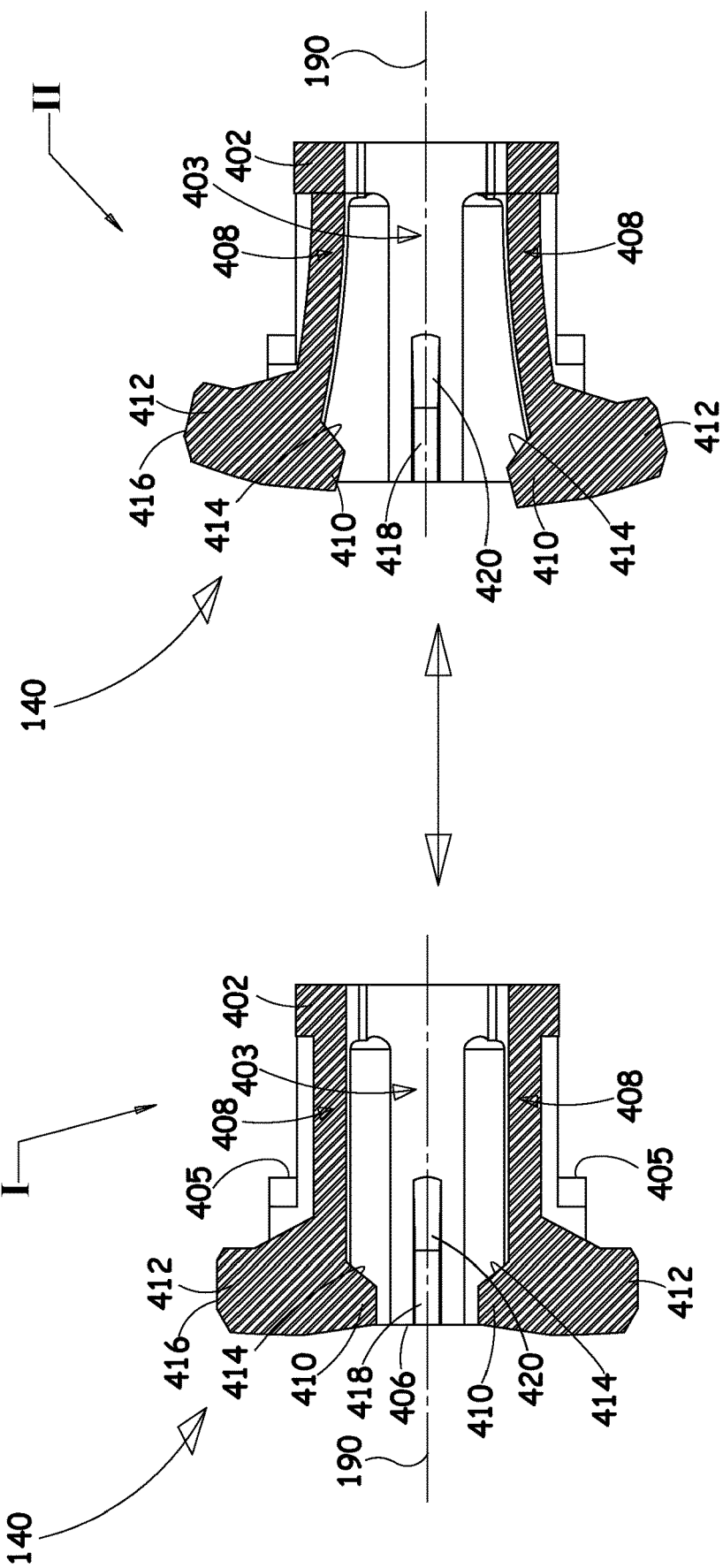

Referring now to FIGS. 5A & 5B, it is seen that the engagement fingers 408 have two operative orientations, an at rest orientation, shown at I, wherein the inwardly directed protrusions 410 are closest to each other, and a spread orientation, shown at II, wherein the inwardly directed protrusions 410 are furthest from each other.

Figure 6A:
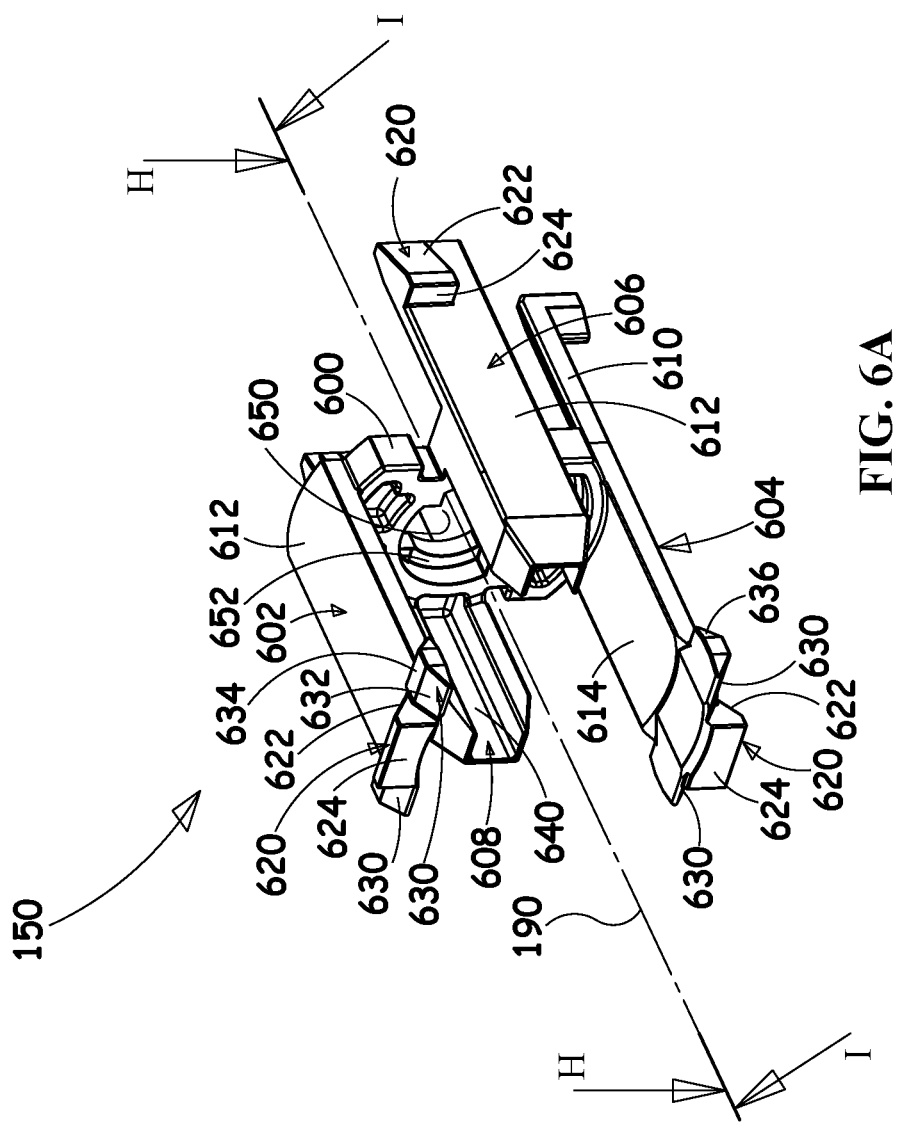

Reference is now made to FIGS. 6A, 6B, 6C, 6D, 6E, 6F, 6G, 6H and 6I, which are respectively a simplified perspective view of a forward-facing portion, a simplified plan view of the forward-facing portion, a simplified top plan view, a simplified bottom plan view, a simplified first side plan view, a simplified second side plan view, a simplified plan view of a rearward-facing portion, a simplified sectional view taken along lines H-H in FIG. 6A and a simplified sectional view taken along lines I-I in FIG. 6A of multifunctional retaining element 150, forming part of the reusable automatic injection assembly of FIGS. 1A & 1B.

As seen in FIG. 6A-6I, multifunctional retaining element 150 is preferably an integrally formed element, preferably injection molded of plastic, and is arranged along longitudinal axis 190. Multifunctional retaining element 150 is preferably formed with a generally planar base 600, which extends perpendicular to longitudinal axis 190, having general axial symmetry.

Extending forwardly from base 600 and perpendicularly thereto and parallel to longitudinal axis 190 are a pair of generally identical fingers 602 and 604.

Extending forwardly and rearwardly from base 600 and perpendicularly thereto and parallel to longitudinal axis 190 are a pair of generally identical fingers 606 and 608.

Extending forwardly from base 600 is a finger 610, which is preferably formed as a forward extension of finger 604.

Fingers 602, 604, 606, 608 and 610 are each formed with an elongate outwardly-facing curved surface 612 and an inwardly-facing curved surface 614. Each of fingers 602, 604, 606, 608 and 610 is also formed with outwardly-facing tapered protrusion 620, having an inclined surface 622 and an engagement surface 624, lying generally perpendicular to axis 190. Additionally each of fingers 602 and 604 is provided with a pair of side outwardly-facing double tapered protrusions 630. Each of protrusions 630 has a forwardly-facing tapered surface 632, an axial planar surface 634, extending in a plane parallel to axis 190, and a rearwardly-facing tapered surface 636.

Each of fingers 606 and 608 is formed with an inwardly-facing longitudinal channel 640, extending parallel to axis 190, on a forwardly-extending portion thereof and is formed with an inwardly facing longitudinal rib 642 on a rearwardly-extending portion thereof.

Base 600 is preferably formed with a central aperture 650 surrounded by a pair of forward-facing recessed partially circumferential surfaces 652. Base 600 is also formed with a rearwardly-facing surface 654.

Figure 7A:
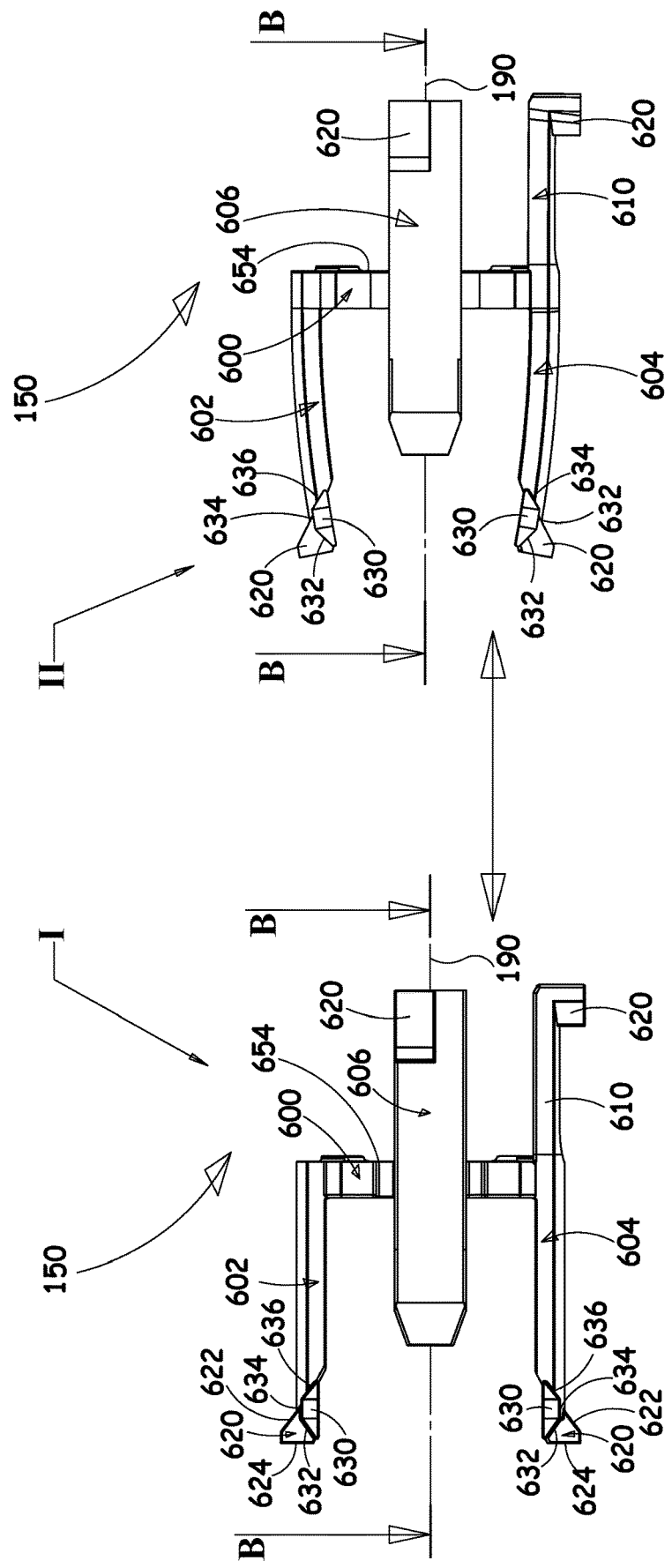
FIGS. 7A and 7B are respectively a simplified plan view illustration and a simplified sectional illustration taken along lines H-H in FIG. 6A of a transition between first engaged and disengaged operative orientations of a first portion of the multifunctional retaining element of FIGS. 6A-6I.
Figure 7B:
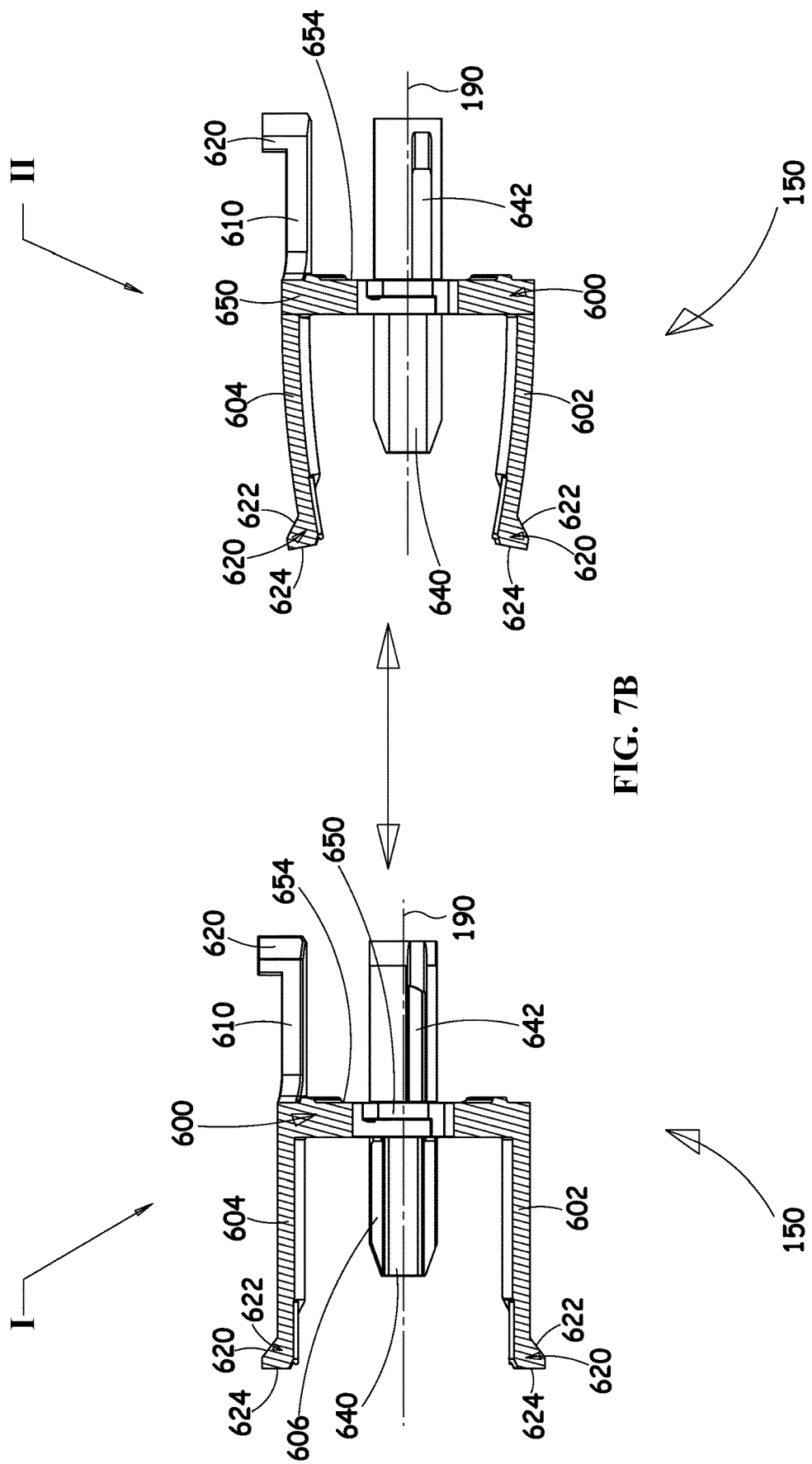

Reference is now made to FIGS. 7A and 7B, which are respectively a simplified plan view illustration and a simplified sectional illustration taken along lines H-H in FIG. 6A of a transition between first engaged and disengaged operative orientations of a first portion of the multifunctional retaining element of FIGS. 6A-6I.

As seen in FIGS. 7A and 7B at I, in a steady state operative orientation, fingers 602 and 604 each extend generally parallel to axis 190. At a given, momentary point in time during operation of the reusable automatic injection assembly 100, as will be described in detail hereinbelow, the operative orientation of fingers 602 and 604 is as seen at II in FIGS. 7A and 7B. In this momentary operative orientation, the forward ends of fingers 602 and 604 are bent inwardly as shown.

Figure 8:
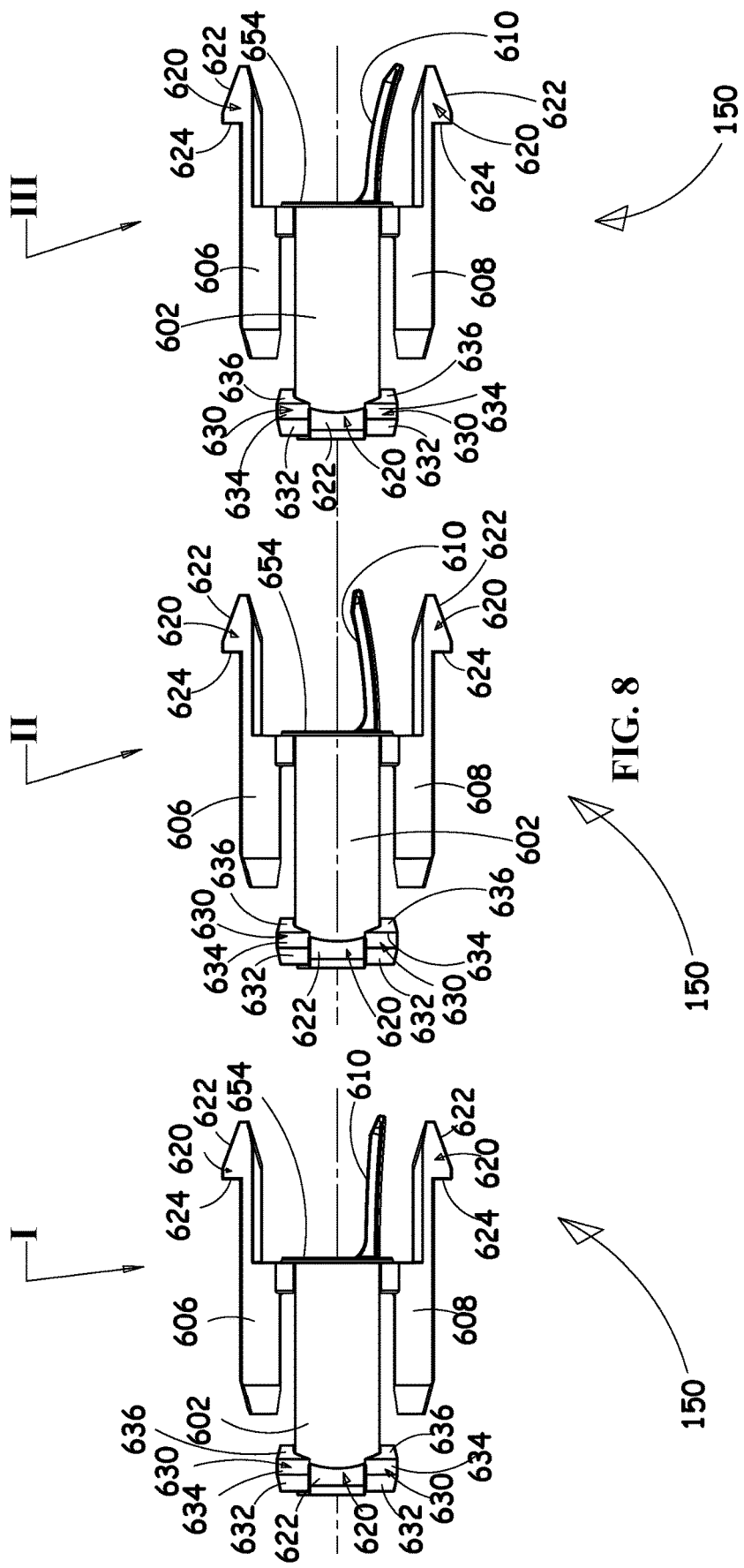
FIG. 8 is a simplified plan view illustration of a transition between second engaged and disengaged operative orientations of a second portion of the multifunctional retaining element of FIGS. 6A-6I.

Reference is now made to FIG. 8, which is simplified plan view illustration of a transition between second engaged and disengaged operative orientations of a second portion of the multifunctional retaining element of FIGS. 6A-6I.

As seen in FIG. 8 at I, in a steady state operative orientation, finger 610 extends generally parallel to axis 190. At a given, momentary point in time during operation of the reusable automatic injection assembly 100, as will be described in detail hereinbelow, the operative orientation of finger 610 is as seen at II in FIG. 8. In this momentary operative orientation, the rearward end of finger 610 is bent inwardly as shown. Immediately thereafter at III, finger 610 is bent outwardly.

Figure 9A:
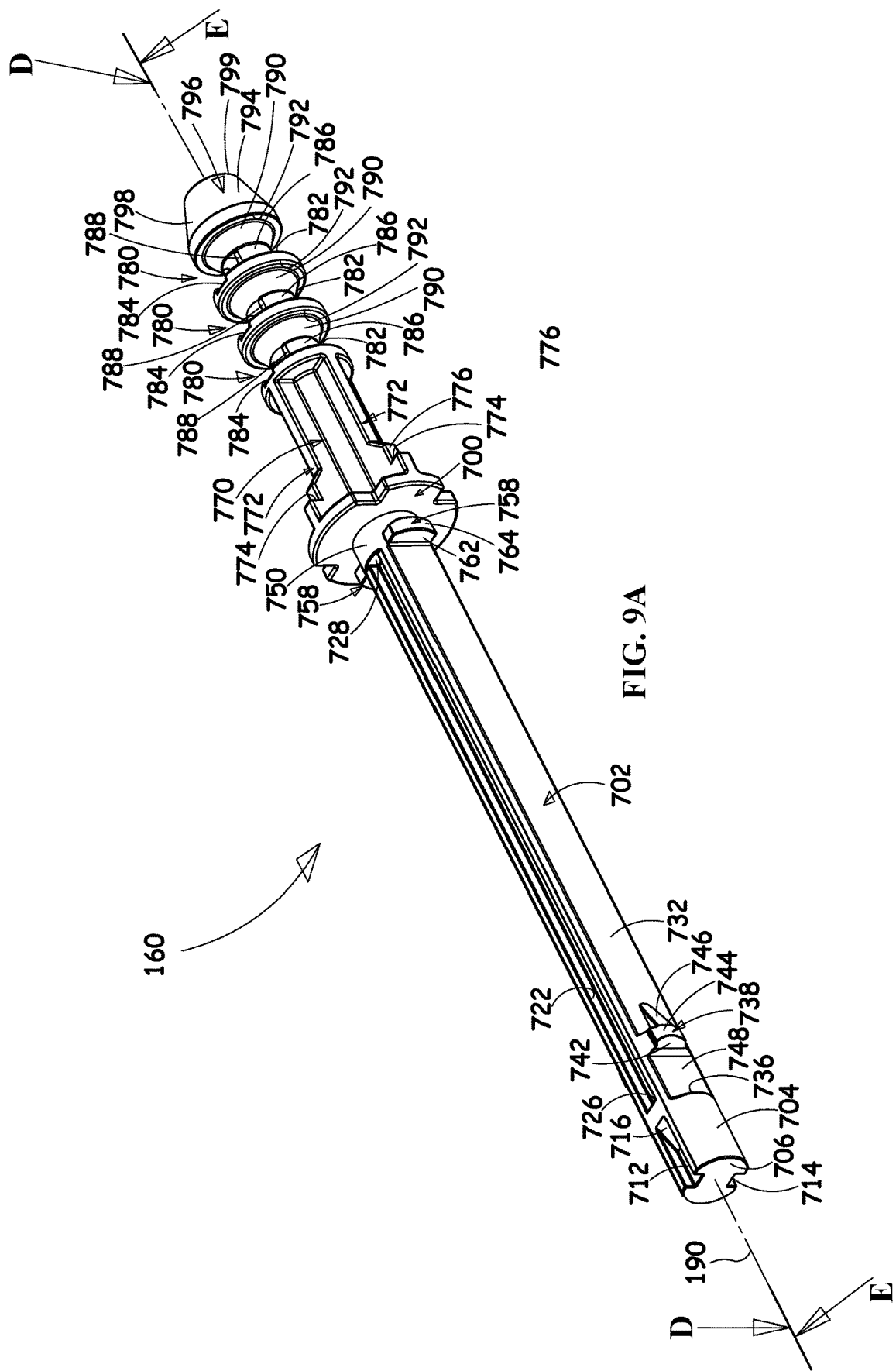
FIGS. 9A, 9B, 9C, 9D and 9E are respectively a simplified perspective view of forward-facing portion, a simplified first side plan view, a simplified second side plan view; a simplified sectional view taken along lines D-D in FIG. 9A and a simplified sectional view taken along lines E-E in FIG. 9A of an elongate damping driver element forming part of the reusable automatic injection assembly of FIGS. 1A & 1B.
Figure 9B:
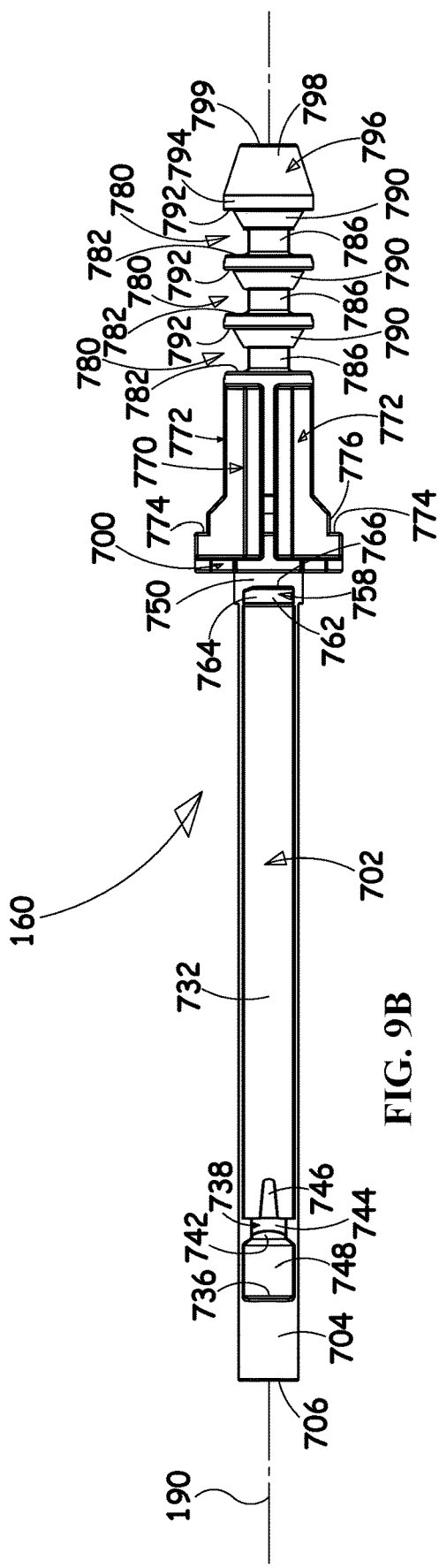
Figure 9C:
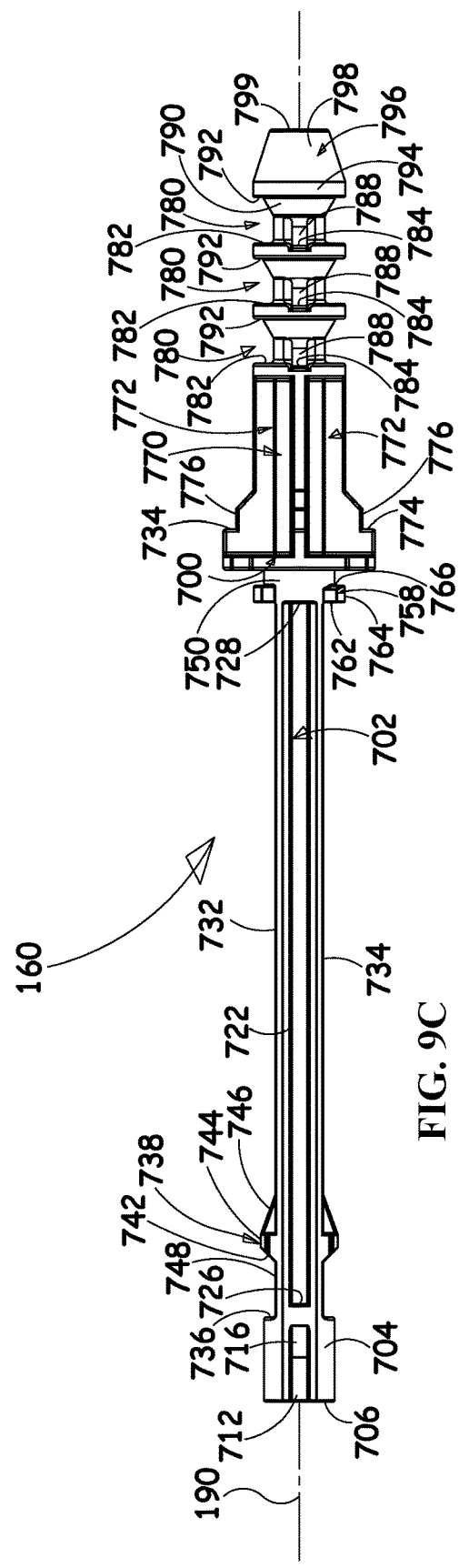
Figure 9D:
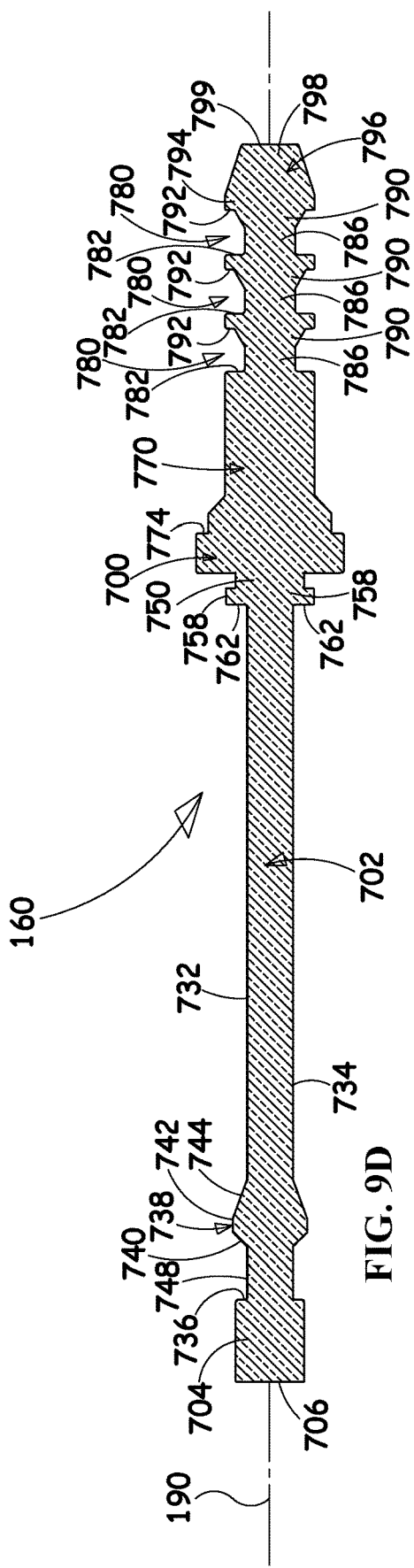
Figure 9E:
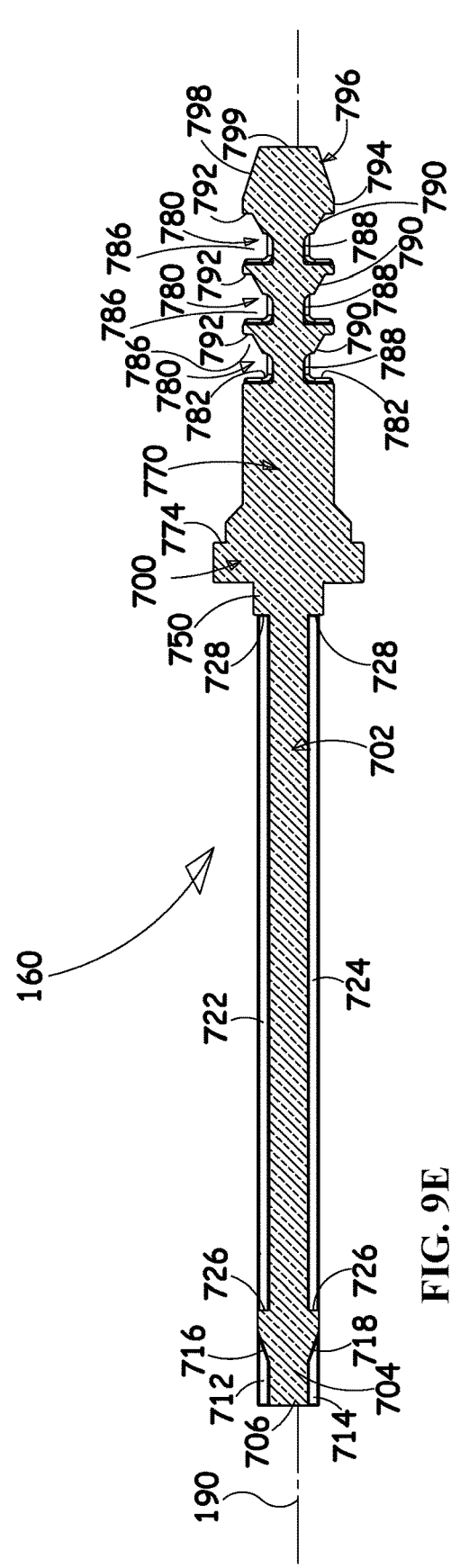

Reference is now made to FIGS. 9A, 9B, 9C, 9D and 9E, which are respectively a simplified perspective view of forward-facing portion, a simplified first side plan view, a simplified second side plan view; a simplified sectional view taken along lines D-D in FIG. 9A and a simplified sectional view taken along lines E-E in FIG. 9A of elongate damping driver element 160, forming part of the reusable automatic injection assembly of FIGS. 1A & 1B.

As seen in FIGS. 9A-9E elongate damping driver element 160 preferably is an integrally-formed element, preferably injection molded of plastic, and is arranged along longitudinal axis 190. Elongate damping driver element 160 preferably has top to bottom and side to side general axial symmetry, and includes a generally planar base 700 from which extends forwardly along axis 190 a generally cylindrical rod 702 having a generally rectangular cross section. Rod 702 terminates at a generally circular cylindrical portion 704, having a forwardly-facing surface 706, which lies in a plane perpendicular to axis 190. Generally circular cylindrical portion 704 is formed with respective top and bottom facing channels 712 and 714, having respective outwardly-tapered, rearwardly extending surfaces 716 and 718.

Generally cylindrical rod 702 is formed with respective top and bottom facing channels 722 and 724, each having respective forward and rearward bulkhead surface 726 and 728.

Generally cylindrical rod 702 is formed with generally planar side-facing surfaces 732 and 734, each terminating at a rearwardly-facing shoulder surface 736 and each having a forward side protrusion 738. Each side protrusion 738 preferably includes a tapered planar forward-facing surface 742, a convex, radially outwardly facing surface 744 and a relatively narrowed rearward-facing tapered surface 746. Each of generally planar side-facing surfaces 732 and 734 defines a generally planar forward side surface portion 748 between surface 742 of protrusion 738 and shoulder surface 736.

Adjacent base 700, cylindrical rod 702 includes a generally circular cylindrical portion 750 from which extend a pair of rearward side protrusions 758. Each side protrusion 758 preferably includes a planar forward-facing surface 762, a convex, radially outwardly facing surface 764 and a planar rearward-facing surface 766.

Rearward of base 700 there is formed an intermediate elongate portion 770, preferably having four radially extending stepped ribs 772, each separate by 90 degrees from its neighbors. Each of stepped ribs 772 preferably includes a shoulder 774 which defines a spring seat for a forward facing end of spring 180 (FIG. 1B) and an elongate edge surface 776. Edge surfaces 776 together serve to position spring 180 radially with respect to axis 190.

Rearwardly of intermediate elongate portion 770 are preferably a series of axial movement direction dependent damping control friction element seats 780, preferably three in number and arranged axially one adjacent there other. Each of axial movement direction dependent damping control Friction element seats 780 includes a rearwardly facing planar surface 782, preferably having a pair of mutually oppositely radially outwardly directed slots 784.

Extending rearwardly from surface 782 is a generally circular cylindrical axial portion 786, preferably having a pair of mutually oppositely radially outwardly directed slots 788, which communicate with slots 784.

Extending rearwardly from generally circular cylindrical axial portion 786 is a generally circularly symmetric rearwardly and outwardly tapered axial portion 790, which terminates at a rearwardly facing planar annular surface 792.

It is appreciated that planar annular surface 792 of a forwardmost axial movement direction dependent damping control friction element seat 780 and planar surface 782 of an axial movement direction dependent damping control friction element seat 780 disposed immediately rearwardly thereof may be defined on a single radially extending bulkhead, such as a bulkhead designated by reference numeral 794.

Rearwardly of the rearwardmost axial movement direction dependent damping control Friction element seat 780 there is preferably defined a rearward end portion 796 having a rearwardly and inwardly tapered circumferential surface 798 and a generally planar rearward facing surface 799.

Figure 10A:
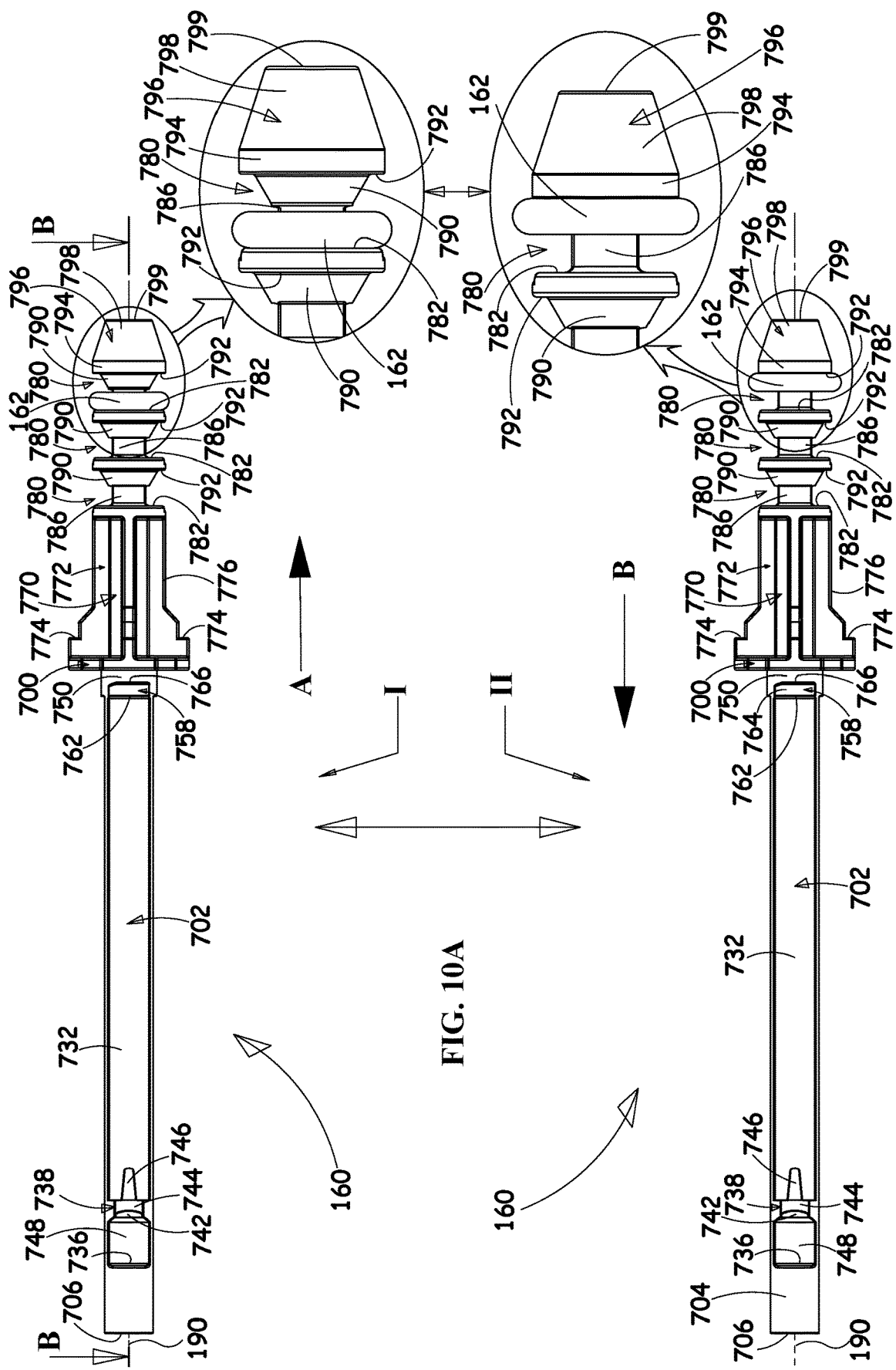
FIGS. 10A and 10B are respectively a simplified plan view illustration and a simplified sectional illustration taken along lines B-B in FIG. 10A of a transition between respective relatively weak and relatively strong damping operative orientations of the elongate damping driver element of FIGS. 9A-9E, having a single friction element mounted thereon.
Figure 10B:
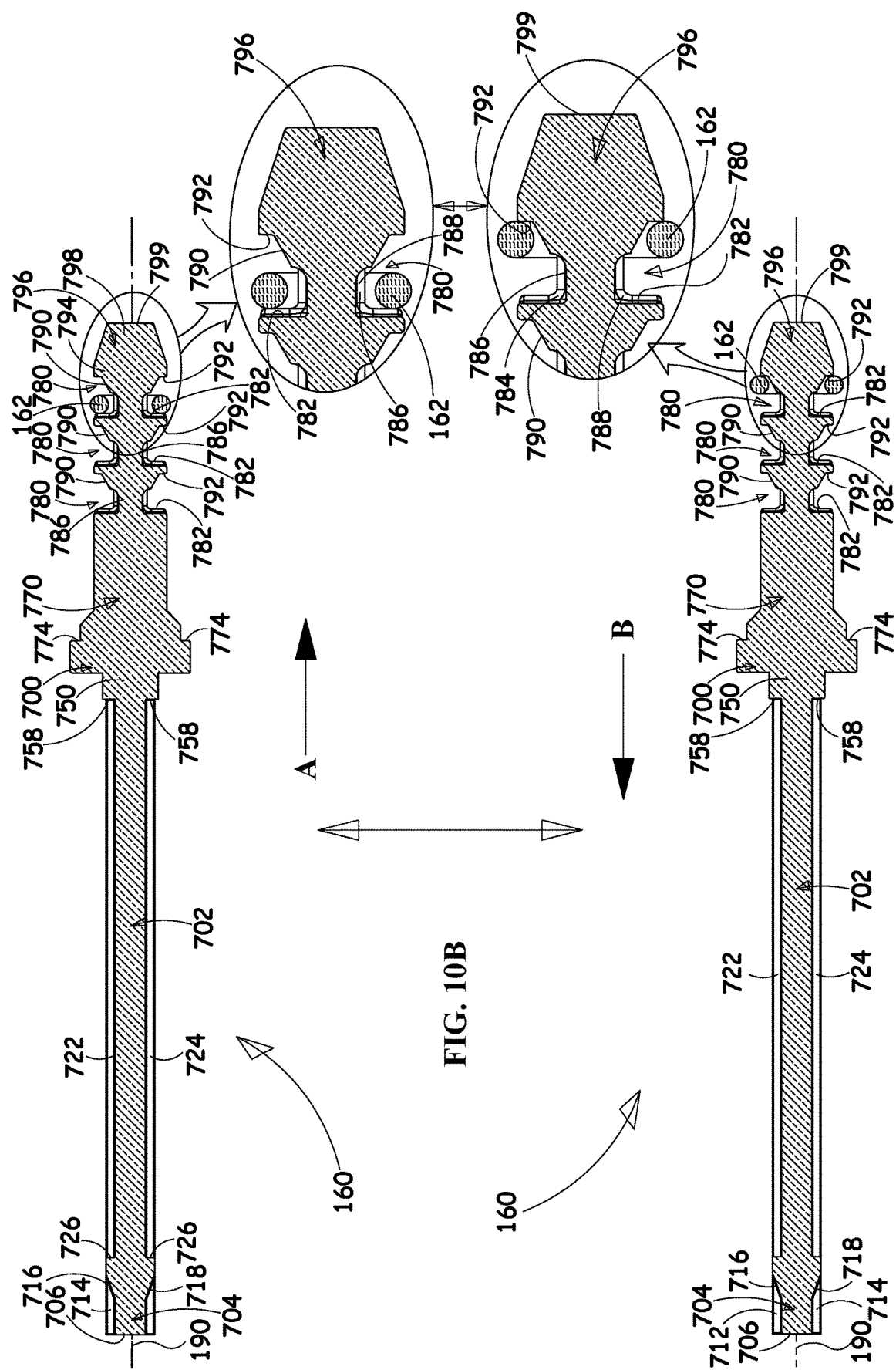

Reference is now made to FIGS. 10A and 10B, which are respectively a simplified plan view illustration and a simplified sectional illustration taken along lines B-B in FIG. 10A of a transition between respective relatively weak and relatively strong damping operative orientations of the elongate damping driver element of FIGS. 9A-9E, having a single Friction element mounted thereon.

As seen in FIGS. 10A and 10B, it is a particular feature of an embodiment of the present invention that when the elongate damping driver element 160 is in rearward motion, relative to main housing portion 102 as indicated by an arrow A, a friction element 162 located in the rearwardmost axial movement direction dependent damping control friction element seat 780 is forced forwardly by frictional engagement with end cover 105 (FIG. 1B) into engagement with rearward facing planar surface 782 and surrounds generally circular cylindrical axial portion 786 and is generally at rest, thus providing a relatively low level of damping of axial motion of the elongate damping driver element 160 in rearward motion.

When the elongate damping driver element 160 is in forward motion, relative to main housing portion 102 as indicated by an arrow B, friction element 162 located in the rearwardmost axial movement direction dependent damping control friction element seat 780 is forced rearwardly by frictional engagement with end cover 105 (FIG. 1B) into engagement with forward facing planar surface 792 and surrounds generally tapered surface 790. Engagement of friction element 162 with generally tapered surface 790 forces friction element 162 radially outwardly and thus increases its frictional engagement with end cover 105, thus providing a relatively high level of damping of axial motion of the elongate damping driver element 160 in forward motion.

It is an additional particular feature of an embodiment of the present invention that under rearward motion of the elongate damping drive element 160, air which would otherwise be trapped between the friction element 162 and the end cover 105 is released via slots and 784 and 788. Were this air not to be released, it would resist required rearward motion of the elongate damping drive element 160.

It is an a further particular feature of an embodiment of the present invention that under forward motion of the elongate damping drive element 160, a partial vacuum is created between friction element 162 and the end cover 105, which enhances damping of forward axial motion of the elongate damping drive element 160 relative to the main housing portion 102.

Figure 11A:
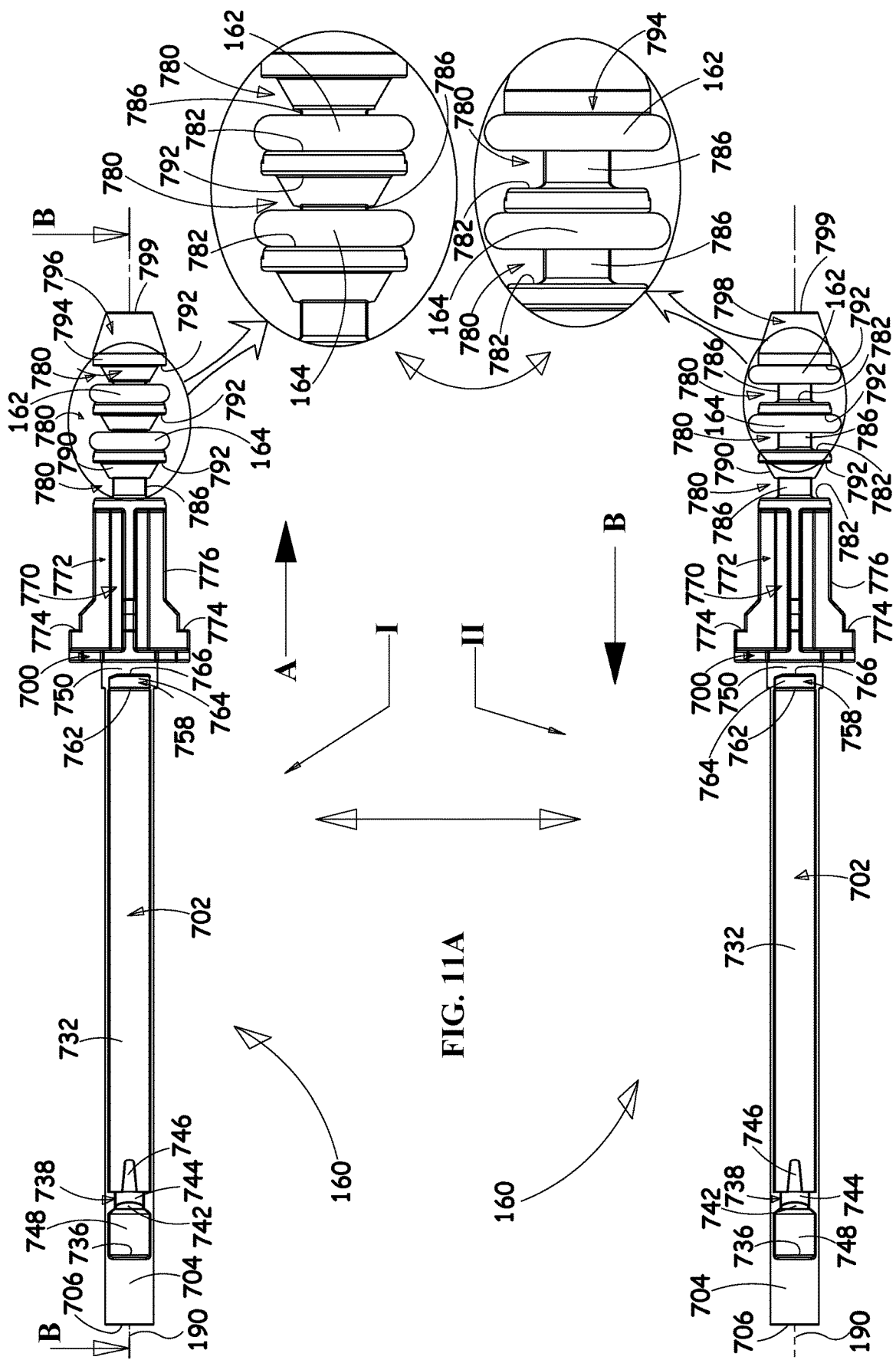
FIGS. 11A and 11B are respectively a simplified plan view illustration and a simplified sectional illustration taken along lines B-B in FIG. 11A of a transition between respective relatively weak and relatively strong damping operative orientations of the elongate damping driver element of FIGS. 9A-9E, having two friction elements mounted thereon.
Figure 11B:
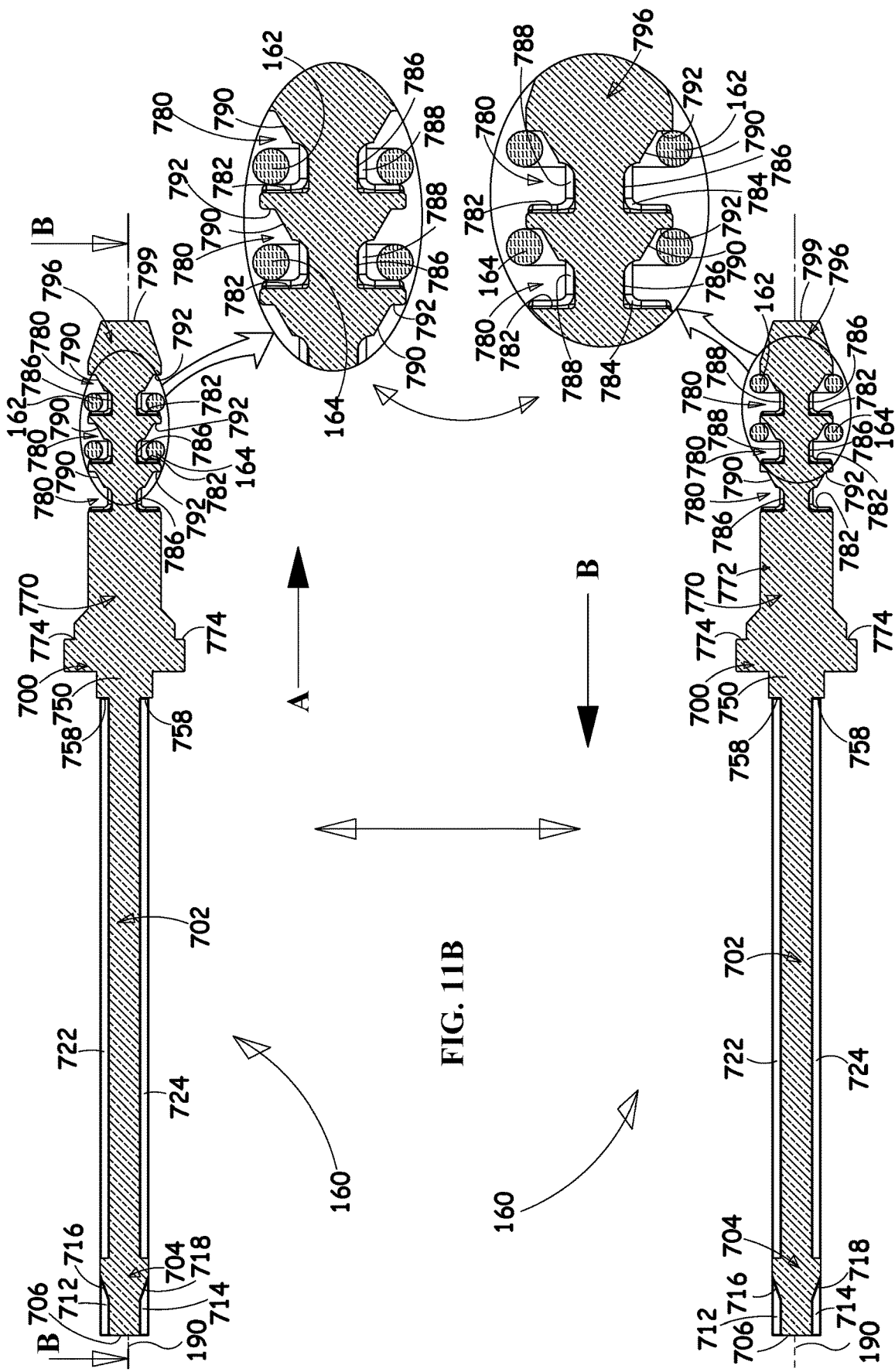

Reference is now made to FIGS. 11A and 11B, which are respectively a simplified plan view illustration and a simplified sectional illustration taken along lines B-B in FIG. 11A of a transition between respective relatively weak and relatively strong damping operative orientations of the elongate damping driver element 160 of FIGS. 10A-10E, having two friction elements mounted thereon.

As seen in FIGS. 11A and 11B, it is a particular feature of an embodiment of the present invention that when the elongate damping driver element 160 is in rearward motion, relative to main housing portion 102 as indicated by an arrow A, friction elements 162 and 164 are located in the rearwardmost axial movement direction dependent damping control friction element seat 780 and the adjacent seat 780 located forwardly thereof and are forced forwardly by frictional engagement with end cover 105 (FIG. 1B) into engagement with rearward facing planar surfaces 782 and surrounds generally circular cylindrical axial portion 786 and is generally at rest, thus providing a relatively low level of damping of axial motion of the elongate damping driver element 160 in rearward motion.

When the elongate damping driver element 160 is in forward motion, relative to main housing portion 102 as indicated by an arrow B, friction elements 162 and 164 are located in the rearwardmost axial movement direction dependent damping control friction element seat 780 and the adjacent seat 780 located forwardly thereof, are forced rearwardly by frictional engagement with end cover 105 (FIG. 1B) into engagement with forward facing planar surfaces 792 and surrounds generally tapered surface 790. Engagement of friction elements 162 and 164 with generally tapered surfaces 790 forces friction elements 162 and 164 radially outwardly and thus increases its frictional engagement with end cover 105, thus providing a relatively high level of damping of axial motion of the elongate damping driver element 160 in forward motion.

It is an additional particular feature of an embodiment of the present invention that under rearward motion of the elongate damping drive element 160, air which would otherwise be trapped between friction elements 162, 164 and the end cover 105 is released via slots and 784 and 788. Were this air not to be released, it would resist required rearward motion of the elongate damping drive element 160.

It is an a further particular feature of an embodiment of the present invention that under forward motion of the elongate damping drive element 160, a partial vacuum is created between friction elements 162, 164 and the end cover 105, which enhances damping of forward axial motion of the elongate damping drive element 160 relative to the main housing portion 102.

Figure 12A:
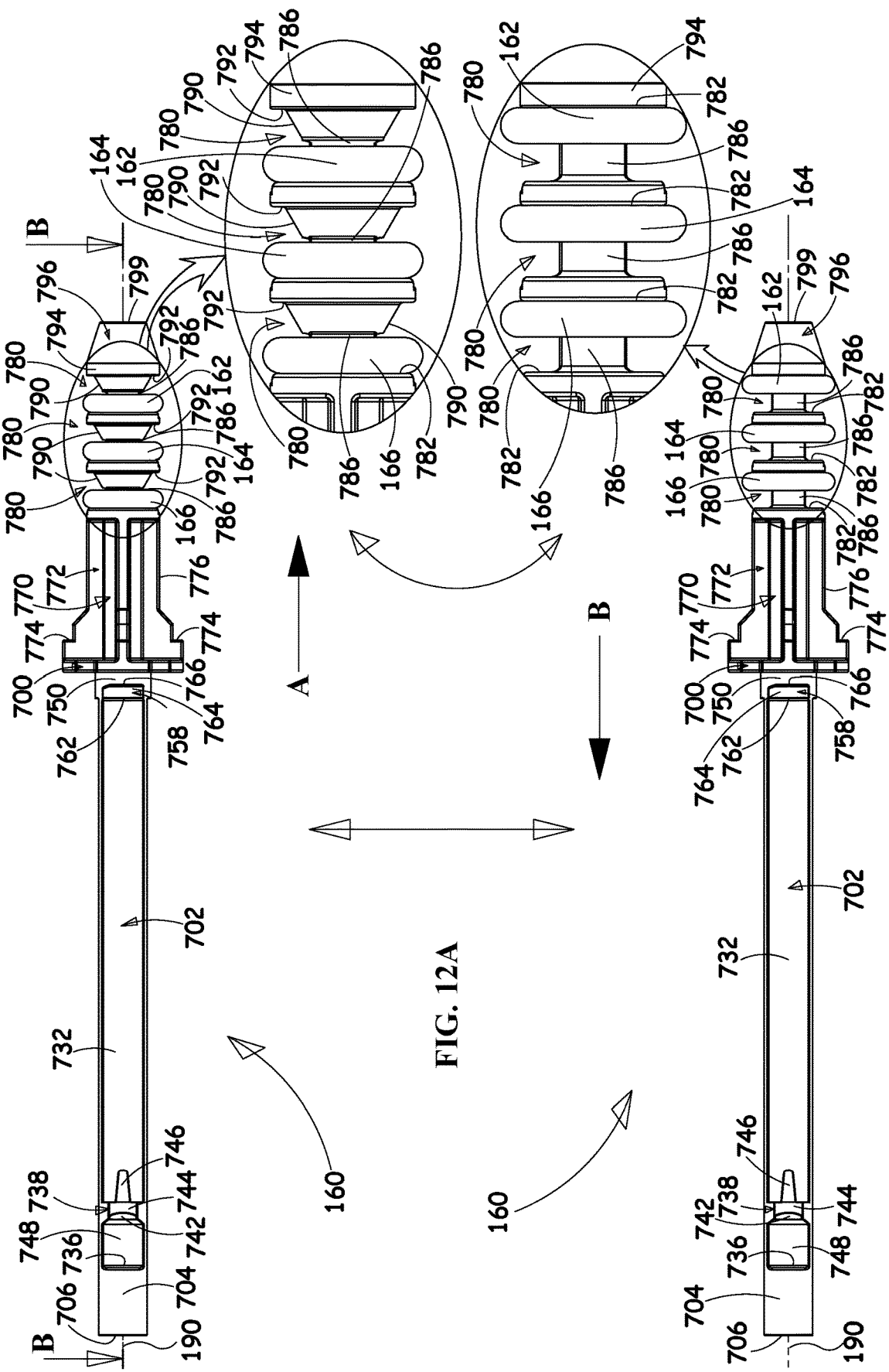
FIGS. 12A and 12B are respectively a simplified plan view illustration and a simplified sectional illustration taken along lines B-B in FIG. 12A of a transition between respective relatively weak and relatively strong damping operative orientations of the elongate damping driver element of FIGS. 9A-9E, having three friction elements mounted thereon.
Figure 12B:
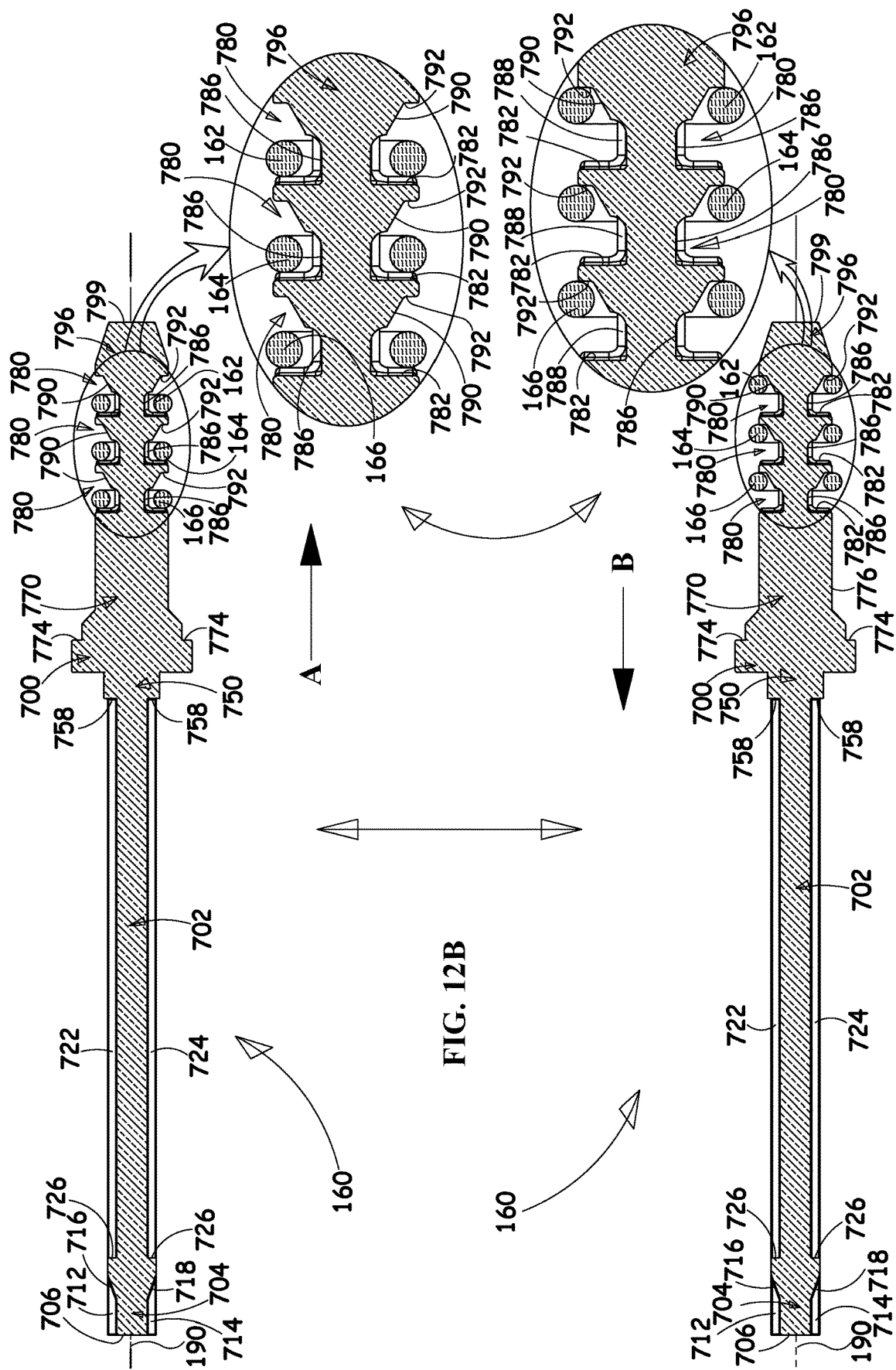

Reference is now made to FIGS. 12A and 12B, which are respectively a simplified plan view illustration and a simplified sectional illustration taken along lines B-B in FIG. 12A of a transition between respective relatively weak and relatively strong damping operative orientations of the elongate damping driver element 160 of FIGS. 10A-10E, having three friction elements mounted thereon.

As seen in FIGS. 12A and 12B, it is a particular feature of an embodiment of the present invention that when the elongate damping driver element 160 is in rearward motion, relative to main housing portion 102 as indicated by an arrow A, friction elements 162, 164 and 166 are each located in a respective axial movement direction dependent damping control friction element seat 780 and are forced forwardly by frictional engagement with end cover 105 (FIG. 1B) into engagement with rearward facing planar surfaces 782 and surrounds generally circular cylindrical axial portions 786 and are generally at rest, thus providing a relatively low level of damping of axial motion of the elongate damping driver element 160 in rearward motion.

When the elongate damping driver element 160 is in forward motion, relative to main housing portion 102 as indicated by an arrow B, friction elements 162, 164 and 166 are located each in a respective axial movement direction dependent damping control friction element seat 780 and are forced rearwardly by frictional engagement with end cover 105 (FIG. 1B) into engagement with forward facing planar surfaces 792 and surrounds generally tapered surfaces 790. Engagement of friction elements 162, 164 and 166 with generally tapered surfaces 790 forces friction elements 162, 164 and 166 radially outwardly and thus increases its frictional engagement with end cover 105, thus providing a relatively high level of damping of axial motion of the elongate damping driver element 160 in forward motion.

It is an additional particular feature of an embodiment of the present invention that under rearward motion of the elongate damping drive element 160, air which would otherwise be trapped between friction elements 162, 164, 166 and the end cover 105 is released via slots and 784 and 788. Were this air not to be released, it would resist required rearward motion of the elongate damping drive element 160.

It is an a further particular feature of an embodiment of the present invention that under forward motion of the elongate damping drive element 160, a partial vacuum is created between friction elements 162, 164, 166 and the end cover 105, which enhances damping of forward axial motion of the elongate damping drive element 160 relative to the main housing portion 102.

Figure 13A:
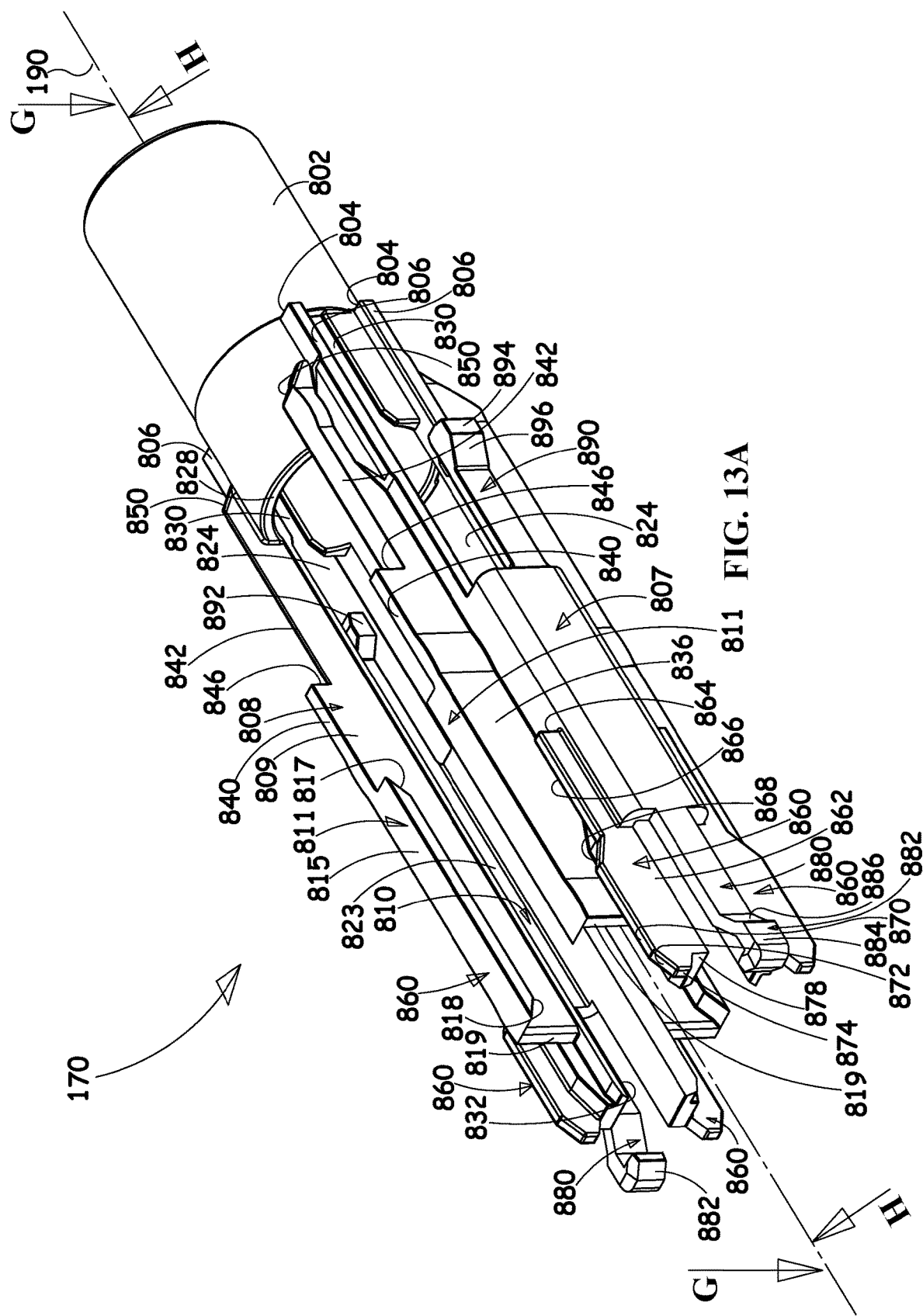
Figure 13B:
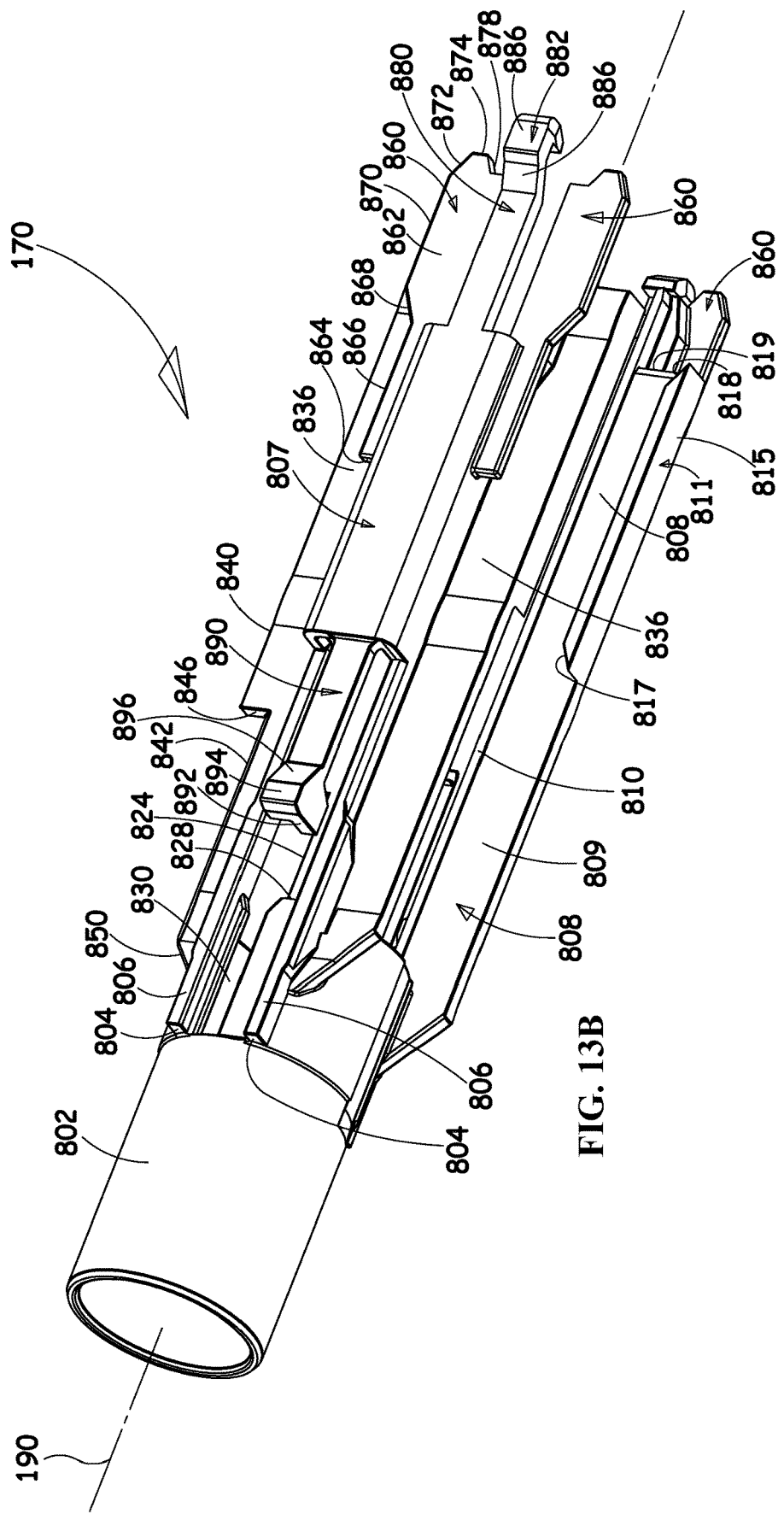
Figure 13D:
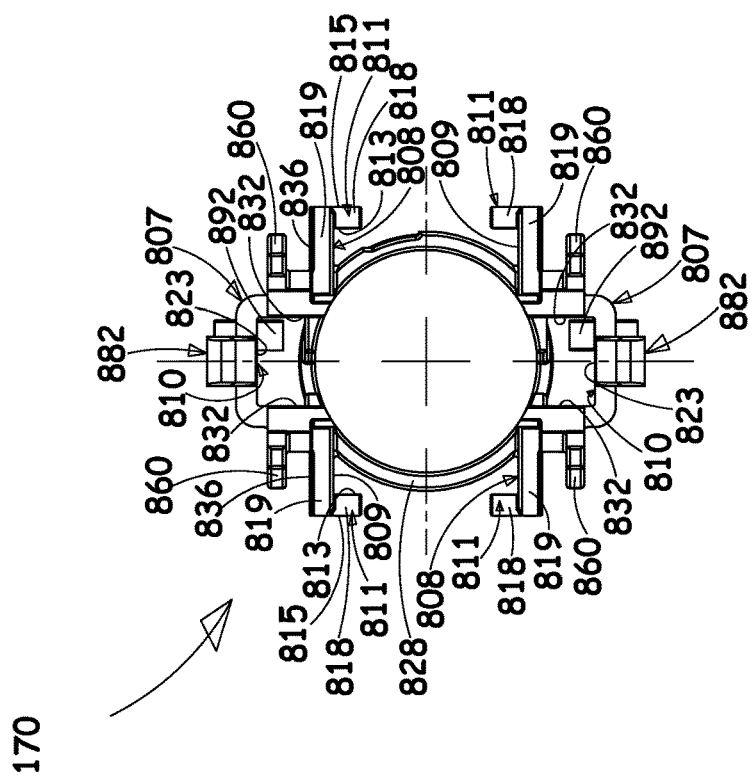
Figure 13C:
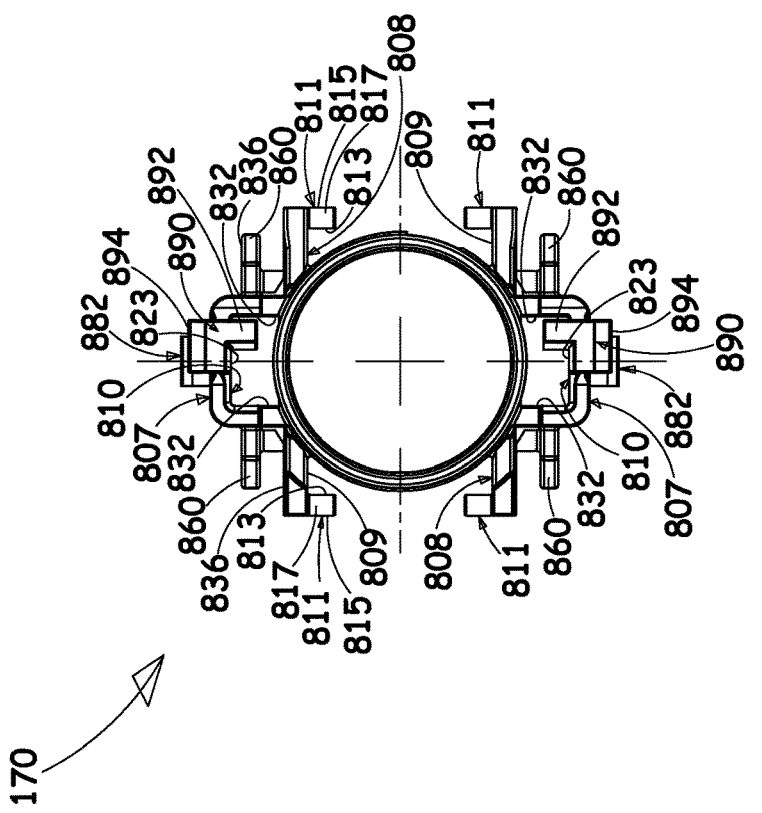
Figure 13G:
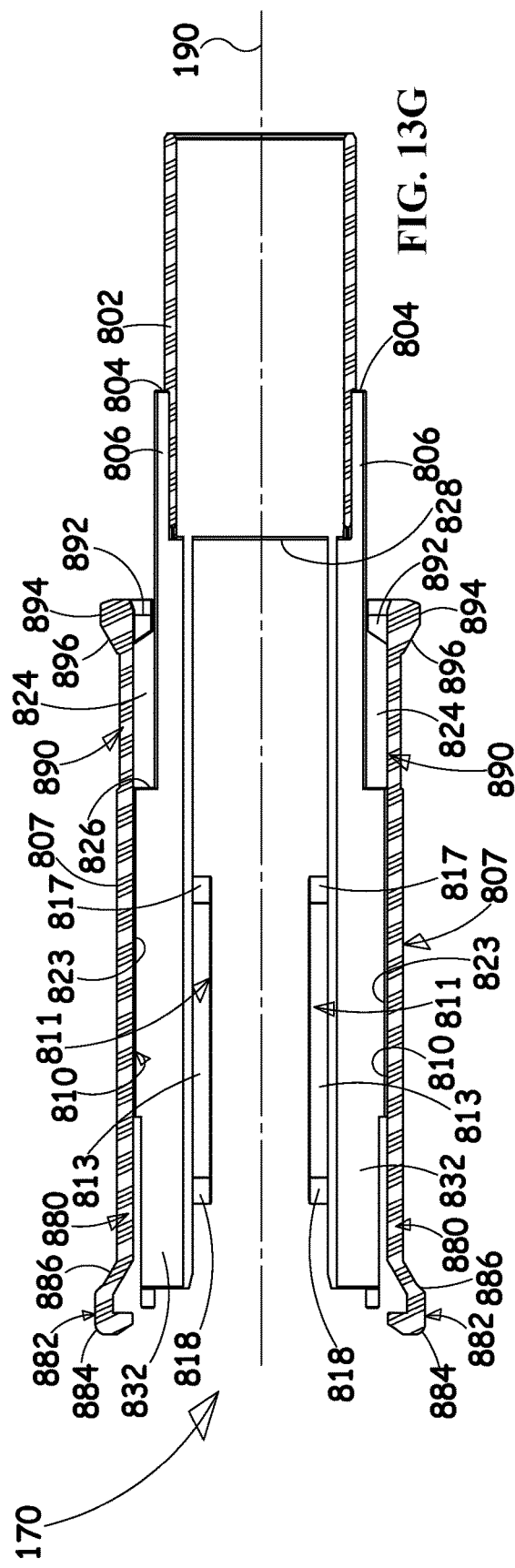
Figure 13H:
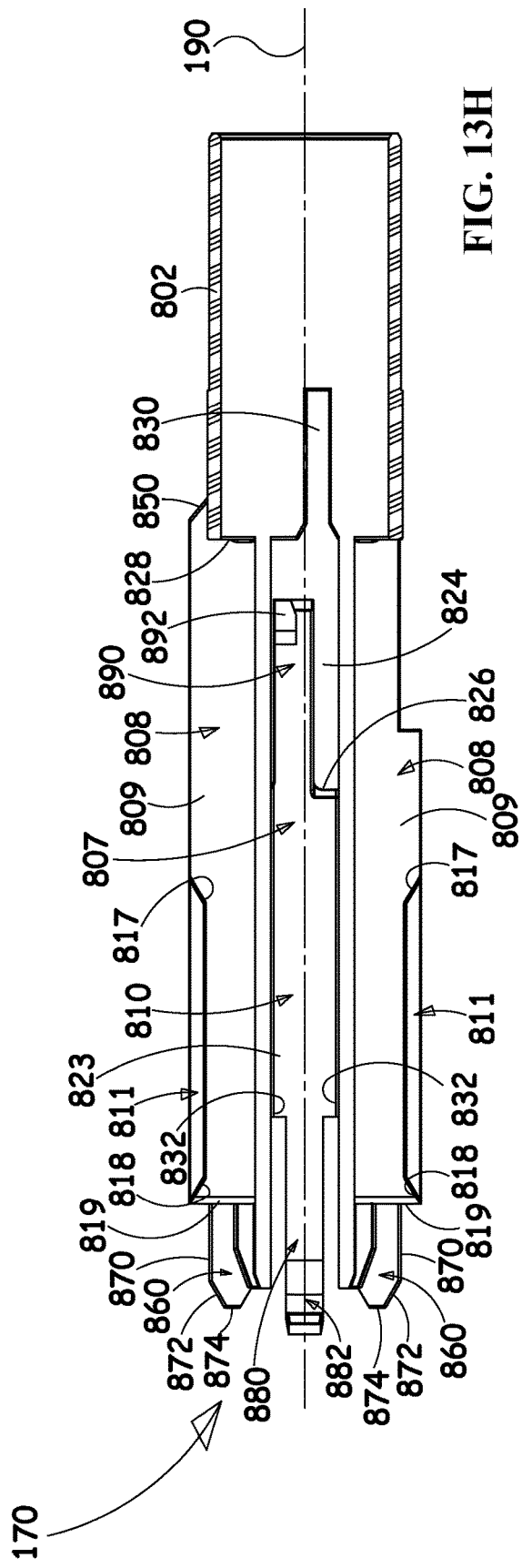

Reference is now made to FIGS. 13A, 13B, 13C, 13D, 13E, 13F, 13G and 13H, which are respectively a simplified perspective view of a forward-facing portion, a simplified perspective view of a rearward-facing portion, a simplified plan view of the rearward-facing portion, a simplified plan view of the forward-facing portion, a simplified top/bottom plan view, a simplified side plan view, a simplified sectional view taken along lines G-G in FIG. 13A and a simplified sectional view taken along lines H-H in FIG. 13A of multifunctional engagement element 170, forming part of the reusable automatic injection assembly of FIGS. 1A & 1B.

As seen in FIGS. 13A-13H, multifunctional engagement element 170 preferably is an integrally formed element, preferably injection molded of plastic, which is arranged along longitudinal axis 190, and includes a generally rearward circular cylindrical portion 802, the interior of which accommodates spring 180 (FIG. 1B) and the exterior of which defines a spring seat for spring 194 (FIG. 1B).

The spring seat is also defined by end surfaces 804 of a plurality of mutually parallel axial protrusions 806, which extend forwardly along a portion of circular cylindrical portion 802 and forwardly thereof, generally parallel to longitudinal axis 190. The plurality of axial protrusions 806 preferably includes two pairs of axial protrusions 806, each pair being associated with an axial arm 807, which extends forwardly partially along a portion of circular cylindrical portion 802 and mainly forwardly thereof. Axial arms are preferably confirmed to define generally mirror images of each other.

Each axial arm 807 defines an axial wall 808 having a generally planar mutually inwardly facing surface 809 having a central axial recess 810. Each surface 809 is bounded along part of its length by an inwardly facing edge wall 811, each having respective inner axial wall surface 813 and respective outer axial wall surface 815 and rearwardly facing tapered surface 817. Axial walls 811 define forwardly facing tapered surfaces 818. Axial walls 808 further define a generally planar forward facing surfaces 819.

Each axial recess 810 is defined by an axial wall 823 along part of its length and is formed with a cut out 824 which extends between a rearward edge 826 of axial wall 823 and a forward edge 828 of cylindrical portion 802. A further cut out 830, which is narrower than cut out 824, is formed in a forward part of cylindrical portion 802 and extends rearwardly from edge 828 to an axial location coincident with end surfaces 804 of protrusions 806.

A pair of axial side walls 832 extend generally perpendicularly to axial wall 823 and join axial wall 823 to axial wall 811.

Axial wall 808 is also preferably formed with outwardly facing surface 836. Axial wall 808 defines an axial edge surface 840, which extends rearwardly of axial wall surface 815 and terminates in a planar edge surface 842, defining a shoulder 846 therebetween. Rearwardly of planar edge surface 842 is a tapered edge surface 850.

At a forward-facing end thereof, axial arm 807 preferably defines a pair of mutually spaced ribs 860, which are spaced from respective outwardly facing surfaces 836. Ribs 860 each define an outer facing surface 862 bounded by a rearwardly facing edge surface 864, a rearward axial edge surface 866, a tapered edge surface 868, a forwardmost axial edge surface 870, a forward tapered outer edge surface 872, a forward facing surface 874, a forward tapered inner edge surface 876, a forward facing edge surface 878 and one of axial side walls 832.

Disposed intermediate ribs 860 is a forward facing resilient finger 880 having an inwardly facing hook portion 882 and outwardly facing protruding surfaces 884.

Disposed intermediate axial protrusions 806 is a rearward facing resilient finger 890 having an inwardly facing protrusion 892 and outwardly facing protruding surfaces 894 and 896.

Reference is now made to FIG. 14, which is a simplified plan view illustration of a transition between disengaged and engaged operative orientations of a first portion of the multifunctional engagement element of FIGS. 13A-13H.

As seen in FIG. 14, resilient fingers 880 are normally in a spread-apart operative orientation as shown at I, prior to insertion of the medicament module 200/300 into the injection assembly 100. Upon insertion of the medicament module 200/300 into the injection assembly 100, resilient fingers 880 are forced into a needle-shield engagement operative orientation, as shown at II, as will be described hereinbelow in detail.

Figure 15A:
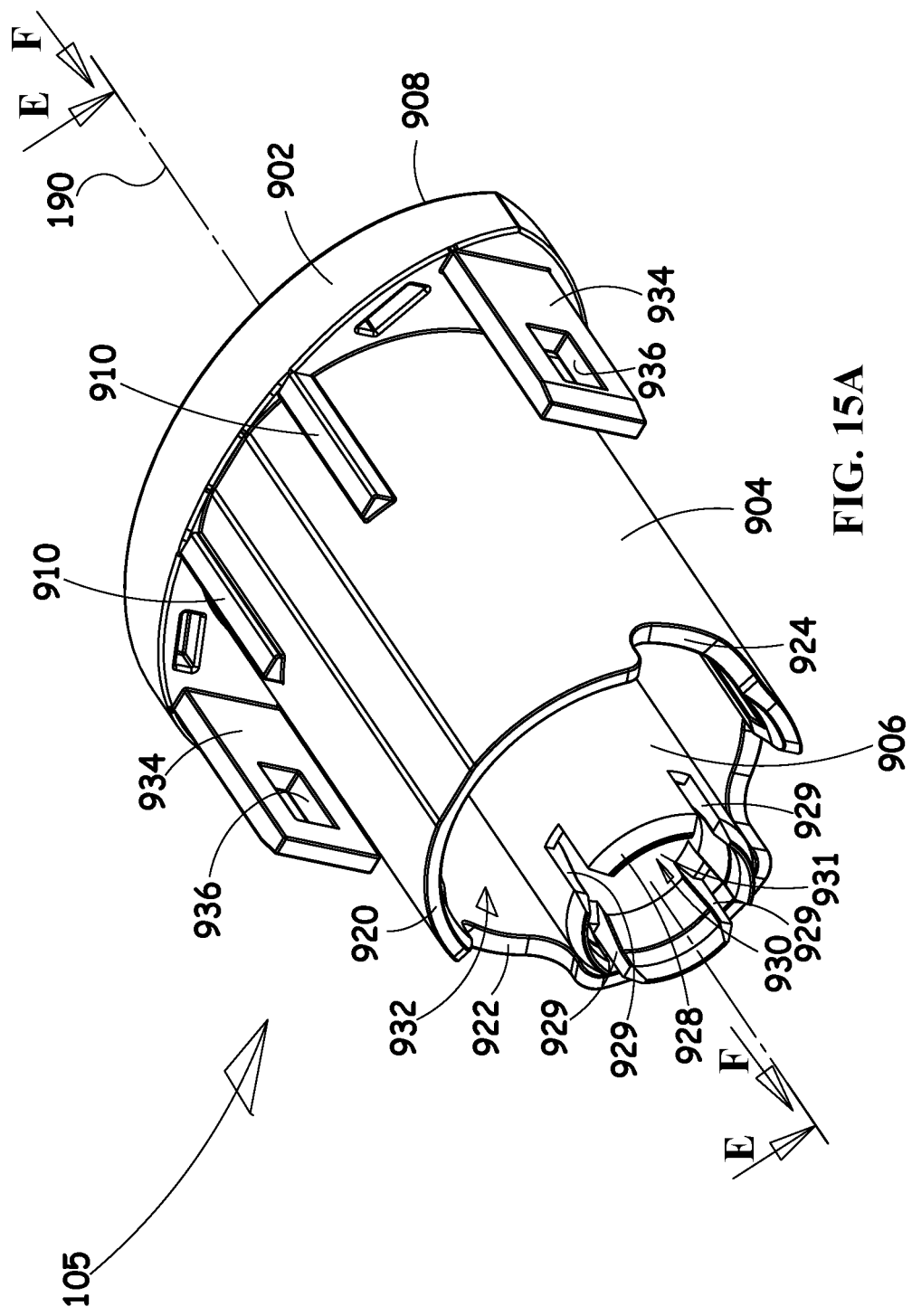
Figure 15B:
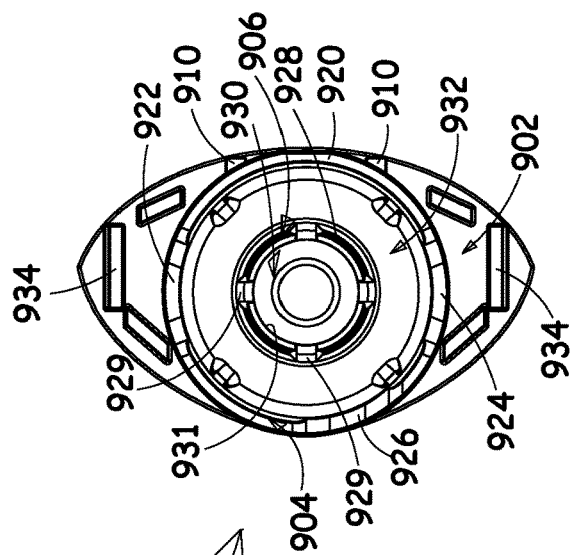
Figure 15C:
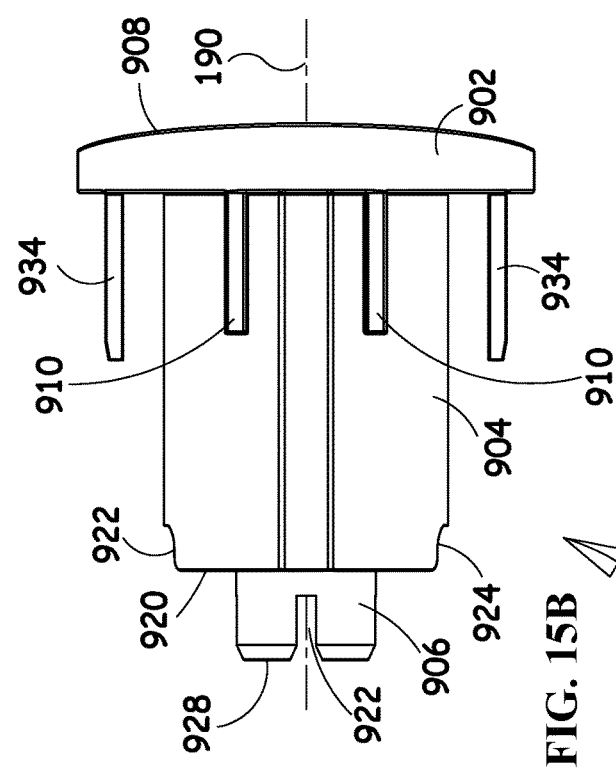
Figure 15D:
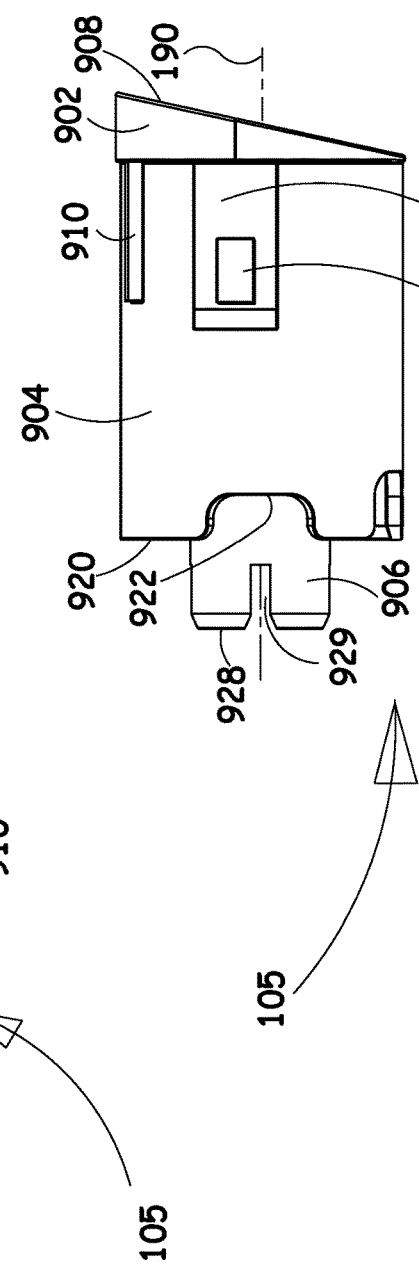

Reference is now made to FIGS. 15A, 15B, 15C, 15D, 15E and 15F, which are simplified respective perspective, first and second side view, planar forward facing end view and first and second sectional illustrations taken along lines E-E and F-F in FIG. 15A of an end cover 105, forming part of the reusable automatic injection assembly of FIGS. 1A & 1B.

As seen in FIGS. 15A-15F, the end cover 105 preferably comprises an integrally formed element, preferably injection molded of plastic, which is arranged along longitudinal axis 190 and includes a generally planar base 902 having first and second mutually spaced, coaxial generally circular cylindrical portions 904 and 906 extending forwardly therefrom, the base has a rearward facing surface 908. It is seen that cylindrical portion 904 is preferably formed with a pair of mutually spaced outwardly extending guide ribs 910.

Generally circular cylindrical portion 904 is preferably formed with a multiply notched forward facing edge 920 defining first and second oppositely positioned notches 922 and 924 and an additional notch 926.

Generally circular cylindrical portion 906 is preferably formed with a multiply notched forward facing edge 928 preferably defining four narrow notches 929, mutually separated by 90 degrees. Generally circular cylindrical portion 906 defines an inner cylindrical volume 930 having an inner facing surface 931. Generally circular cylindrical portions 904 and 906 defined therebetween an annular volume 932.

A pair of generally flat rectangular protrusions 934 extend forwardly of base 902 on mutually opposite sides of generally circular cylindrical portion 904 and each include a generally rectangular aperture 936.

Annular volume 932 serves as a rear spring seat for springs 180 and 194 (FIG. 1B) and inner cylindrical surface 931 preferably provides a friction engagement surface for engagement by one or more friction elements 162, 164 and 166 (FIG. 1B).

Figure 16D:
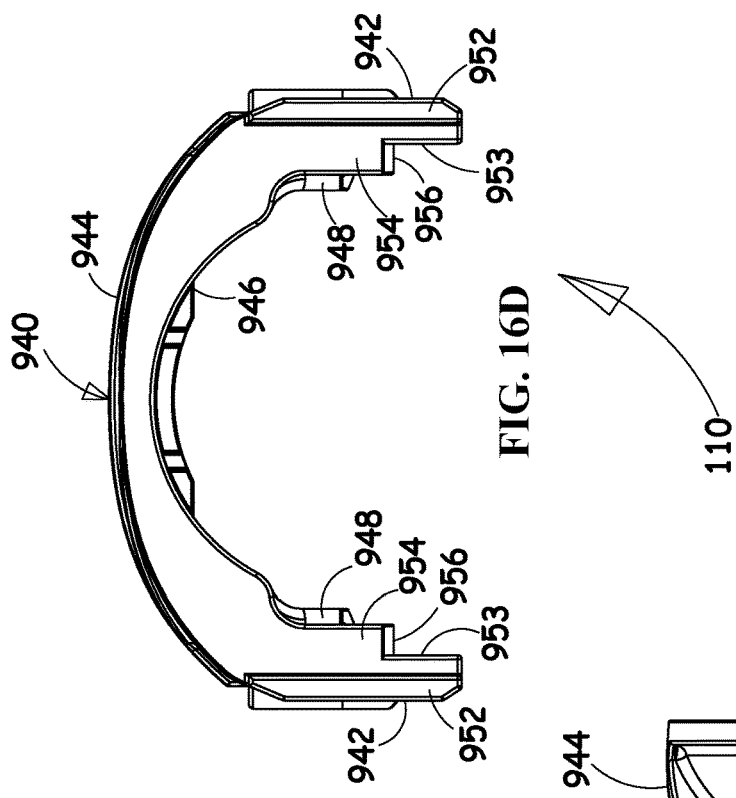
Figure 16E:
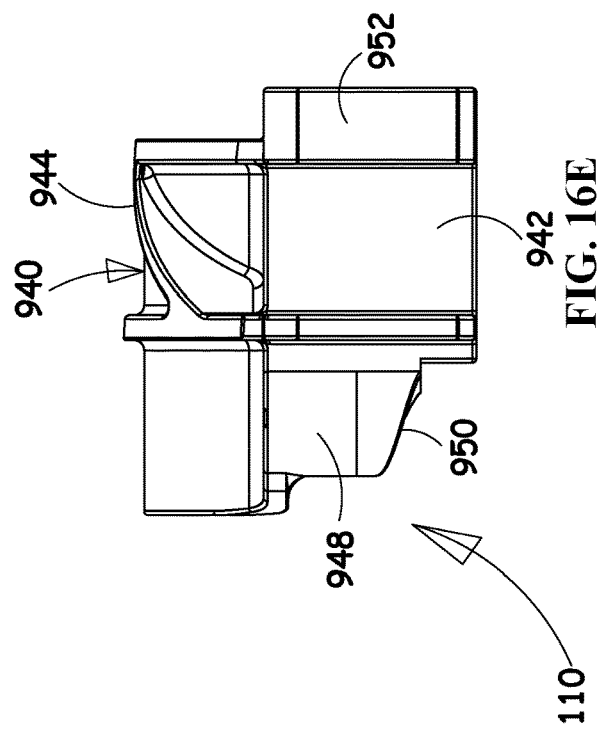
Figure 16C:
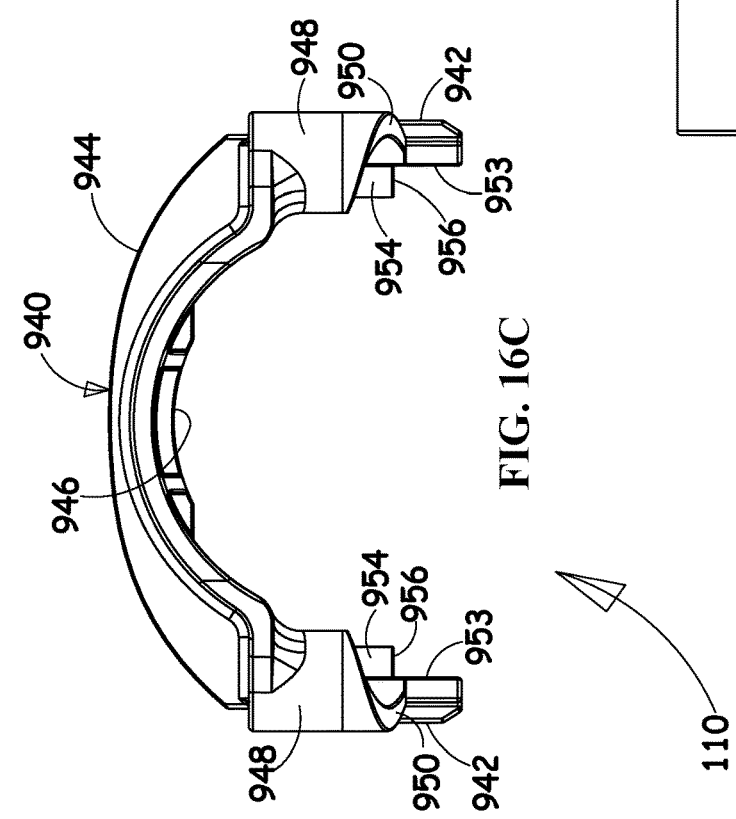

Reference is now made to FIGS. 16A, 16B, 16C, 16D, 16E, 16F, 16G and 16H, which are simplified respective top and bottom perspective, first and second end view, side view, top and bottom view and a sectional illustration taken along lines H-H in FIG. 16A of trigger element 110 (FIG. 1B), forming part of the reusable automatic injection assembly of FIGS. 1A & 1B.

As seen in FIGS. 16A-16H, trigger element 110 preferably is an integrally formed element, preferably injection molded of plastic and includes a top portion 940 and a pair of side portions 942. Top portion 940 preferably has a generally convex outer-facing surface 944 and a generally concave inner-facing surface 946.

Rearward of side portions 942 there are provided a pair of aperture pin receiving channels 948, each of which preferably has a helically-curved latch-engaging surface 950. Forward of side portions 942, there are provided a pair of side protrusions 952. Along an inwardly-facing surface 953 of side portions 942, there is provided a pair of generally rectangular protrusions 954 each having a downward-facing edge surface 956 and a tapered rearward facing surface 958. Side portions 942 have a rearward-facing edge 959.

Figures 17A, 17B:
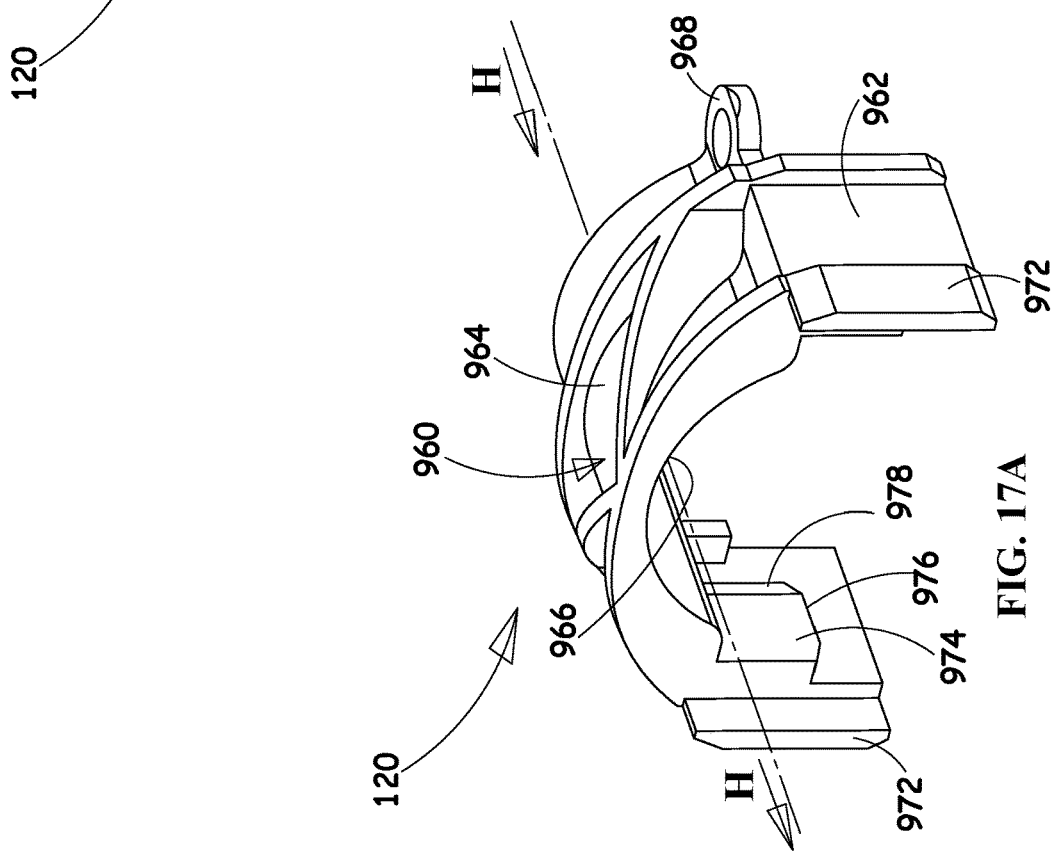
Figure 17D:
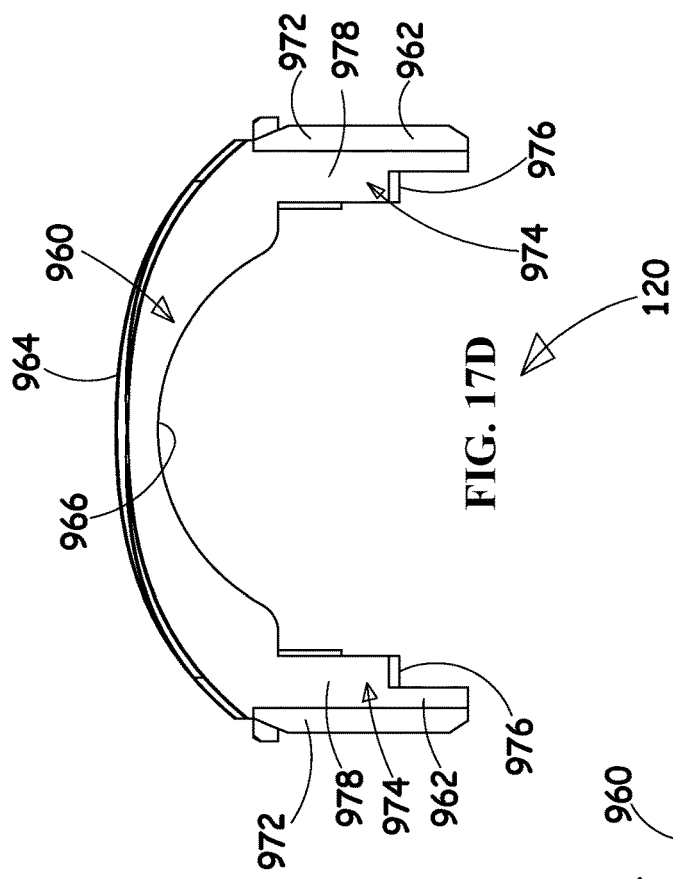
Figure 17E:
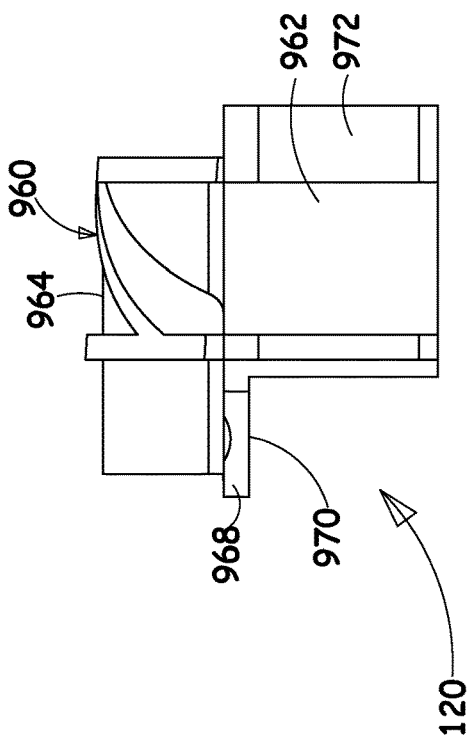
Figure 17C:
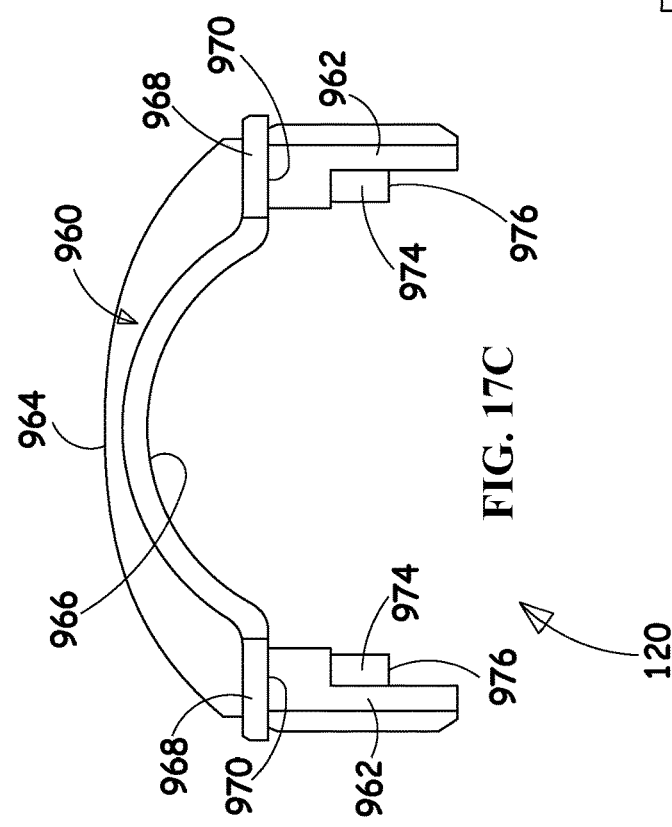

Reference is now made to FIGS. 17A, 17B, 17C, 17D, 17E, 17F, 17G and 17H, which are simplified respective top and bottom perspective, first and second end view, side view, top and bottom view and a sectional illustration taken along lines H-H in FIG. 17A of trigger element 120 (FIG. 1B), forming part of the reusable automatic injection assembly of FIGS. 1A & 1B;

As seen in FIGS. 17A-17H, trigger element 120 preferably is an integrally formed element, preferably injection molded of plastic and includes a top portion 960 and a pair of side portions 962. Top portion 960 preferably has a generally convex outer-facing surface 964 and a generally concave inner-facing surface 966.

Rearward of side portions 942 there are provided a pair of pin receiving channels 968, each of which preferably has a generally flat latch element-engaging surface 970. Forward of side portions 962, there are provided a pair of side protrusions 972. Inward of side portions 962, there are provided a pair of generally rectangular protrusions 974 each having a downward-facing edge surface 976 and a tapered rearward facing surface 978.

Figure 18A:
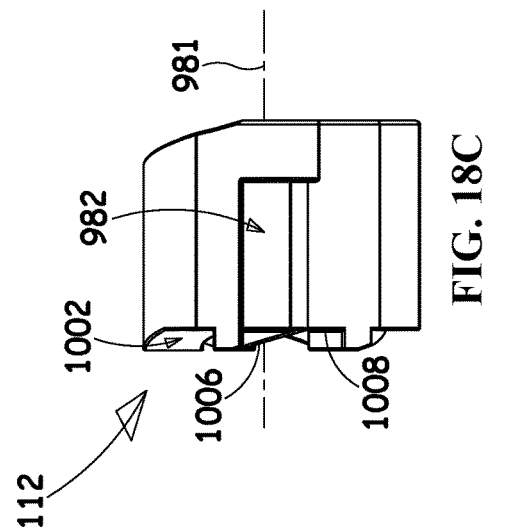
FIGS. 18A, 18B, 18C, 18D, 18E and 18F are simplified respective top and bottom perspective, side view, first and second end view and a sectional illustration taken along lines F-F in FIG. 18A of a latch, forming part of one embodiment of the reusable automatic injection assembly of FIGS. 1A & 1B.

Reference is now made to FIGS. 18A, 18B, 18C, 18D, 18E and 18F, which are simplified respective top and bottom perspective, side view, first and second end view and a sectional illustration taken along lines F-F in FIG. 18A of latch 112 (FIG. 1B, forming part of one embodiment of the reusable automatic injection assembly of FIGS. 1A & 1B.

As seen in FIGS. 18A-18F, latch 112 preferably is an integrally formed element, preferably injection molded of plastic and has an overall generally tubular configuration including a central pin receiving bore 980 extending along a latch rotation axis 981, and first and second radially outwardly extending ribs 982 and 984, which are mutually separated by approximately 90 degrees.

Figure 18B:
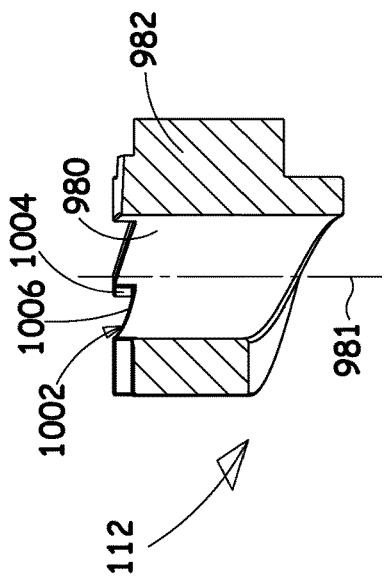
Figure 18C:
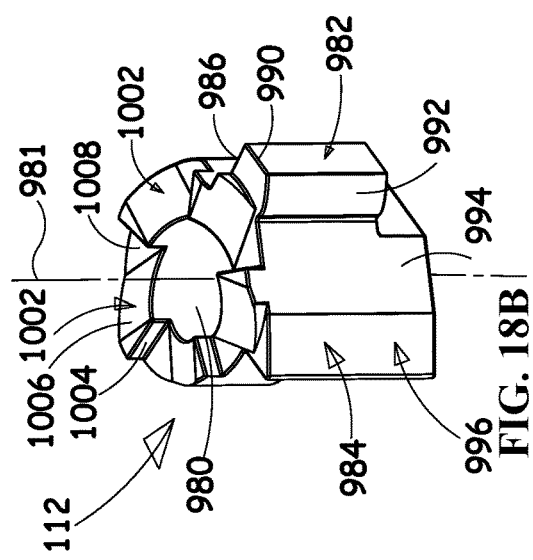
Figure 18D:
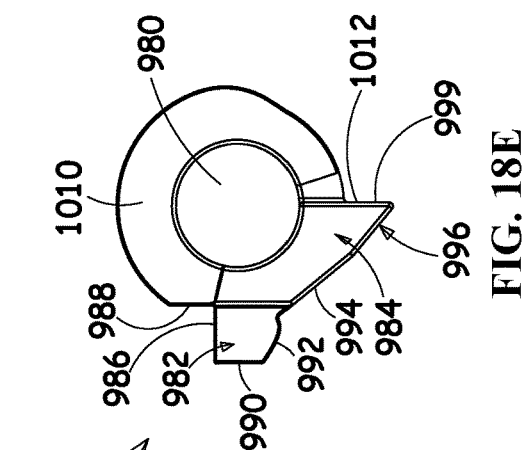
Figure 18E:
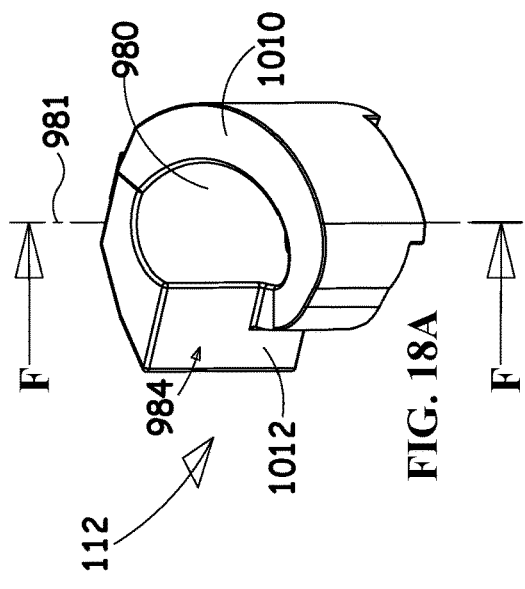
Figure 18F:
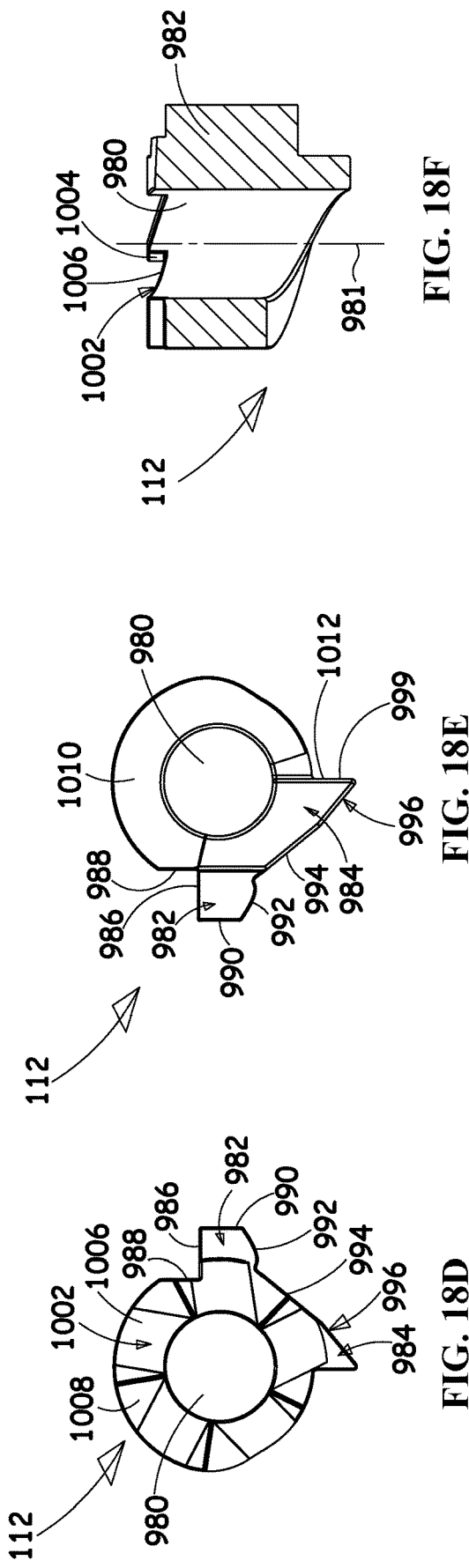

As seen particularly clearly in FIG. 18D, rib 982 has a generally rectangular cross section defining a radially extending wall 986, which extends generally at right angles to a generally flat inner surface 988 and to a generally flat radially outwardly facing protruding surface 990. A curved surface 992 joins surface 990 to a generally flat surface 994, which extends to rib 984 and terminates thereat in a skewed, generally radially directed pointed portion 996.

As seen particularly clearly in FIG. 18B, a bottom surface of latch 112 defines about bore 980 a plurality of teeth 1002 each preferably including a generally axial surface 1004 extending parallel to bore 980, a tapered surface 1006 and a surface 1008, which is generally perpendicular to axis 981.

As seen particularly in FIG. 18A, a top surface of latch 112 preferably defines a helically spiral surface 1010, which terminates at an retaining surface 1012, extending in radially in a plane parallel to axis 981. Helically spiral surface 1010 is preferably configured to slidably mate with helical surface 950 of trigger element 110.

It is appreciated that latches 112 are constructed so as to define mirror images of one another.

Figure 19E:
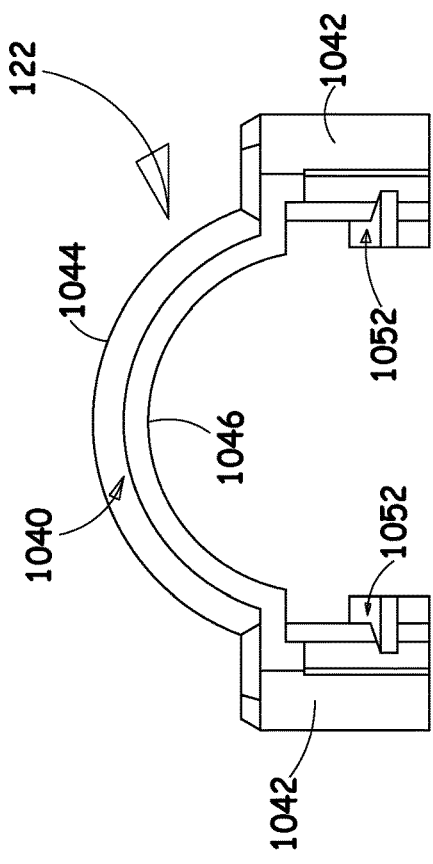
Figure 19D:
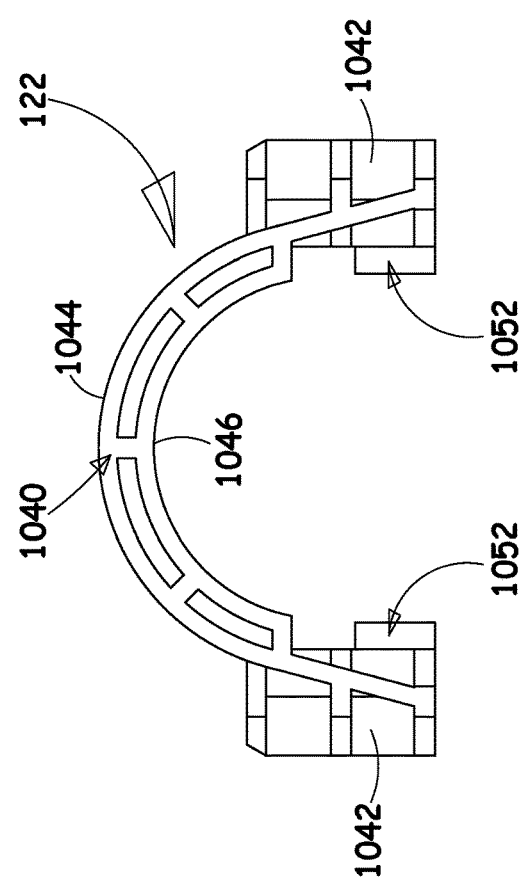
Figure 19F:
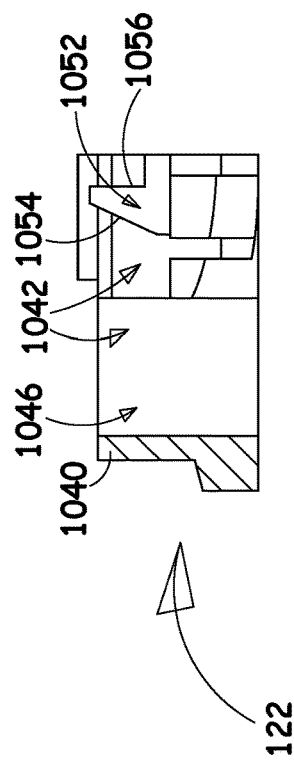

Reference is now made to FIGS. 19A, 19B, 19C, 19D, 19E and 19F, which are simplified respective top and bottom perspective, side view, first and second end view and a sectional illustration taken along lines F-F in FIG. 19A of unitary latch element 122 (FIG. 1B), forming part of another embodiment of the reusable automatic injection assembly of FIGS. 1A & 1B.

As seen in FIGS. 19A-19F, unitary latch element 122 preferably is an integrally formed element, preferably injection molded of plastic and includes a top portion 1040 and a pair of side portions 1042. Top portion 1040 preferably has a generally convex outer-facing surface 1044 and a generally concave inner-facing surface 1046.

Side portions 1042 preferably each define a pin receiving channel 1048. Inwardly of each of side portions 1042, there are provided a pair of side protrusions 1052, each defining a tapered upwardly-facing surface 1054 and a rearward facing surface 1056.

Figure 20A:
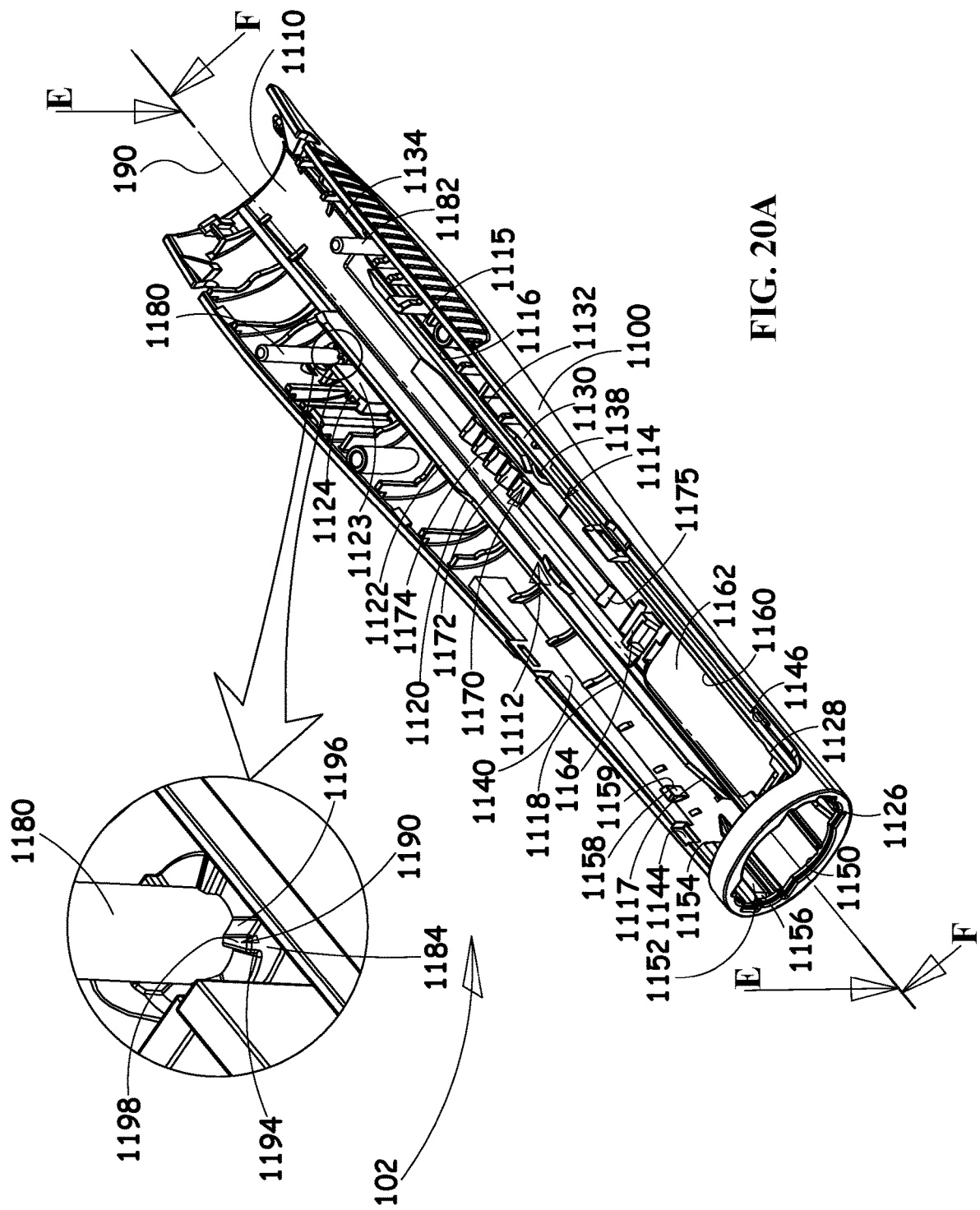
FIGS. 20A, 20B, 20C, 20D, 20E and 20F are simplified respective top perspective, top plan view first and second end view and sectional illustrations taken along lines E-E and F-F in FIG. 20A of a main housing portion forming part of the reusable automatic injection assembly of FIGS. 1A & 1B.
Figure 20B:
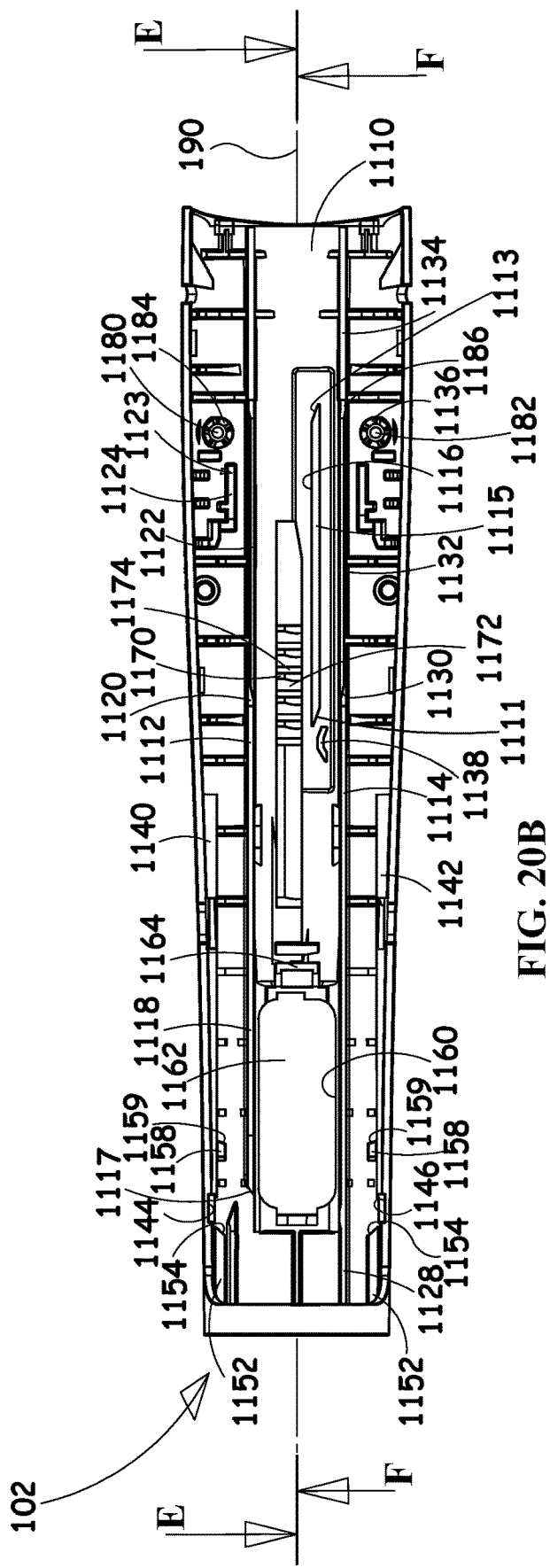
Figure 20D:
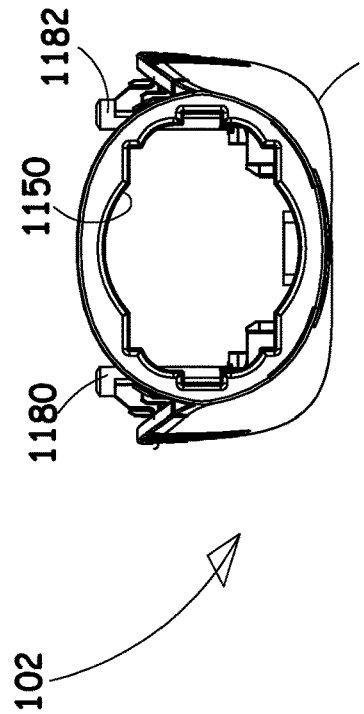
Figure 20C:
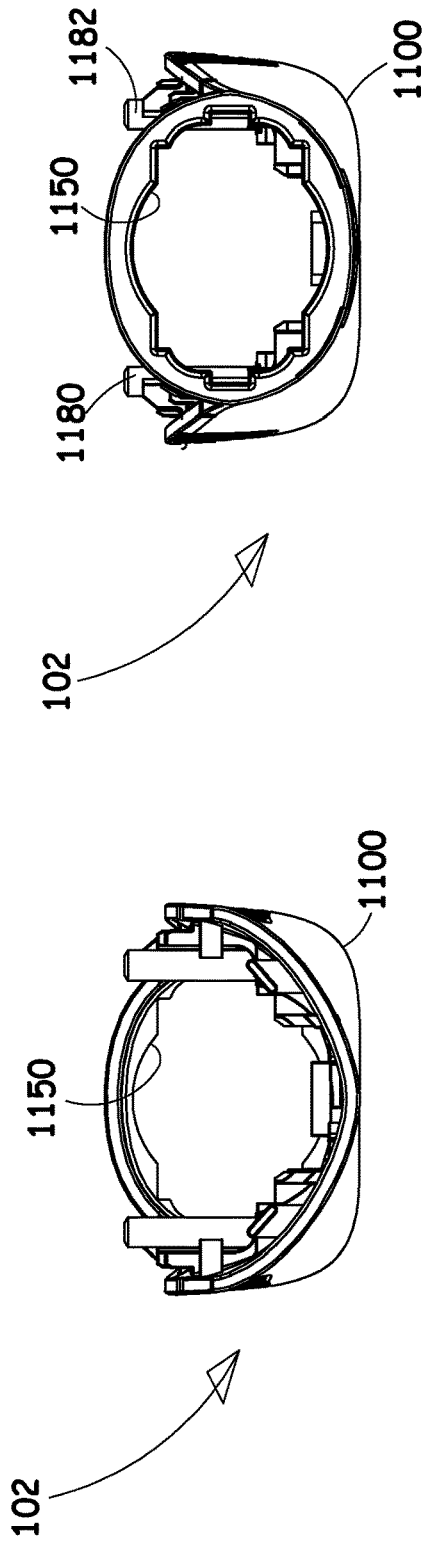
Figure 20E:
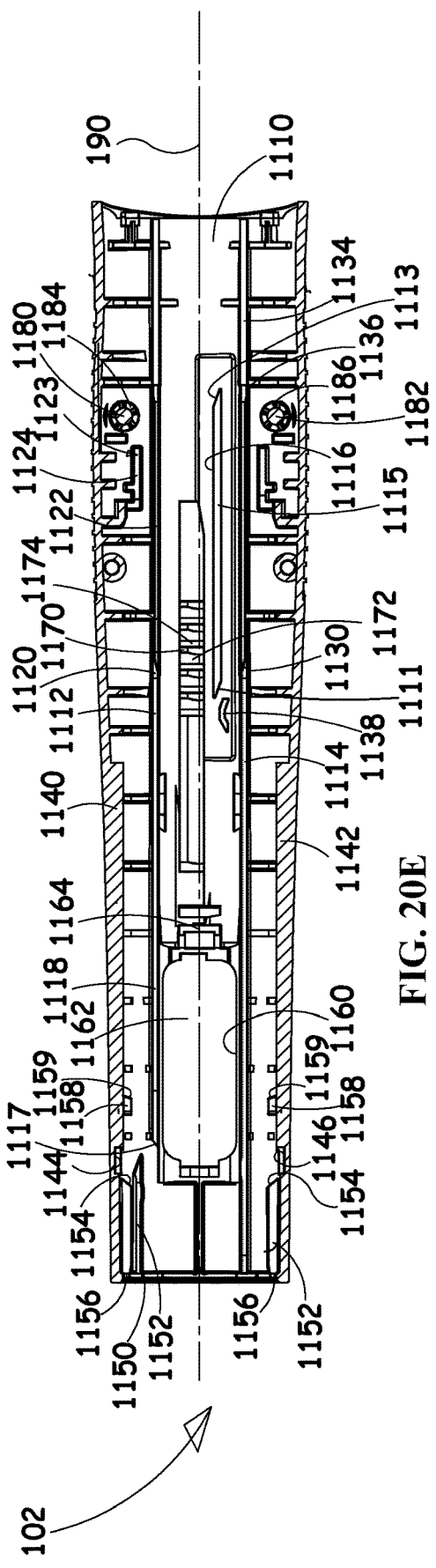
Figure 20F:
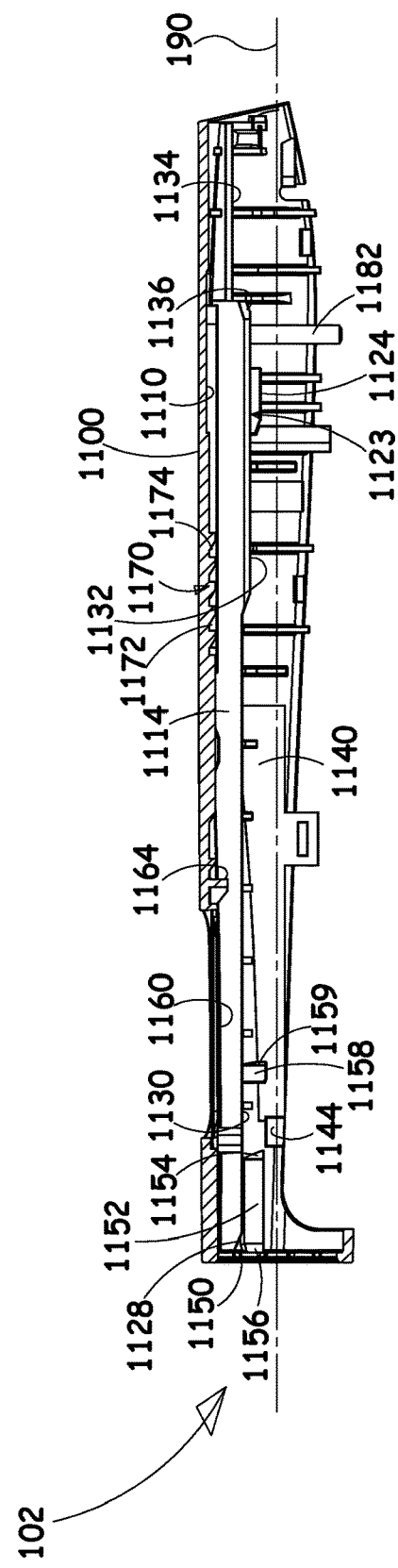

Reference is now made to FIGS. 20A, 20B, 20C, 20D, 20E and 20F are simplified respective top perspective, top plan view first and second end view and sectional illustrations taken along lines E-E and F-F in FIG. 20A of main housing portion 102 (FIG. 1) forming part of the reusable automatic injection assembly of FIGS. 1A & 1B.

As seen in FIGS. 20A-20F, main housing portion 102 preferably is an integrally formed element, preferably injection molded of plastic, extending along longitudinal axis 190 and defines an outer surface 1100, having a generally convex cross section, and an inner surface 1110, having a generally concave cross section and preferably including a pair of axially extending mutually spaced elongate ribs 1112 and 1114. An additional rib 1115 having a forwardly tapered forward end 1111, a rearwardly tapered rearward end 1113 and an inwardly facing surface 1116 is also provided on inner surface 1110.

Elongate rib 1112 includes a tapered forward edge portion 1117, an elongate forward edge portion 1118, a tapered intermediate portion 1120, an elongate rearward edge portion 1122. An inwardly facing protrusion 1123 is positioned alongside rib 1112 and generally outwardly thereof, which is provided with an upper-facing edge 1124.

Elongate rib 1114 includes a tapered forward edge portion 1126, an elongate forward edge portion 1128, a tapered forward intermediate portion 1130, an elongate rearward intermediate portion 1132 and an elongate rearward edge portion 1134, which defines a shoulder 1136 with respect to elongate rearward intermediate portion 1132.

A protrusion 1138 is also provided on inner surface 1110, positioned slightly forwardly with respect to rib 1115.

Main housing portion 102 also includes a pair of mutually facing tapered inwardly facing side surfaces 1140 and 1142 and a pair of mutually facing recesses 1144 and 1146 formed at the ends thereof.

Main housing portion 102 has a forwardly-facing generally ringed surface 1149, which defines a ringed opening 1150 at a forward edge thereof and a pair of protrusions 1152 adjacent a rearward edge thereof. Protrusions 1152 preferably each define a rearwardly-facing tapered surface 1154 and a forwardly facing surface 1156. Rearwardly of protrusions 1152 there are two mutually opposed protrusions 1158 each having a tapered rearwardly facing surface 1159.

Rearwardly of ringed opening 1150 there is defined an aperture 1160, which is preferably fitted with a transparent window 1162, rearwardly of which is formed an inwardly-facing protrusion 1164. Rearwardly of protrusion 1164 and intermediate ribs 1112 and 1114 are an axially disposed array of mutually axially spaced ratchet teeth 1170, each of which has a forward-facing tapered surface 1172 and a rearward-facing retaining surface 1174. The array of mutually axially spaced ratchet teeth 1170 also defines a forwardly facing tapered surface 1175.

Main housing portion 102 defines a pair of mutually spaced inwardly facing pins 1180 and 1182 which are configured for slidable engagement with latches 112, trigger element 110 in a first embodiment and latch element 122 and trigger element 120 in a second embodiment. Pins 1180 and 1182 extend from respective base surfaces 1184 and 1186, which define spring seats for springs 114 (FIG. 1B).

As seen particularly clearly in the enlargement of FIG. 20A, surfaces 1184 and 1186 define about respective pins 1180 and 1182 a plurality of teeth 1190 each preferably including a generally axial surface 1194 extending parallel to pins 1180 or 1182, a tapered surface 1196 and a surface 1198, which is generally perpendicular to pins 1180 or 1182.

Reference is now made to FIGS. 21A, 21B, 21C, 21D, 21E, 21F and 21G, which are simplified respective top and bottom perspective view, bottom plan view, first and second end view and sectional illustrations taken along lines F-F and G-G in FIG. 21A of cover portion 104 (FIG. 1B), forming part of the reusable automatic injection assembly of FIGS. 1A & 1B.

As seen in FIGS. 21A-21G, the cover portion 104 preferably is an integrally formed element, preferably injection molded of plastic, extending along longitudinal axis 190, and includes an outer surface 1300 having a generally convex cross section and an inner surface 1310 having a generally concave cross section and preferably including a pair of axially extending mutually spaced elongate ribs 1312 and 1314 as well as another elongate rib 1315.

Elongate rib 1312 includes a tapered forward edge portion 1316, an elongate forward edge portion 1318, a tapered intermediate portion 1320 and an elongate rearward edge portion 1322.

Elongate rib 1314 includes a tapered forward edge portion 1326, an elongate forward edge portion 1328, a tapered intermediate portion 1330 and an elongate rearward edge portion 1334.

Engagement walls 1335 extend generally outwardly with respect to longitudinal axis 190 from each of rearward edge portion 1322 and rearward edge portion 1334.

Inner surface 1310 also defines a pair of mutually spaced protrusions 1336, which define a seating location for pins 1180 and 1182 of the main housing portion 102. Additional protrusions 1337 are formed slightly inwardly of protrusions 1336 and define a seating location for a lip of user engageable button 108, when it is in a non-actuated operative orientation.

Cover portion 104 also defines an aperture 1360, which is preferably fitted with transparent window 106 (FIG. 1B), rearwardly of which is formed an inwardly-facing protrusion 1364. Rearwardly of protrusion 1364 and intermediate ribs 1312 and 1314 are an axially disposed array of mutually axially spaced ratchet teeth 1370, each of which has a forward-facing tapered surface 1372 and a rearward-facing retaining surface 1374. The array of mutually axially spaced ratchet teeth 1370 also defines a forwardly facing tapered surface 1375, Alongside and forward of aperture 1360, there are provided a pair of recesses 1376 and 1378.

Cover portion 104 defines an aperture 1380 for accommodating button 108 (FIG. 1B).

As seen particularly in FIGS. 21B and G, the cover portion 104 includes a pair of protrusions 1390 which are configured to retain in pivotably snap fit engagement a pivot axle of actuation button 108.

There are two mutually opposed protrusions 1392 rearwardly of tapered forward edge portion 1316, each having a tapered rearwardly facing surface 1394.

Figure 22A:
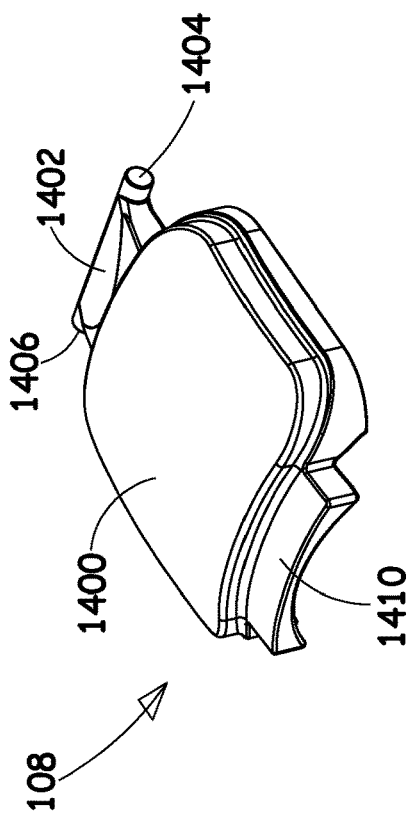
FIGS. 22A, 22B, 22C and 22D are simplified respective perspective, planar top and side views and a sectional view taking along lines D-D in FIG. 22B of a user-engageable actuation button forming part of the reusable automatic injection assembly of FIGS. 1A & 1B.
Figure 22D:
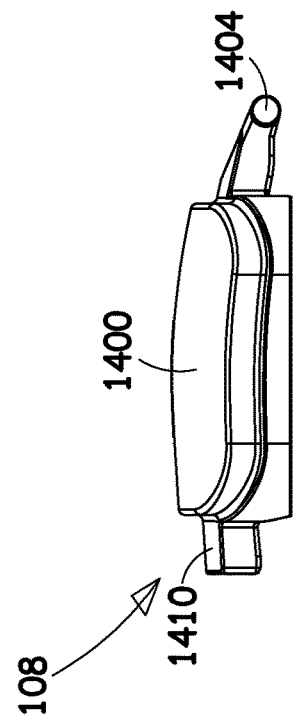
Figure 22B:
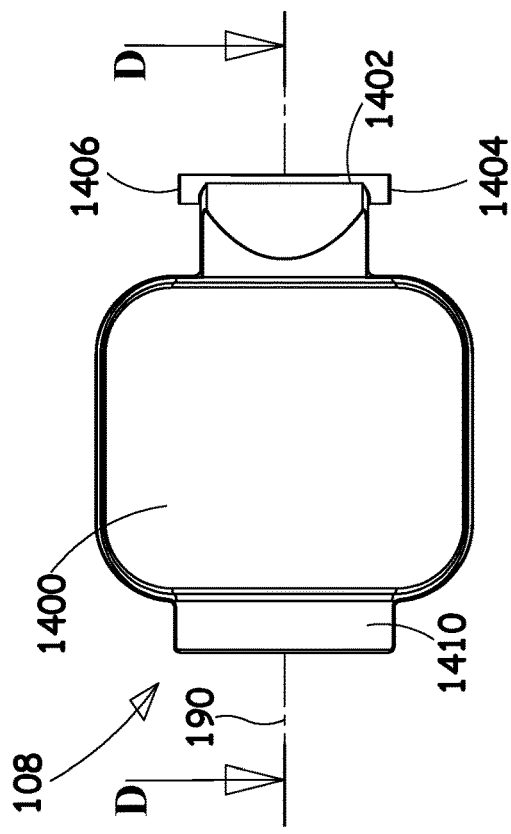
Figure 22C:
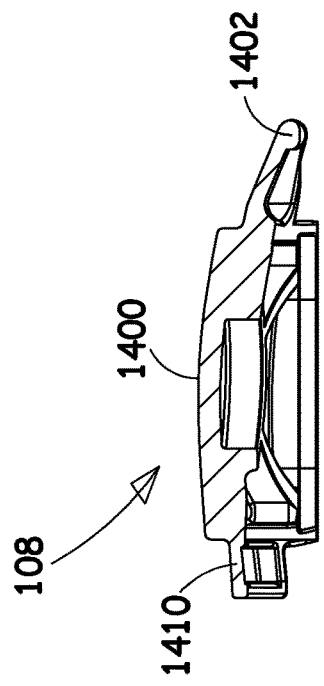

Reference is now made to FIGS. 22A, 22B, 22C and 22D, which are simplified respective perspective, planar top and side views and a sectional view taken along lines D-D in FIG. 22B of user-engageable actuation button 108 (FIG. 1B) forming part of the reusable automatic injection assembly of FIGS. 1A & 1B.

As seen in FIGS. 22A-22D, the actuation button 108 preferably is an integrally formed element, preferably injection molded of plastic and has a generally convex user engagement surface 1400.

Rearwardly of engagement surface 1400, the actuation button 108 is formed to define a pivot axle 1402 having pivot axle ends 1404 and 1406, which are pivotably snap fit retained in protrusions 1390 formed on inner facing surface 1310 of cover portion 104. Forwardly of engagement surface 1400 there is defined a lip 1410, which seats between protrusions 1337 formed on inner facing surface 1310 of cover portion 104.

Reference is now made to FIGS. 23A, 23B, 23C, 23D, 23E, 23F, 23G, 23H, 23I, 23J, 23K and 23L, which are simplified drawings of the reusable automatic injection assembly of FIGS. 1A, 1B and 4A-22D.

Figure 23A:
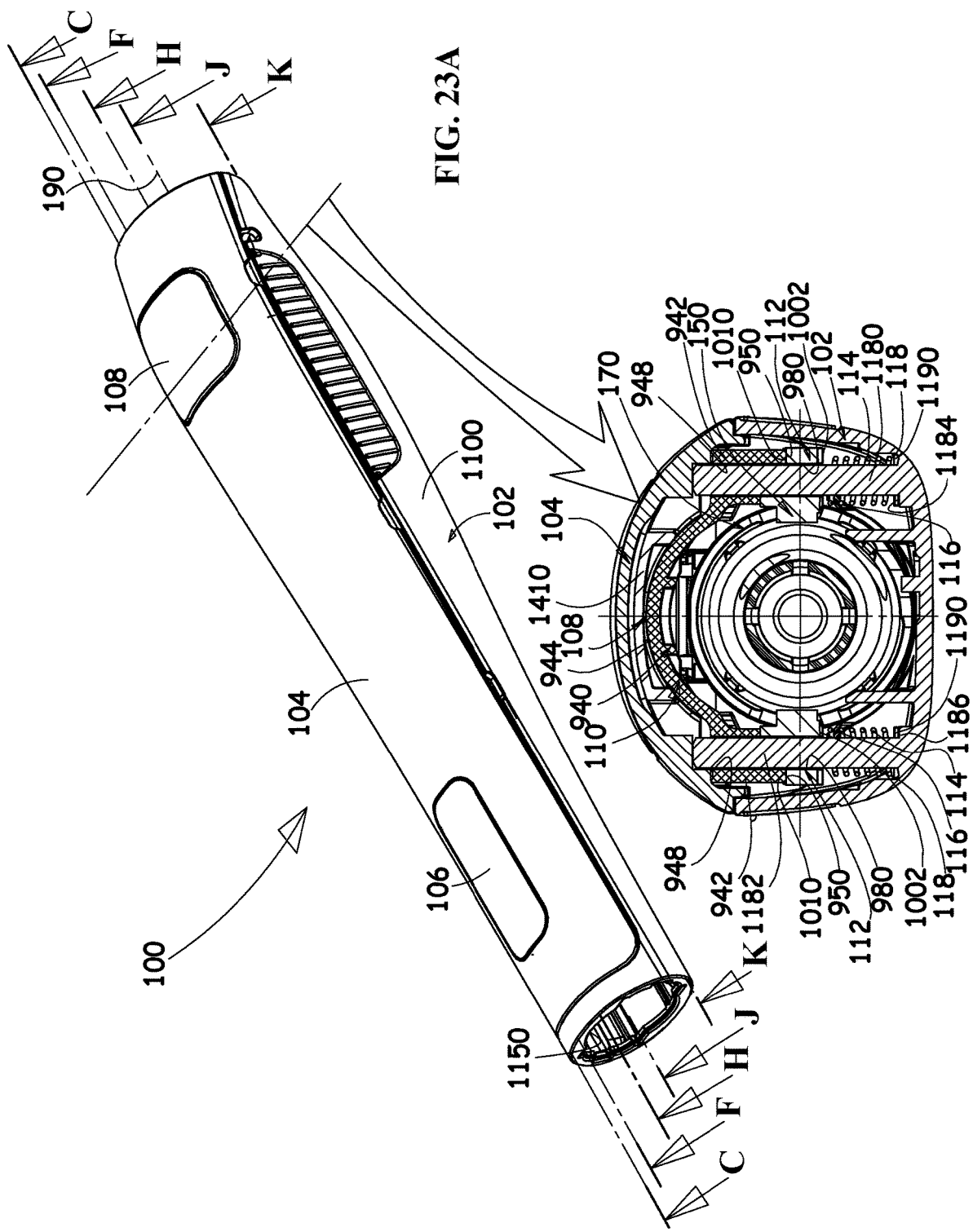

FIG. 23A illustrates the exterior of the reusable automatic injection assembly and is similar to FIG. 1A, except for the direction of view. FIG. 23A also includes a sectional enlargement.

Figure 23B:
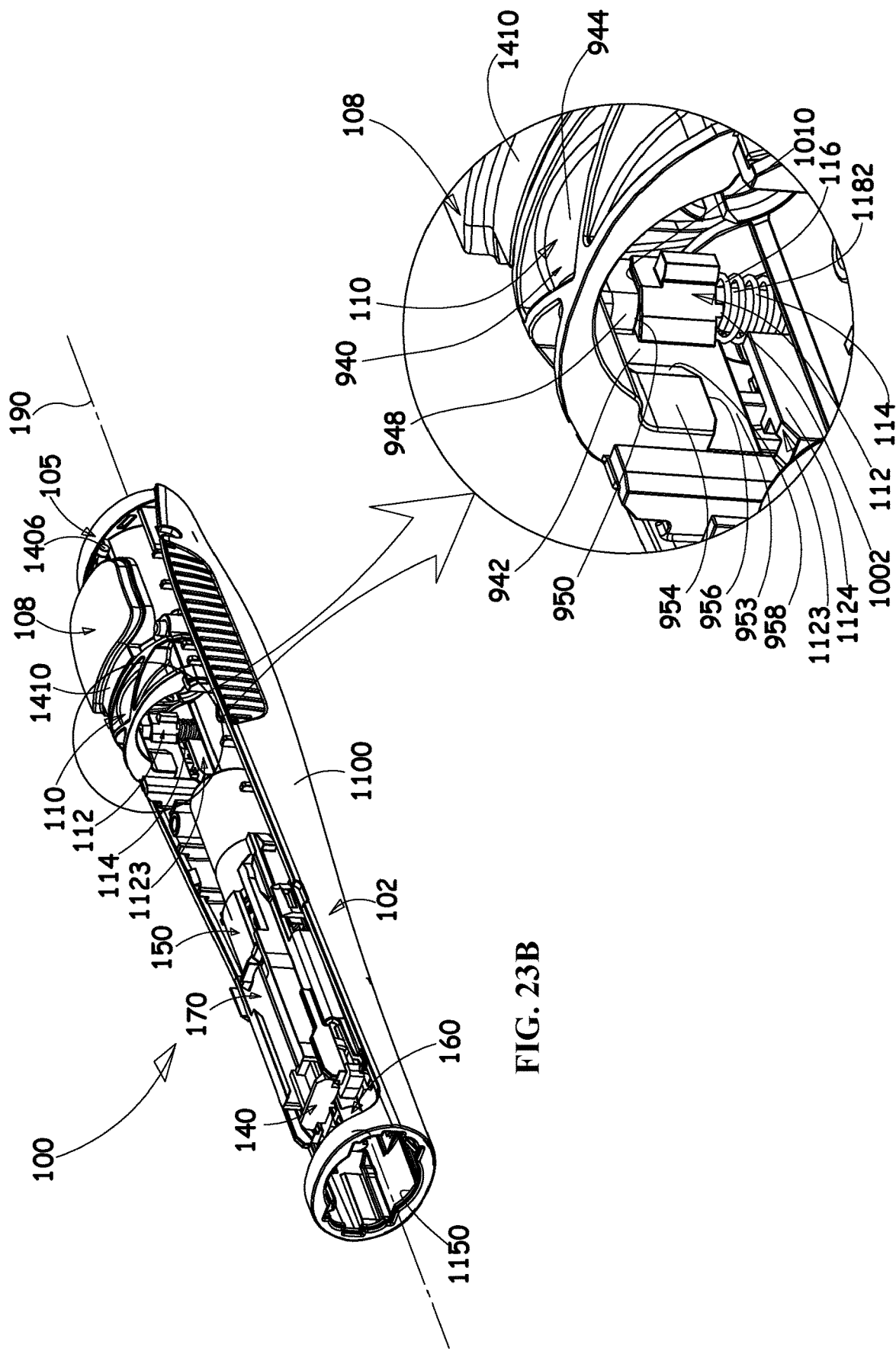
Figure 23C:
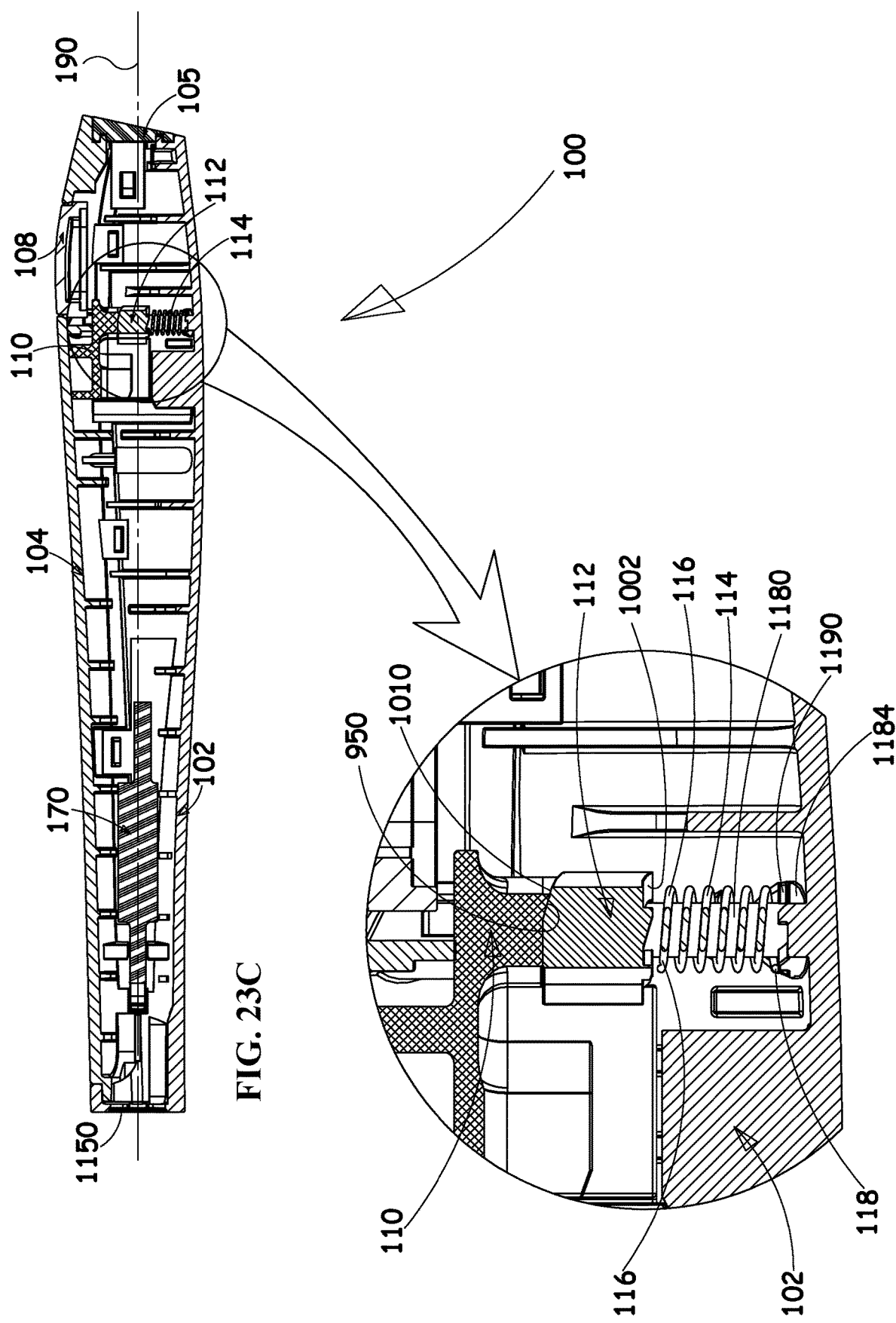
Figure 23D:
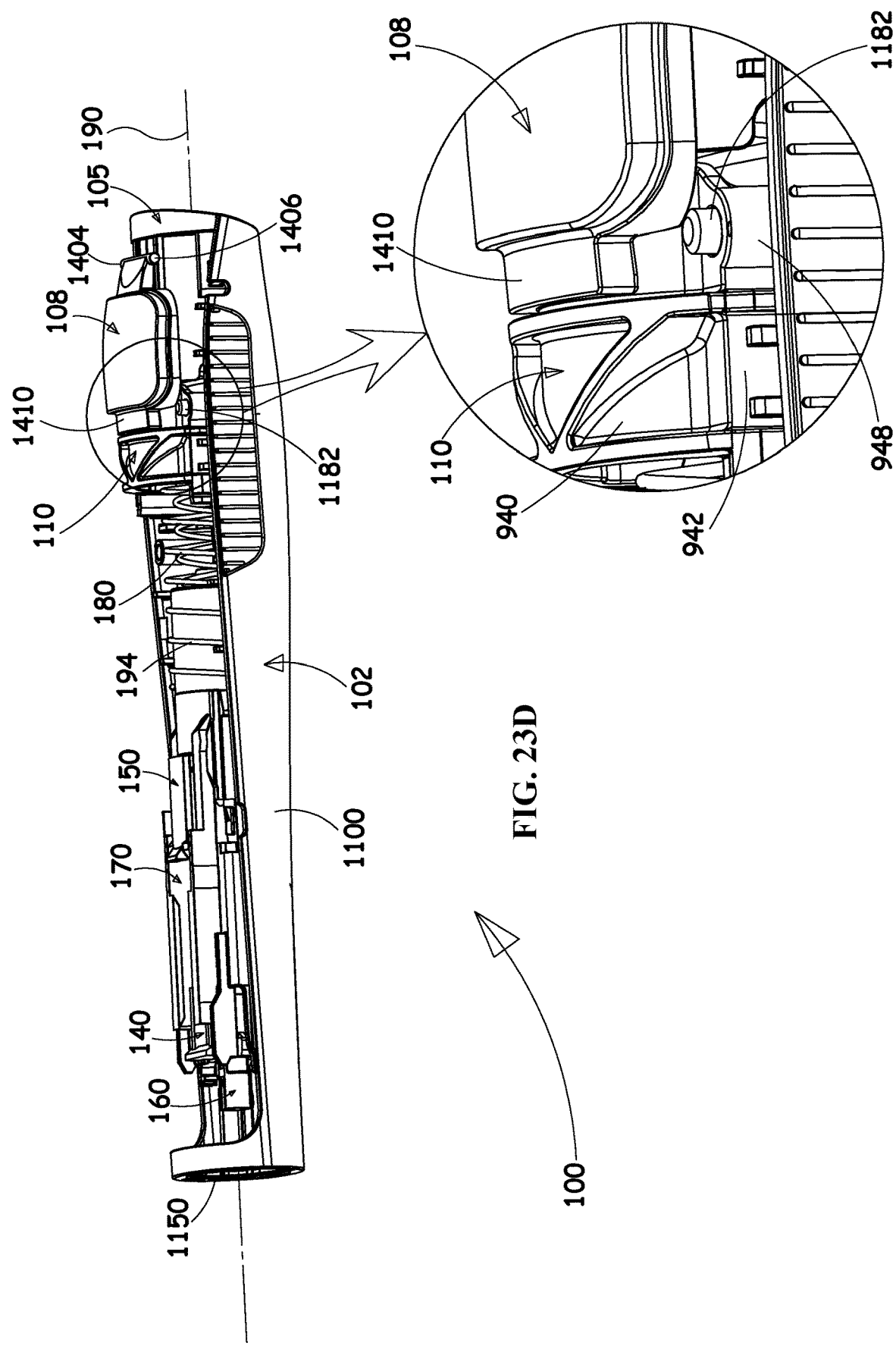
Figure 23E:
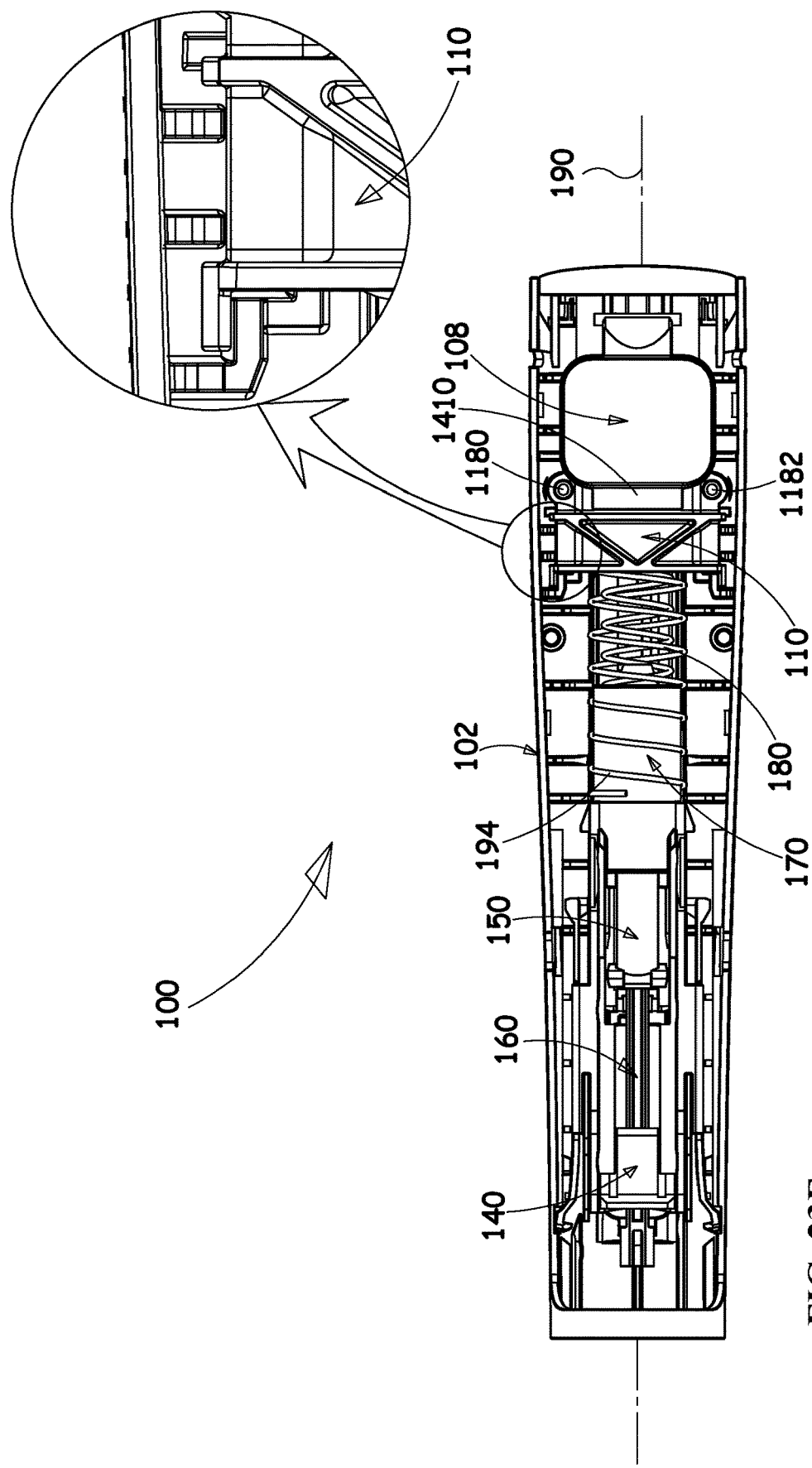
Figure 23F:
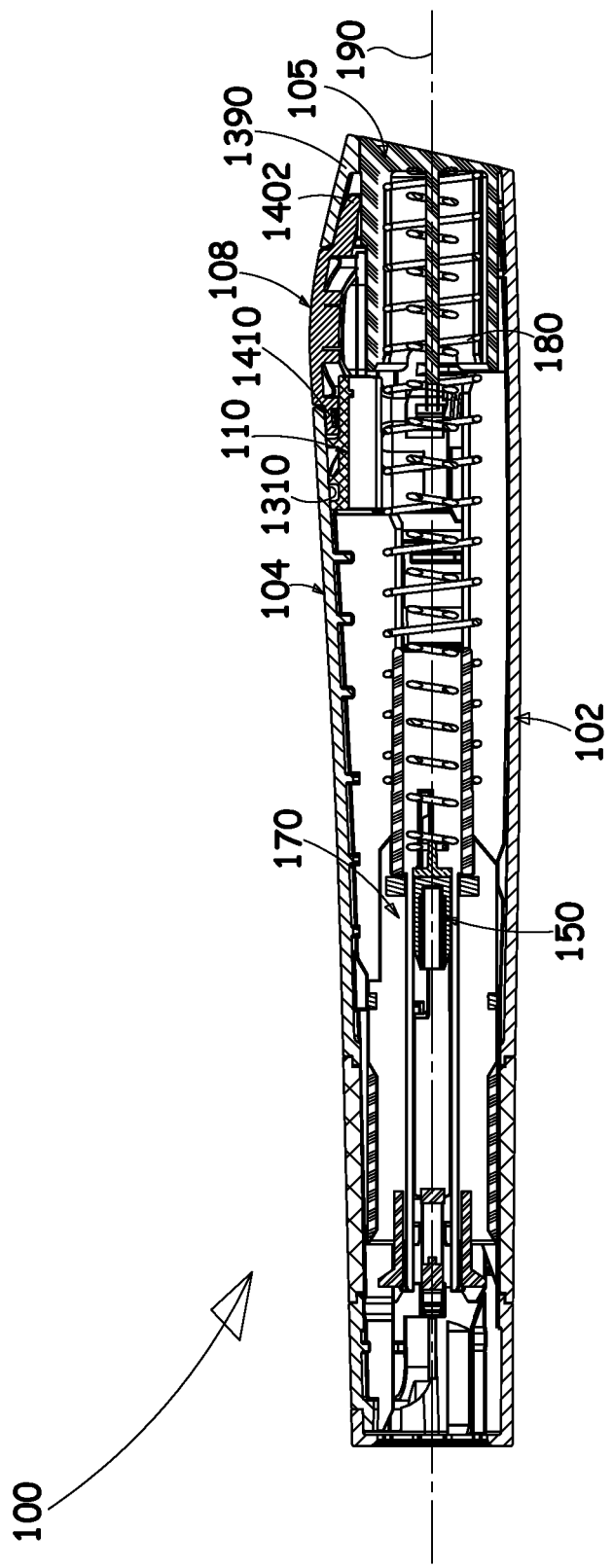

FIGS. 23B-23F particularly illustrate the structural relationship between user engageable actuation button 108, trigger element 110 and latches 112 in a "storage" operative orientation, as the reusable automatic injection assembly would be delivered to the user. FIG. 23B is a simplified partial top view pictorial illustration of the automatic injection assembly wherein the cover portion 104 and springs 180 and 194 are not shown. FIG. 23C is a simplified sectional illustration of the reusable automatic injection assembly, taken along lines C-C in FIG. 23A. FIG. 23D is a simplified partial side view pictorial illustration of the automatic injection assembly wherein the cover portion 104 is not shown. FIG. 23E is a simplified top view illustration wherein the cover portion 104 is not shown. FIG. 23F is a simplified sectional illustration of the reusable automatic injection assembly, taken along lines F-F in FIG. 23A.

As seen particularly in FIGS. 23A-23F, it is seen that trigger element 110 and latches 112 are slidably mounted on pins 1180 and 1182 (FIG. 20A) of main housing portion 102 for selectable vertical positioning therealong, in the sense of the enlargement in FIG. 23A. Latches 112 are rotatably mounted about pins 1180 and 1182.

It is additionally seen that in this storage operative orientation, retaining surface 1012 of each latch 112 engages inwardly-facing surface 953 of trigger element 110.

As seen particularly in the enlargement of FIG. 23A, springs 114, which are seated on respective upward-facing surfaces 1184 and 1186 underlying respective pins 1180 and 1182, urges latches 112 upwardly along pins 1180 and 1182 respectively into engagement with trigger element 110 (FIGS. 16A-16H) and urges the trigger element 110 upwardly into engagement with cover portion 104 and with the lip 1410 of the user engageable actuation button 108, thereby urging lip 1410 against cover portion 104.

More specifically, the teeth 1190 on each of upward-facing surfaces 1184 and 1186 are engaged by a bottom coil end 118 of a spring 114, as seen in an enlargement A in FIG. 23C, and the teeth 1002 on the bottom surface of each latch 112 are engaged by a top coil end 116 of a spring 114, as seen in an enlargement B in FIG. 23. Helically spiral surface 1010 of each latch 112 slidably engages helical surface 950 of trigger element 110.

The pivotable mounting of user engageable button 108 onto cover portion 104 is clearly shown in FIG. 23F, wherein it is seen that pivot axle 1402 having pivot axle ends 1404 and 1406, are pivotably snap fit retained in protrusions 1390 formed on inner facing surface 1310 of cover portion 104.

FIGS. 23G-23L particularly illustrate the driving assembly 130 and more specifically, the structural relationship between control element 140 (FIGS. 4A-5B), multifunctional retaining element 150 (FIGS. 6A-8), elongate damping driver element 160 (FIGS. 9A-12B) and multifunctional engagement element 170 (FIGS. 13A-14B) in a "storage" operative orientation, as the reusable automatic injection assembly would be delivered to the user.

Figure 23G:
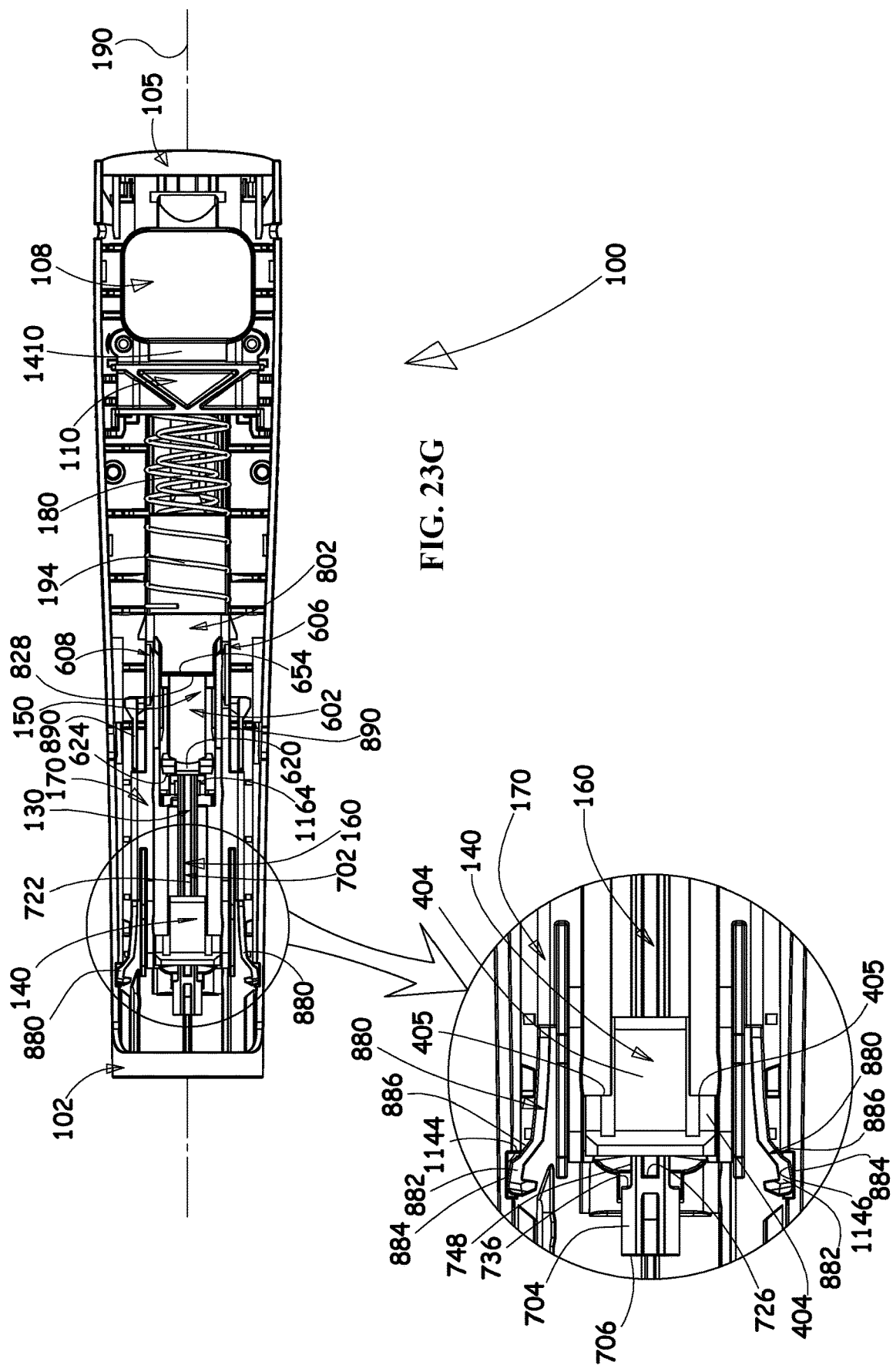
Figure 23L:
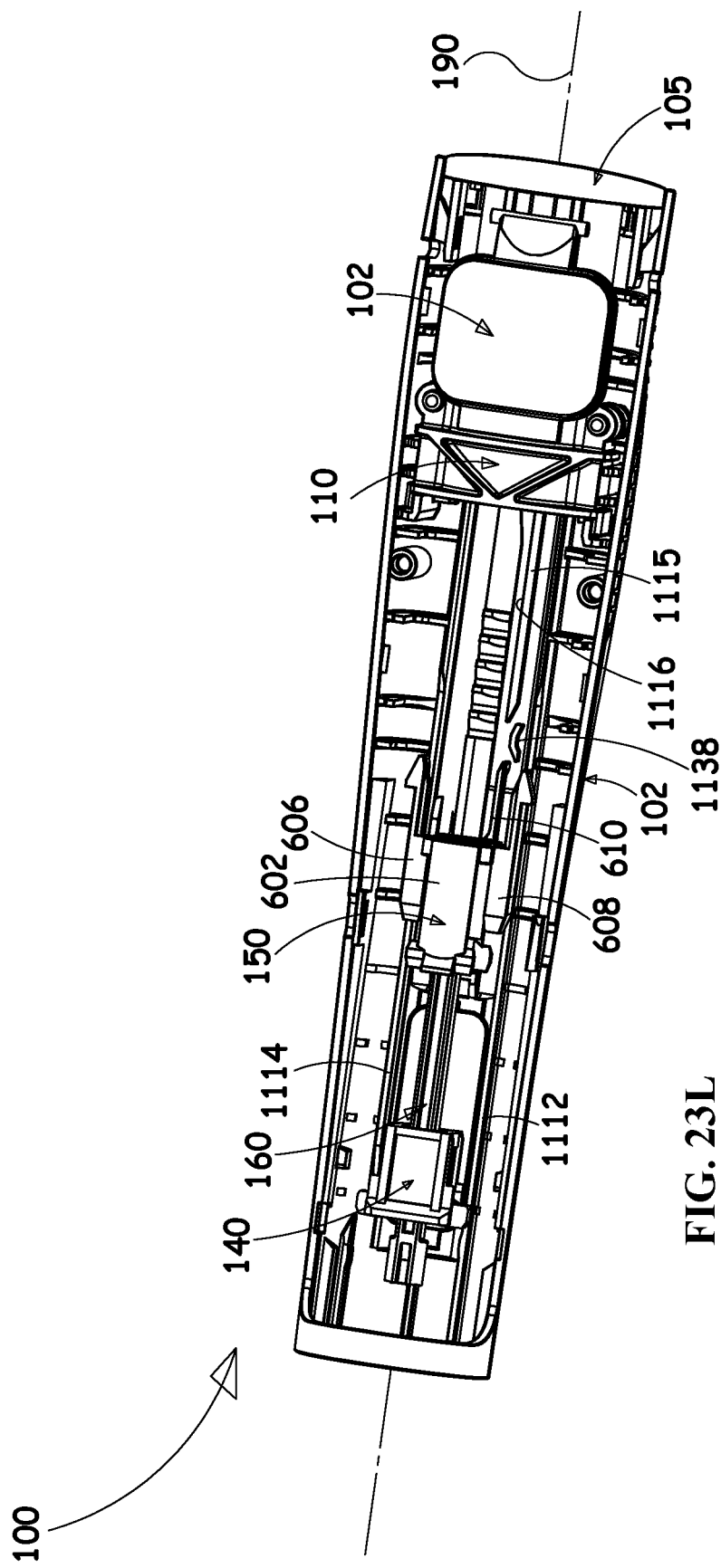

FIG. 23G is a simplified partial top view pictorial illustration of the automatic injection assembly wherein the cover portion 104 is not shown. FIG. 23H is a simplified sectional illustration of the reusable automatic injection assembly, taken along lines H-H in FIG. 23A. FIG. 23I is a simplified front view illustration taken along an arrow I in FIG. 23H. FIG. 23J simplified sectional illustration of the reusable automatic injection assembly, taken along lines J-J in FIG. 23A. FIG. 23K simplified sectional illustration of the reusable automatic injection assembly, taken along lines K-K in FIG. 23A. FIG. 23L is a simplified partial bottom view pictorial illustration of the automatic injection assembly wherein the cover portion 104, multifunctional engagement element 170 and springs 180 and 194 are not shown.

Turning initially to FIGS. 23G and 23K, it is seen that control element 140 (FIGS. 4A-5B) is axially slidably positioned along elongate damping driver element 160 (FIGS. 9A-12B), wherein rearwardly-facing tapered surface 414 of control element 140 engage tapered planar forward-facing surface 742 of cylindrical rod 702 and thereby prevent rearward axial displacement of control element 140 relative to elongate damping driver element 160. It is also seen that inwardly-facing protrusions 418 of control element 140 axially slidably engage channels 722 and 724 of elongate damping driver element 160.

It is also seen that multifunctional engagement element 170 (FIGS. 13A-14B) is in its forwardmost position wherein forward-facing resilient fingers 880 are in a mutually spread at rest operative orientation as seen at I in FIG. 14A. When forward-facing resilient fingers 880 are in this at rest operative orientation the outwardly-facing protruding surfaces 884 of multi-functional engagement element 170 are located within respective recesses 1144 and 1146 of main housing portion 102 and respective recesses 1376 and 1378 of cover portion 104 (not shown).

It is appreciated that in the storage operative orientation, the control element 140 is in the operative orientation shown and described hereinabove with reference to FIG. 5A at state I.

As seen clearly in FIG. 23J, first compression spring 180 is arranged along axis 190 and is seated at a rearward end thereof in annular volume 930 defined by end cover 105. A forward end of first compression spring 180 is seated against shoulders 774 of elongate damping driver element 160 (FIGS. 9A-12B).

As also seen particularly clearly in FIG. 23J, second compression spring 194 is arranged along axis 190 and is seated at a rearward end thereof in an annular volume 930 defined by end cover 105. A forward end of second compression spring 194 is seated against end surfaces 804 of multifunctional engagement element 170 (FIGS. 13A-14B).

As further seen particularly clearly in FIGS. 23G and 23J, multifunctional retaining element 150 is disposed along axis 190 relative to the multifunctional engagement element 170 such that rearwardly-facing surface 654 of multifunctional retaining element 150 engages the forward edge 828 of cylindrical portion 802 of multifunctional engagement element 170, thus preventing forward displacement of the multifunctional engagement along axis 190 relative to the multifunctional retaining element. Multifunctional retaining element 150 is restrained from forward axial displacement with respect to main housing portion 102 and cover portion 104 by engagement of engagement surfaces 624 of fingers 602 and 604 of multifunctional retaining element 150 with corresponding inwardly facing protrusions 1164 of main housing portion 102 and 1364 of cover portion 104.

As seen particularly clearly in FIG. 23H, outer facing surfaces 862 of ribs 860 of multifunctional engagement element 170 slidably engage axial extending mutually spaced ribs 1112 and 1114 of the main housing portion 102 and axial extending mutually spaced ribs 1312 and 1314 of the cover portion 104.

As additionally seen clearly in FIG. 23J, engagement surface 624 of outwardly-facing tapered protrusions 620 of generally identical fingers 602 and 604 operatively engage inwardly-facing protrusion 1164 of main housing portion 102 and inwardly-facing protrusion 1364 of cover portion 104, thus retaining elongate damping driver element 160 against forward motion along axis 190.

As further seen clearly in FIG. 23J, the elongate damping driver element 160 extends through central aperture 650 formed in multifunctional retaining element 150 and is axially positioned relative thereto such that protrusions 758 of elongate damping driver element 160 are located in engagement with forward-facing recessed partially circumferential surfaces 652 of base 600.

As seen clearly in FIGS. 23G and 23K, and as seen in FIGS. 7A and 7B at I, in a storage operative orientation, fingers 602 and 604 each extend generally parallel to axis 190 and engage generally rearward circular cylindrical portion 802 of multifunctional engagement element 170, thus preventing forward displacement of the multifunctional engagement element 170.

As seen clearly in FIG. 23L and as seen in FIG. 8 at I, in a steady state operative orientation, finger 610 of multifunctional retaining element 150 extends generally parallel to axis 190.

It is further seen clearly in FIG. 23K that multifunctional retaining element 150 is slidably seated within multifunctional engagement element 170 by means of engagement of fingers 606 and 608 of the multifunctional retaining element 150 within axial recesses 810 of the multifunctional engagement element 170.

Figure 24A:
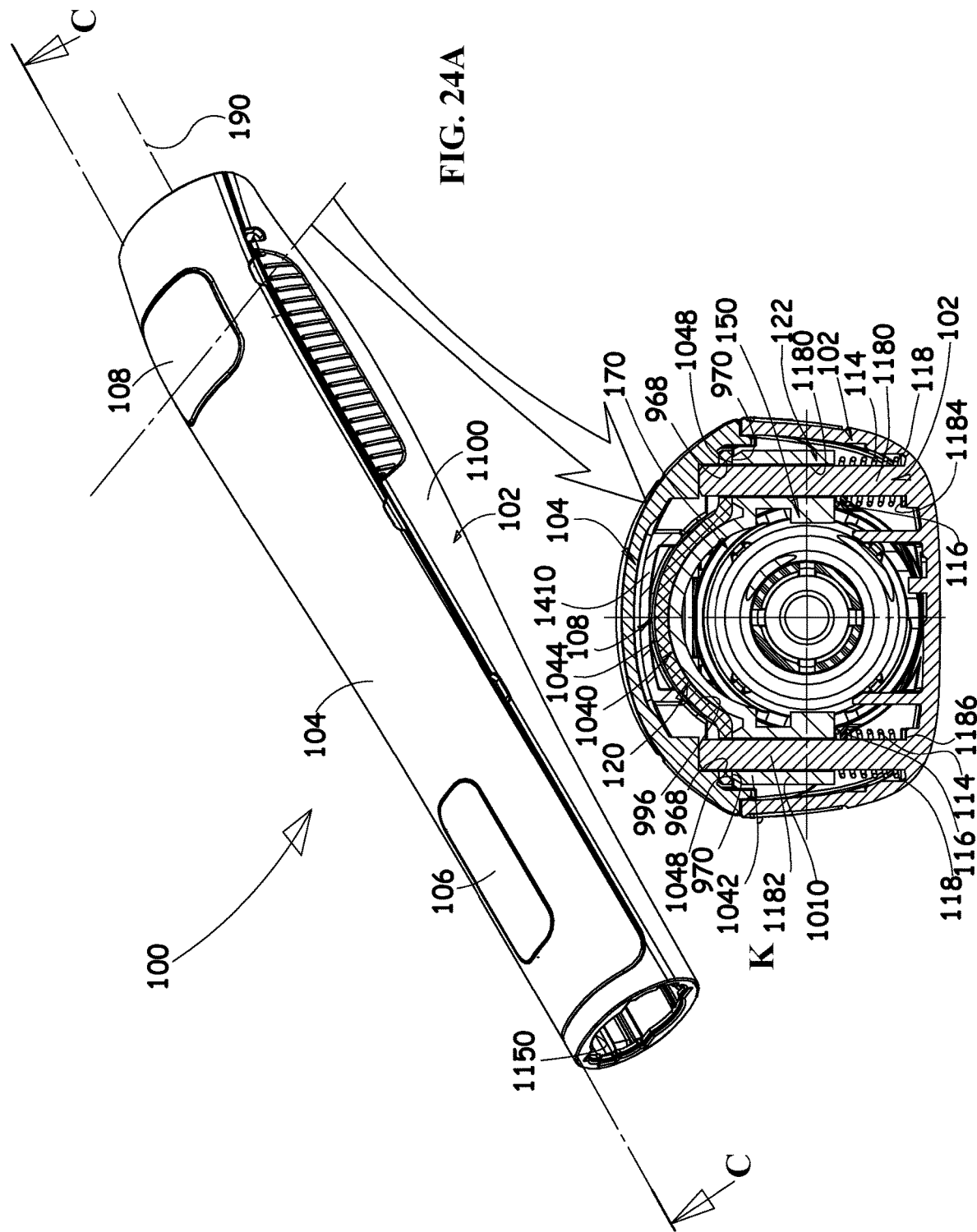
FIGS. 24A, 24B and 24C are simplified drawings of the reusable automatic injection assembly of FIGS. 1A, 1B, 17A-17H, 19A-19F and 22A-22D in a "storage" operative orientation.
Figure 24B:
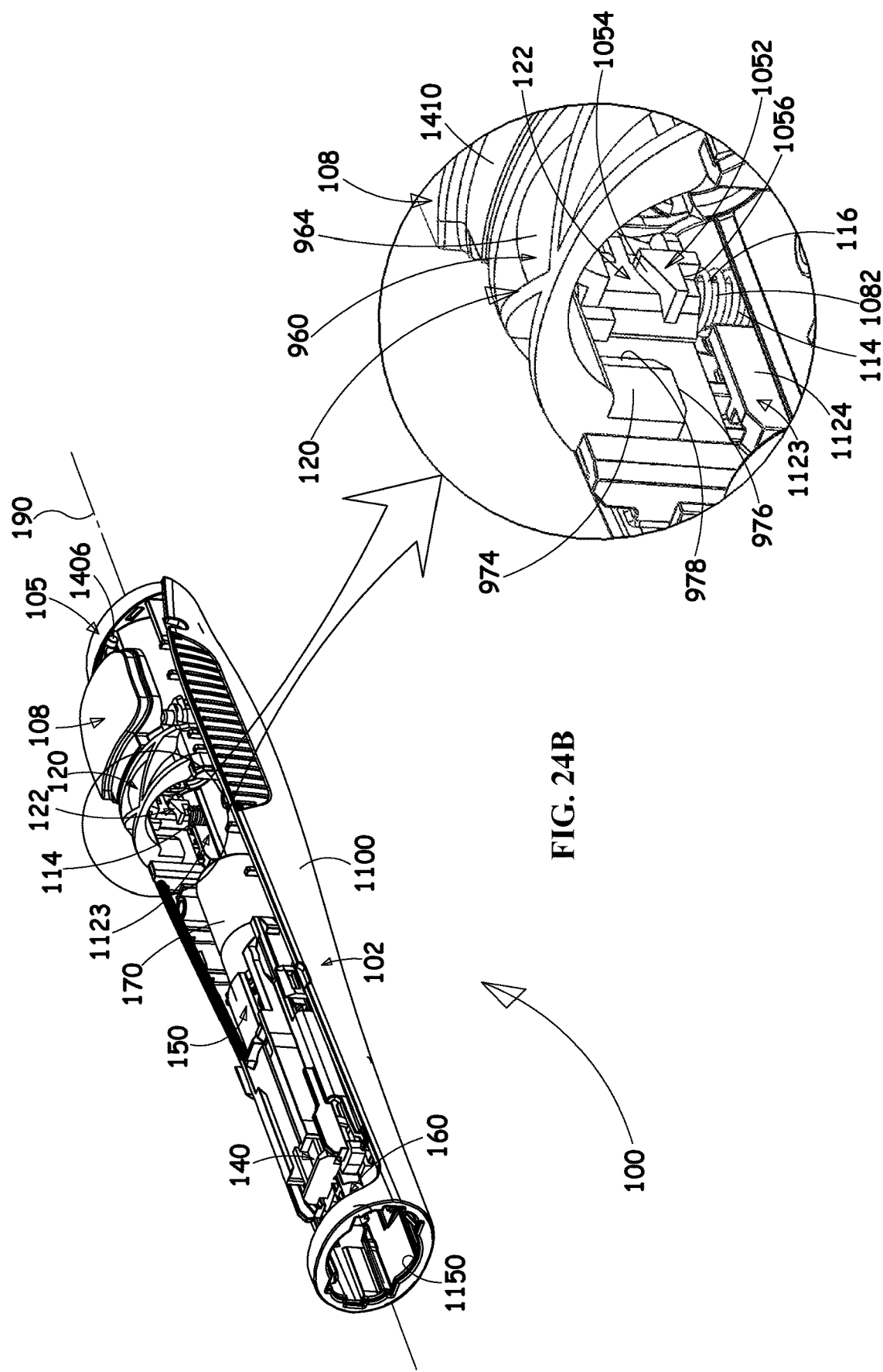
Figure 24C:
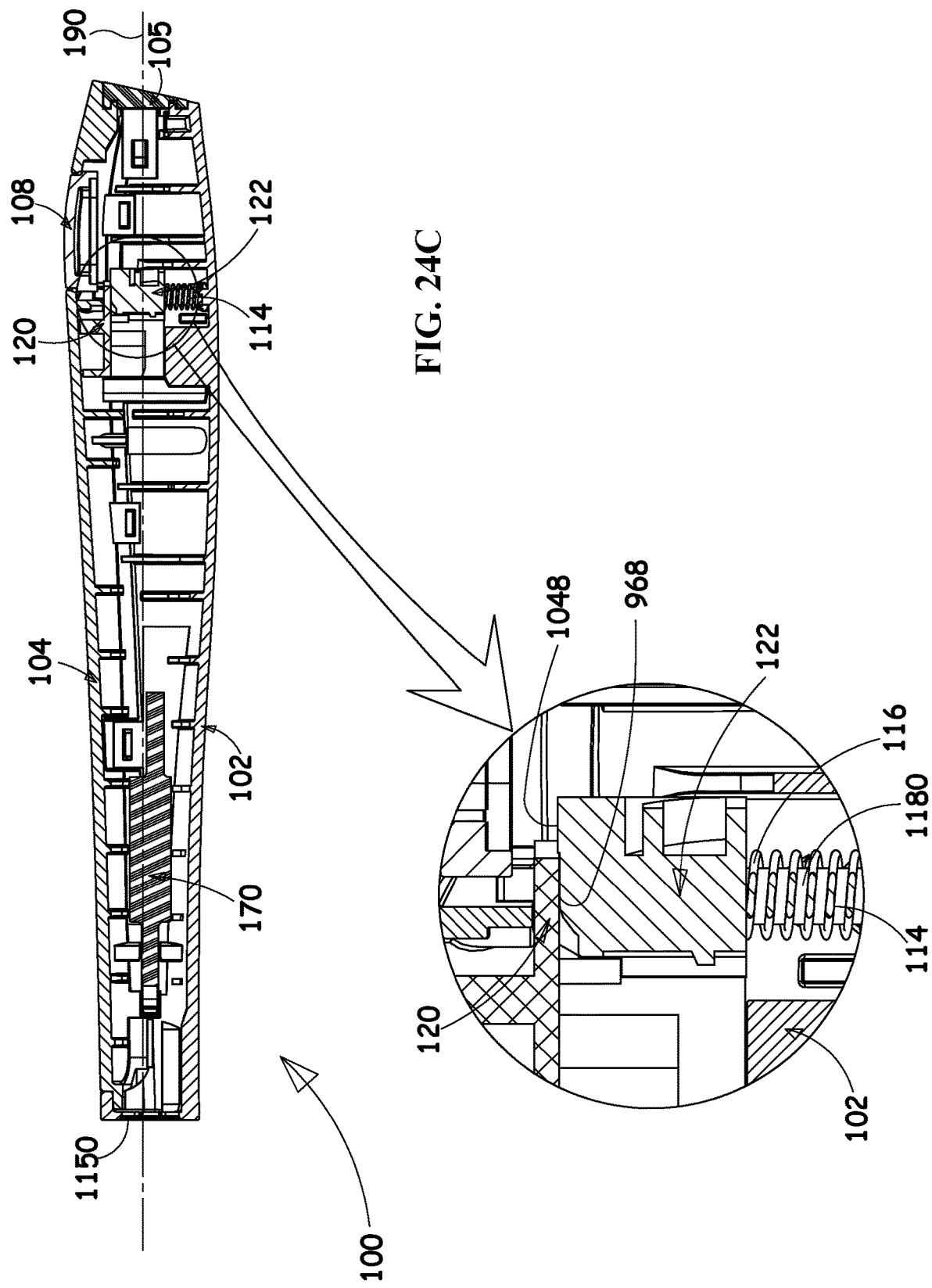

Reference is now made to FIGS. 24A, 24B and 24C, which are simplified drawings of the reusable automatic injection assembly of FIGS. 1A, 1B, 17A-17H, 19A-19F and 22A-22D.

FIGS. 24A, 24B and 24C particularly illustrate the structural relationship between user engageable actuation button 108, trigger element 120 and unitary latch element 122 in a "storage" operative orientation, as the reusable automatic injection assembly would be delivered to the user.

FIG. 24A illustrates the exterior of the reusable automatic injection assembly of FIGS. 1A, 1B, 17A-17H, 19A-19F and 22A-22D and is similar to FIG. 1A, except for the direction of view and is identical to FIG. 23A. FIG. 24A also includes a sectional enlargement which differs from the sectional enlargement of FIG. 23A.

FIG. 24B is a simplified partial top view pictorial illustration of the automatic injection assembly of FIGS. 1A, 1B, 17A-17H, 19A-19F and 22A-22D wherein the cover portion 104 and springs 180 and 194 are not shown. FIG. 24C is a simplified sectional illustration of the reusable automatic injection assembly of FIGS. 1A, 1B, 17A-17H, 19A-19F and 22A-22D, taken along lines C-C in FIG. 24A.

As seen particularly in FIGS. 24A-24C, it is seen that trigger element 120 and unitary latch element 122 are slidably mounted on pins 1180 and 1182 (FIG. 20A) of main housing portion 102 for selectable vertical positioning therealong, in the sense of the sectional enlargement in FIG. 24A.

As seen particularly in the enlargement of FIG. 24A, springs 114, which are seated on respective upward-facing surfaces 1184 and 1186 underlying respective pins 1180 and 1182, urges unitary latch element 122 upwardly along pins 1180 and 1182 respectively into engagement with trigger element 120 (FIGS. 17A-17H) and urges the trigger element 120 upwardly into engagement with cover portion 104 and with the lip 1410 of the user engageable actuation button 108, thereby urging lip 1410 against cover portion 104.

More specifically it is seen that convex outer-facing surface 1044 of unitary latch element 122 engages concave inner-facing surface 966 of trigger element 120.

As distinct from the embodiment of FIGS. 23A-23L, in the embodiment of FIGS. 24A-24C, upward-facing surfaces 1184 and 1186 of the main housing portion 102 and the unitary latch element 122 does not have any teeth formed thereon and does not include a helical surface and is not rotatable.

The remainder of the structure described hereinabove with respect to FIGS. 23G-23L may be identical to that in the embodiment of FIGS. 1A, 1B, 17A-17H, 19A-19F and 22A-22D and is not again described or shown for the sake of conciseness.

Figure 25A:
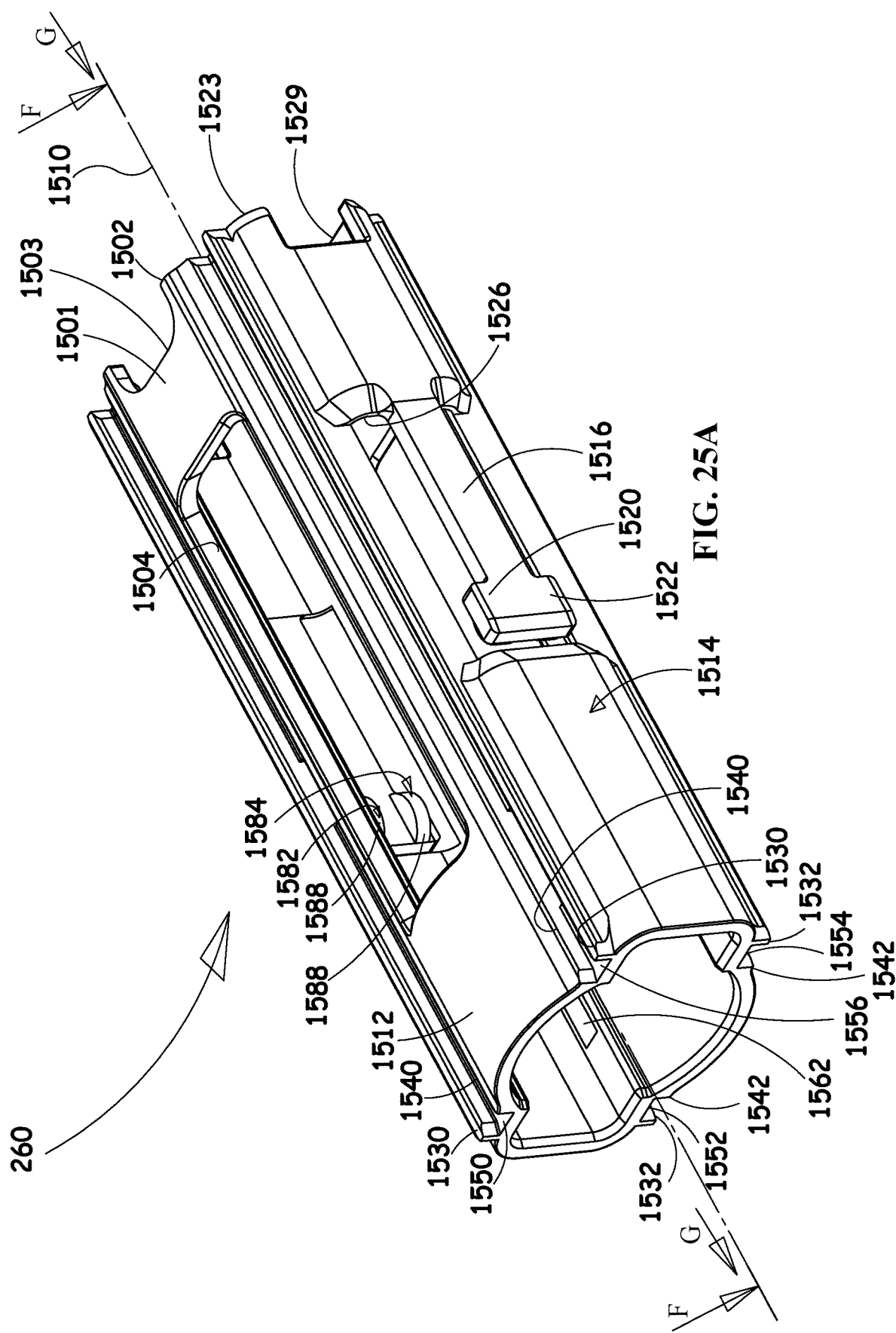
Figure 25E:
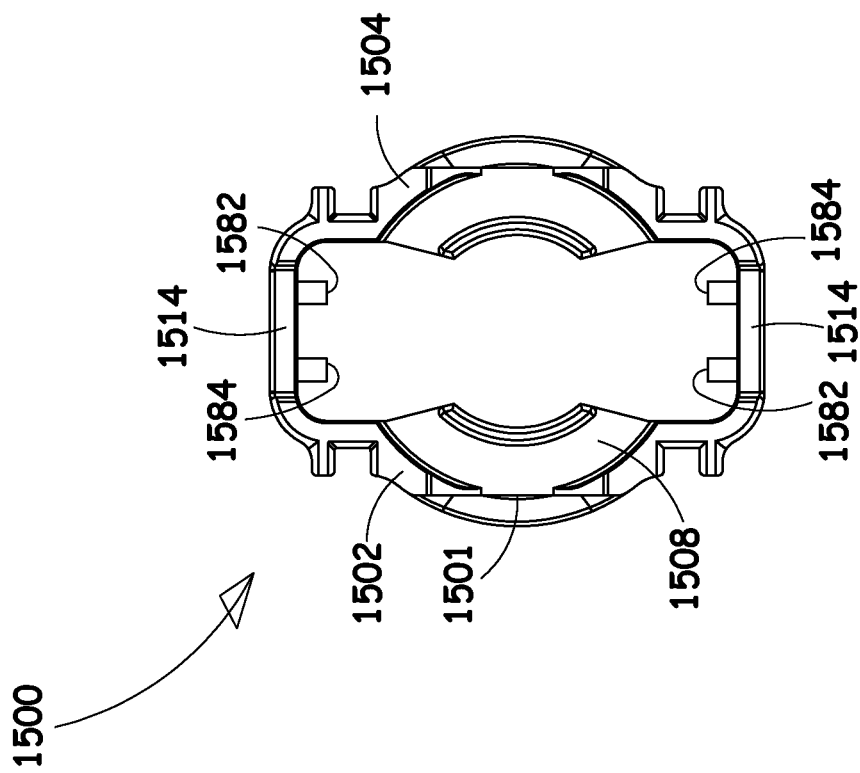
Figure 25D:
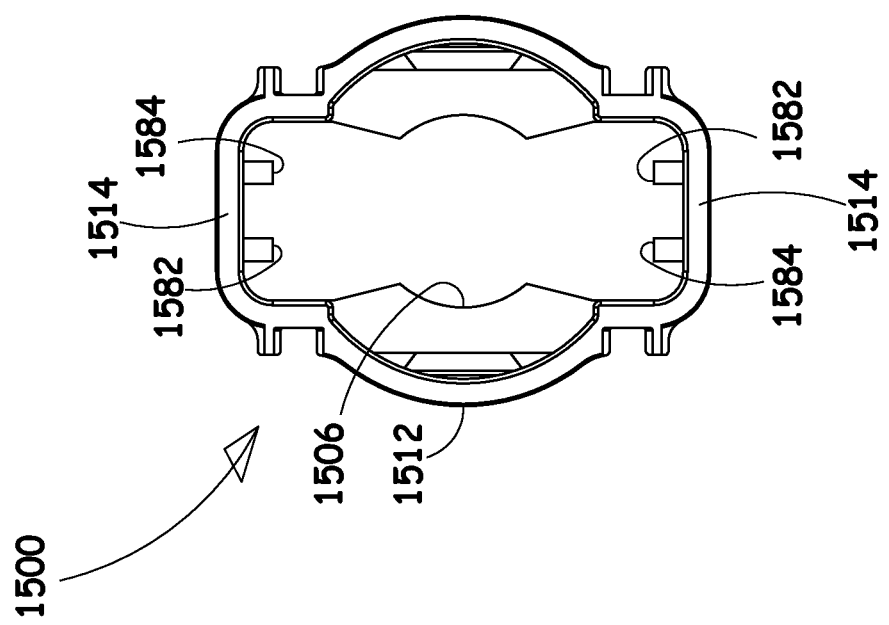

Reference is now made to FIGS. 25A, 25B, 25C, 25D, 25E, 25F and 25G, which are simplified respective perspective, top and bottom view, side view, first and second end view and sectional illustrations taken along lines F-F and G-G in FIG. 25A of a module housing 260 (FIG. 2B) or 360 (FIG. 2C), forming part of the medicament module of FIGS. 2A & 2B and 3A & 3B.

As seen in FIGS. 25A-25G, the module housing, which was previously indicated by reference numeral 260 (FIGS. 2A & 2B) and 360 (FIGS. 3A & 3B), here indicated by reference numeral 1500, preferably is an integrally formed element, preferably injection molded of plastic and preferably has a generally cylindrical configuration including a generally tubular portion 1501, which defines backward-facing generally symmetric edges 1502 having cutouts 1503 and generally symmetric top/bottom facing windows 1504. Top-bottom facing windows 1504 may be obviated, if module housing 1500 is formed of a transparent material. Generally axially coincident with base portions of cutouts 1503 are a pair of inwardly directed partially azimuthal bulkheads 1506, having rearwardly-facing surfaces 1508.

Module housing 1500 is preferably side-to-side symmetric about a longitudinal axis 1510, which is coaxial with axis 190 when the medicament module is inserted into the reusable automatic injection assembly 100. Module housing 1500 is preferably formed with a central, generally circular cylindrical portion 1512 and a pair of generally symmetric side-disposed longitudinal wall portions 1514.

Fingers 1516 and 1518 extend forwardly in respective cut outs 1526 and 1528 formed in longitudinal wall portions 1514 and parallel to longitudinal axis 1510, each of fingers 1516 and 1518 preferably terminating in side-to-side facing protrusions 1520 and 1522.

Longitudinal wall portions 1514 preferably each terminate rearwardly at a rearward edge 1523, which defines a generally rectangular cut-out 1529.

A pair of mutually spaced longitudinal ribs 1530 and 1532 are formed on opposite sides of each wall portions 1514. Ribs 1530 and 1532 each define, together with an adjacent respective mutually facing rib 1540 and 1542 a longitudinal channel. The channels are respective designated by reference numerals 1550, 1552, 1554 and 1556.

Forward slots 1560 and 1562 are formed along channels 1552 and 1556 respectively and central slots 1564 and 1566 are defined along channels 1550 and 1554 respectively. Forward slots 1560 and 1562 each include a forward facing edge 1568 and a rearward facing edge 1570. Central slots 1564 and 1566 each include a forward facing edge 1578 and a rearward facing edge 1580.

A pair of inwardly directed side protrusions 1582 and 1584 extend inwardly from each of arms 1516 and 1518 in a plane perpendicular to axis 1510 and each define a generally circular inwardly facing edge 1588.

Figure 26A:
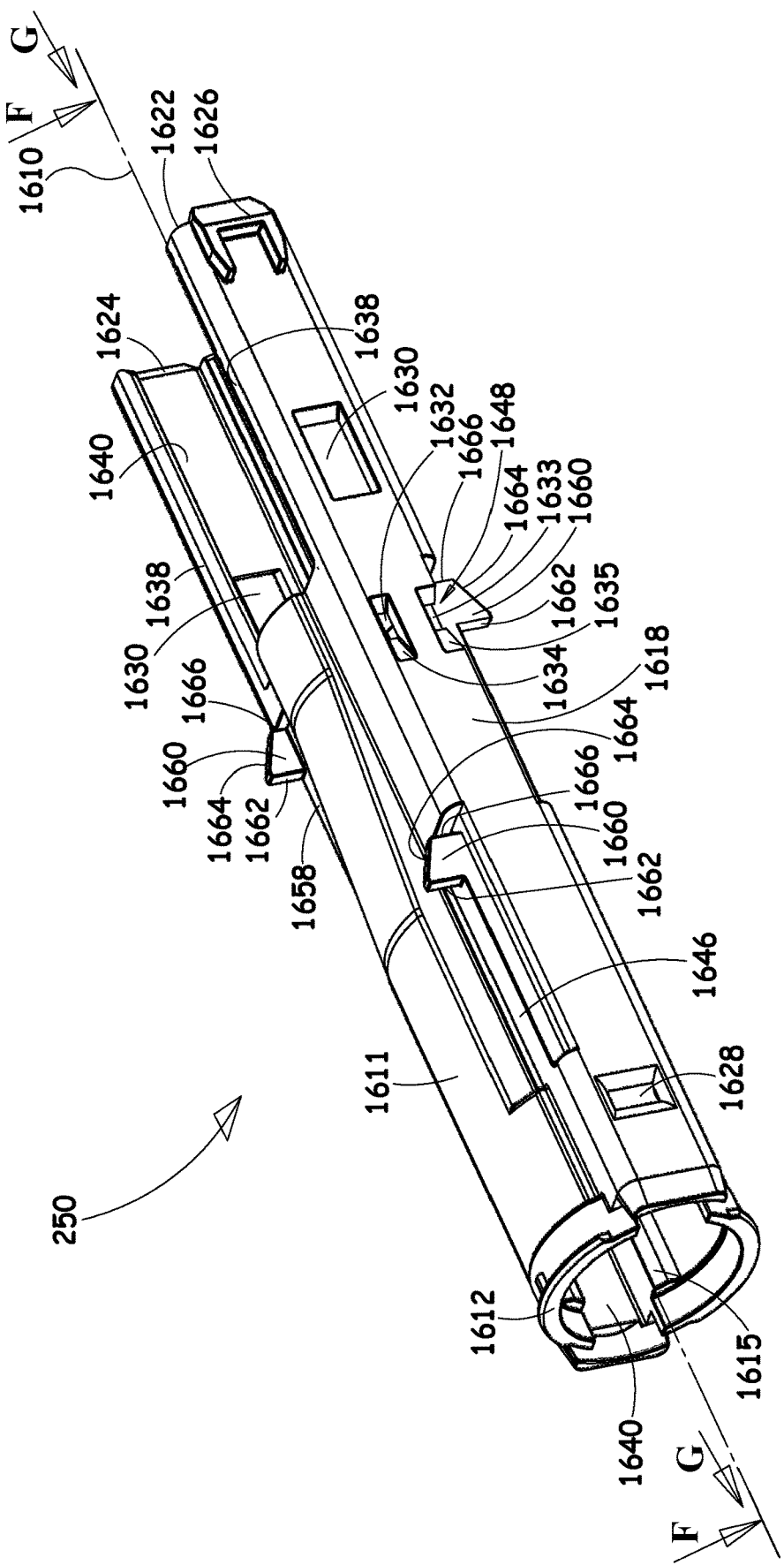
Figure 26E:
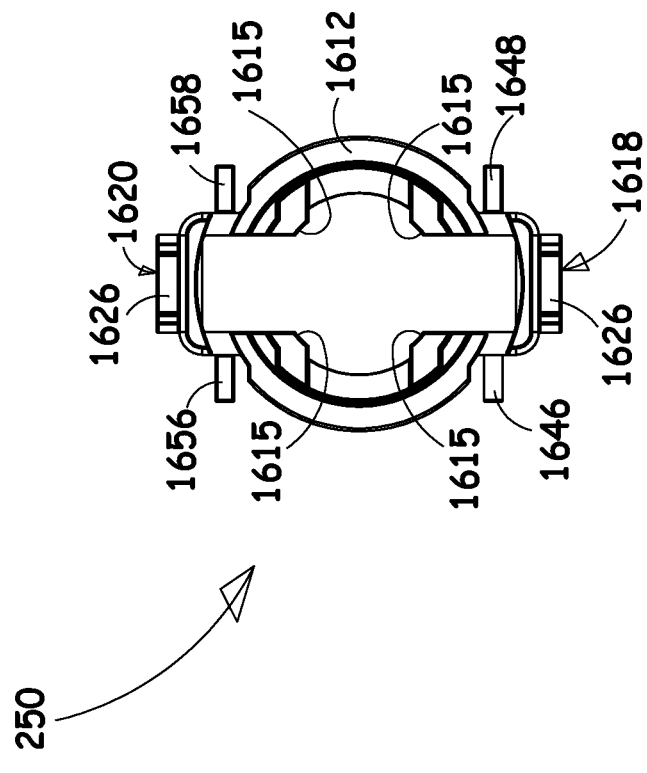
Figure 26D:
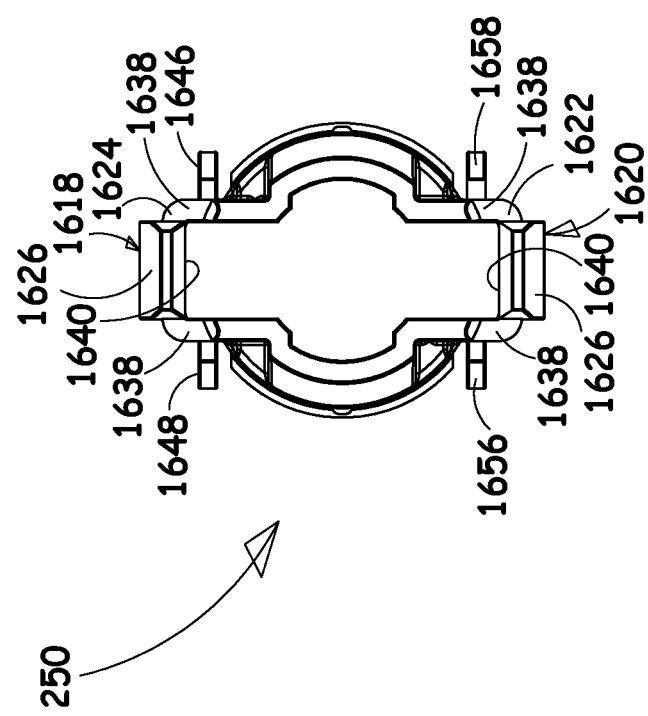

Reference is now made to FIGS. 26A, 26B, 26C, 26D, 26E, 26F and 26G, which are simplified respective perspective, top and bottom view, side view, first and second end view and sectional illustrations taken along lines F-F and G-G in FIG. 26A of one embodiment of needle shield 250 (FIG. 2B), forming part of one embodiment of the medicament module as seen in FIG. 2B.

As seen in FIGS. 26A-26G, needle shield 250 preferably is an integrally formed element, preferably injection molded of plastic and preferably has a generally cylindrical configuration arranged about a longitudinal axis 1610, which is normally coaxial with longitudinal axis 1510 of module housing 1500, when the needle shield 250 is operatively engaged with the module housing 1500.

Needle shield 250 preferably includes a generally conical tubular portion 1611 terminating at a partially circumferential rim 1612 extending radially outwardly therefrom. Conical tubular portion 1611 defines a generally circular cylindrical hollow bore. Generally conical tubular portion 1611 preferably defines a plurality of generally longitudinal guide surfaces 1615 which serve to guide the axial travel of a syringe therein. Needle shield 250 preferably includes a pair of side mounting arms 1618 and 1620, extending rearwardly from tubular portion 1611 and having respective rearward facing edges 1622 and 1624. Each of mounting arms 1618 and 1620 is formed with a generally U-shaped outer facing protrusion 1626 adjacent a rearward facing edge thereof 1622. Each of mounting arms 1618 and 1620 is formed with a forward recess 1628 and a rearward slot 1630 as well as a pair of narrow slots 1632 and 1633, forwardly of which are formed tapered surfaces 1634 and 1635 respectively.

Each of mounting arms 1618 and 1620 is preferably formed with an axial inwardly-facing surface 1636, which together with side ribs 1638 defines a channel 1640.

Mounting arm 1618 is formed with respective forward and rearward resilient finger portions 1646 and 1648. Mounting arm 1620 is formed with respective forward and rearward resilient finger portions 1656 and 1658.

Finger portions 1646, 1648, 1656 and 1658 each include an outwardly-facing protrusion 1660 having a forward-facing surface 1662, a rearward-facing tapered surface 1664 and a rearward facing edge 1666.

Figure 27A:
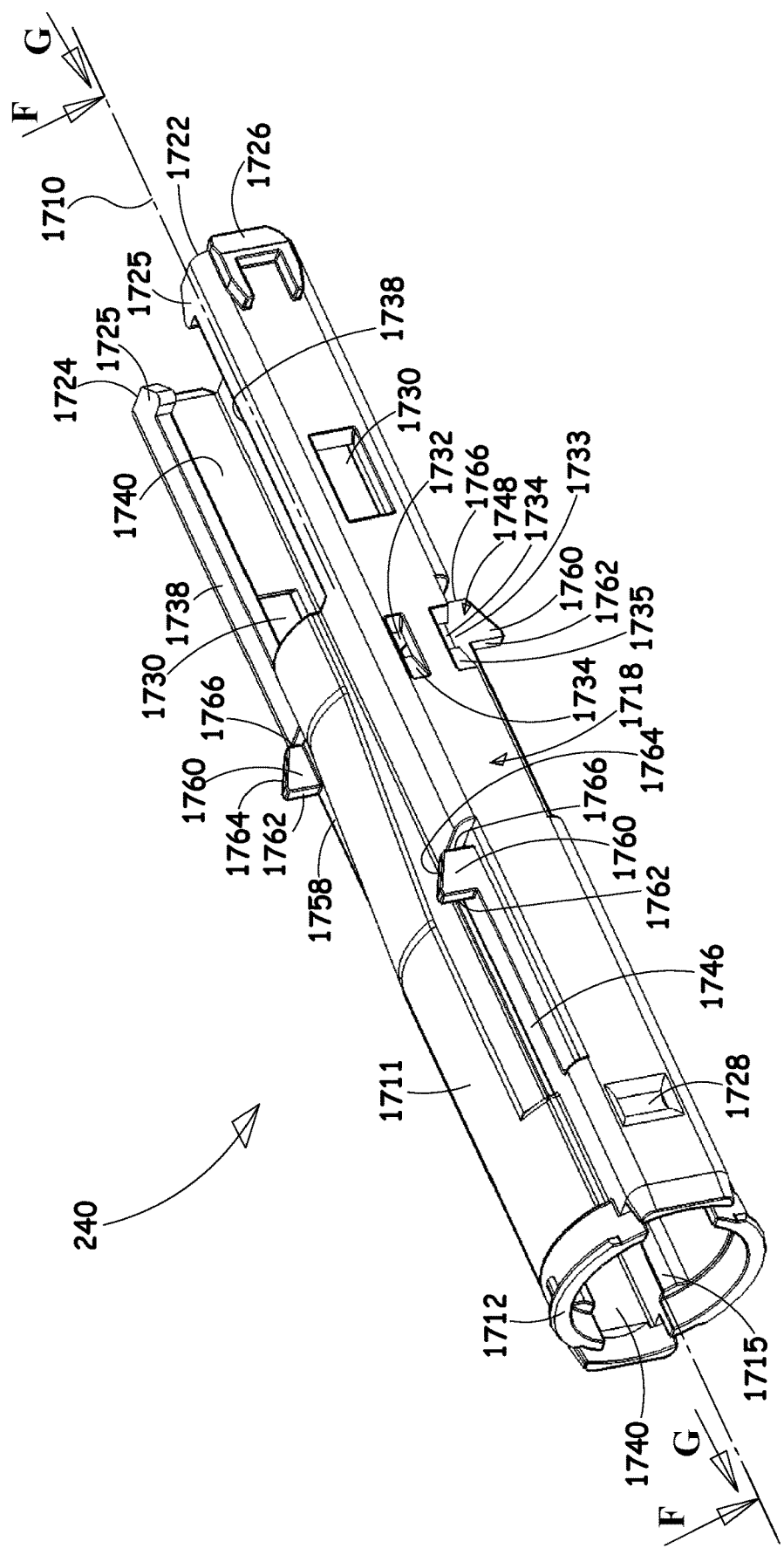
Figure 27B:
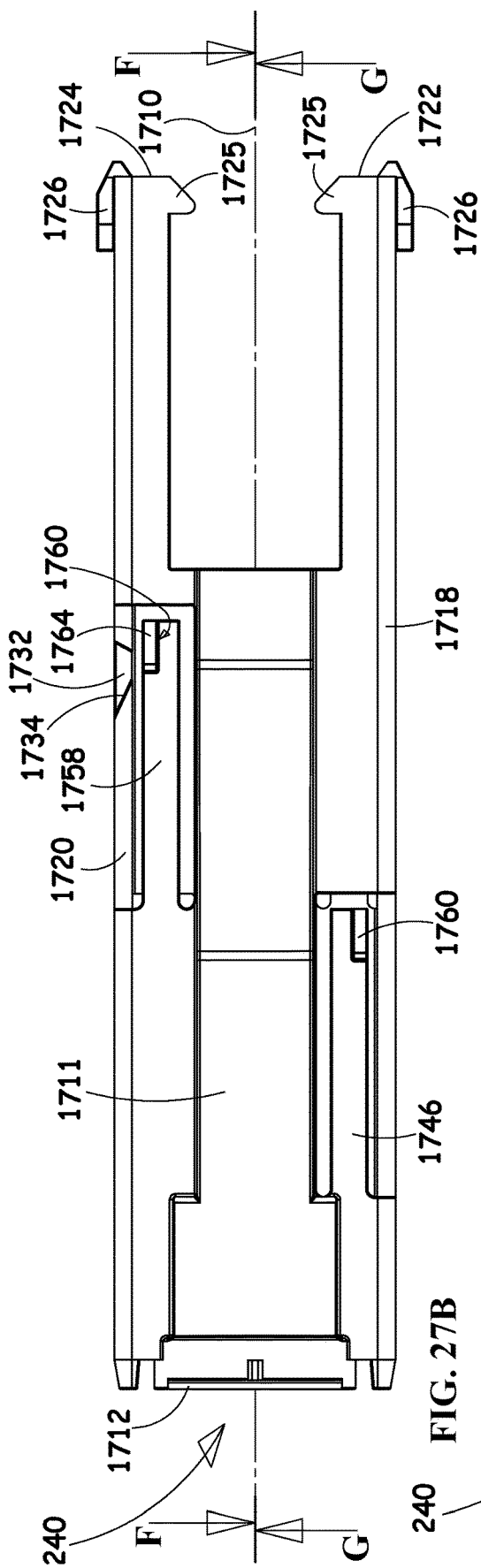
Figure 27C:
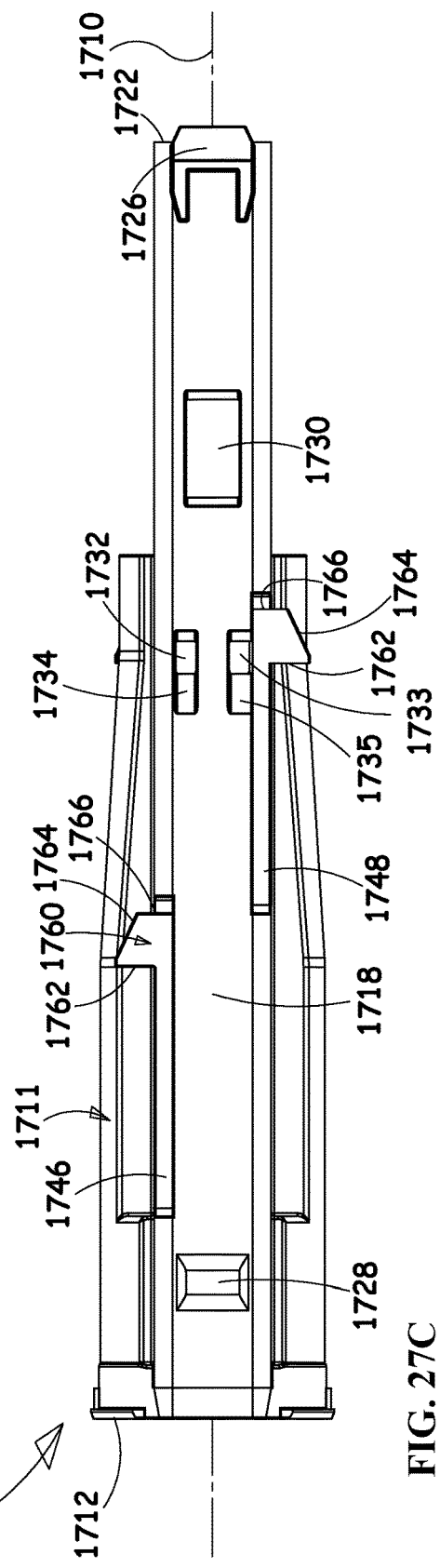
Figure 27E:
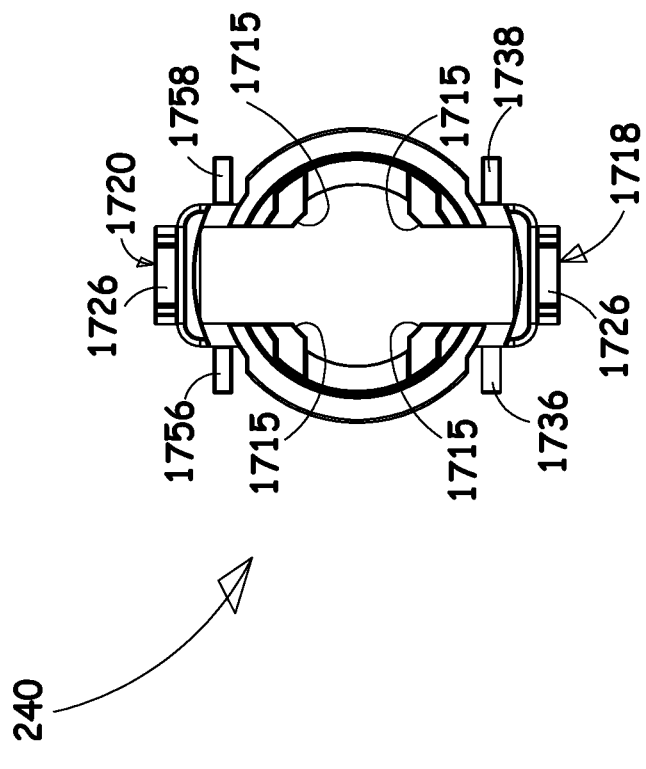
Figure 27D:
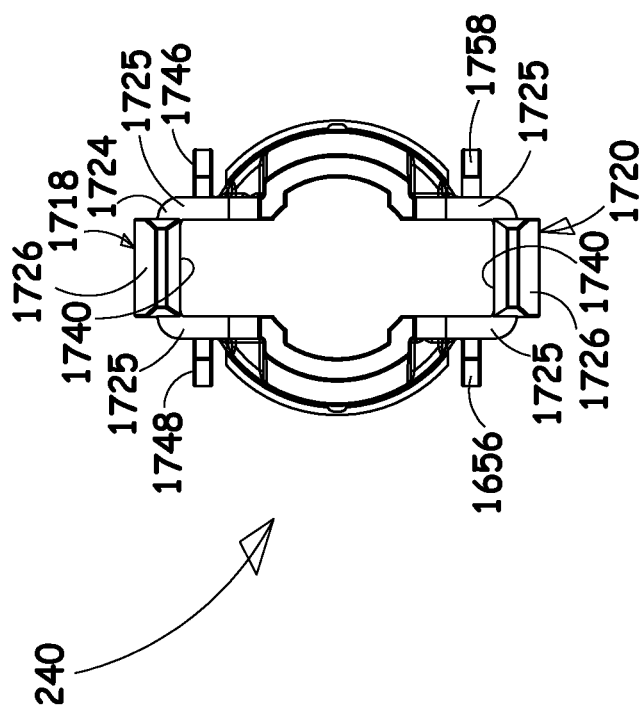

Reference is now made to FIGS. 27A, 27B, 27C, 27D, 27E, 27F and 27G are simplified respective perspective, top and bottom view, side view, first and second end view and sectional illustrations taken along lines F-F and G-G in FIG. 27A of another embodiment of a needle shield, designated by reference numeral 240, forming part of the medicament module as seen in FIG. 2B.

As seen in FIGS. 27A-27G, needle shield 240 preferably is an integrally formed element, preferably injection molded of plastic and preferably has a generally cylindrical configuration arranged about a longitudinal axis 1710, which is normally coaxial with longitudinal axis 1510 of module housing 1500, when the needle shield 240 is operatively engaged with the module housing 1500.

Needle shield 240 preferably includes a generally conical tubular portion 1711 terminating at a partially circumferential rim 1712 extending radially outwardly therefrom and defining a generally circular cylindrical hollow bore. Generally conical tubular portion 1711 preferably defines a plurality of generally longitudinal guide surfaces 1715 which serve to guide the axial travel of a syringe therein. Needle shield 240 preferably includes a pair of side mounting arms 1718 and 1720, extending rearwardly from tubular portion 1711 and having respective rearward facing edges 1722 and 1724.

Adjacent each of rearward facing edges 1722 and 1724 there are preferably formed a pair of mutually spaced inwardly directed toothed syringe retaining protrusions 1725.

Each of mounting arms 1718 and 1720 is formed with a generally U-shaped outer facing protrusion 1726 adjacent respective edges 1722 and 1724. Each of mounting arms 1718 and 1720 is formed with a forward recess 1728 and a rearward slot 1730 as well as a pair of narrow slots 1732 and 1733, forwardly of which are formed tapered surfaces 1734 and 1735 respectively.

Each of mounting arms 1718 and 1720 is preferably formed with an axial inwardly-facing surface 1736, which together with side ribs 1738 defines a channel 1740.

Mounting arm 1718 is formed with respective forward and rearward resilient finger portions 1746 and 1748. Mounting arm 1720 is formed with respective forward and rearward resilient finger portions 1756 and 1758.

Finger portions 1746, 1748, 1756 and 1758 each include an outwardly-facing protrusion 1760 having a forward-facing surface 1762, a rearward-facing tapered surface 1674 and a rearward facing edge 1766.

Figure 28A:
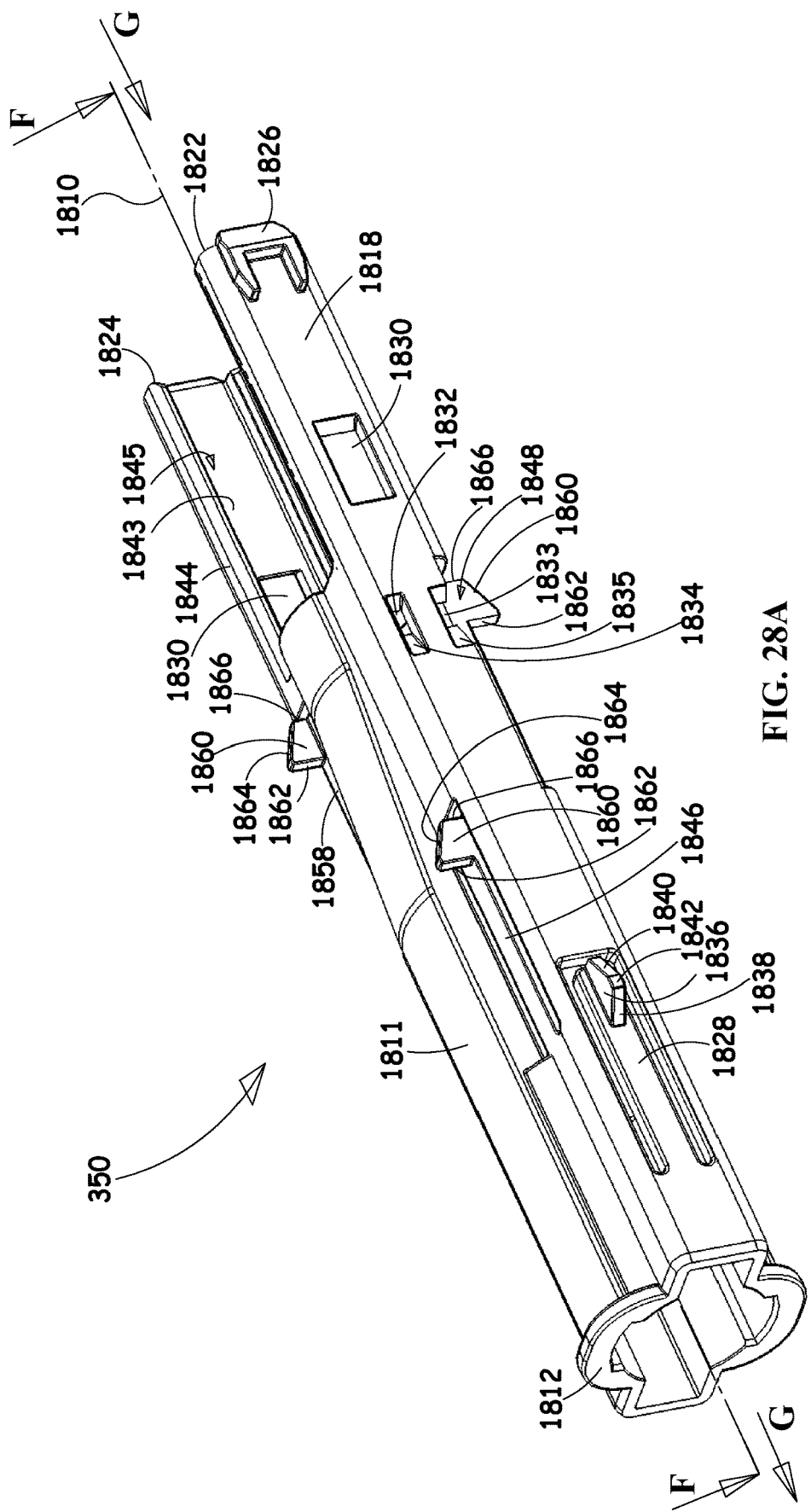
Figure 28E:
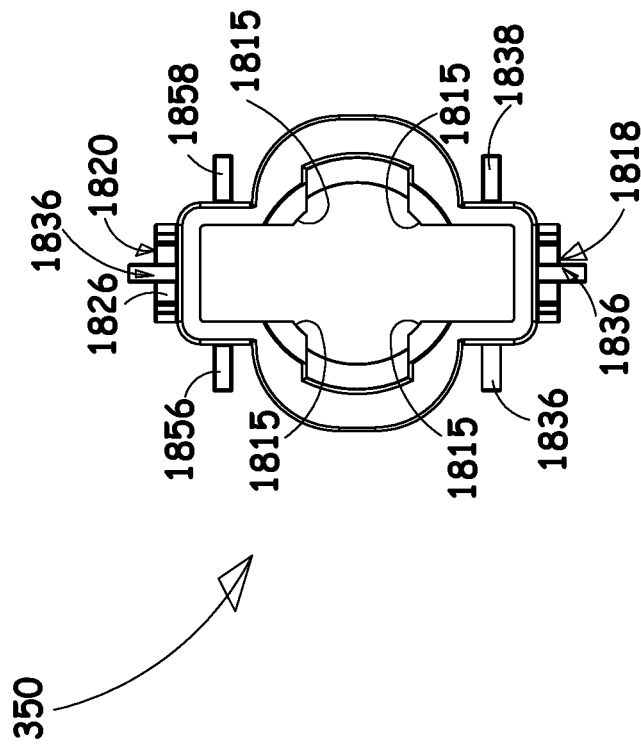
Figure 28D:
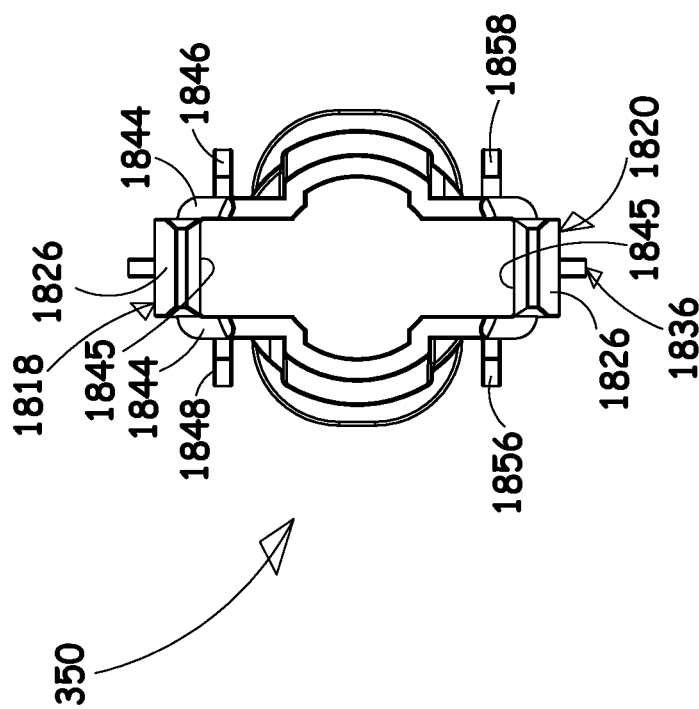
Figure 28F:
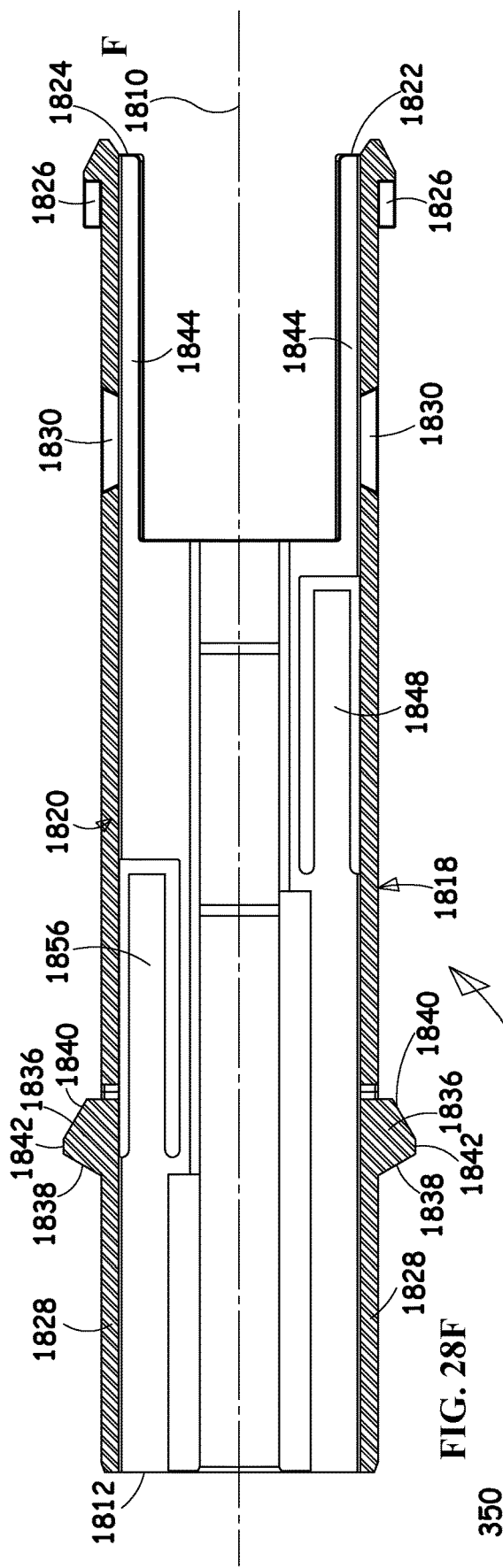
Figure 28G:
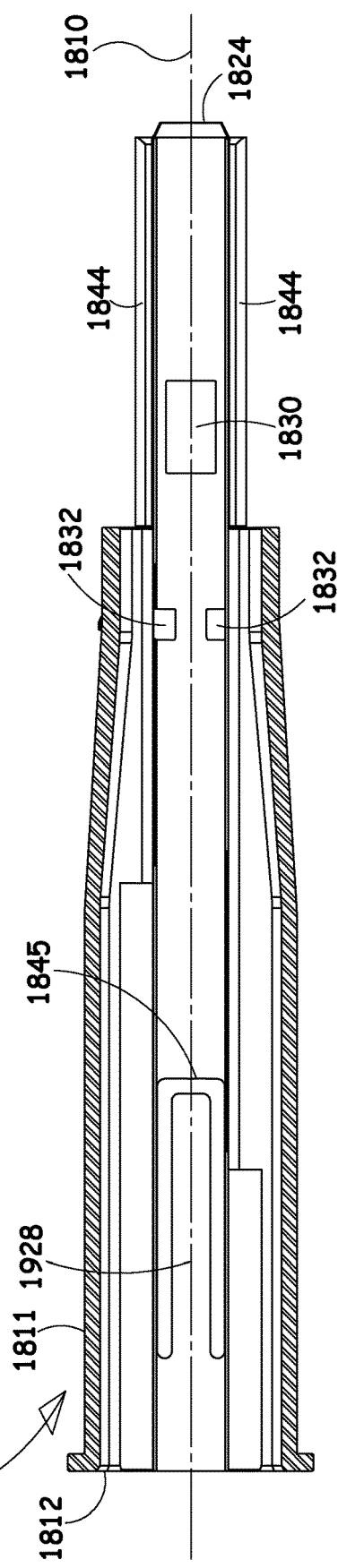

Reference is now made to FIGS. 28A, 28B, 28C, 28D, 28E, 28F and 28G, which are simplified respective perspective, top and bottom view, side view, first and second end view and sectional illustrations taken along lines F-F and G-G in FIG. 28A of yet another embodiment of a needle shield, designated by reference 350, forming part of the medicament module as seen in FIG. 3B.

As seen in FIGS. 28A-28G, needle shield 350 preferably is an integrally formed element, preferably injection molded of plastic and preferably has a generally cylindrical configuration arranged about a longitudinal axis 1810, which is normally coaxial with longitudinal axis 1510 of module housing 1500, when the needle shield 350 is operatively engaged with the module housing 1500.

Needle shield 350 preferably includes a generally conical tubular portion 1811 terminating at a partially circumferential rim 1812 extending radially outwardly therefrom and defining a generally circular cylindrical hollow bore. Generally conical tubular portion 1811 preferably defines a plurality of generally longitudinal guide surfaces 1815 which serve to guide the axial travel of a syringe therein. Needle shield 350 preferably includes a pair of side mounting arms 1818 and 1820, extending rearwardly from tubular portion 1811 and having respective rearward facing edges 1822 and 1824. Each of mounting arms 1818 and 1820 is formed with a generally U-shaped outer facing protrusion 1826 adjacent respective edges 1822 and 1824. Each of mounting arms 1818 and 1820 is formed with a rearward-facing flexible finger 1828 and a rearward slot 1830 as well as a pair of narrow slots 1832 and 1833, forwardly of which are formed tapered surfaces 1834 and 1835 respectively.

Rearward-facing flexible finger 1828 preferably is formed with an outwardly-facing protrusion 1836 having a forwardly-facing tapered surface 1838 and a rearwardly-facing tapered surface 1840 joined at an outermost flat surface 1842.

Each of mounting arms 1818 and 1820 is preferably formed with an axial inwardly-facing surface 1843, which together with side ribs 1844 defines a channel 1845.

Mounting arm 1818 is formed with respective forward and rearward resilient finger portions 1846 and 1848. Mounting arm 1820 is formed with respective forward and rearward resilient finger portions 1856 and 1858.

Finger portions 1846, 1848, 1856 and 1858 each include an outwardly-facing protrusion 1860 having a forward-facing surface 1862, a rearward-facing tapered surface 1864 and a rearward facing edge 1866.

Figure 29A:
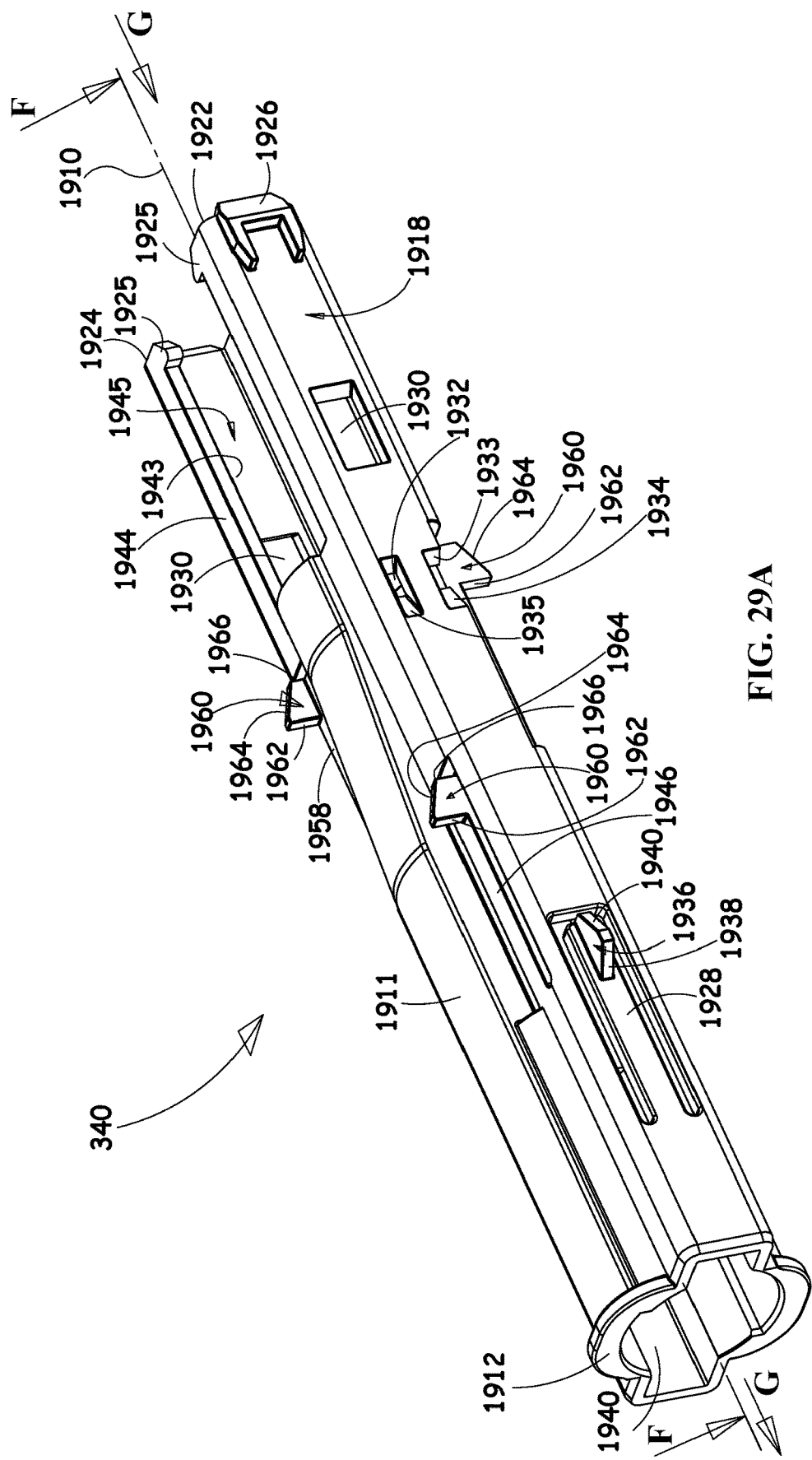
Figure 29B:
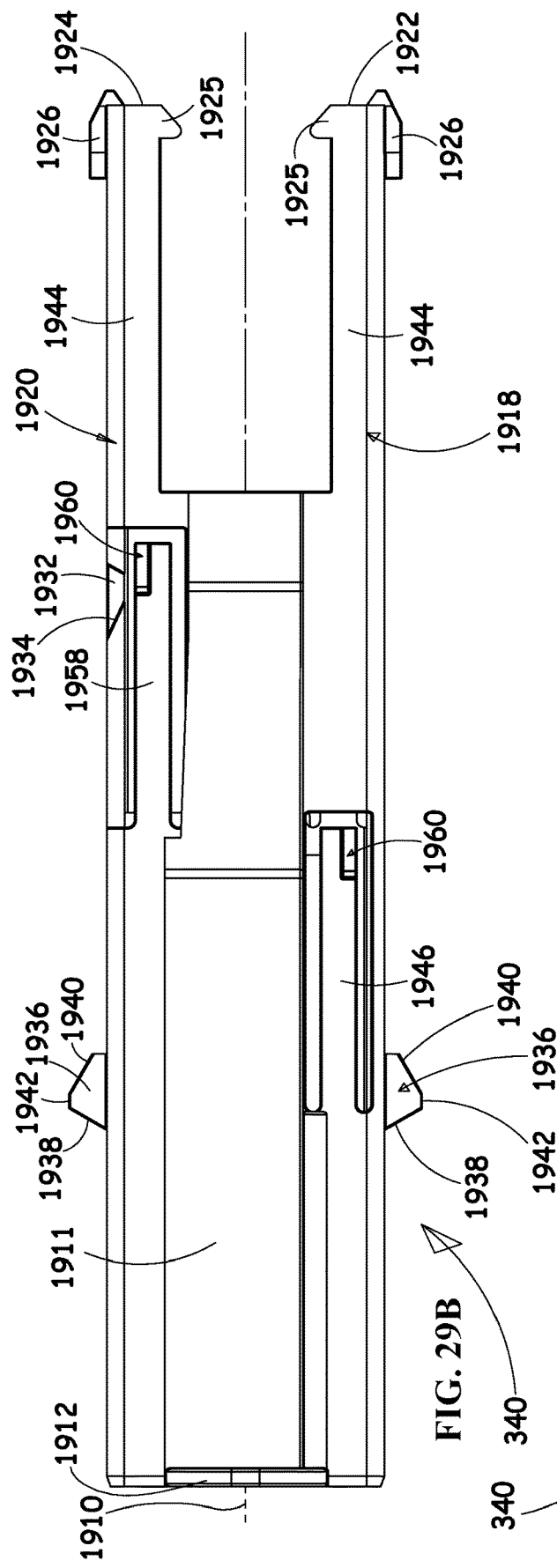
Figure 29C:
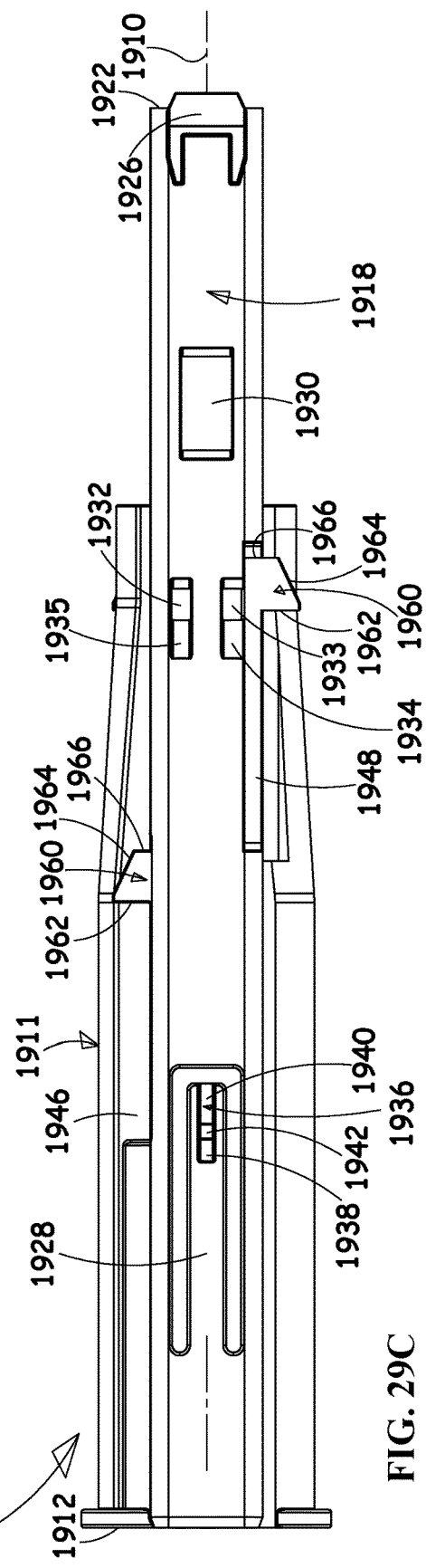
Figure 29E:
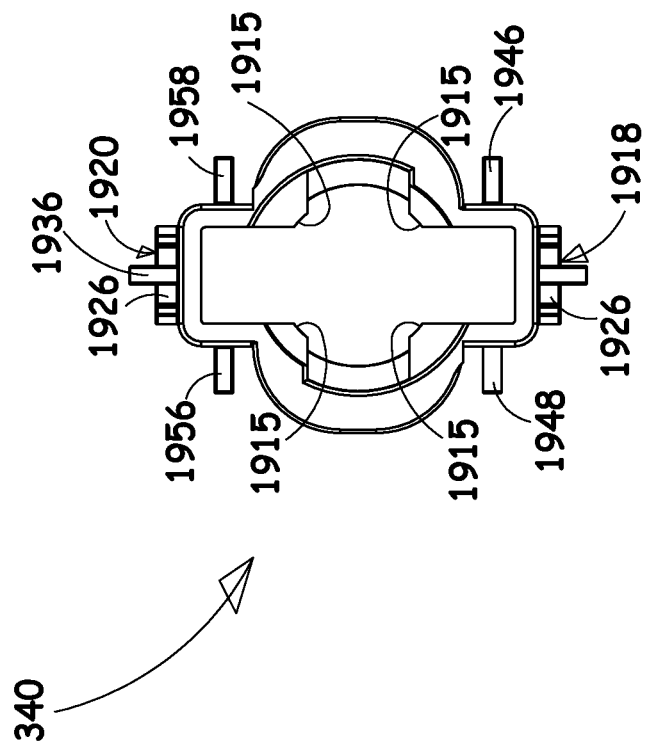
Figure 29D:
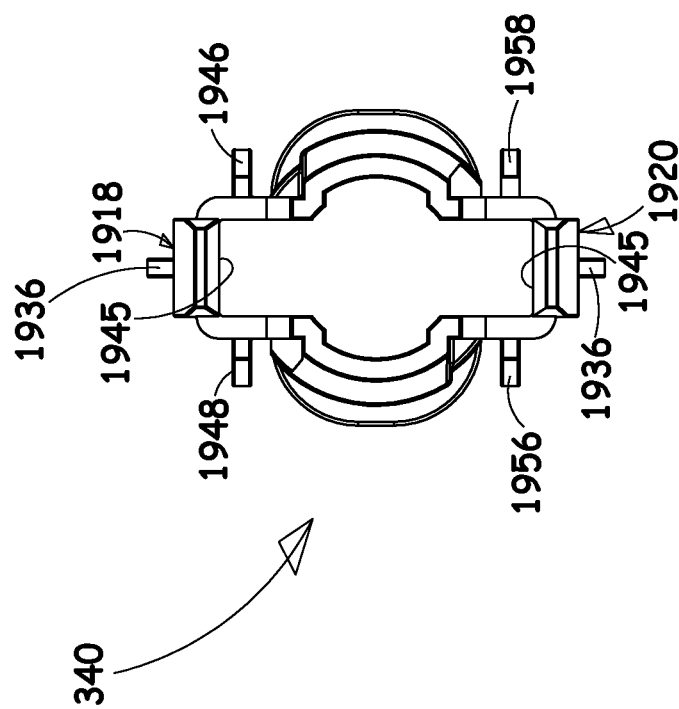

Reference is now made to FIGS. 29A, 29B, 29C, 29D, 29E, 29F and 29G, which are simplified respective perspective, top and bottom view, side view, first and second end view and sectional illustrations taken along lines F-F and G-G in FIG. 29A of another embodiment of needle shield 340, forming part of the medicament module as seen in FIG. 3B.

As seen in FIGS. 29A-29G, needle shield 340 preferably is an integrally formed element, preferably injection molded of plastic and preferably has a generally cylindrical configuration arranged about a longitudinal axis 1910, which is normally coaxial with longitudinal axis 1510 of module housing 1500, when the needle shield 340 is operatively engaged with the module housing 1500.

Needle shield 340 preferably includes a generally conical tubular portion 1911 terminating at a partially circumferential rim 1912 extending radially outwardly therefrom and defining a generally circular cylindrical hollow bore. Generally conical tubular portion 1911 preferably defines a plurality of generally longitudinal guide surfaces 1915 which serve to guide the axial travel of a syringe therein. Needle shield 340 preferably includes a pair of side mounting arms 1918 and 1920, extending rearwardly from tubular portion 1911 and having respective rearward facing edges 1922 and 1924.

Adjacent each of rearward facing edges 1922 and 1924 there are preferably formed a pair of mutually spaced inwardly directed toothed syringe retaining protrusions 1925.

Each of mounting arms 1918 and 1920 is formed with a generally U-shaped outer facing protrusion 1926 adjacent respective edges 1922 and 1924. Each of mounting arms 1918 and 1920 is formed with a rearward-facing flexible finger 1928 and a rearward slot 1930 as well as a pair of narrow slots 1932 and 1933, forwardly of which are formed tapered surfaces 1934 and 1935 respectively.

Rearward-facing flexible finger 1928 preferably is formed with an outwardly-facing protrusion 1936 having a forwardly-facing tapered surface 1938 and a rearwardly-facing tapered surface 1940 joined at an outermost flat surface 1942.

Each of mounting arms 1918 and 1920 is preferably formed with an axial inwardly-facing surface 1943, which together with side ribs 1944 defines a channel 1945.

Mounting arm 1918 is formed with respective forward and rearward resilient finger portions 1946 and 1948. Mounting arm 1920 is formed with respective forward and rearward resilient finger portions 1956 and 1958.

Finger portions 1946, 1948, 1956 and 1958 each include an outwardly-facing protrusion 1960 having a forward-facing surface 1962, a rearward-facing tapered surface 1964 and a rearward facing edge 1966.

Reference is now made to FIGS. 30A-30C, which are simplified pictorial illustrations of forward needle depth adjustment element 220 (FIG. 2B) forming part of the medicament module as seen in FIG. 2B and a sectional illustration of forward needle depth adjustment element 220, section line being taken along lines C-C in FIG. 30A.

As seen in FIGS. 30A and 30B, forward needle depth adjustment element 220 includes a generally cylindrical portion 1970 having an internal screw threading 1971, a generally ring-like rearward edge 1972 and a forward edge 1973 having a pair of cut-outs 1974. An inner cylindrical surface of forward needle depth adjustment element 220 is formed with a circumferential undercut 1975 disposed adjacent the rearward end 1972 and pair of generally oppositely directed recesses 1976. An outer cylindrical surface 1977 of forward needle depth adjustment element 220 preferably has a surface configuration which assists gripping thereof.

Reference is now made to FIGS. 31A and 31B, which are simplified pictorial illustrations of rearward needle depth adjustment element 230 (FIG. 2B) forming part of the medicament module as seen in FIG. 2B.

As seen in FIGS. 31A and 31B, rearward needle depth adjustment element 230 includes a generally cylindrical portion 1978 having a generally circular cylindrical hollow bore and a pair of rearwardly extending arms 1979. The generally cylindrical portion 1978 and part of arms 1979 have an external screw threading 1980 formed thereon. Generally cylindrical portion 1978 has a generally ring-like forwardly-directed injection site contact edge 1981.

Rearwardly extending arms 1979 each define a pair of outwardly extending mutually spaced generally rectangular protrusions 1982, forwardly of each of which is formed a somewhat rounded protrusion 1983. An outer cylindrical surface 1984 of generally cylindrical portion 1978 is preferably formed with a visually sensible scale 1985, which is useful in indicating a setting of an injection depth.

Figure 32D:
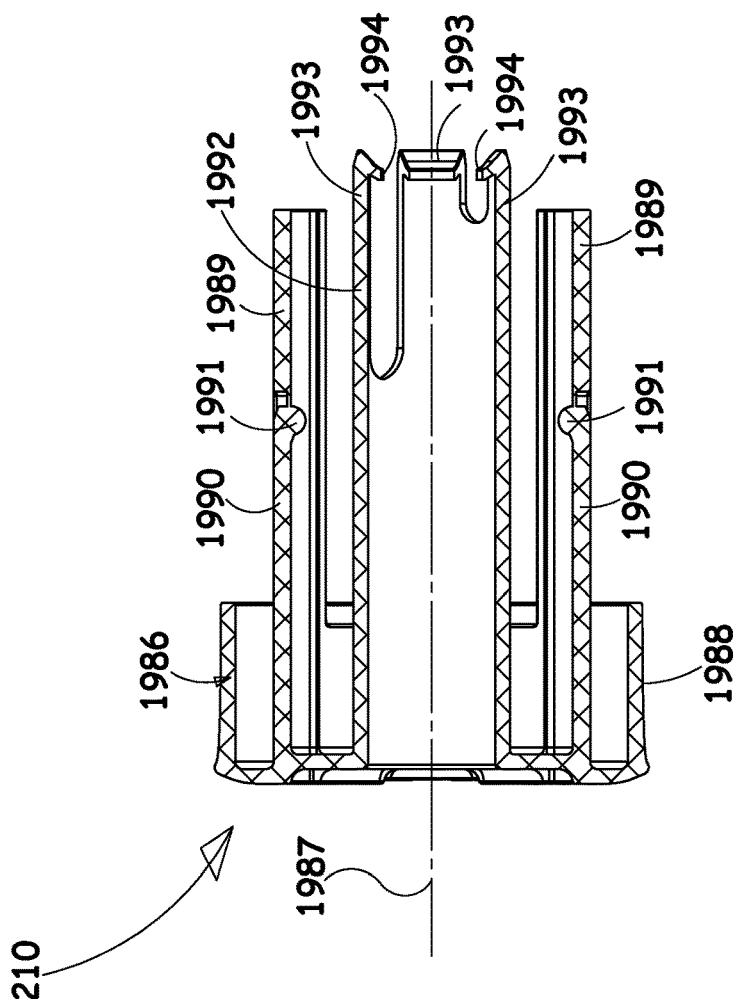
Figure 32C:
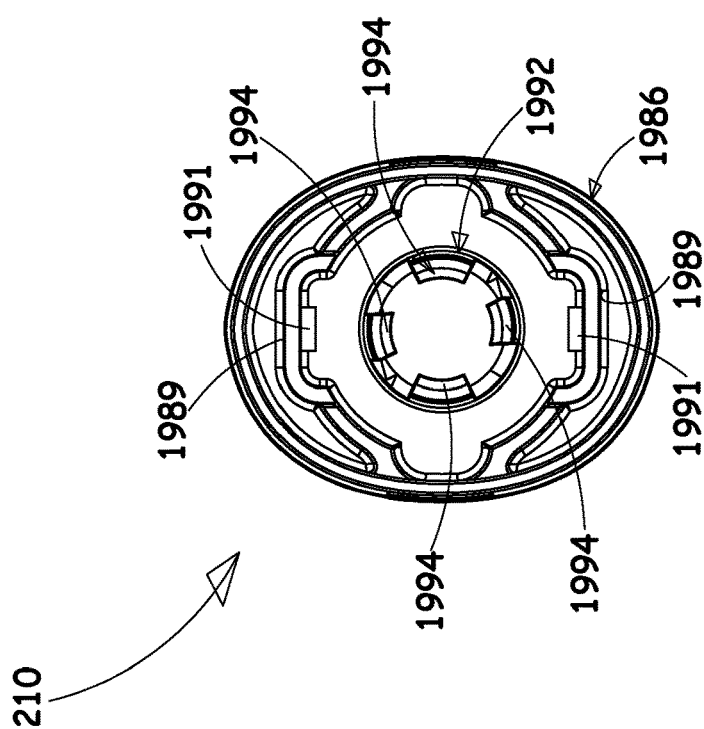

Reference is now made to FIGS. 32A, 32B, 32C and 32D, which are simplified respective first and second perspective views, end view and a sectional view taken along lines D-D in FIG. 32A showing RNS remover 210, forming part of a medicament module as shown in FIGS. 2A & 2B.

As seen in FIGS. 32A-32D, the RNS remover 210 preferably is an integrally formed element preferably injection molded of plastic and includes a generally tubular portion 1986, preferably of oval cross section, arranged about a longitudinal axis 1987, which is normally coaxial with longitudinal axis 1510 of module housing 1500, when the RNS remover 210 is operatively engaged with the module housing 1500. Tubular portion 1986 defines external oval cylindrical user finger engagement surface 1988.

RNS remover 210 preferably includes a pair of generally rectangular rearward arms 1989 which extend rearward of the generally tubular portion 1986 Arms are each formed with a rearwardly-extending resilient finger 1990 having inwardly-facing protrusions 1991.

Extending rearwardly from tubular portion 1986 between arms 1989 is a generally circularly cylindrical hollow tube portion 1992 having an opening therethrough and defining a plurality of azimuthally distributed rearwardly facing inner fingers 1993, each having an inwardly directed protrusion 1994.

Figure 33B:
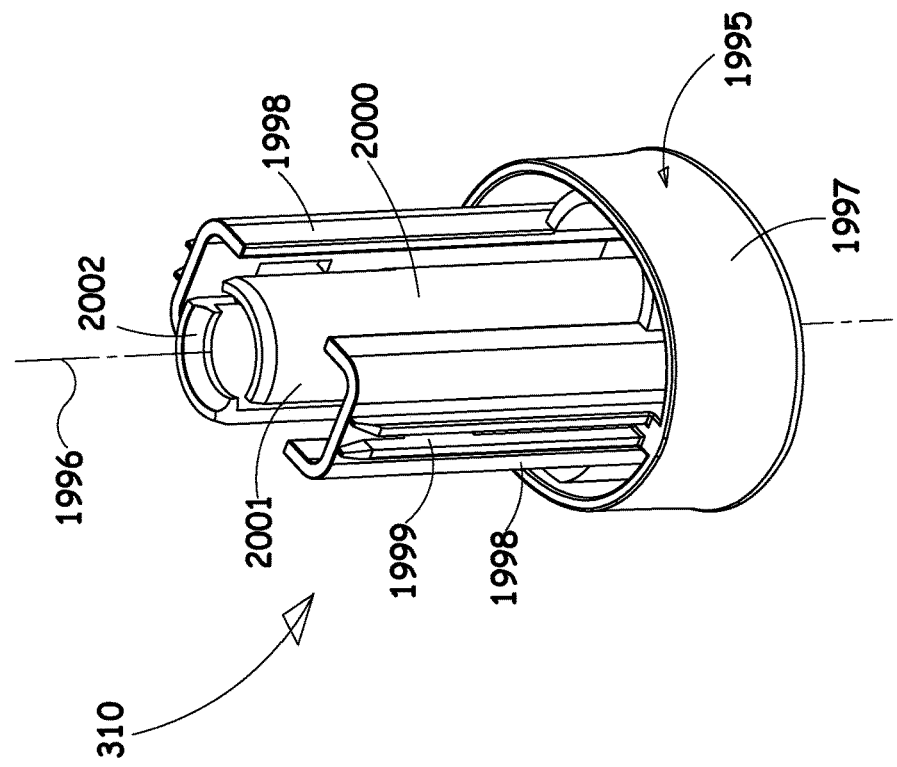
FIGS. 33A, 33B, 33C and 33D are simplified respective first and second perspective views, end view and a sectional view taken along lines D-D in FIG. 33A showing a RNS remover, preferably forming part of a medicament module as in FIGS. 3A & 3B.
Figure 33A:
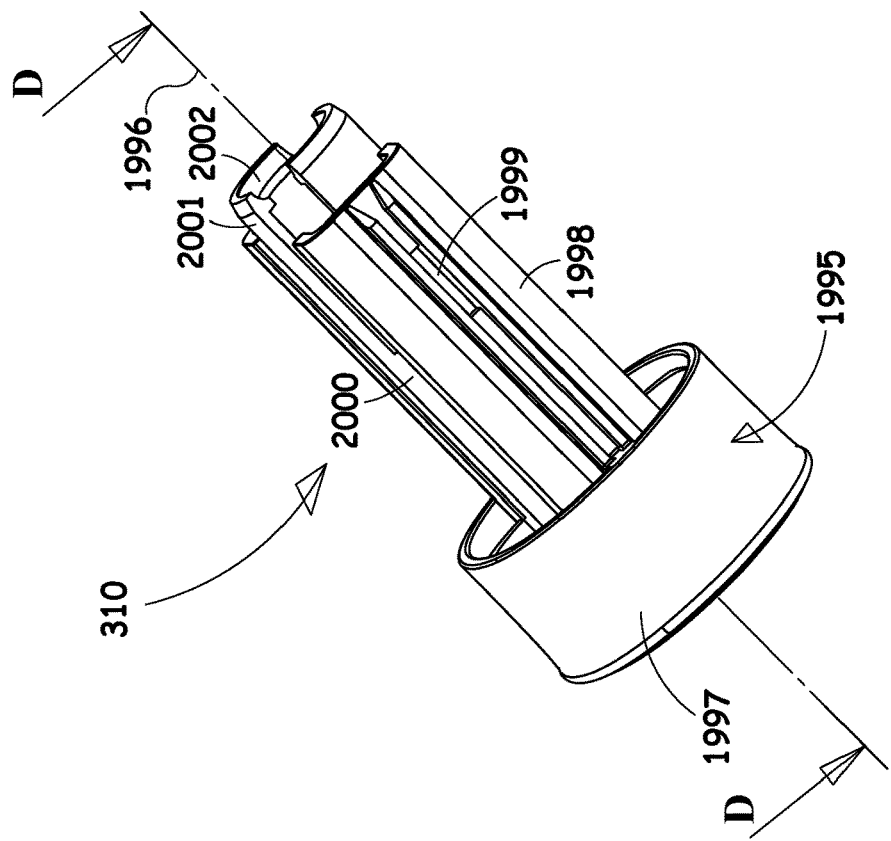
Figure 33D:
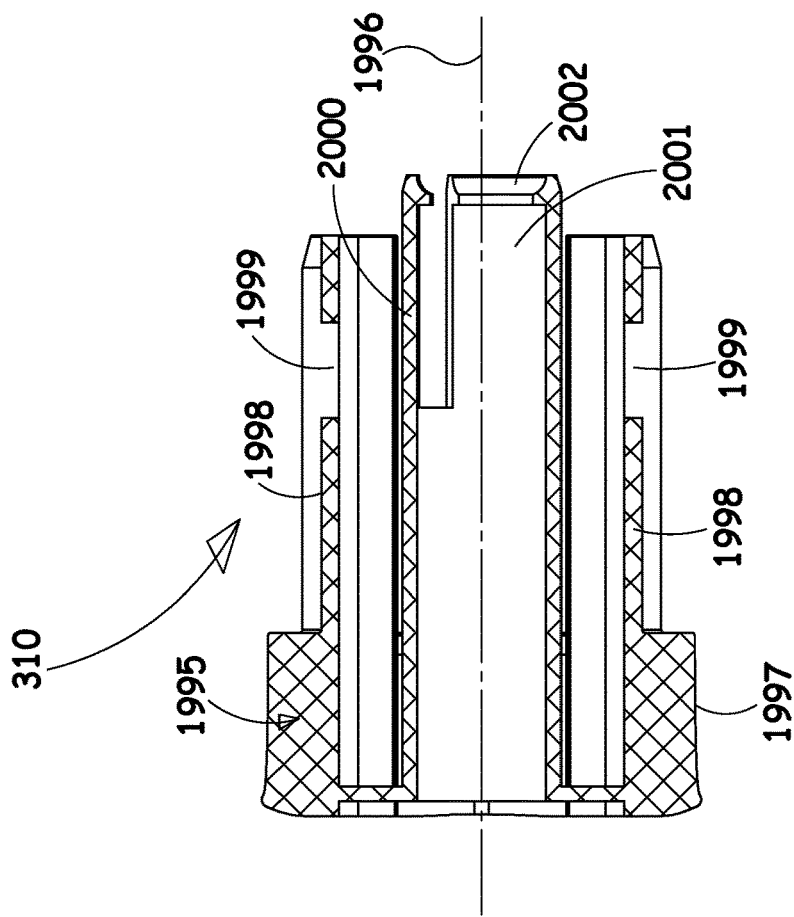
Figure 33C:
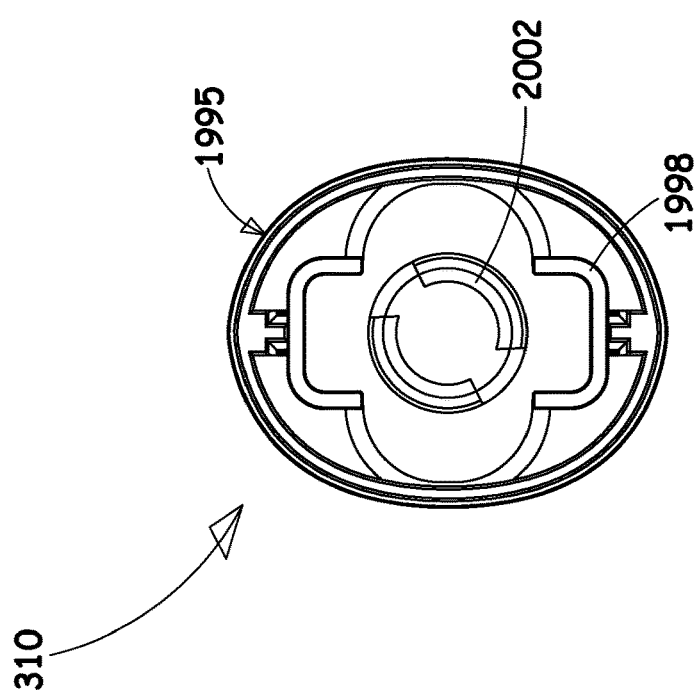

Reference is now made to FIGS. 33A, 33B, 33C and 33D, which are simplified respective first and second perspective views, end view and a sectional view taken along lines D-D in FIG. 33A showing RNS remover 310 forming part of a medicament module as seen in FIGS. 3A & 3B.

As seen in FIGS. 33A-33D, the RNS remover 310 preferably is an integrally formed element preferably injection molded of plastic and includes a generally tubular hollow portion 1995 having an opening therethrough, preferably of oval cross section, arranged about a longitudinal axis 1996, which is normally coaxial with longitudinal axis 1510 of module housing 1500, when the RNS remover 310 is operatively engaged with the module housing 1500. Tubular portion 1995 defines external oval cylindrical user finger engagement surface 1997.

RNS remover 310 preferably includes a pair of generally rectangular rearward arms 1998 which extend rearward of the generally tubular portion 1995 Arms are each formed with an aperture 1999. Extending rearwardly from tubular portion 1995 between arms 1998 is a generally circularly cylindrical tubular portion 2000 defining a plurality of azimuthally distributed rearwardly facing inner fingers 2001, each having an inwardly directed protrusion 2002.

Reference is now made to FIGS. 34A, 34B, 34C and 34D, which are simplified drawings of one embodiment of a medicament module of FIGS. 2A & 2B in a "storage" operative orientation.

FIGS. 34A and 34B are respective top and side views of medicament module 200 (FIGS. 2A and 2B) including needle shield 250. FIGS. 34C & 34D are sectional illustrations taken along respective lines C-C and D-D in FIGS. 34A and 34B respectively.

FIGS. 34A-34D particularly illustrate the structural relationship of needle shield 250 (FIGS. 26A-26G) and module housing 1500 (FIGS. 25A-25G), as well as the structural relationship between RNS remover 210 (FIGS. 32A-32D), forward needle depth adjustment element 220 (FIGS. 30A & 30B) and a rearward needle depth adjustment element 230 (FIGS. 31A & 31B).

As seen particularly in FIGS. 34A-34D, needle shield 250 is located generally inside and coaxial with module housing 1500, such that respective axes 1510 and 1610 are coaxial.

It is also seen that in a "storage" operative orientation, the needle shield 250 is fixedly retained in the module housing 1500 against axial relative movement therebetween. Needle shield 250 is retained against forward axial displacement relative to module housing 1500 along coaxial axes 1510 and 1610 by engagement of protrusions 1626 at the rearward end of the needle shield 250 in cutouts 1503 at the edge 1502 of the module housing 1500.

It is seen in FIGS. 34A-34D that needle shield 250 is retained against forward or rearward axial displacement relative to module housing 1500 along coaxial axes 1510 and 1610 by engagement of protrusions 1660 of finger protrusions 1646 and 1656 of needle shield 250 in slots 1560 and 1562 of the module housing. Additionally, needle shield 250 is retained against rearward or forward axial displacement relative to module housing 1500 along coaxial axes 1510 and 1610 by engagement of protrusions 1660 of finger protrusions 1648 and 1658 of needle shield 250 in slots 1564 and 1566 of the module housing.

Additionally it is seen that protrusions 1582 and 1584 on fingers 1516 and 1518 respectively of module housing 1500 are seated in narrow slots 1632 and 1633 of the needle shield 250.

It is further seen that rearwardly extending arms 1979 of rearward needle depth adjustment element 230 lie in channels 1640 of needle shield 250. It is also seen that internal screw threading 1971 of forward needle depth adjustment element 220 is threadably engaged with external screw threading 1980 of rearward needle depth adjustment element 230.

It is also seen that RNS remover 210 is arranged is located generally forwardly of the module housing 1500 and both inside and outside of needle shield 250 and coaxially therewith such that, respective axes 1987, 1510 and 1610 are coaxial. More specifically, generally circularly cylindrical tube portion 1992 of RNS remover 210 is located in the generally circular cylindrical hollow bore of rearward needle depth adjustment element 230 and rearwardly thereof in the generally circular cylindrical hollow bore of needle shield 250.

It is additionally seen that the generally rectangular arms 1989 of RNS remover 210 are located outside and partially enclosing side mounting arms 1618 and 1620 of needle shield 250.

It is further seen that protrusions 1991 of RNS remover 210 are seated in corresponding recesses 1628 of the needle shield 250.

It is seen that forward needle depth adjustment element 220 is fixedly attached to needle shield 250 by means of snap fit engagement between partially circumferential rim 1612 of needle shield 250 and recesses 1976 of forward needle depth adjuster 220.

Reference is now made to FIGS. 35A, 35B, 35C and 35D, which are simplified drawings of another embodiment of a medicament module of FIGS. 2A & 2B in a "storage" operative orientation. This embodiment of a medicament module includes syringe 242 and a removable needle shield 244.

FIGS. 35A and 35B are respective top and side views of medicament module 200 (FIGS. 2A and 2B) including needle shield 240. FIGS. 35C & 35D are sectional illustrations taken along respective lines C-C and D-D in FIGS. 35A and 35B respectively.

FIGS. 35A-35D particularly illustrate the structural relationship of needle shield 240 (FIGS. 27A-27G) and module housing 1500 (FIGS. 25A-25G), as well as the structural relationship between RNS remover 210 (FIGS. 32A-32D), forward needle depth adjustment element 220 (FIGS. 30A & 30B) and a rearward needle depth adjustment element 230 (FIGS. 31A & 31B).

As seen particularly in FIGS. 35A-35D, needle shield 240 is located generally inside and coaxial with module housing 1500, such that respective axes 1510 and 1710 are coaxial.

It is also seen that in a "storage" operative orientation, the needle shield 240, is fixedly retained in the module housing 1500 against axial relative movement therebetween. Needle shield 240 is retained against forward axial displacement relative to module housing 1500 along coaxial axes 1510 and 1710 by engagement of protrusions 1726 at the rearward end of the needle shield 240 in cutouts 1503 at the edge 1502 of the module housing 1500.

It is additionally seen that syringe 242 is fixedly retained against rearward axial motion along axis 1710 relative to needle shield 240 and module housing 1500 by engagement of protrusion 1725 of needle shield 240 with flange 248 of syringe 242.

It is further seen that syringe 242 is fixedly retained against forward axial motion along axis 1710 relative to needle shield 240 and module housing 1500 by engagement of flange 248 of syringe 242 with rearwardly-facing surfaces 1508 of bulkheads 1506 of module housing 1500.

It is seen in FIGS. 35A-35D that needle shield 240 is retained against forward or rearward axial displacement relative to module housing 1500 along coaxial axes 1510 and 1710 by engagement of protrusions 1760 of finger protrusions 1746 and 1756 of needle shield 240 in slots 1560 and 1562 of the module housing. Additionally, needle shield 240 is retained against rearward or forward axial displacement relative to module housing 1500 along coaxial axes 1510 and 1710 by engagement of protrusions 1760 of finger protrusions 1748 and 1758 of needle shield 240 in slots 1564 and 1566 of the module housing.

Additionally it is seen that protrusions 1582 and 1584 on fingers 1516 and 1518 respectively of module housing 1500 are seated in narrow slots 1732 and 1733 of the needle shield 240.

It is further seen that rearwardly extending arms 1979 of rearward needle depth adjustment element 230 lie in channels 1740 of needle shield 240. It is also seen that internal screw threading 1971 of forward needle depth adjustment element 220 is threadably engaged with external screw threading 1980 of rearward needle depth adjustment element 230.

It is also seen that RNS remover 210 is arranged is located generally forwardly of the module housing 1500 and both inside and outside of needle shield 240 and coaxially therewith such that, respective axes 1987, 1510 and 1710 are coaxial. More specifically, generally circularly cylindrical tube portion 1992 of RNS remover 210 is located in the generally circular cylindrical hollow bore of rearward needle depth adjustment element 230 and rearwardly thereof in the generally circular cylindrical hollow bore of needle shield 240. Generally circularly cylindrical tube portion 1992 of RNS remover 210 generally surrounds attachably engages removable needle cover 244 by virtue of the engagement of inwardly directed protrusion 1994 of RNS remover 210 with a rearward edge of removable needle cover 244.

It is additionally seen that the generally rectangular arms 1989 of RNS remover 210 are located outside and partially enclosing side mounting arms 1718 and 1720 of needle shield 240.

It is further seen that protrusions 1991 of RNS remover 210 are seated in corresponding recesses 1728 of the needle shield 240.

It is seen that forward needle depth adjustment element 220 is fixedly attached to needle shield 250 by means of snap fit engagement between partially circumferential rim 1712 of needle shield 250 and recesses 1976 of forward needle depth adjuster 220.

Reference is now made to FIGS. 36A, 36B, 36C and 36D, which are simplified drawings of one embodiment of a medicament module of FIGS. 3A & 3B in a "storage" operative orientation.

Figure 36A:
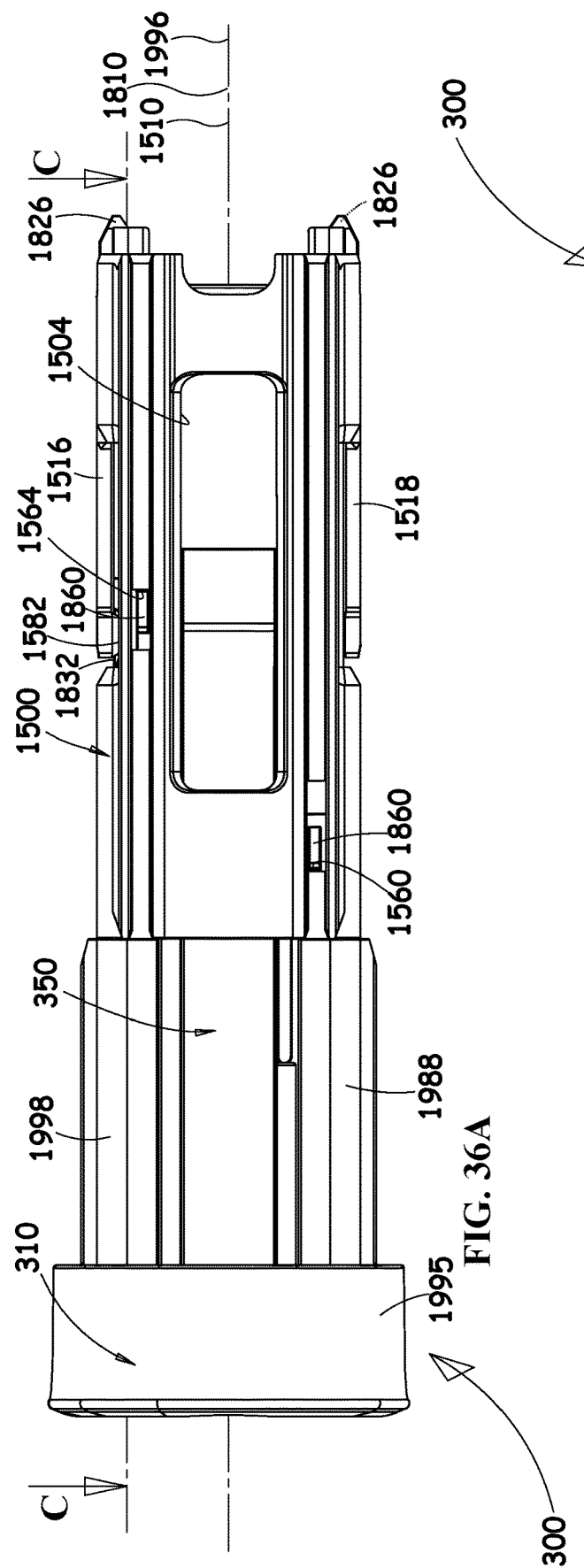
Figure 36B:
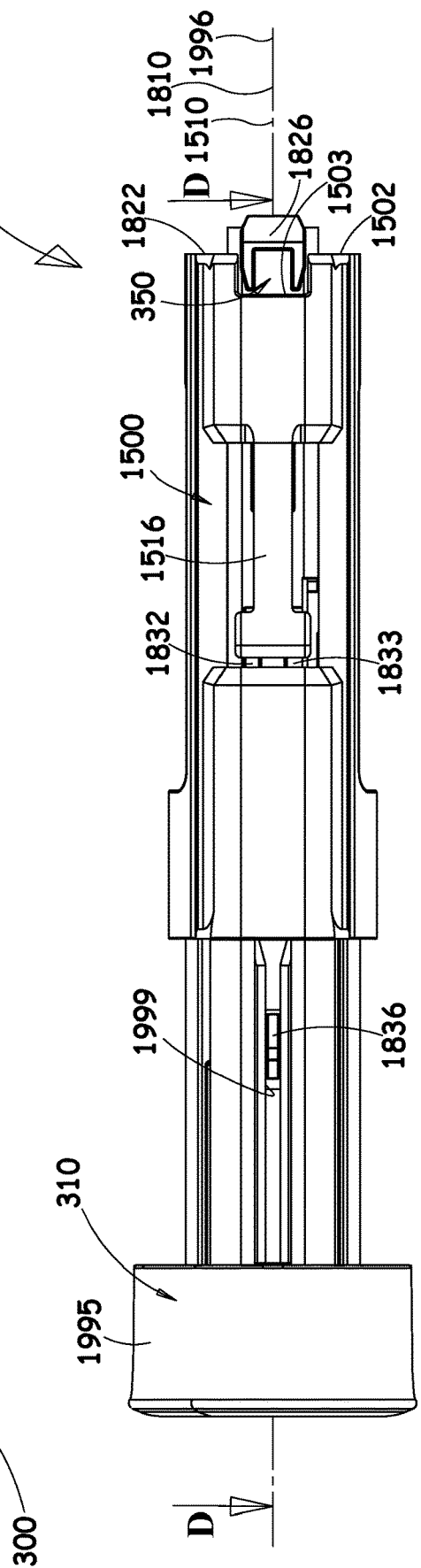

FIGS. 36A and 36B are respective top and side views of medicament module 300 (FIGS. 3A and 3B) including needle shield 350. FIGS. 36C & 36D are sectional illustrations taken along respective lines C-C and D-D in FIGS. 36A and 36B respectively.

FIGS. 36A-36D particularly illustrate the structural relationship of needle shield 350 (FIGS. 28A-28G), module housing 1500 (FIGS. 25A-25G) and RNS remover 310 (FIGS. 33A-33D)

As seen particularly in FIGS. 36A-36D, needle shield 350 is located generally inside and coaxial with module housing 1500, such that respective axes 1510 and 1810 are coaxial.

It is also seen that in a "storage" operative orientation, the needle shield 350 is fixedly retained in the module housing 1500 against axial relative movement therebetween. Needle shield 350 is retained against forward axial displacement relative to module housing 1500 along coaxial axes 1510 and 1810 by engagement of protrusions 1826 at the rearward end of the needle shield 350 in cutouts 1503 at the edge 1502 of the module housing 1500.

It is seen in FIGS. 36A-36D that needle shield 350 is retained against forward or rearward axial displacement relative to module housing 1500 along coaxial axes 1510 and 1810 by engagement of protrusions 1860 of finger protrusions 1846 and 1856 of needle shield 350 in slots 1560 and 1562 of the module housing. Additionally, needle shield 350 is retained against rearward or forward axial displacement relative to module housing 1500 along coaxial axes 1510 and 1810 by engagement of protrusions 1860 of finger protrusions 1848 and 1858 of needle shield 350 in slots 1564 and 1566 of the module housing.

Additionally it is seen that protrusions 1582 and 1584 on fingers 1516 and 1518 respectively of module housing 1500 are seated in narrow slots 1832 and 1833 of the needle shield 350.

It is also seen that RNS remover 310 is arranged is located generally forwardly of the module housing 1500 and both inside and outside of needle shield 350 and coaxially therewith such that, respective axes 1996, 1510 and 1810 are coaxial. More specifically, generally circularly cylindrical tube portion 2000 of RNS remover 310 is located in the generally circular cylindrical hollow bore of needle shield 350.

It is additionally seen that the generally rectangular arms 1998 of RNS remover 310 are located outside and partially enclosing side mounting arms 1818 and 1820 of needle shield 350.

It is further seen that outwardly-facing protrusions 1836 of rearward-facing flexible fingers 1828 of the needle shield 350 are seated in apertures 1999 of RNS remover 310, thereby locking RNS remover 310 onto needle shield 350.

Reference is now made to FIGS. 37A, 37B, 37C and 37D, which are simplified drawings of another embodiment of a medicament module of FIGS. 3A & 3B in a "storage" operative orientation. This embodiment of a medicament module includes syringe 342 and a removable needle shield 344 surrounding a needle 346, which extends forwardly of a syringe flange 348.

Figure 37A:
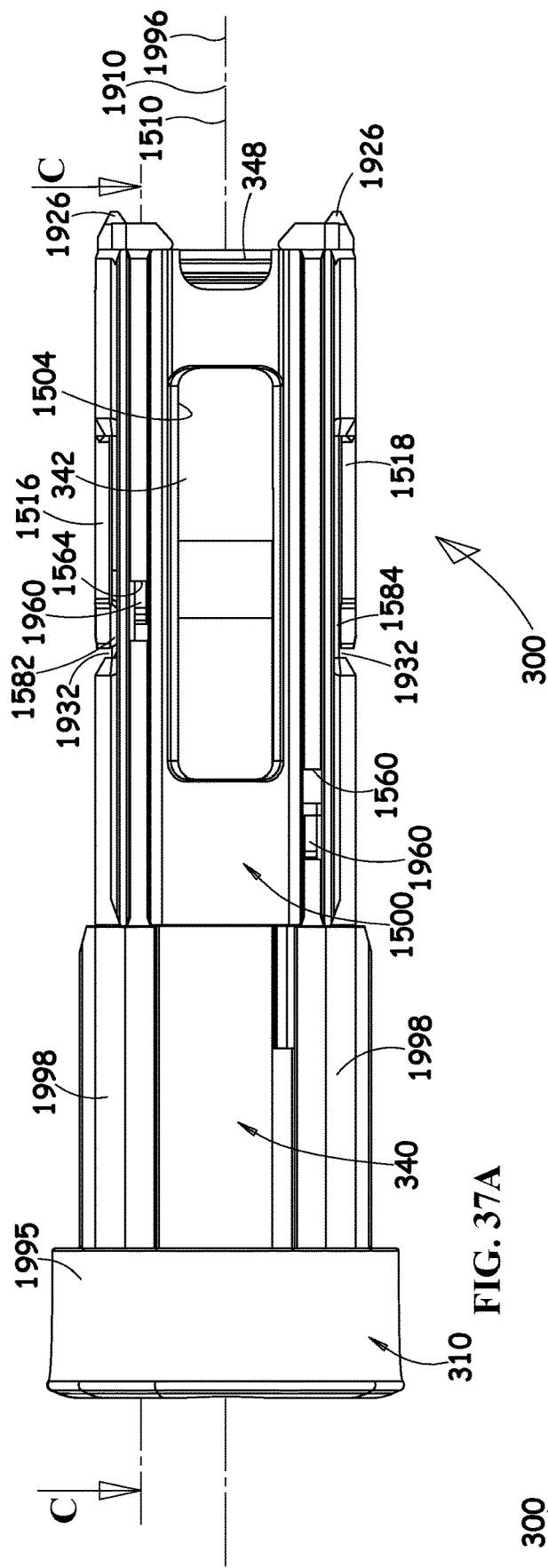
FIGS. 37A, 37B, 37C and 37D are simplified drawings of another embodiment of a medicament module of FIGS. 3A & 3B in a "storage" operative orientation.
Figure 37B:
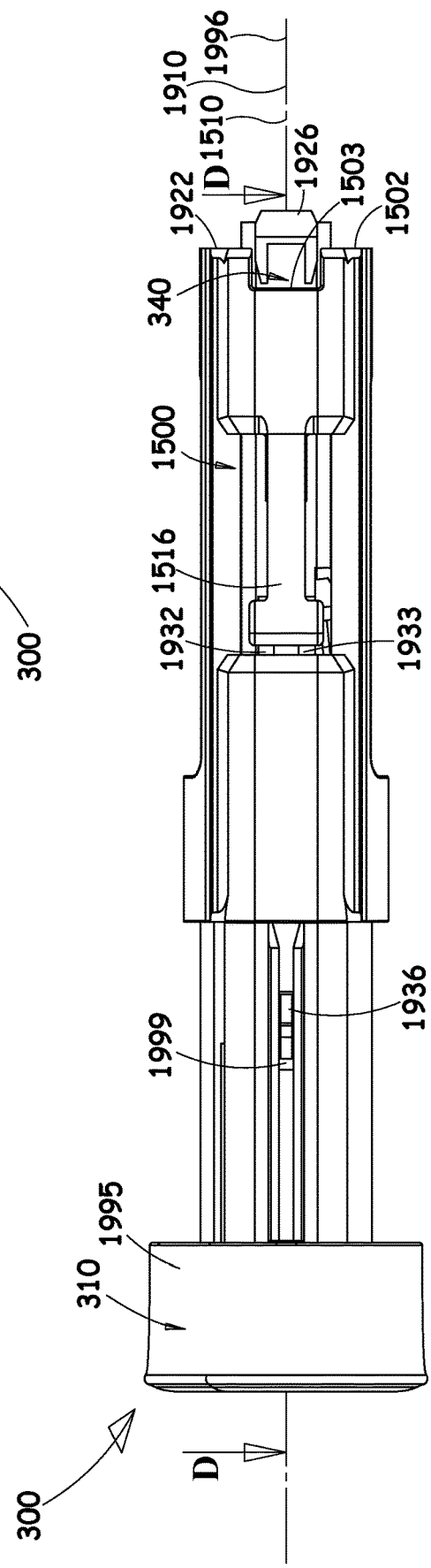
Figure 37C:
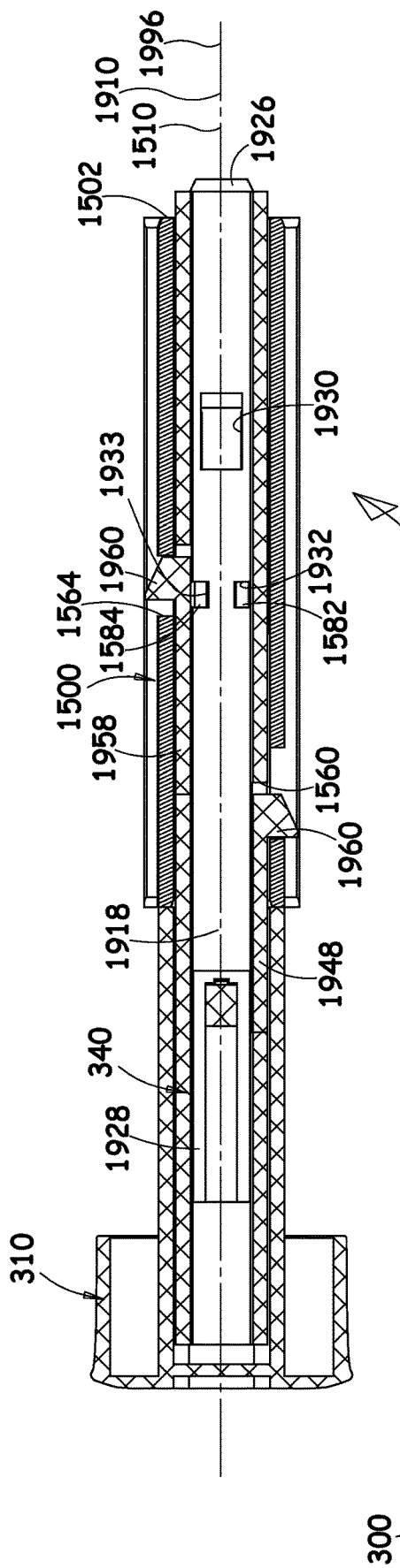
Figure 37D:
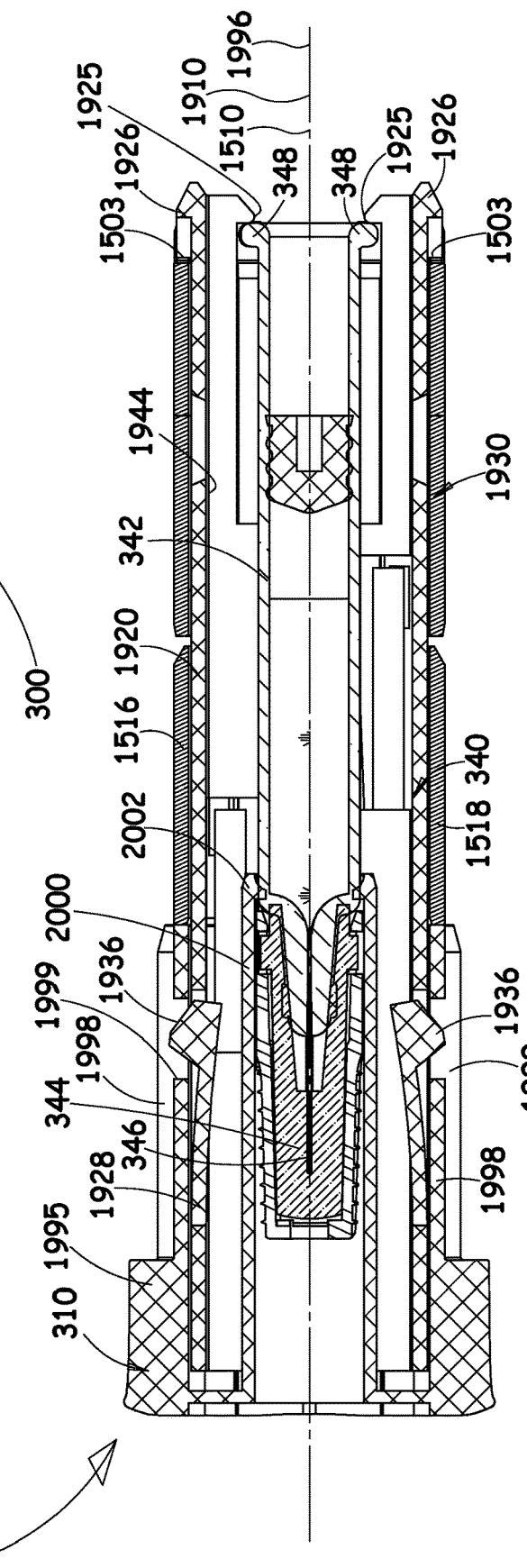

FIGS. 37A and 37B are respective top and side views of medicament module 300 (FIGS. 3A and 3B) including needle shield 340. FIGS. 37C & 37D are sectional illustrations taken along respective lines C-C and D-D in FIGS. 37A and 37B respectively.

FIGS. 37A-37D particularly illustrate the structural relationship of needle shield 340 (FIGS. 29A-29G), module housing 1500 (FIGS. 25A-25G) and RNS remover 310 (FIGS. 33A-33D)

As seen particularly in FIGS. 37A-37D, needle shield 340 is located generally inside and coaxial with module housing 1500, such that respective axes 1510 and 1910 are coaxial.

It is also seen that in a "storage" operative orientation, the needle shield 340, is fixedly retained in the module housing 1500 against axial relative movement therebetween. Needle shield 340 is retained against forward axial displacement relative to module housing 1500 along coaxial axes 1510 and 1910 by engagement of protrusions 1926 at the rearward end of the needle shield 340 in cutouts 1503 at the edge 1502 of the module housing 1500.

It is additionally seen that syringe 342 is fixedly retained against rearward axial motion along axis 1910 relative to needle shield 340 and module housing 1500 by engagement of protrusion 1925 of needle shield 340 with flange 348 of syringe 342.

It is further seen that syringe 342 is fixedly retained against forward axial motion along axis 1910 relative to needle shield 340 and module housing 1500 by engagement of flange 348 of syringe 342 with rearwardly-facing surfaces 1508 of bulkheads 1506 of module housing 1500.

It is seen in FIGS. 37A-37D that needle shield 340 is retained against forward or rearward axial displacement relative to module housing 1500 along coaxial axes 1510 and 1910 by engagement of protrusions 1960 of finger protrusions 1946 and 1956 of needle shield 340 in slots 1560 and 1562 of the module housing. Additionally, needle shield 340 is retained against rearward or forward axial displacement relative to module housing 1500 along coaxial axes 1510 and 1910 by engagement of protrusions 1960 of finger protrusions 1948 and 1958 of needle shield 340 in slots 1564 and 1566 of the module housing.

Additionally it is seen that protrusions 1582 and 1584 on fingers 1516 and 1518 respectively of module housing 1500 are seated in narrow slots 1932 and 1933 of the needle shield 340.

It is also seen that RNS remover 310 is arranged is located generally forwardly of the module housing 1500 and both inside and outside of needle shield 340 and coaxially therewith such that, respective axes 1996, 1510 and 1910 are coaxial. More specifically, generally circularly cylindrical tube portion 2000 of RNS remover 310 is located in the generally circular cylindrical hollow bore of needle shield 340. Generally circularly cylindrical tube portion 2000 of RNS remover 310 generally surrounds attachably engages removable needle cover 344 by virtue of the engagement of inwardly directed protrusion 2002 of RNS remover 310 with a rearward edge of removable needle cover 344.

It is additionally seen that the generally rectangular arms 1998 of RNS remover 310 are located outside and partially enclosing side mounting arms 1918 and 1920 of needle shield 340.

It is further seen that protrusions 1936 of rearward-facing flexible fingers 1928 of needle shield 340 are seated in corresponding apertures 1999 of the RNS remover 310, thereby locking the needle shield 340 to the RNS remover 310.

Reference is now made to FIGS. 38A, 38B, 38C and 38D, which are simplified illustrations of preparatory steps required prior insertion of the medicament module 200 of FIGS. 34A-34D into operative engagement with the reusable injection assembly 100 of FIGS. 1A-24C.

Figure 38B:
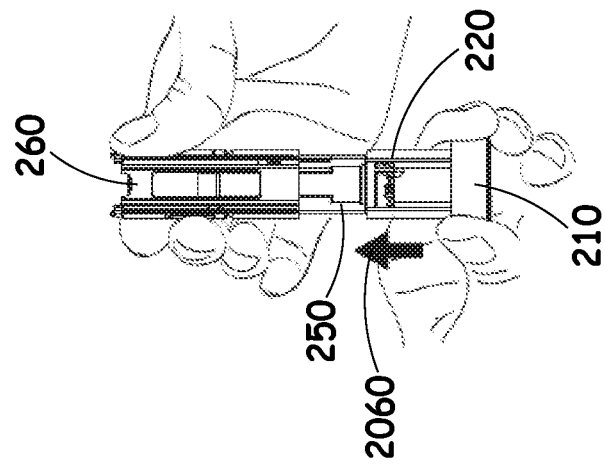
FIGS. 38A, 38B, 38C and 38D are simplified illustrations of preparatory steps required prior insertion of the medicament module of FIGS. 34A-34D into operative engagement with the reusable injection assembly of FIGS. 1A-24C.
Figure 38A:
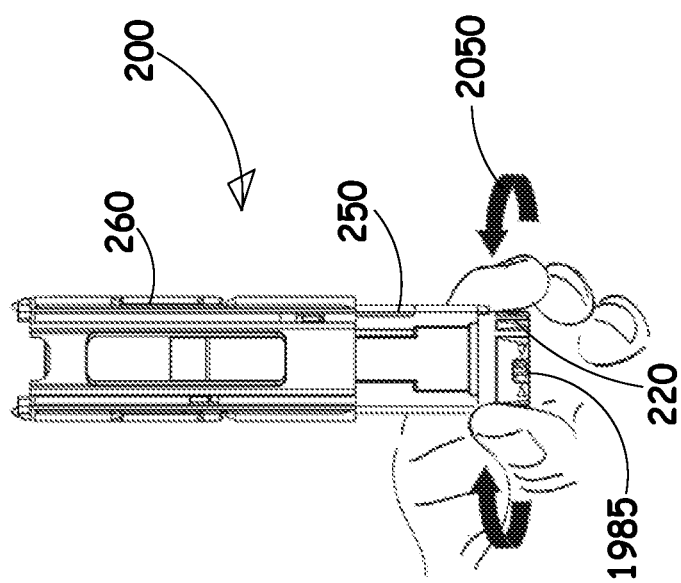

It is seen in FIG. 38A that a user rotates forward needle depth adjustment element 220 of medicament module 200 in a direction indicated by an arrow 2050, so that the desired injection depth is indicated on the visually sensible scale 1985.

It is further seen in FIG. 38B that following injection depth adjustment, the user places the RNS remover 210 onto the medicament module 200 in a direction indicated by an arrow 2060.

Figure 38D:
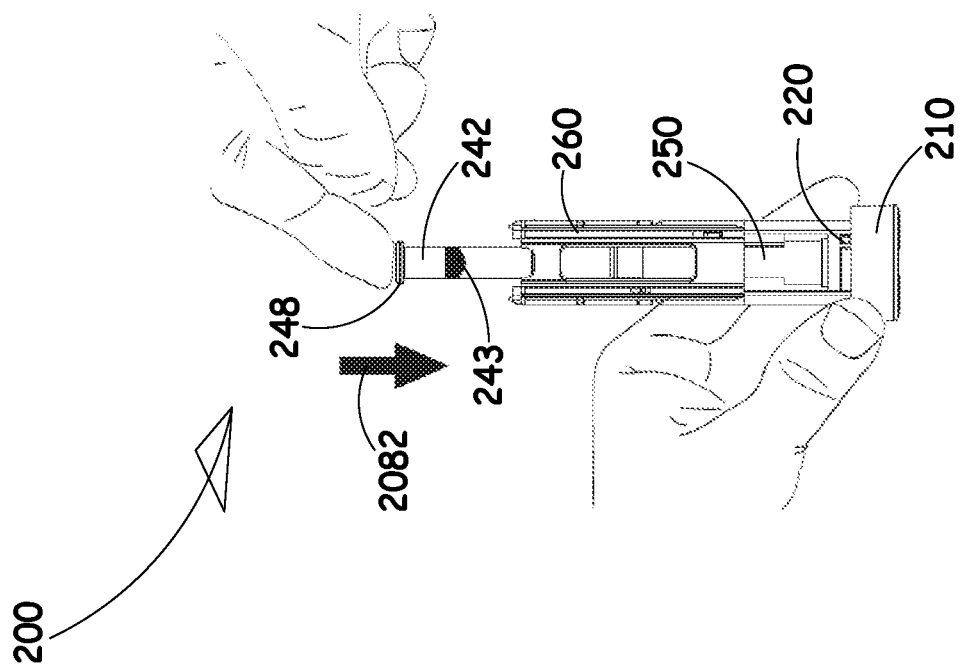
Figure 38C:
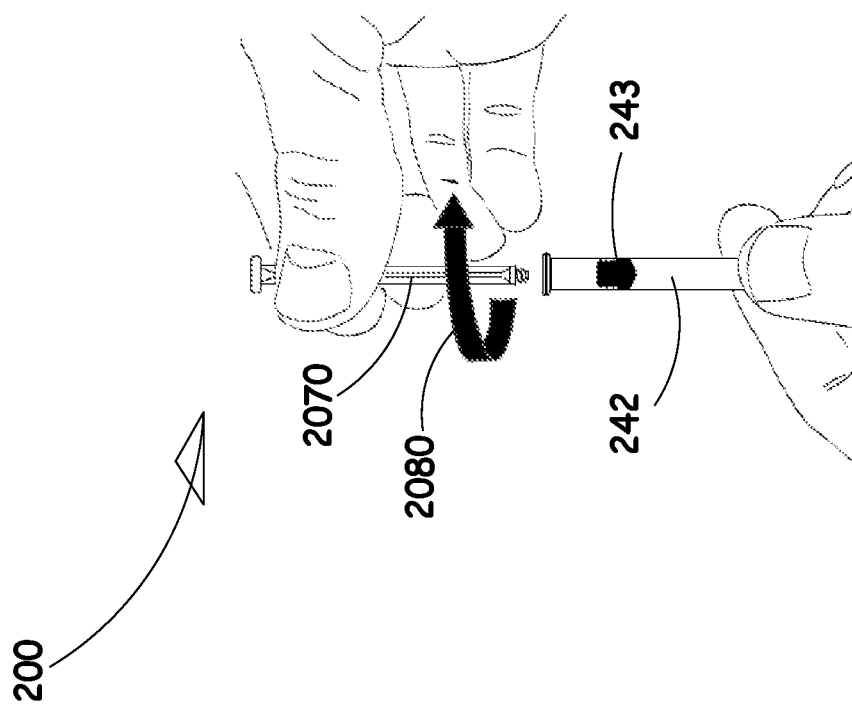

An additional preparatory step required prior to insertion of the medicament module 200 of FIGS. 34A-34D into operative engagement with the reusable injection assembly 100 is seen in FIG. 38C, where the user detaches a standard plunger rod 2070 from the piston 243 of syringe 242 in a direction indicated by an arrow 2080.

It is additionally seen in FIG. 38D that the syringe 242 without the plunger rod 2070 is placed by the user into the medicament module 200 in the direction indicated by an arrow 2082. At this stage, the medicament module 200 of FIGS. 34A-34D is ready for insertion into operative engagement with the reusable injection assembly 100.

Reference is now made to FIGS. 39A and 39B, which are simplified illustrations of preparatory steps required prior insertion of the medicament module 200 of FIGS. 35A-35D into operative engagement with the reusable injection assembly of FIGS. 1A-24C.

It is seen in FIG. 39A that a user rotates forward needle depth adjustment element 220 of medicament module 200 in a direction indicated by an arrow 2050, so that the desired injection depth is indicated on the visually sensible scale 1985.

It is further seen in FIG. 39B that following injection depth adjustment, the user places the RNS remover 210 onto the medicament module 200 in a direction indicated by an arrow 2060. As distinguished from FIGS. 38A-38D, the medicament module 200 of FIGS. 35A-35D already retains syringe 242 within the medicament module 200, due to engagement of flange 248 with syringe retaining protrusions 1725 of needle shield 240. At this stage, the medicament module 200 of FIGS. 35A-35D is ready for insertion into operative engagement with the reusable injection assembly 100.

Figure 40B:
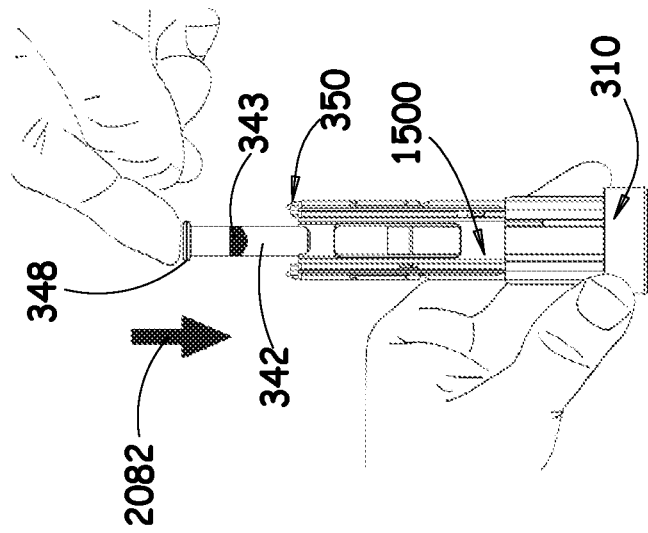
FIGS. 40A and 40B are simplified illustrations of preparatory steps required prior insertion of the medicament module of FIGS. 36A-36D into operative engagement with the reusable injection assembly of FIGS. 1A-24C.
Figure 40A:
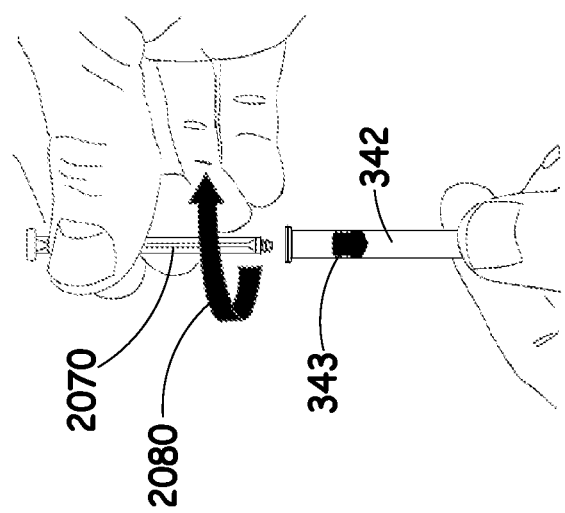

Reference is now made to FIGS. 40A and 40B, which are simplified illustrations of preparatory steps required prior insertion of the medicament module 300 of FIGS. 36A-36D into operative engagement with the reusable injection assembly 100 of FIGS. 1A-24C.

The medicament module 300 of FIGS. 36A-36D does not include a needle depth adjustment function, thus it is preferably supplied with the RNS remover 310 already assembled and preferably locked to needle shield 350.

The first preparatory step required for use of medicament module 300 of FIGS. 36A-36D is seen in FIG. 40A, where the user detaches standard plunger rod 2070 from the piston 343 of syringe 342 in a direction indicated by an arrow 2080.

It is additionally seen in FIG. 40B that the syringe 342 without the plunger rod 2070 is placed by the user into the medicament module 300 in the direction indicated by an arrow 2082. At this stage, the medicament module 300 of FIGS. 36A-36D is ready for insertion into operative engagement with the reusable injection assembly 100.

Figure 41:
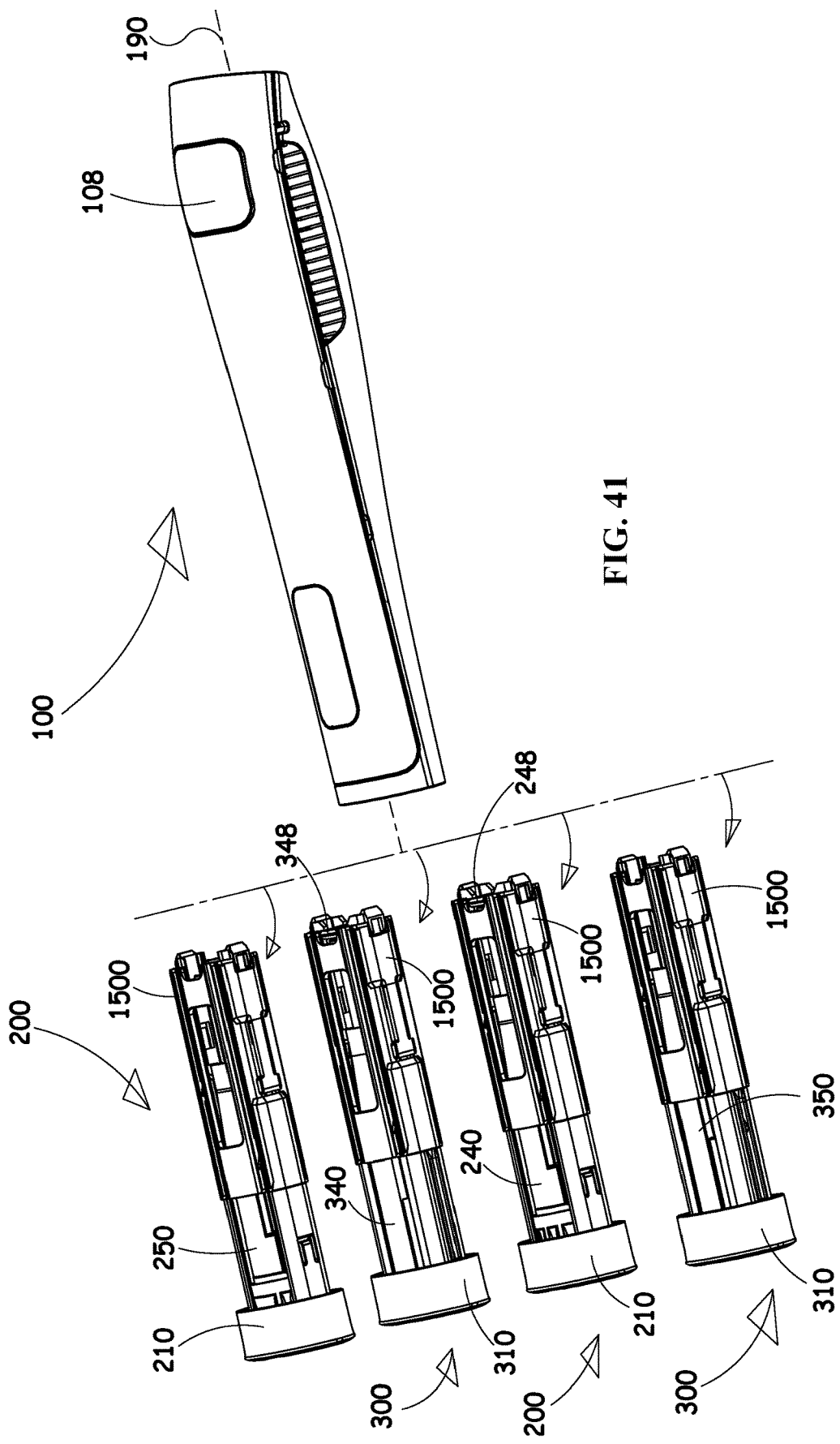
FIG. 41 is a simplified drawing illustrating the reusable automatic injection assembly of FIGS. 1A-24C and the four alternative embodiments of medicament modules shown in FIGS. 2A-3B, just prior to operative engagement of a medicament module with the reusable automatic injection assembly.

Reference is now made to FIG. 41, which is a simplified drawing illustrating the reusable automatic injection assembly 100 of FIGS. 1A-24C and the four alternative embodiments of medicament modules shown in FIGS. 2A-3B, just prior to operative engagement of a medicament module with the reusable automatic injection assembly 100.

It is seen in FIG. 41 that preferably four different medicament modules 200 of FIGS. 34A-34D, 200 of FIG. 35A-35D, 300 of FIGS. 36A-36D and 300 of FIGS. 37A-37D can be inserted into operative engagement with the reusable injection assembly 100 of FIGS. 1A-24C.

It is appreciated that several preparatory steps are required before insertion of medicament module 200 of FIGS. 34A-34D into the reusable injection assembly 100, as detailed with reference to FIGS. 38A-38D. Several preparatory steps are required before insertion of medicament module 200 of FIGS. 35A-35D into the reusable injection assembly 100, as detailed with reference to FIGS. 39A-39B. Several preparatory steps are required before insertion of medicament module 300 of FIGS. 36A-36D into the reusable injection assembly 100, as detailed with reference to FIGS. 40A-40B. It is also appreciated that no preparatory steps are required in order to insert medicament module 300 of FIGS. 37A-37D into the reusable injection assembly 100 since there is no injection depth adjustment function and the syringe 342 is retained within the medicament assembly 300.

Figure 42A:
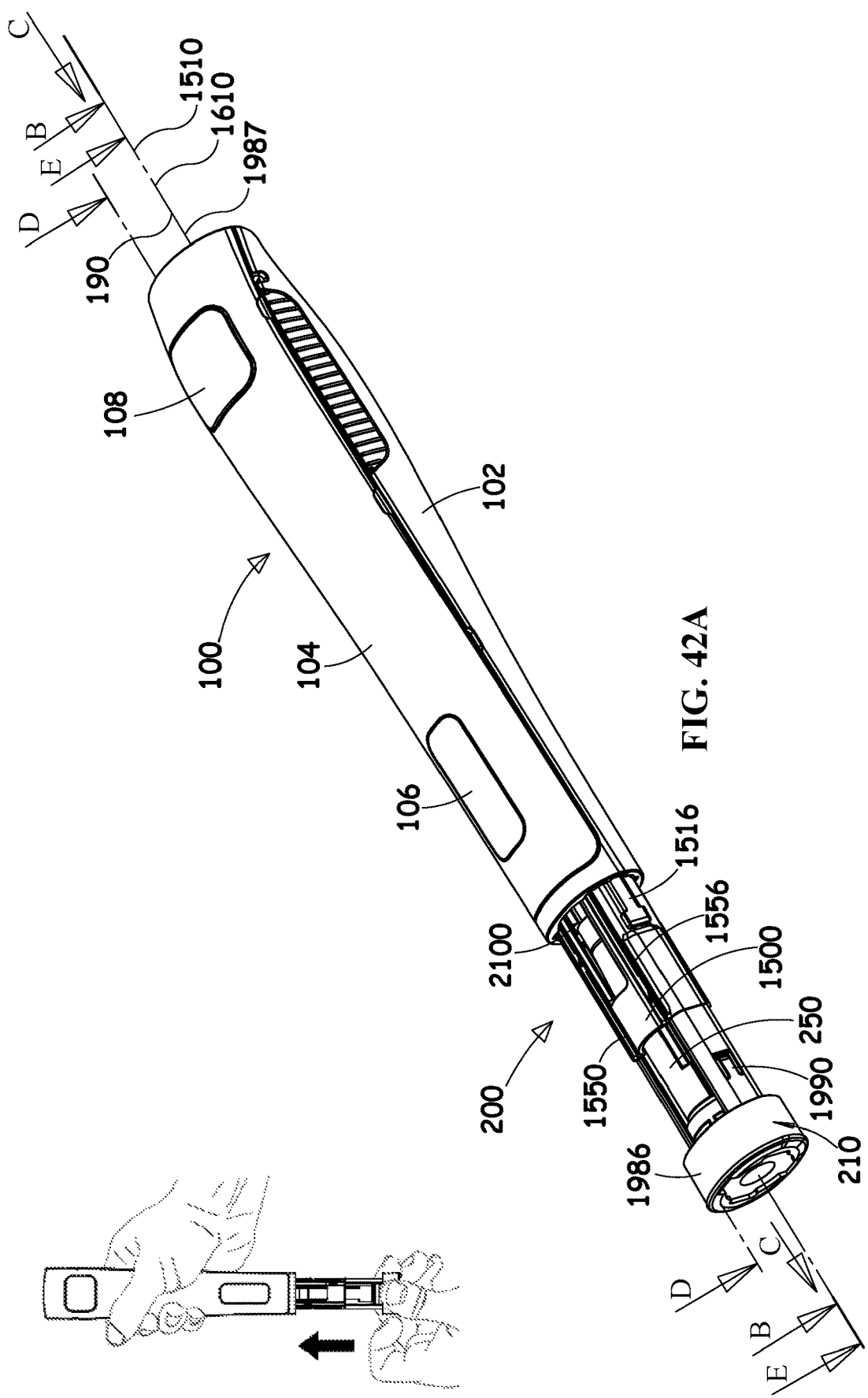
Figure 42B:
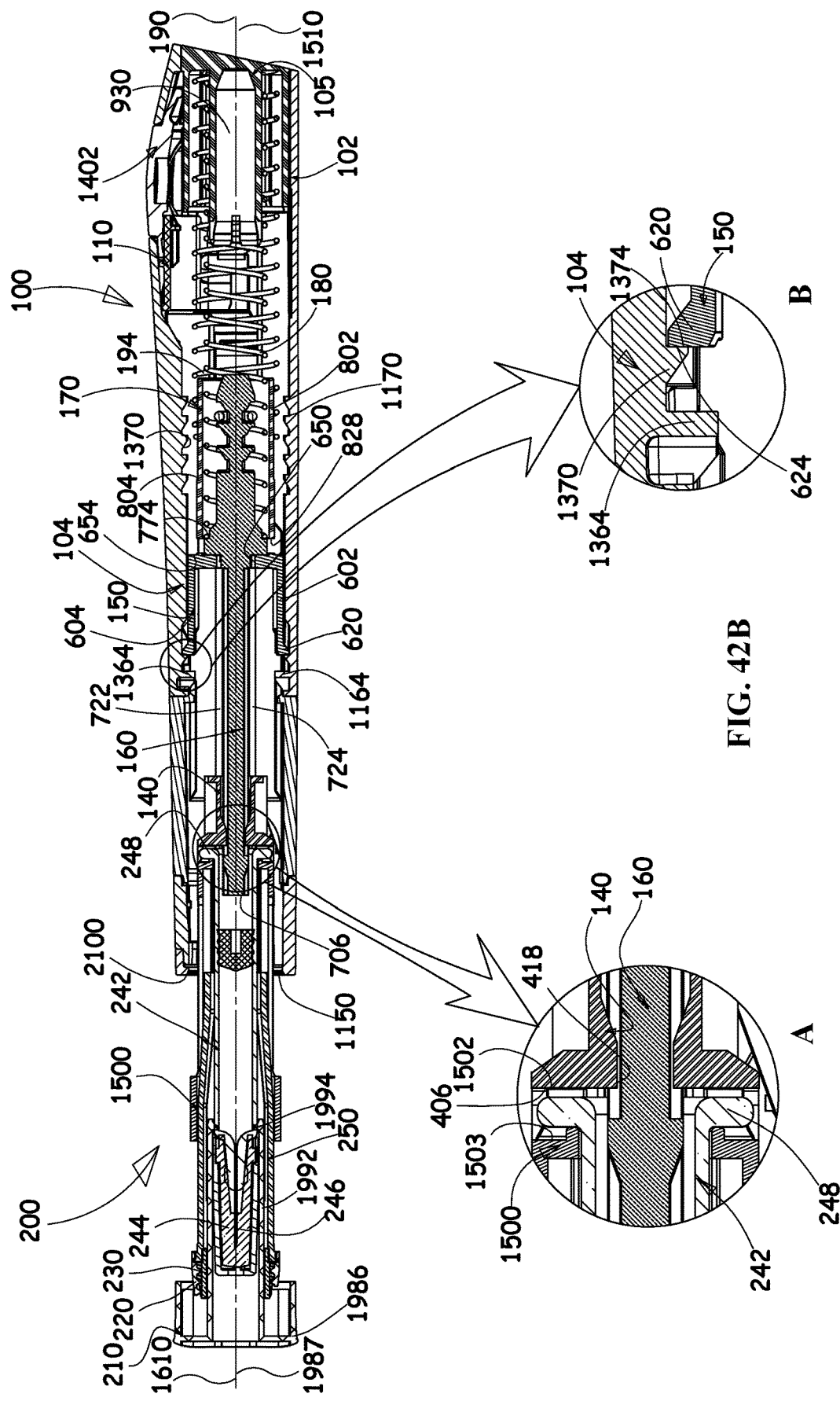
Figure 42C:
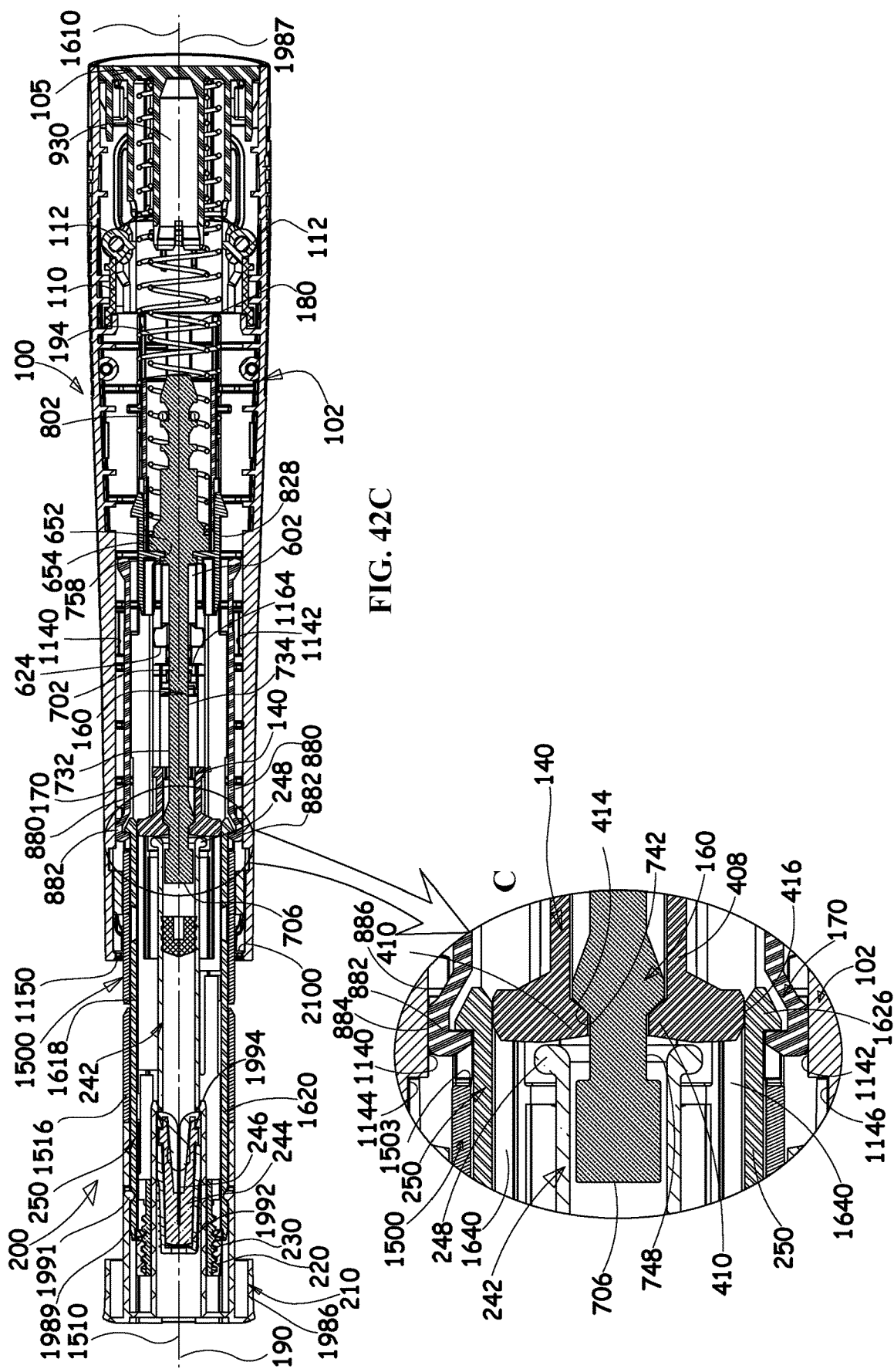

Reference is now made to FIGS. 42A, 42B, 42C, 42D and 42E, which are simplified illustrations of a first stage in the insertion of the medicament module 200/300 of FIGS. 34A-34D into the reusable automatic injection assembly 100 of FIGS. 1A-16H, 18A-18F and 20A-24C, following the preparatory steps shown in FIGS. 38A-38D. FIGS. 42B, 42C and 42D are sectional illustrations taken along respective lines B-B, C-C and D-D in FIG. 42A and FIG. 42E is a simplified partially cut-away illustration of FIG. 42A.

As seen in FIGS. 42A-42E, a rearward portion of the medicament module 200/300 is partially inserted into a forward cavity 2100 of the reusable automatic injection assembly 100 by a user pushing RNS remover 210 axially rearwardly along axis 190.

More specifically, it is seen that at this stage elongate ribs 1112 and 1114 of main housing portion 102 and elongate ribs 1312 and 1314 of cover portion 104 of the reusable automatic injection assembly engage respective longitudinal channels 1550, 1552, 1554 and 1556 of the module housing 1500.

As seen in enlargement C in FIG. 42C, inwardly-facing hook portions 882 (FIGS. 13A-13H) of multifunctional engagement element 170 engage corresponding generally U-shaped outer facing protrusions 1626 of needle shield 250, thereby attaching needle shield 250 to multifunctional engagement element 170 for axial movement together along axis 190. Hook portions 882 are retained in engagement with corresponding protrusions 1626 by virtue of engagement of an inwardly-facing side surfaces 1140 and 1142 of the main housing portion 102 with respective outwardly-facing protruding surfaces 884 of hook portions 882.

As additionally seen in enlargement C in FIG. 42C, rearwardly-facing tapered surface 414 of control element 140 engages tapered planar forward-facing surface 742 of elongate damping driver element 160.

As also seen in enlargement C in FIG. 42C, outwardly-facing surfaces 416 of forwardly-extending engagement fingers 408 of control element 140 engage corresponding channels 1640 formed in needle shield 250. This engagement retains fingers 408 from outward deflection and thus allow charging force to be transferred from the control element 140 to the elongate damping driver element 160 by means of engagement between rearwardly-facing tapered surface 414 of control element 140 and tapered planar forward-facing surface 742 of elongate damping driver element 160.

As seen in enlargement A in FIG. 42B, the rearwardmost portions of edge 1502 of module housing 1500 engage forward facing surfaces 406 of control element 140 and urge the control element 140, the multifunctional retaining element 150 and the elongate damping driver element 160 axially rearwardly along axis 190, against the urging of spring 180.

As seen in enlargement D in FIG. 42D, the rearward facing edges 1622 and 1624 of mounting arms 1618 and 1620 of the needle shield 250 engage forward-facing surfaces 878 of multifunctional engagement element 170 and urge it axially rearwardly along axis 190, against the urging of spring 194.

As seen in enlargement B in FIG. 42B, an outwardly-facing tapered protrusion 620 of multifunctional retaining element 150 is retained against forward axial displacement along axis 190 relative to the main housing portion 102 and cover portion 104 by engagement of forward engagement surface 624 of outwardly-facing tapered protrusion 620 with a corresponding rearward retaining surface 1174 of a forwardmost one of ratchet teeth 1170 of the main housing portion 102 and with a corresponding rearward retaining surface 1374 of a forwardmost one of ratchet teeth 1370 of the cover portion 104.

As seen in FIG. 42E, finger 610 (FIGS. 6A-6I) of multifunctional retaining element 150 is in a steady state operative orientation so that finger 610 extends generally parallel to axis 190 as seen in FIG. 8 at I.

Figure 43A:
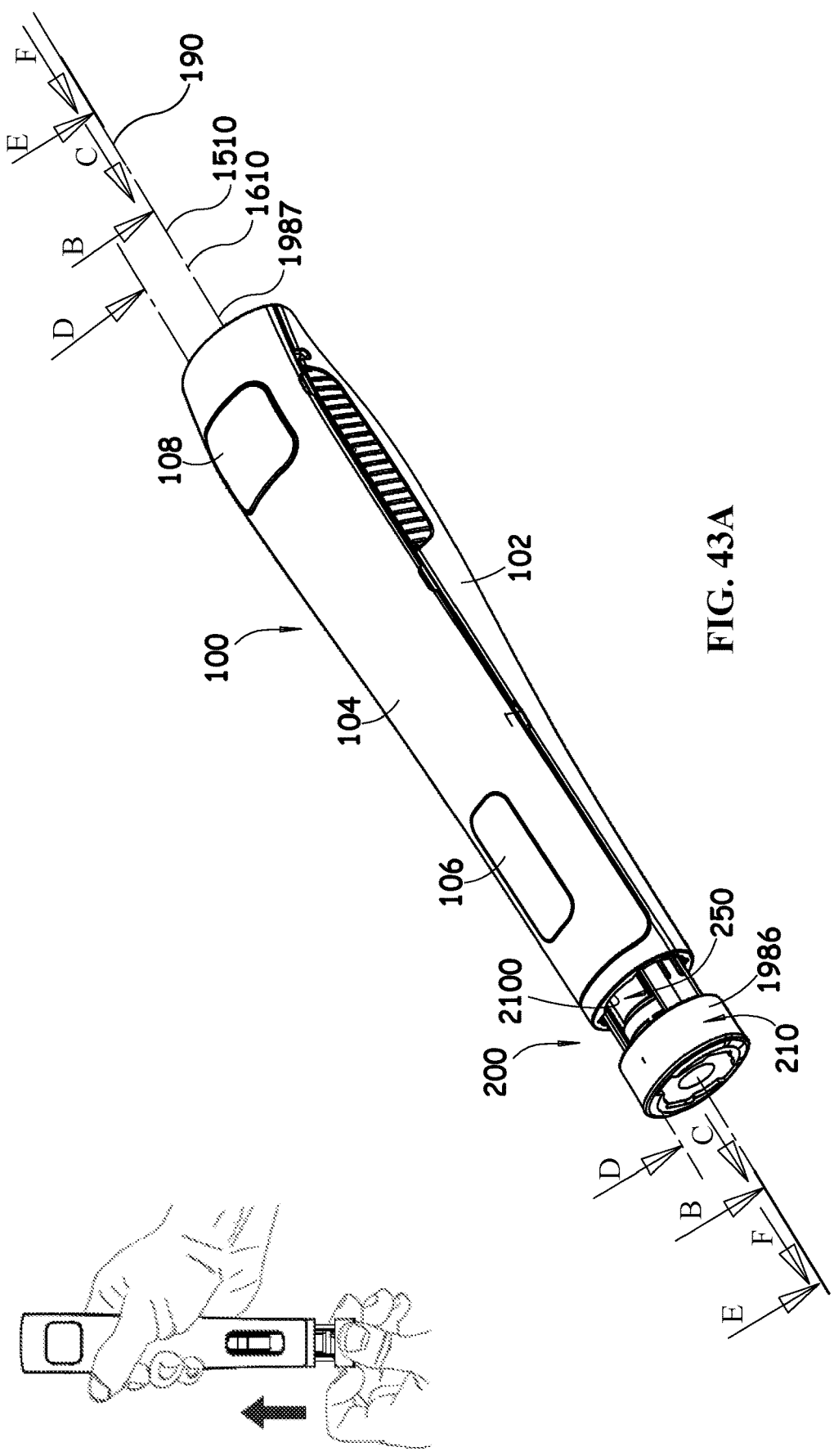

Reference is now made to FIGS. 43A, 43B, 43C, 43D and 43E, which are simplified illustrations of a second stage in the insertion of the medicament module of FIGS. 34A-34D into the reusable automatic injection assembly of FIGS. 1A-16H, 18A-18F and 20A-24C, following the preparatory steps shown in and described above with respect to FIGS. 38A-38E and following the first stage subsequent thereto, described un and described above with respect to FIGS. 42A-42D. FIGS. 43B, 43C and 43D are sectional illustrations taken along respective lines B-B, C-C and D-D in FIG. 43A and FIG. 43E is a simplified partially cut-away illustration of FIG. 43A.

As seen in FIGS. 43A-43E, a rearward portion of the medicament module 200/300 is inserted more fully into a forward cavity 2100 of the reusable automatic injection assembly 100 by a user pushing RNS remover 210 axially rearwardly along axis 190.

More specifically, it is seen that also at this stage elongate ribs 1112 and 1114 of main housing portion 102 and elongate ribs 1312 and 1314 of cover portion 104 of the reusable automatic injection assembly engage respective longitudinal channels 1550, 1552, 1554 and 1556 of the module housing 1500.

As seen in FIG. 43C, inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190. Hook portions 882 are still retained in engagement with corresponding protrusions 1626 by virtue of engagement of an inwardly-facing side surfaces 1140 and 1142 of the main housing portion 102 with respective outwardly-facing protruding surfaces 884 of hook portions 882.

As additionally seen in enlargement A in FIG. 43C, at this second stage, inwardly-facing protrusions 418 of control element 140 still engages forward side surface portion 748 of elongate damping driver element 160.

As also seen in FIG. 43C, outwardly-facing surfaces 416 of forwardly-extending engagement fingers 408 of control element 140 still engage corresponding channels 1640 formed in needle shield 250.

As additionally seen in FIG. 43B, the rearwardmost portions of edge 1502 of module housing 1500 still engage forward facing surfaces 406 of control element 140 and urge the control element 140, the multifunctional retaining element 150 and the elongate damping driver element 160 axially rearwardly along axis 190, against the urging of spring 180.

As seen in FIG. 43D, the rearward facing edges 1622 of mounting arms 1618 and 1620 of the needle shield 250 still engage forward-facing surfaces 878 of multifunctional engagement element 170 and urge it axially rearwardly along axis 190, against the urging of spring 194.

As seen in FIG. 43E, finger 610 (FIGS. 6A-6I) of multifunctional retaining element 150 is preferably deflected outwardly with respect to longitudinal axis 190, as seen at II in FIG. 8, by virtue of engagement of finger 610 with forwardly tapered forward end 1111 of main housing portion 102.

As seen in enlargement B in FIG. 43C, and as distinguished from the operative orientation described hereinabove with reference to FIG. 23K, engagement surface 1010 of each latch 112 no longer engages inwardly-facing surface 953 of trigger element 110. Rather inclined surfaces 622 of outwardly-facing tapered protrusions 620 of each of generally identical fingers 606 and 608 of multifunctional retaining element 150 engage curved surfaces 992 of latches 112 and rotate one latch 112 in a counterclockwise rotational direction in the sense of enlargement B and another latch 112 in a clockwise rotational direction, about axis 981 (FIGS. 18A-18F) in order to disengage surface 1010 of each latch 112 from inwardly-facing surface 953 of trigger element 110.

As seen in enlargement C in FIG. 43B, a rearward portion of elongate damping driver element 160 including a rearward portion of intermediate elongate portion 770 and the series of axial movement direction dependent damping control friction element seats 780, is partially inserted in inner cylindrical volume 930 of generally circular cylindrical portion 906 of end cover 105, such that friction element 162 (FIG. 10A, stage I) is located adjacent a rearwardly-facing planar surface 782 of elongate damping driver element 160 opposite single bulkhead 794 of a forwardmost axial movement direction dependent damping control friction element seat 780, inwardly of inner-facing surface 931 of generally circular cylindrical portion 906 of end cover 105, thus exerting less frictional resistance to rearward displacement of the elongate damping driver element 160, as seen in state A in FIGS. 10A & 10B.

It is appreciated from a consideration of enlargement C in FIG. 43B that air compressed behind friction element 162 in generally circular cylindrical portion 906 of end cover 105 is vented to the atmosphere via mutually radially outwardly directed slots 784 and 788 (FIGS. 9A-12B).

It is also appreciated that, as seen in FIG. 43D, protrusions 1660 of finger portions 1648 and 1658 of needle shield 250 do not fully engage slots 1564 and 1566 of the module housing 1500 by virtue of engagement of rib 1114 of the main housing portion 102 and rib 1314 of the cover portion 104 with protrusions 1660 of finger portions 1648 and 1658.

It is also seen in FIG. 43D that protrusions 1660 of finger portions 1646 and 1656 of needle shield 250 remain fully engaged with slots 1560 and 1562 of the module housing 1500 in this operative orientation.

Reference is now made to FIGS. 44A, 44B, 44C, 44D and 44E, which are simplified illustrations of a third, momentary, stage in the insertion of the medicament module of FIGS. 34A-34D into the reusable automatic injection assembly of FIGS. 1A-16H, 18A-18F and 20A-24C, following the preparatory steps shown in and described above with respect to FIGS. 38A-38E and following the first and second stages subsequent thereto, shown in and described above with respect to FIGS. 42A-42D and FIGS. 43A-43D. FIGS. 44B, 44C and 44D are sectional illustrations taken along respective lines B-B, C-C and D-D in FIG. 44A. FIG. 44E is a simplified partially cut-away illustration of FIG. 44A.

As seen in FIGS. 44A-44E, a rearward portion of the medicament module 200/300 is inserted fully into a forward cavity 2100 of the reusable automatic injection assembly 100 by a user pushing RNS remover 210 axially rearwardly along axis 190.

More specifically, it is seen that also at this stage elongate ribs 1112 and 1114 of main housing portion 102 and elongate ribs 1312 and 1314 of cover portion 104 of the reusable automatic injection assembly still engage respective longitudinal channels 1550, 1552, 1554 and 1556 of the module housing 1500.

As seen in FIG. 44C, inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190. Hook portions 882 are still retained in engagement with corresponding protrusions 1626 by virtue of engagement of an inwardly-facing side surfaces 1140 and 1142 of the main housing portion 102 with respective outwardly-facing protruding surfaces 884 of hook portions 882.

As additionally seen in enlargement A in FIG. 44C, rearwardly-facing tapered surface 414 of control element 140 preferably engages tapered planar forward-facing surface 742 of elongate damping driver element 160.

As also seen in FIG. 44C, outwardly-facing surfaces 416 of forwardly-extending engagement fingers 408 of control element 140 still engage corresponding channels 1640 formed in needle shield 250.

As additionally seen in FIG. 44B, the rearwardmost portions of edge 1502 of module housing 1500 still engage forward facing surfaces 406 of control element 140 and urge it axially rearwardly along axis 190, against the urging of spring 180. Spring 180 is seen to be in its fully compressed operative orientation.

As seen in enlargement D in FIG. 44D, the rearward facing edges 1622 of mounting arms 1618 and 1620 of the needle shield 250 still engage forward-facing surfaces 878 of multifunctional engagement element 170 and urge it axially rearwardly along axis 190, against the urging of spring 194. Spring 194 is seen to be in its fully compressed operative orientation.

As seen in FIG. 44B, an outwardly-facing tapered protrusion 620 of multifunctional retaining element 150 is limited in its possible forward axial displacement along axis 190 relative to the main housing portion 102 and cover portion 104 by location of forward engagement surface 624 of outwardly-facing tapered protrusion 620 rearwardly of ratchet teeth 1170 of the main housing portion 102 and rearwardly of ratchet teeth 1370 of the cover portion 104.

As seen in partially in FIG. 44E, finger 610 (FIGS. 6A-6I) of multifunctional retaining element 150 returns to at rest orientation generally extending parallel to axis 190, as seen in state I in FIG. 8.

As seen in enlargement B in FIG. 44C, and as distinguished from the operative orientation described hereinabove with reference to FIG. 43C, retaining surface 1012 of each latch 112 once again engages inwardly-facing surface 953 of trigger element 110. Inclined surfaces 622 of outwardly-facing tapered protrusions 620 of each of generally identical fingers 606 and 608 of multifunctional retaining element 150 no longer engage curved surfaces 992 of latches 112 and are located axially rearwardly thereof. Thus, as compared with FIG. 43C one latch 112 has been rotated in a clockwise rotational direction in the sense of enlargement B and another latch 112 has been rotated in a counterclockwise rotational direction, about axis 981 (FIGS. 18A-18F) such that surface 1012 of each latch 112 once again engages inwardly-facing surface 953 of trigger element 110 due to engagement between helically-curved latch engagement surface 950 of trigger element 110 and helically spiral surface 1010 of latch element 112, as seen particularly in FIG. 23C.

As seen in enlargement C in FIG. 44B, a rearward portion of elongate damping driver element 160 including a rearward portion of intermediate elongate portion 770 and the series of axial movement direction dependent damping control friction element seats 780, is fully inserted in inner cylindrical volume 930 of generally circular cylindrical portion 906 of end cover 105. Friction element 162 (FIG. 10A, stage I) is disposed axially rearwardly of its location in FIG. 43B and remains located adjacent a rearwardly-facing planar surface 782 of elongate damping driver element 160 opposite single bulkhead 794 of forwardmost axial movement direction dependent damping control friction element seat 780, which has also been displaced axially rearwardly, and remains located inwardly of inner-facing surface 931 of generally circular cylindrical portion 906 of end cover 105.

It is appreciated from a consideration of enlargement C in FIG. 44B that air compressed behind friction element 780 in generally circular cylindrical portion 906 of end cover 105 is vented to the atmosphere via mutually radially outwardly directed slots 784 and 788 (FIGS. 9A-12B).

It is also appreciated that, as seen in FIG. 44D, protrusions 1660 of all finger portions 1646, 1648 and 1656, 1658 of needle shield 250 do not fully engage slots 1560, 1564 and 1562, 1566 of the module housing 1500 by virtue of engagement with ribs 1112 and 1114 of the main housing portion 102 and ribs 1312 and 1314 of the cover portion 104 with protrusions 1660 of finger portions 1646, 1648 and 1656, 1658.

Figure 45A:
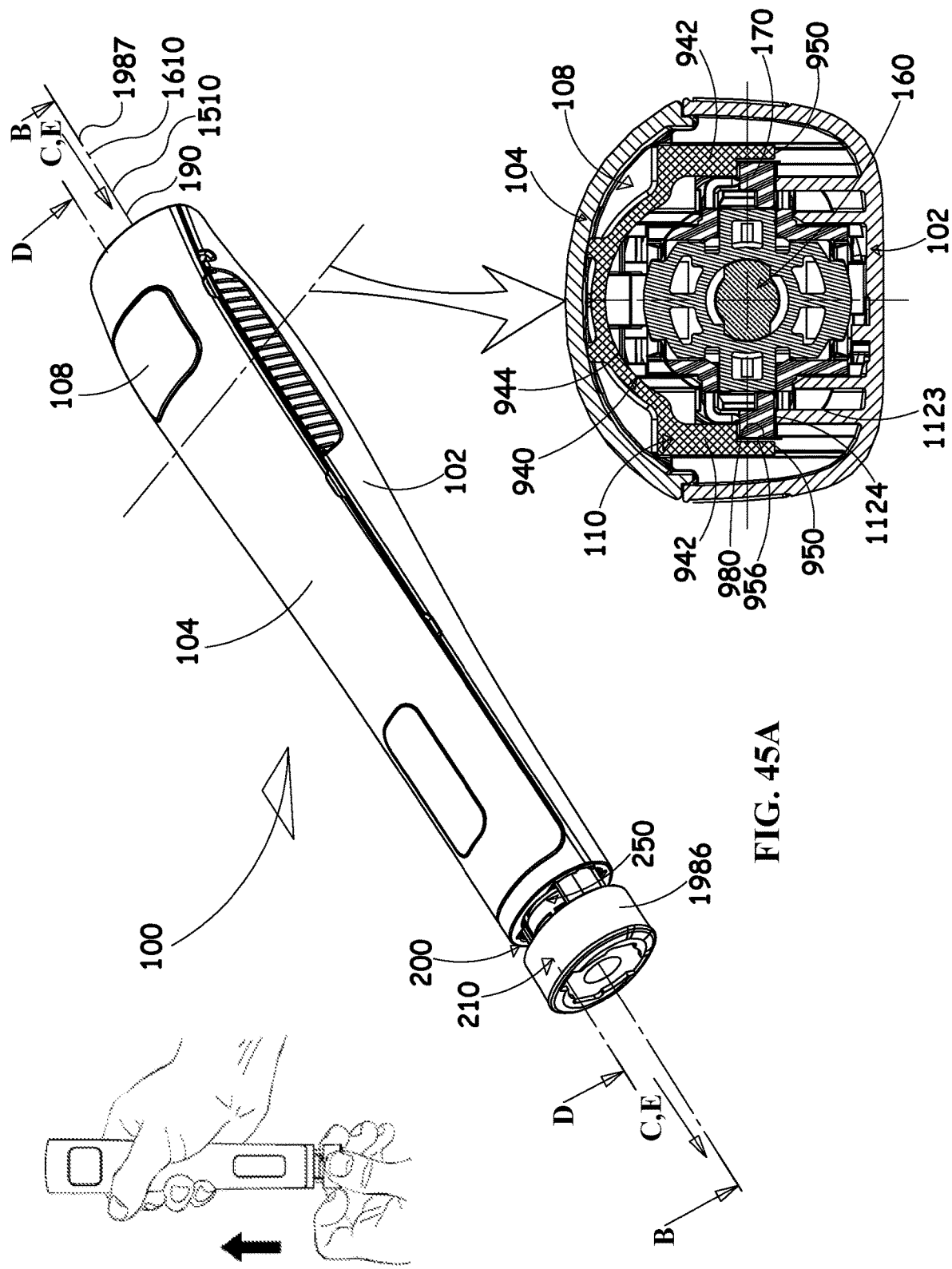
FIGS. 45A, 45B, 45C, 45D and 45E are simplified illustrations of a fourth stage in the insertion of the medicament module of FIGS. 34A-34D, following the preparatory steps shown in FIGS. 38A-38E, into the reusable automatic injection assembly of FIGS. 1A-16H, 18A-18F and 20A-24C.
Figure 45B:
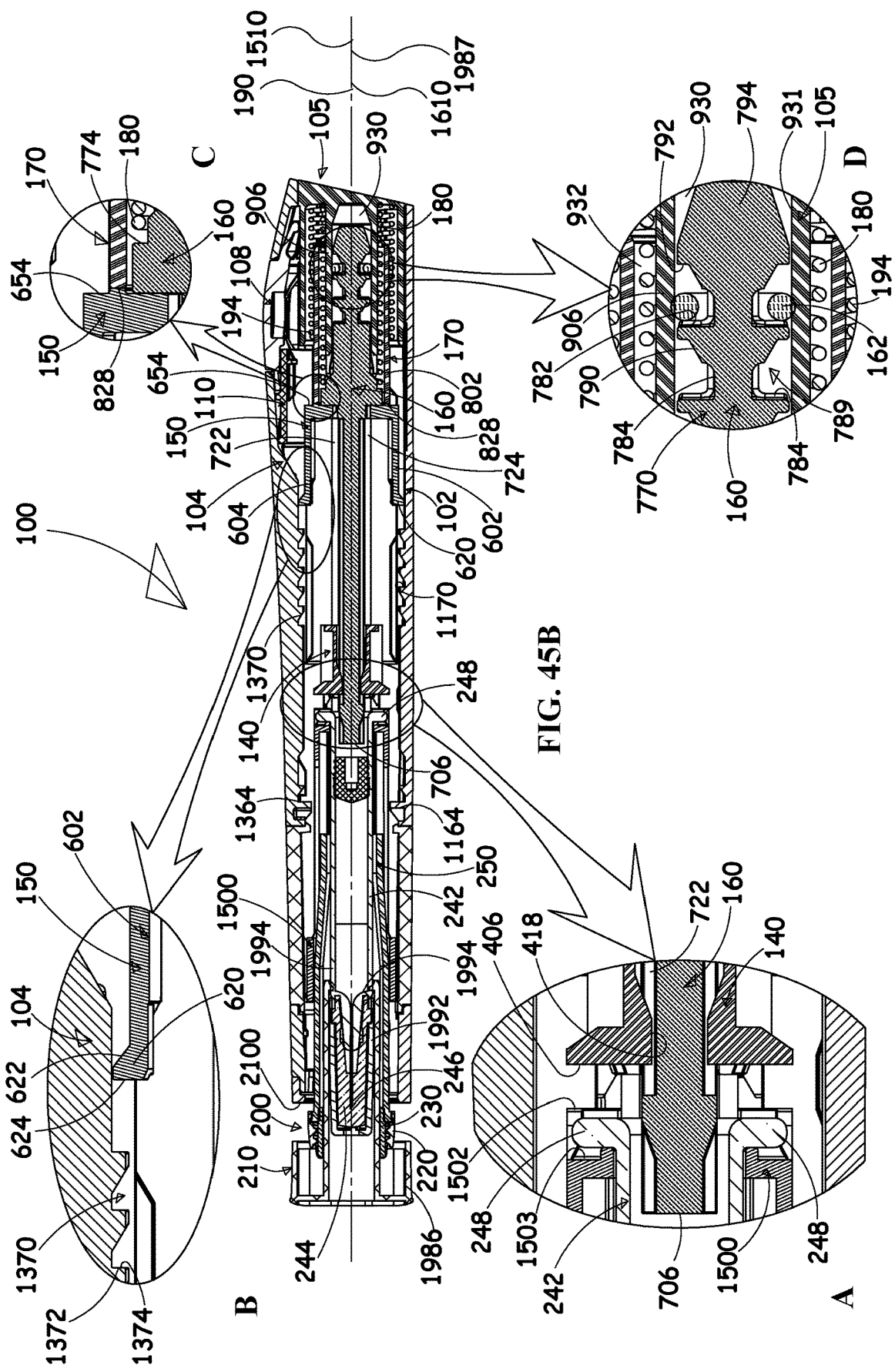
Figure 45C:
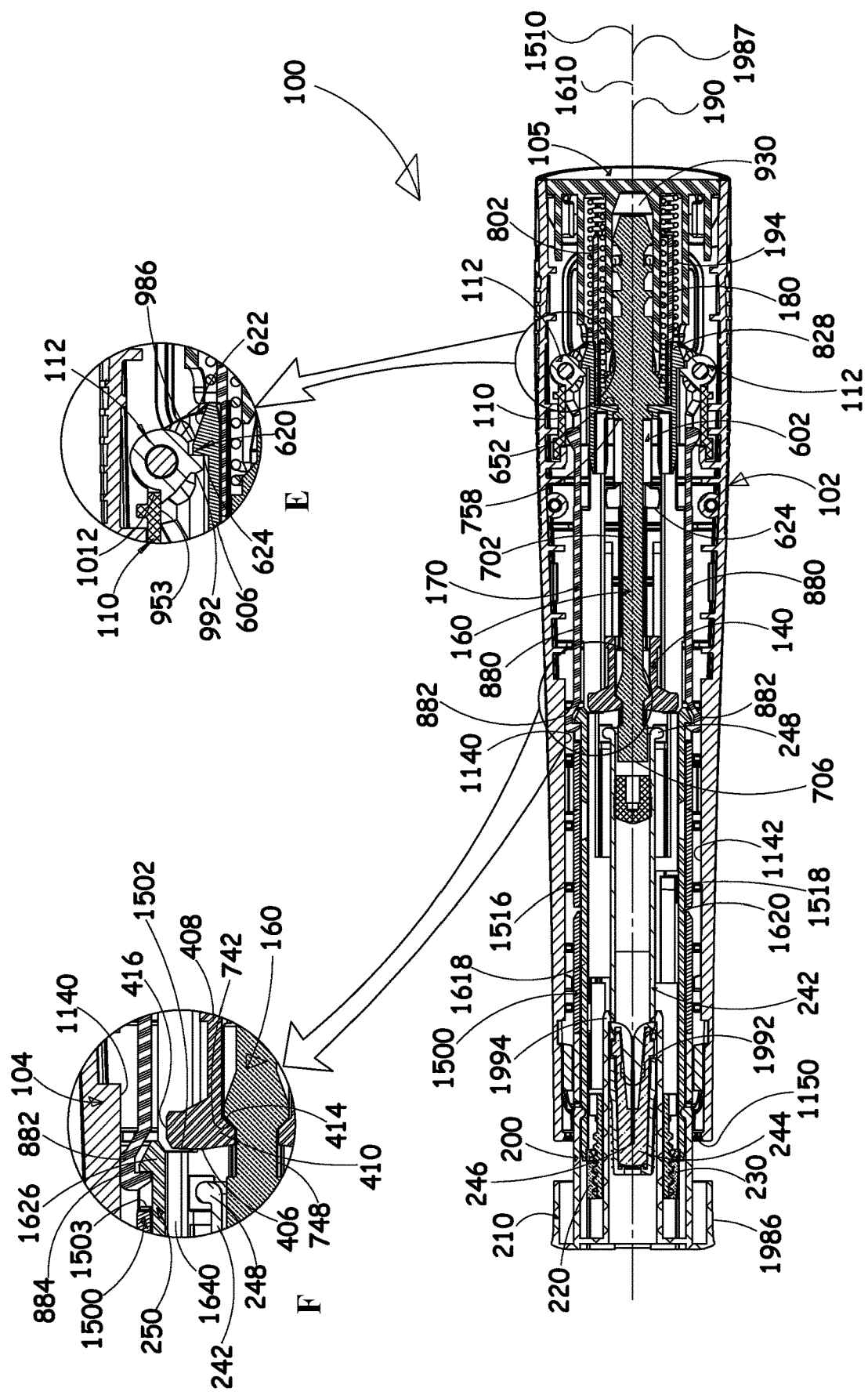
Figure 45D:
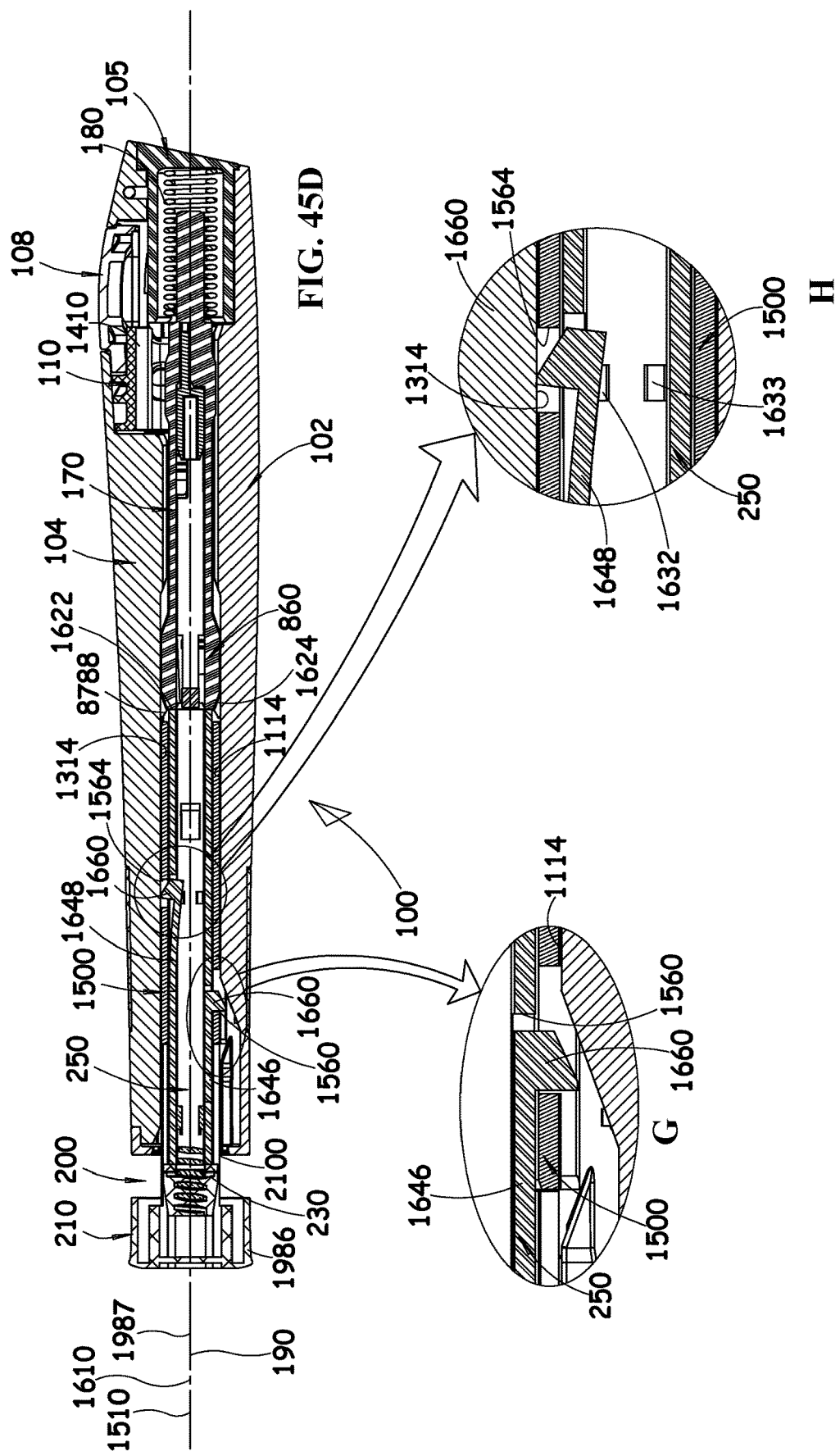
Figure 45E:
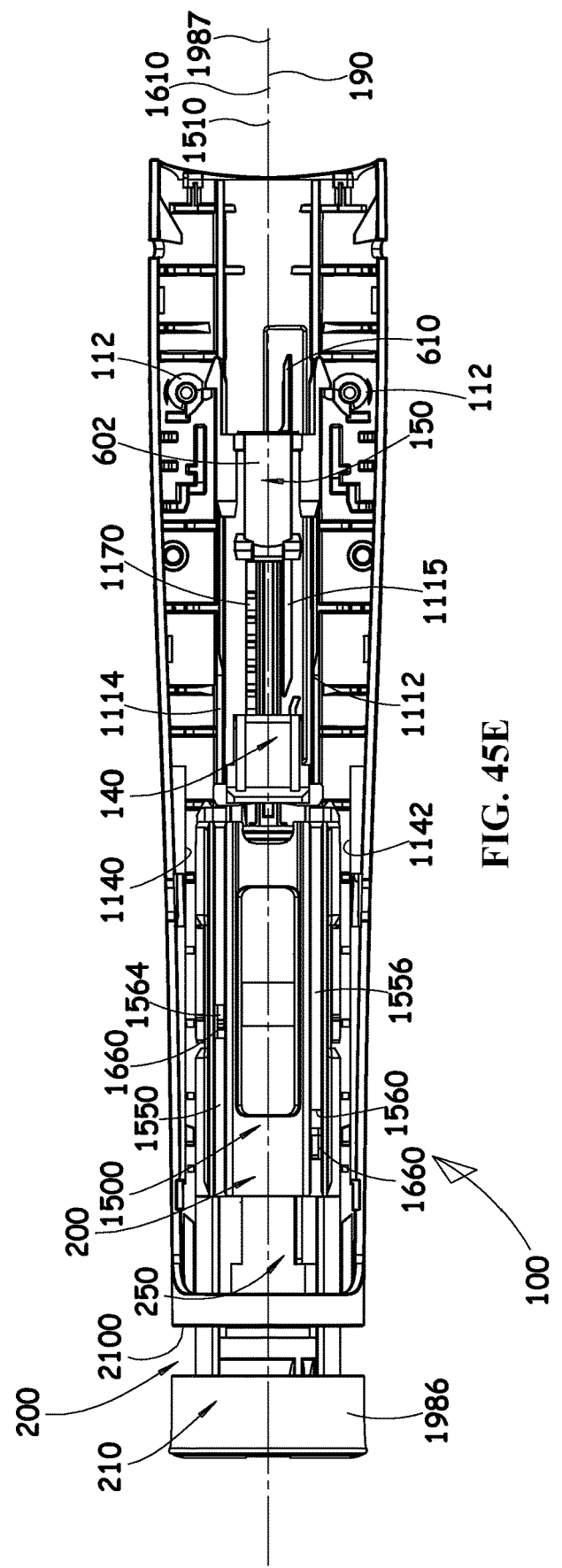

Reference is now made to FIGS. 45A, 45B, 45C, 45D and 45E, which are simplified illustrations of a fourth stage in the insertion of the medicament module of FIGS. 34A-34D into the reusable automatic injection assembly of FIGS. 1A-16H, 18A-18F and 20A-24C, following the preparatory steps shown in and described above with respect to FIGS. 38A-38E and following the first, second and third stages subsequent thereto, shown in and described above with respect to FIGS. 42A-42D, FIGS. 43A-43D and FIGS. 44A-44E. FIGS. 45B, 45C and 45D are sectional illustrations taken along respective lines B-B, C-C and D-D in FIG. 45A. FIG. 45E is a simplified partially cut-away illustration of FIG. 43A.

As seen in FIGS. 45A-45E, the medicament module 200/300 has been forwardly displaced from its fully inserted operative orientation as shown in and described above with respect to FIGS. 44A-44E. This forward displacement takes place when the user lets go of the medicament module 200/300 and allows spring 194 to push the medicament module 200/300 forwardly along axis 190 relative to the reusable automatic injection assembly 100.

More specifically, it is seen that also at this stage elongate ribs 1112 and 1114 of main housing portion 102 and elongate ribs 1312 and 1314 of cover portion 104 of the reusable automatic injection assembly still engage respective longitudinal channels 1550, 1552, 1554 and 1556 of the module housing 1500.

As additionally seen in enlargement E in FIG. 45C, rearwardly-facing tapered surface 414 of control element 140 remains in engagement with tapered planar forward-facing surface 742 of elongate damping driver element 160.

As also seen in FIG. 45C, outwardly-facing surfaces 416 of forwardly-extending engagement fingers 408 of control element 140 still engage corresponding channels 1640 formed in needle shield 250.

As additionally seen in FIG. 45C, the rearwardmost portions of edge 1502 of module housing 1500 no longer engage forward facing surfaces 406 of control element 140 and thus do not urge it axially rearwardly along axis 190, against the urging of spring 180. Module housing 1500 is retained in this axial position notwithstanding that the user is no longer pushing it rearwardly along axis 190 by virtue of the following:

As noted above and as seen in FIG. 45C, inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190. Hook portions 882 are still retained in engagement with corresponding protrusions 1626 by virtue of engagement of an inwardly-facing side surfaces 1140 and 1142 of the main housing portion 102 with respective outwardly-facing protruding surfaces 884 of hook portions 882.

As noted above with respect to FIGS. 34A-34D and as seen in FIG. 45D and enlargements G and H thereof, needle shield 250 is retained against forward axial displacement relative to module housing 1500 along coaxial axes 1510 and 1610 by engagement of protrusions 1660 of finger protrusions 1646 and 1656 of needle shield 250 in slots 1560 and 1562 of the module housing. It is seen in enlargement H in FIG. 45D that finger portions 1648 and 1658 of needle shield 250 are not fully engaged in slots 1564 and 1566 of the module housing 1500 in this operative orientation due to engagement of protrusions 1660 of finger portions 1648 and 1658 with respective ribs 1114 of the main housing portion 102 and 1314 of the cover portion 104.

As noted above with respect to FIGS. 23A-23L and as seen in FIG. 45B, multifunctional retaining element 150 is disposed along axis 190 relative to the multifunctional engagement element 170 such that rearwardly-facing surface 654 of multifunctional retaining element 150 engages the forward edge 828 of cylindrical portion 802 of multifunctional engagement element 170, thus preventing forward displacement of the multifunctional engagement along axis 190 relative to the multifunctional retaining element 150.

As seen in enlargement F in FIG. 45C, forward engagement surface 624 of outwardly-facing tapered protrusion 620 of each of generally identical fingers 606 and 608 of the multifunctional retaining element 150 engages radially extending walls 986 of latch elements 112, thereby preventing forward displacement of the multifunctional retaining element 150 relative to the main housing portion 102 and the cover portion 104. In view of the above-described connections between the multifunctional retaining element 150, the multifunctional engagement element 170, the needle shield 250 and the module housing 1500, this prevents forward displacement of the medicament module 200/300 along axis 190 relative to the reusable automatic injection assembly 100.

As seen in FIG. 45E, finger 610 (FIGS. 6A-6I) of multifunctional retaining element 150 as seen at I in FIG. 8 remains in an at rest orientation generally extending parallel to axis 190.

As seen in enlargement D in FIG. 45B, a rearward portion of elongate damping driver element 160 including a rearward portion of intermediate elongate portion 770 and the series of axial movement direction dependent damping control friction element seats 780, is somewhat less than fully inserted in inner cylindrical volume 930 of generally circular cylindrical portion 906 of end cover 105. Friction element 162 (FIG. 10A, stage I) is disposed axially forwardly of its location in FIG. 44B and remains located adjacent a rearwardly-facing planar surface 782 of elongate damping driver element 160 opposite single bulkhead 794 of forwardmost axial movement direction dependent damping control friction element seat 780, which has also been displaced axially rearwardly, and remains located inwardly of inner-facing surface 931 of generally circular cylindrical portion 906 of end cover 105.

It is appreciated from a consideration of enlargement D in FIG. 45B that air compressed behind friction element 780 in generally circular cylindrical portion 906 of end cover 105 is vented to the atmosphere via mutually radially outwardly directed slots 784 and 788 (FIGS. 9A-12B).

It is also appreciated from sectional enlargement in FIG. 45A that at this stage user engageable actuation button 108 is prevented from being pressed at this stage by virtue of:
engagement of lip 1410 of button 108 on convex outward-facing surface 944 of trigger element 110;
engagement of a downward-facing surface 956 of trigger element 110 with rearward-facing resilient finger 890 of multifunctional engagement element 170; and
support of rearward-facing resilient finger 890 against inward displacement thereof by trigger element 110 by an upper-facing edge 1124 of inwardly-facing protrusion 1123 of main housing portion 102.

Figure 46:
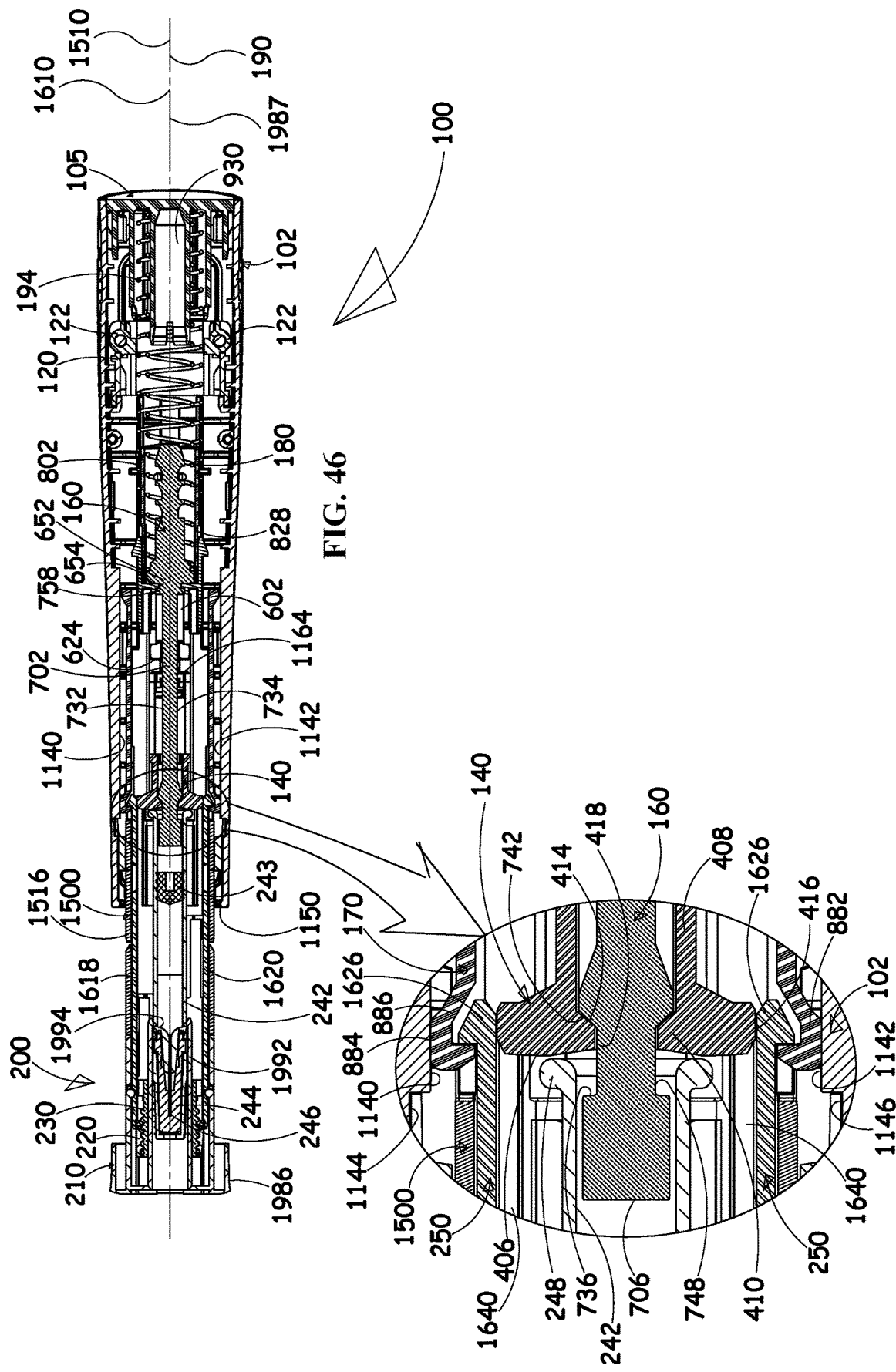
FIG. 46 is a simplified illustration of a first stage in the insertion of the medicament module of FIGS. 34A-34D, following the preparatory steps shown in FIGS. 38A-38E, into the reusable automatic injection assembly of FIGS. 1A-15F, 17A-17H and 19A-24C.

Reference is now made to FIG. 46, which is a simplified illustration of a first stage in the insertion of the medicament module 200/300 of FIGS. 34A-34D, following the preparatory steps shown in FIGS. 38A-38E, into the reusable automatic injection assembly 100 of FIGS. 1A-15F, 17A-17H and 19A-24C. FIG. 46 is a sectional illustration taken along lines E-E in FIG. 42A using the reusable automatic injection assembly 100 of FIGS. 1A-15F, 17A-17H and 19A-24C.

The reusable automatic injection assembly 100 is seen in FIG. 46 in accordance with an alternative embodiment of the present invention, whereas an alternative trigger element 120 and unitary latch element 122 are incorporated into the reusable automatic injection assembly 100.

It is seen that in this first stage in the insertion of the medicament module 200/300 into the reusable automatic injection assembly 100 all spatial relations between all of the components remain preferably the same as in FIGS. 42A-42E, other than the relations between the trigger element 110 and the unitary latch element 122, which preferably remain the same as described with reference to FIGS. 24A-24C, as follows:

Trigger element 120 and latch element 122 are slidably mounted on pins 1180 and 1182 (FIG. 20A) of main housing portion 102 for selectable vertical positioning therealong.

Springs 114, which are seated on respective upward-facing surfaces 1184 and 1186 underlying respective pins 1180 and 1182, urge unitary latch element 122 upwardly along pins 1180 and 1182 respectively into engagement with trigger element 120 (FIGS. 17A-17H) and urges the trigger element 120 upwardly into engagement with cover portion 104 and with the lip 1410 of the user engageable actuation button 108, thereby urging lip 1410 against cover portion 104. More specifically it is noted that convex outer-facing surface 1044 of unitary latch element 122 engages concave inner-facing surface 966 of trigger element 120.

Reference is now made to FIGS. 47A and 47B, which are simplified illustrations of a second stage in the insertion of the medicament module 200/300 of FIGS. 34A-34D, following the preparatory steps shown in FIGS. 38A-38E, into the reusable automatic injection assembly 100 of FIGS. 1A-15F, 17A-17H and 19A-24C. FIGS. 47A and 47B are sectional illustrations taken along lines E-E and F-F in FIG. 43A using the reusable automatic injection assembly 100 of FIGS. 1A-15F, 17A-17H and 19A-24C.

The reusable automatic injection assembly 100 is seen in FIGS. 47A and 47B in accordance with an alternative embodiment of the present invention, whereas an alternative trigger element 120 and unitary latch element 122 are incorporated into the reusable automatic injection assembly 100.

It is seen that in this second stage in the insertion of the medicament module 200/300 into the reusable automatic injection assembly 100 all spatial relations between all of the components remain preferably the same as in FIGS. 43A-43E, other than the relations between the trigger element 110 and the unitary latch element 122, which are preferably as follows:

Trigger element 120 and latch element 122 remain slidably mounted on pins 1180 and 1182 (FIG. 20A) of main housing portion 102 for selectable vertical positioning therealong.

It is noted with reference to FIG. 47 that during insertion of the medicament module 200/300 into the reusable automatic injection assembly 100, multifunctional retaining element 150 is rearwardly displaced such that inclined surfaces 622 of outwardly-facing tapered protrusions 620 of each of generally identical fingers 606 and 608 of multifunctional retaining element 150 engage tapered upwardly-facing surfaces 1054 of unitary latch element 122, thus urging the latch element 122 to be displaced downwardly, in the sense of FIG. 47, against the urging of springs 114, thus allowing further rearward displacement of multifunctional retaining element 150.

During this downward displacement of unitary latch element 122 against the urging of springs 114 along pins 1180 and 1182, latch element 122 disengages from trigger element 120 (FIGS. 17A-17H). More specifically it is noted that convex outer-facing surface 1044 of latch element 122 does not engage concave inner-facing surface 966 of trigger element 120 in this second stage of medicament module 200/300 insertion into the reusable automatic injection assembly 100.

Figure 48:
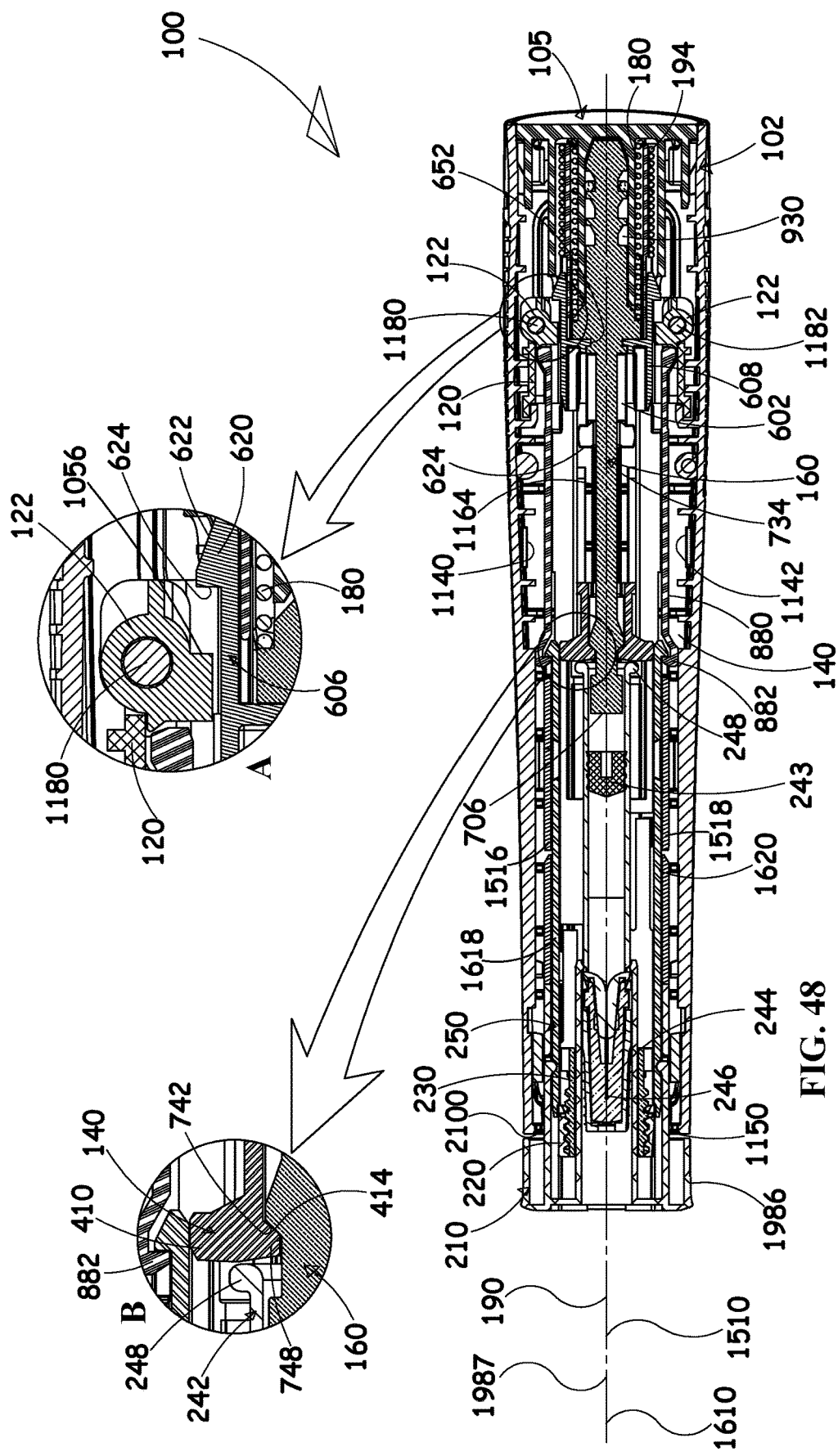
FIG. 48 is a simplified illustration of a third stage in the insertion of the medicament module of FIGS. 34A-34D, following the preparatory steps shown in FIGS. 38A-38E, into the reusable automatic injection assembly of FIGS. 1A-15F, 17A-17H and 19A-24C.

Reference is now made to FIG. 48, which is a simplified illustration of a third stage in the insertion of the medicament module 200 of FIGS. 34A-34D, following the preparatory steps shown in FIGS. 38A-38E, into the reusable automatic injection assembly 100 of FIGS. 1A-15F, 17A-17H and 19A-24C. FIG. 48 is a sectional illustration taken along lines E-E in FIG. 44A using the reusable automatic injection assembly 100 of FIGS. 1A-15F, 17A-17H and 19A-24C.

The reusable automatic injection assembly 100 is seen in FIG. 48 in accordance with an alternative embodiment of the present invention, whereas an alternative trigger element 120 and unitary latch element 122 are incorporated into the reusable automatic injection assembly 100.

It is seen that in this third stage in the insertion of the medicament module 200/300 into the reusable automatic injection assembly 100 all spatial relations between all of the components remain preferably the same as in FIGS. 44A-44E, other than the relations between the trigger element 110 and the unitary latch element 122, which are preferably as follows:

Trigger element 120 and latch element 122 remain slidably mounted on pins 1180 and 1182 (FIG. 20A) of main housing portion 102 for selectable vertical positioning therealong.

It is seen in FIG. 48 that once the multifunctional retaining element 150 is displaced rearwardly with respect to latch element 122, the latch element 122 is returned upwardly, in the sense of FIG. 48, along pins 1180 and 1182 due to the biasing force of springs 114, thus causing the latch element 122 to engage the trigger element 120 (FIGS. 17A-17H) again. More specifically, it is noted that convex outer-facing surface 1044 of latch element 122 once again engages concave inner-facing surface 966 of trigger element 120 in this third stage of medicament module 200/300 insertion into the reusable automatic injection assembly 100.

It is noted with reference to FIG. 48 that during further insertion of the medicament module 200/300 into the reusable automatic injection assembly 100, multifunctional retaining element 150 bypassed the latch element 122 due to its downward displacement as described hereinabove with reference to FIG. 47 and is displaced further rearwardly such that an outwardly-facing tapered protrusion 620 of multifunctional retaining element 150 is limited in its possible forward axial displacement along axis 190 relative to the main housing portion 102 and cover portion 104 by location of forward engagement surface 624 of outwardly-facing tapered protrusion 620 rearwardly and spaced from rearward facing surface 1056 of unitary latch element 122.

Figure 49A:
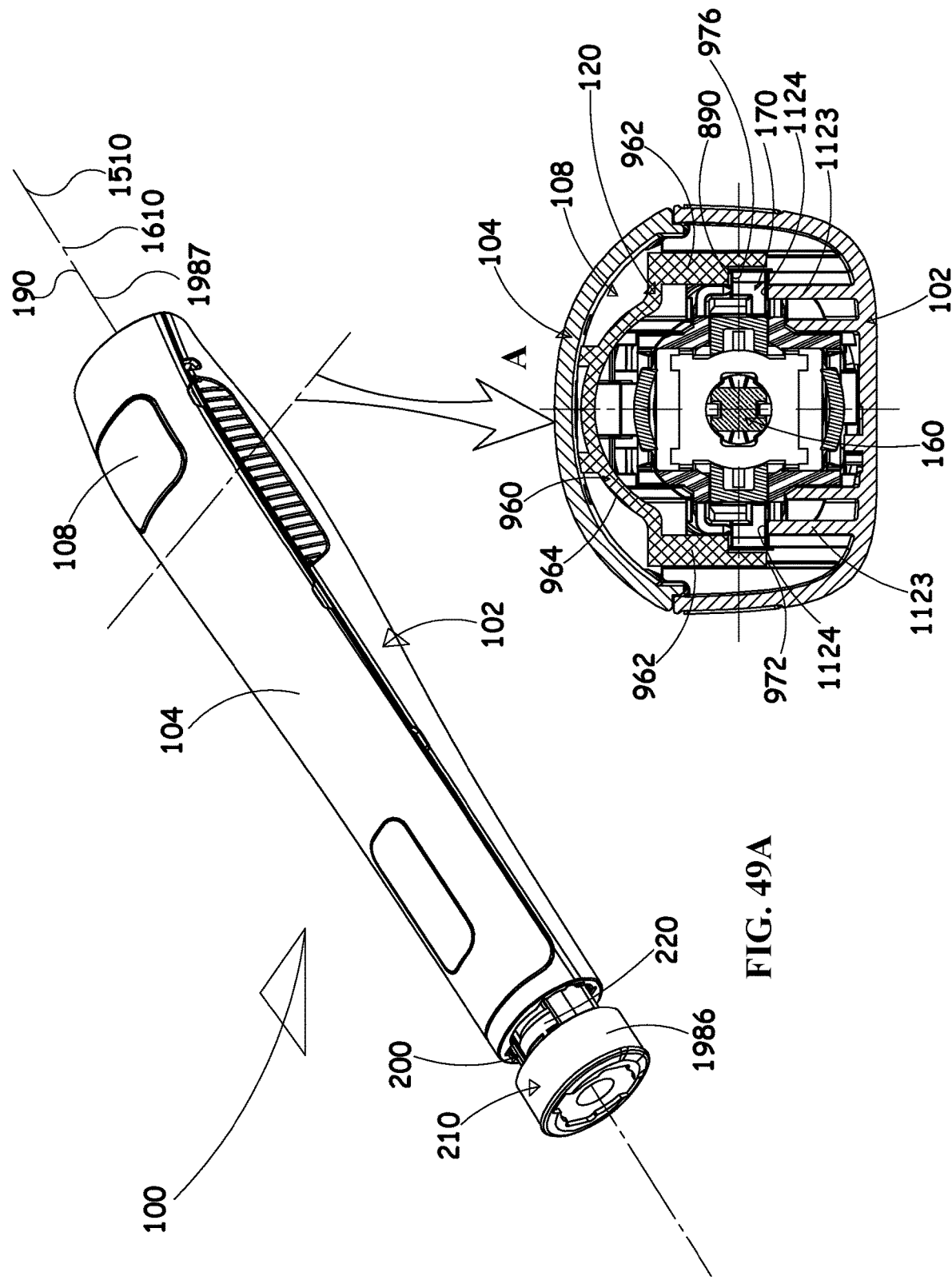
FIGS. 49A and 49B are simplified illustrations of a fourth stage in the insertion of the medicament module of FIGS. 34A-34D, following the preparatory steps shown in FIGS. 38A-38E, into the reusable automatic injection assembly of FIGS. 1A-15F, 17A-17H and 19A-24C.
Figure 49B:
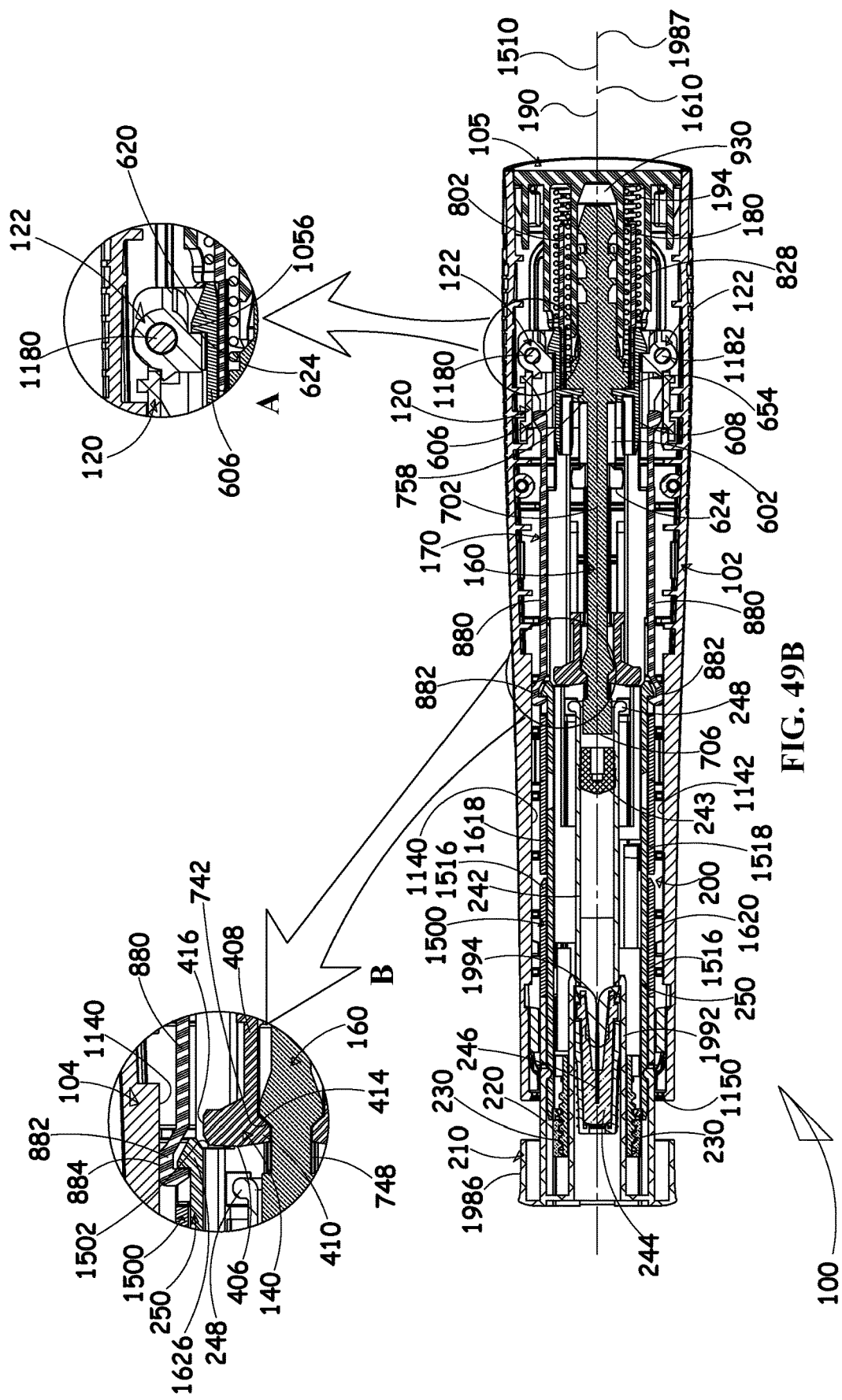

Reference is now made to FIGS. 49A and 49B, which are simplified illustrations of a fourth stage in the insertion of the medicament module 200 of FIGS. 34A-34D, following the preparatory steps shown in FIGS. 38A-38E, into the reusable automatic injection assembly of FIGS. 1A-15F, 17A-17H and 19A-24C and following the first, second and third stages subsequent thereto, shown in and described above with respect to FIGS. 46, 47 and 48. FIGS. 49A and 49B are respective simplified perspective and sectional illustrations taken along lines B-B in FIG. 49A.

As seen in FIGS. 49A-49B, the medicament module 200/300 has been forwardly displaced from its fully inserted operative orientation as shown in and described above with respect to FIG. 48. This forward displacement takes place when the user lets go of the medicament module 200/300 and allows spring 194 to push the medicament module 200/300 forwardly along axis 190 relative to the reusable automatic injection assembly 100.

The reusable automatic injection assembly 100 is seen in FIGS. 49A and 49B in accordance with an alternative embodiment of the present invention, whereas an alternative trigger element 120 and unitary latch element 122 are incorporated into the reusable automatic injection assembly 100.

It is seen that in this fourth stage in the insertion of the medicament module 200/300 into the reusable automatic injection assembly 100 all spatial relations between all of the components remain preferably the same as in FIGS. 45A-45E, other than the relations between the trigger element 110 and the unitary latch element 122, which are preferably as follows:

Trigger element 120 and latch element 122 remain slidably mounted on pins 1180 and 1182 (FIG. 20A) of main housing portion 102 for selectable vertical positioning therealong.

It is seen in FIGS. 49A and 49B that the latch element 122 is positioned upwardly, in the sense of FIGS. 49A and 49B thus the latch element 122 engages the trigger element 120 (FIGS. 17A-17H). More specifically, it is noted that convex outer-facing surface 1044 of latch element 122 engages concave inner-facing surface 966 of trigger element 120 in this fourth stage of medicament module 200/300 insertion into the reusable automatic injection assembly 100.

It is further seen in FIGS. 49A and 49B that during release of the medicament module 200/300 by a user, the medicament module 200/300 is slightly displaced forwardly out of the reusable automatic injection assembly 100, such that multifunctional retaining element 150 is also displaced forwardly and is retained from further forward displacement due to engagement between engagement surface 624 of tapered protrusion 620 of multifunctional retaining element 150 and rearward facing surface 1056 of latch element 122.

It is particularly seen in an enlargement B in FIG. 49B that forward engagement surface 624 of outwardly-facing tapered protrusion 620 of each of generally identical fingers 606 and 608 of the multifunctional retaining element 150 engages rearward facing surface 1056 of latch element 122, thereby preventing forward displacement of the multifunctional retaining element 150 relative to the main housing portion 102 and the cover portion 104. In view of the connections described above with reference to FIG. 45A-45E, between the multifunctional retaining element 150, the multifunctional engagement element 170, the needle shield 250 and the module housing 1500, this prevents forward displacement of the medicament module 200/300 along axis 190 relative to the reusable automatic injection assembly 100.

It is also appreciated from sectional enlargement A in FIG. 49A that at this stage user engageable actuation button 108 is prevented from being pressed at this stage by virtue of:
engagement of lip 1410 of button 108 on convex outward-facing surface 964 of trigger element 120;
engagement of a downward-facing surface 976 of trigger element 110 with rearward-facing resilient finger 890 of multifunctional engagement element 170; and
support of rearward-facing resilient finger 890 against inward displacement thereof by trigger element 110 by an upper-facing edge 1124 of inwardly-facing protrusion 1123 of main housing portion 102.

Figures 50A, 50B:
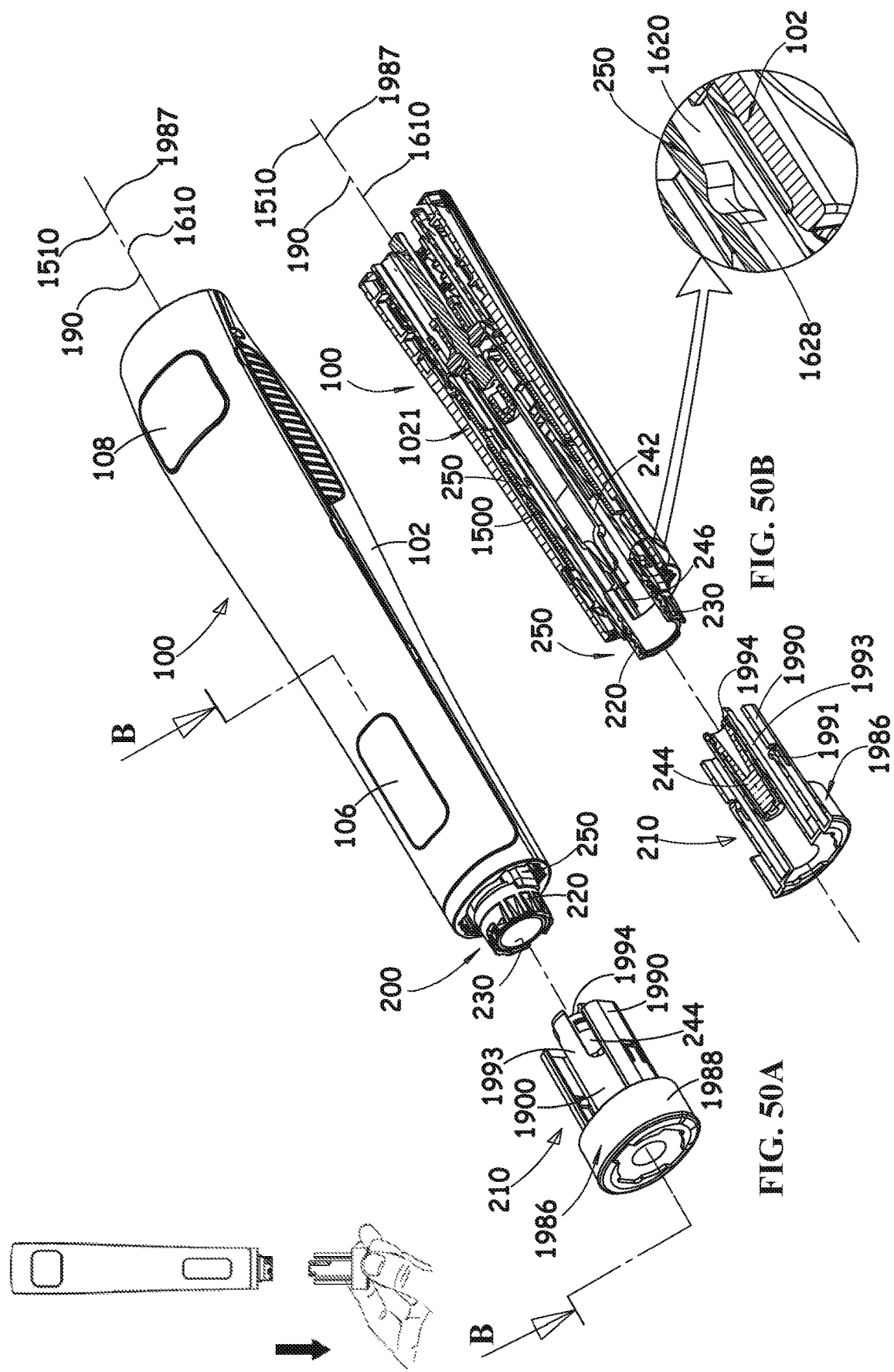
FIGS. 50A and 50B are simplified respective pictorial and sectional illustrations of an RNS removal stage following the insertion of the medicament module of FIGS. 34A-35D into the reusable automatic injection assembly 100 of FIGS. 1-24C.

Reference is now made to FIGS. 50A and 50B are simplified respective pictorial and sectional illustrations of an RNS removal stage following the insertion of the medicament module of FIGS. 34A-35D into the reusable automatic injection assembly 100 of FIGS. 1-24C. FIG. 50B is taken along lines B-B in FIG. 50A.

As seen in FIGS. 50A and 50B, when the RNS remover 210 (FIGS. 32A-32D) is disengaged from the needle shield 250 of the medicament module 200/300, as by axial forward pulling on the RNS remover 210 along axis 190, which causes protrusions 1991 to disengage from recesses 1628 on needle shield 250, the rigid needle shield 244 is retained interiorly of the RNS remover 210, preferably by engagement of inwardly directed protrusions 1994 of rearwardly facing inner fingers 1993 of the RNS remover 210 with a rearward-facing edge of rigid needle shield 244.

It is noted that if a multi-use medicament module 200/300 is used in association with reusable automatic injection assembly 100, such as shown in FIGS. 34A-34D and 36A-36D, the rigid needle shield 244 is preferably removeable from the RNS remover 210/310 through the central opening of the cylindrical hollow tube portion 1992/2000. It is further noted that if a single-use medicament module 200/300 is used in association with reusable automatic injection assembly 100, such as shown in FIGS. 35A-35D and 37A-37D, the rigid needle shield 244 is preferably retained within the RNS remover 210/310, due to a particular design of RNS remover, which is shown and described in U.S. Pat. No. 8,992,477, which is hereby incorporated by reference in its entirety.

Figures 51A, 51B:
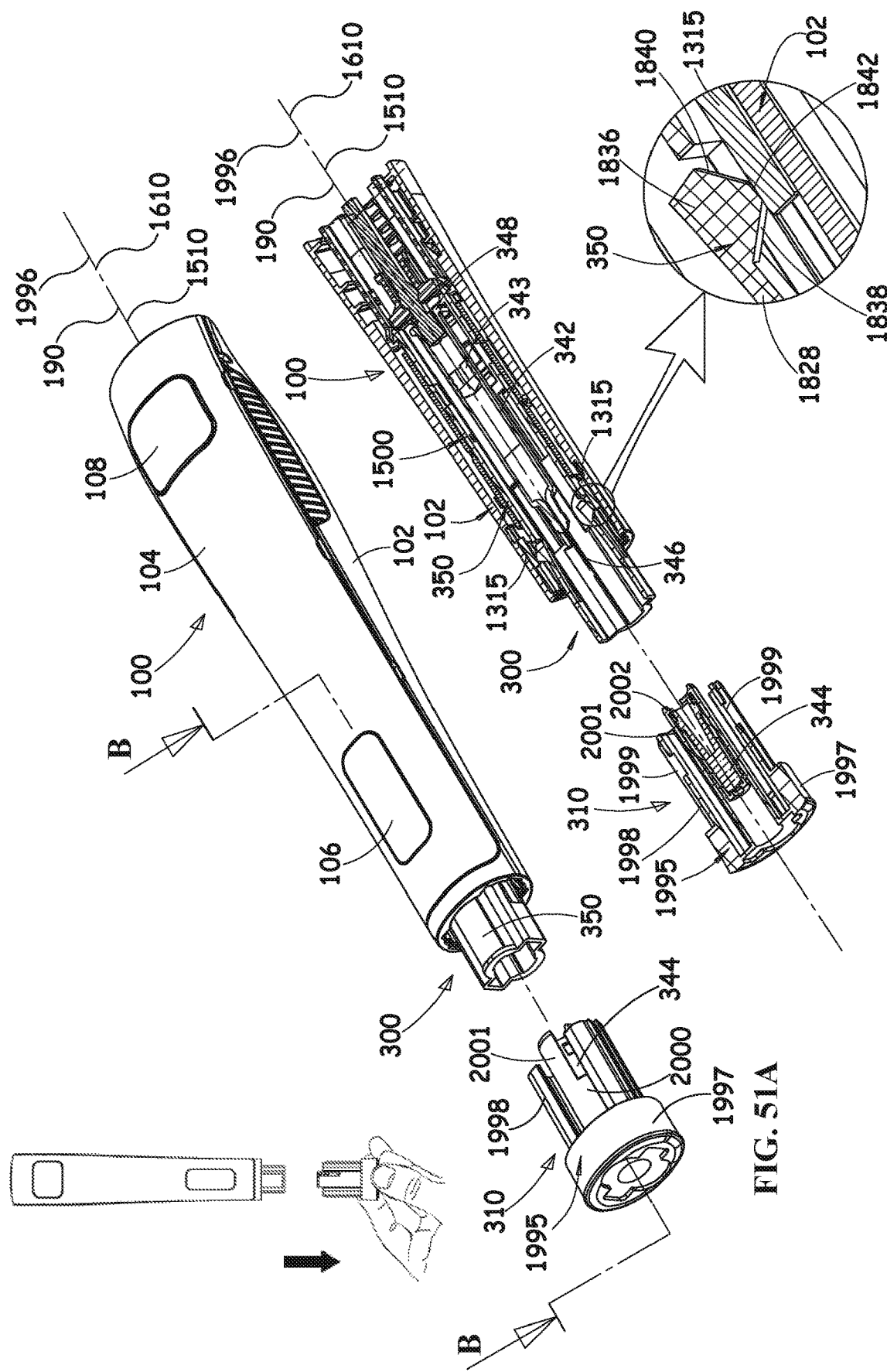
FIGS. 51A and 51B are simplified respective pictorial and sectional illustrations of an RNS removal stage following the insertion of the medicament module of FIGS. 36A-37D into the reusable automatic injection assembly 100 of FIGS. 1-24C.

Reference is now made to FIGS. 51A and 51B, which are simplified respective pictorial and sectional illustrations of an RNS removal stage following the insertion of the medicament module of FIGS. 36A-37D into the reusable automatic injection assembly 100 of FIGS. 1-24C.

As seen in FIGS. 51A and 51B, when the RNS remover 310 (FIGS. 33A-33D) is disengaged from the needle shield 350 of the medicament module 200, as by axial forward pulling on the RNS remover 310 along axis 190, which causes outwardly-facing protrusions 1836 of needle shield 350 to disengage from apertures 1999 of RNS remover 310. It is a particular feature of an embodiment of the present invention that this disengagement is only possible only when the medicament module 300 and the reusable automatic injection assembly 100 are in an axial operative orientation corresponding to that shown in FIGS. 45A-45D such that ribs 1315 (FIGS. 21A-21G engage protrusions 1836 (FIGS. 36A-37D).

The rigid needle shield 344 is retained interiorly of the RNS remover 310, preferably by engagement of inwardly directed protrusions 2002 of rearwardly facing inner fingers 2001 of the RNS remover 310 with a rearward-facing edge of rigid needle shield 344.

Figure 52B:
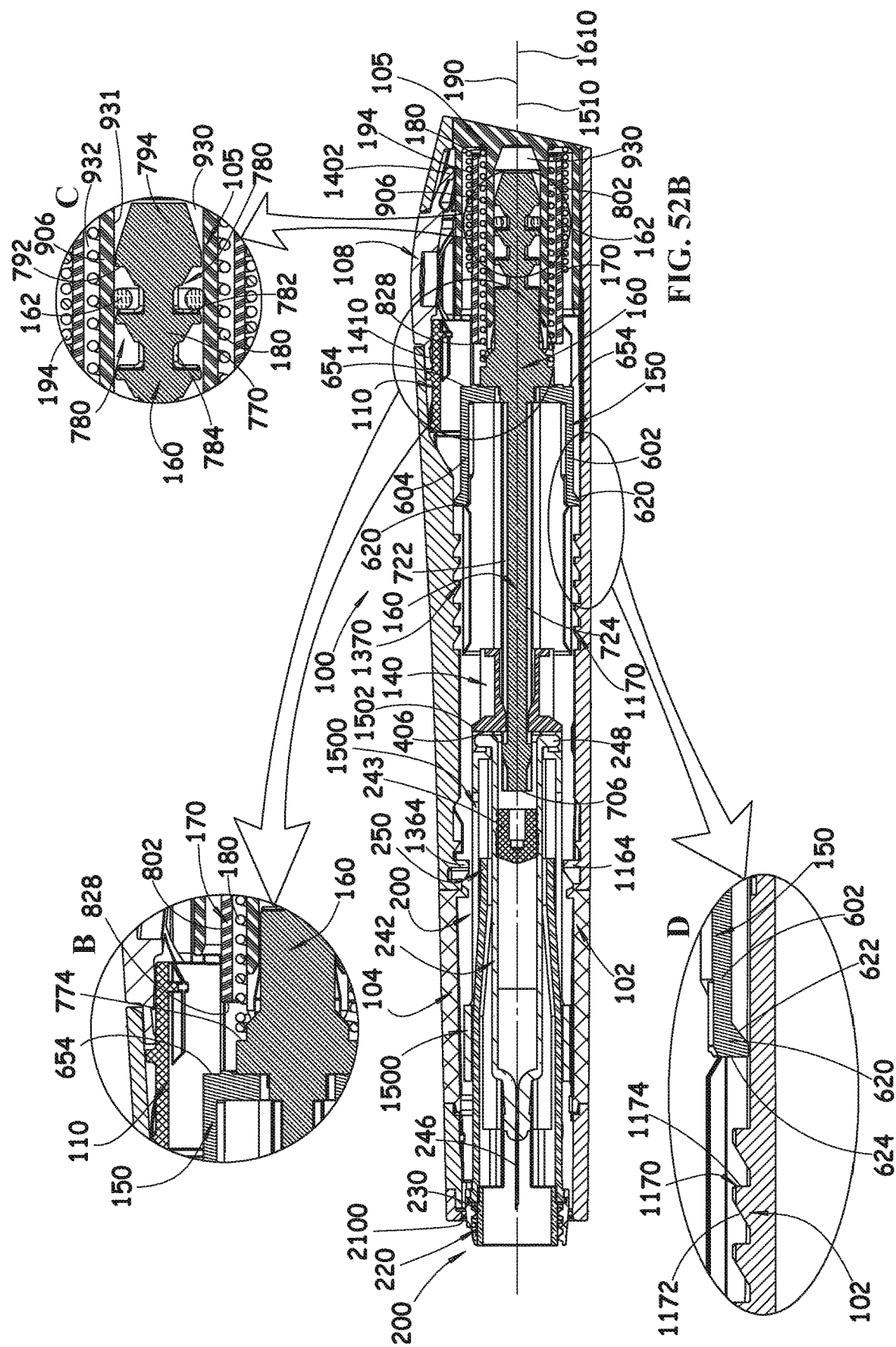
Figure 52C:
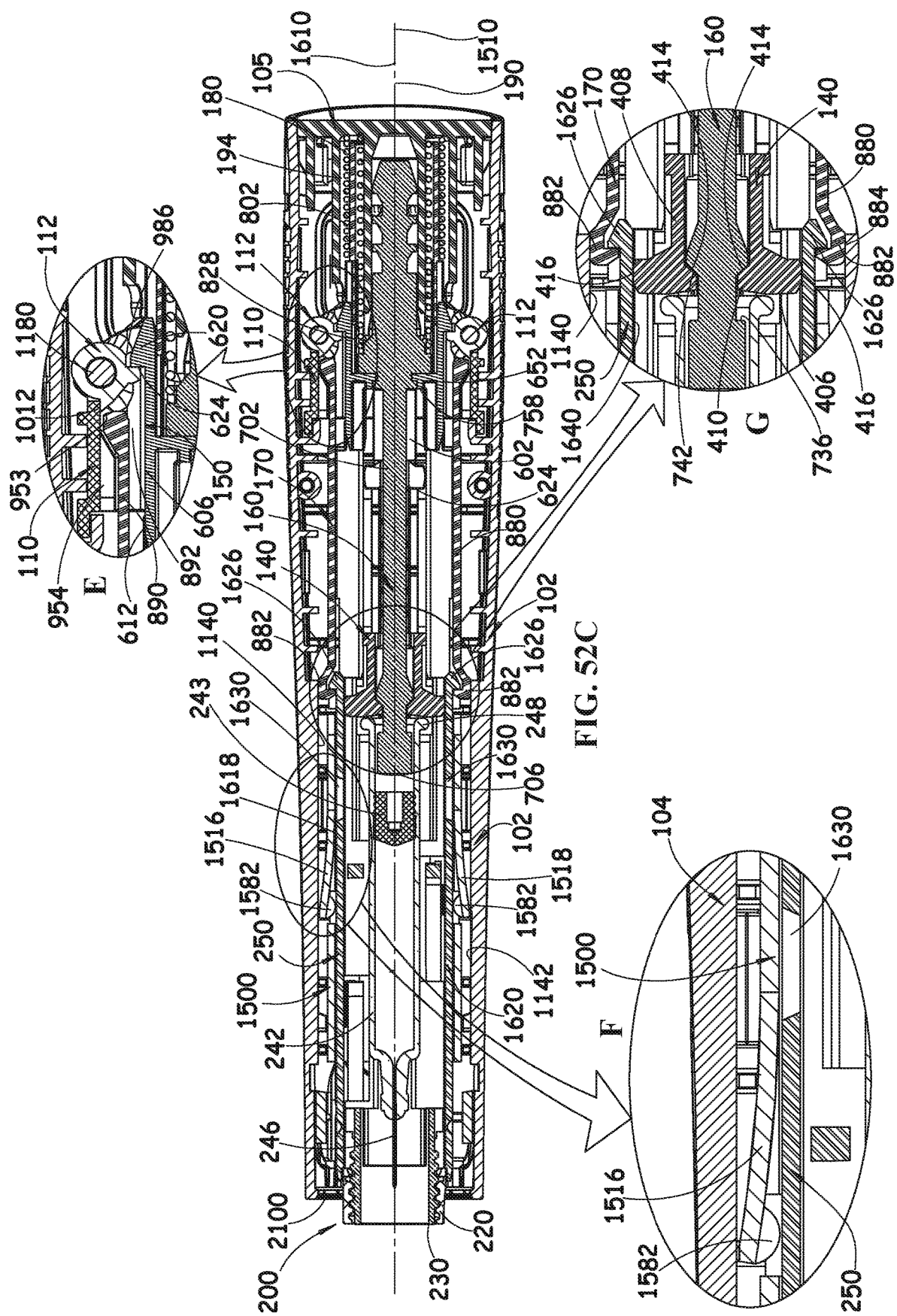
Figure 52D:
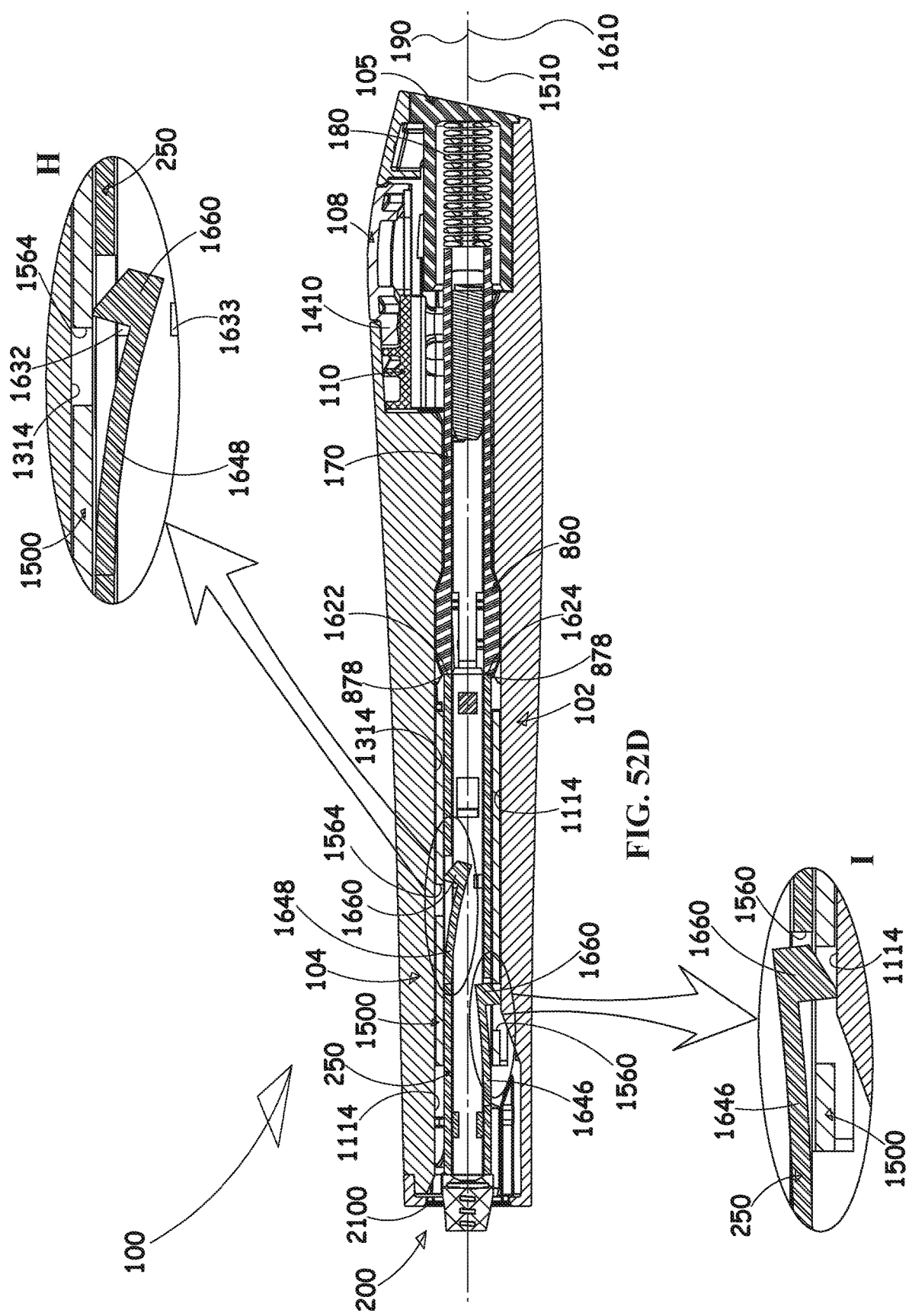

Reference is now made to FIGS. 52A, 52B, 52C and 52D, which are simplified illustrations of an injection site engagement stage of the reusable automatic injection assembly of FIGS. 1A-16H, 18A-18F and 20A-24C following the RNS removal stage. FIG. 52A is a perspective illustration and FIGS. 52B, 52C and 52D are sectional illustrations taken along respective lines B-B, C-C and D-D in FIG. 52A.

As seen in FIGS. 52A-52D, the medicament module 200/300, without the RNS remover 210/310, is displaced rearwardly with respect to the operative orientation as shown in and described above with respect to FIGS. 45A-45D. This rearward displacement takes place when the user presses the reusable automatic injection assembly of FIGS. 1A-16H, 18A-18F and 20A-24C axially along axis 190 against the injection site on the user's body against the urging of spring 194.

It is seen in enlargement G in FIG. 52C that rearwardly-facing tapered surface 414 of control element 140 remains in engagement with tapered planar forward-facing surface 742 of elongate damping driver element 160. At this stage, forward facing surfaces 406 of control element 140 still does not engage rearwardly-facing shoulder surfaces 736 of elongate damping driver element 160.

As also seen in enlargement G in FIG. 52C, outwardly-facing surfaces 416 of forwardly-extending engagement fingers 408 of control element 140 still engage corresponding channels 1640 formed in needle shield 250.

As seen in FIG. 52B, the rearwardmost portions of edge 1502 of module housing 1500 still engage forward facing surfaces 406 of control element 140 and urge it axially rearwardly along axis 190. Module housing 1500 is retained in this axial position since the user is urging the medicament module 200/300 rearwardly along axis 190 by axial engagement thereof with the injection site.

It is appreciated that inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190.

It is also appreciated that, as seen in FIG. 52D and enlargements H and I thereof that protrusions 1660 of finger portions 1648 and 1658 of needle shield 250 do not engage slots 1560 and 1564 of the module housing 1500 by virtue of engagement with ribs 1114 of the main housing portion 102 and ribs 1314 of the cover portion 104 with protrusions 1660 of finger portions 1648 and 1658, thus permitting relative movement of module housing 1500 relative to needle shield 250. It is further seen in enlargement I in FIG. 52D that finger portions 1646 and 1656 do not fully engage slots 1560 and 1562 of the module housing 1500.

As noted above with respect to FIGS. 23A-23L and as seen in enlargement B in FIG. 52B, multifunctional retaining element 150 is disposed along axis 190 relative to the multifunctional engagement element 170 such that rearwardly-facing surface 654 of multifunctional retaining element 150 no longer engages the forward edge 828 of cylindrical portion 802 of multifunctional engagement element 170.

As seen in enlargement E in FIG. 52C, forward engagement surface 624 of outwardly-facing tapered protrusion 620 of each of generally identical fingers 606 and 608 of the multifunctional retaining element 150 still engages radially extending walls 986 of latch elements 112, thereby preventing forward displacement of the multifunctional retaining element 150 relative to the main housing portion 102 and the cover portion 104.

As seen in enlargement C in FIG. 52B, a rearward portion of elongate damping driver element 160 including a rearward portion of intermediate elongate portion 770 and the series of axial movement direction dependent damping control friction element seats 780, is nearly but not completely fully inserted in inner cylindrical volume 930 of generally circular cylindrical portion 906 of end cover 105. Friction element 162 (FIG. 10A, stage I) is disposed axially forwardly of its location in FIG. 44B and remains located adjacent a rearwardly-facing planar surface 782 of elongate damping driver element 160 opposite single bulkhead 794 of forwardmost axial movement direction dependent damping control friction element seat 780, which has also been displaced axially rearwardly, and remains located inwardly of inner-facing surface 931 of generally circular cylindrical portion 906 of end cover 105.

It is also appreciated from sectional enlargement A in FIG. 52A that at this stage user engageable actuation button 108 is not prevented from being pressed at this stage by virtue of disengagement of downward-facing surface 956 of trigger element 110 from rearward-facing resilient finger 890 of multifunctional engagement element 170 due to rearward axial displacement of finger 890.

It is seen in enlargement E in FIG. 52C that rearward-facing resilient finger 890 is supported against inward displacement thereof by rectangular protrusions 954 of trigger element 110.

It is seen in enlargement F in FIG. 52C and sectional enlargement in FIG. 52A that inwardly directed side protrusions 1582 and 1584 of fingers 1516 and 1518 of module housing 1500 are disengaged from narrow slots 1632 and 1633, having been deflected outwardly by engagement thereof with respective tapered surfaces 1634 and 1635.

Figure 53A:
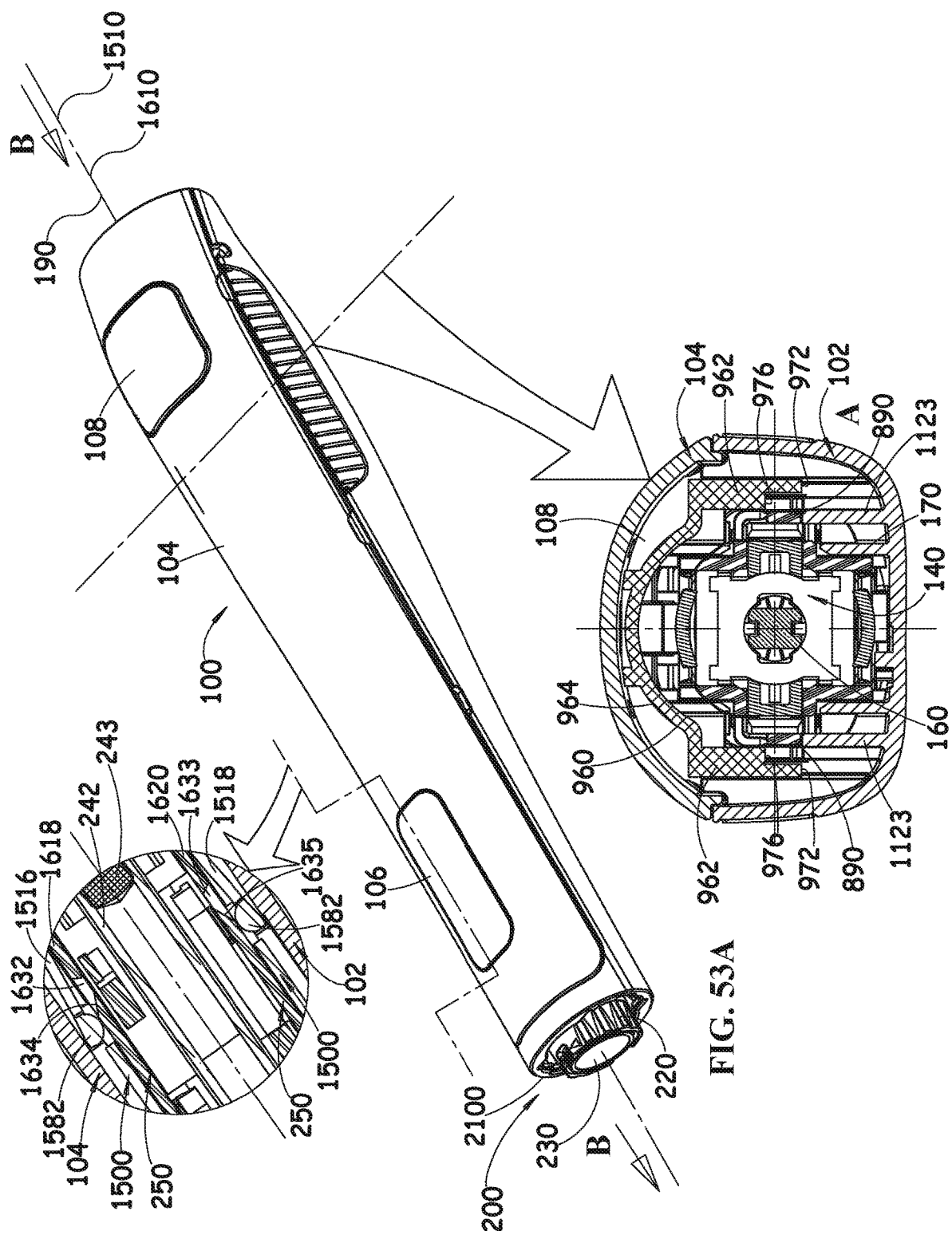

Reference is now made to FIGS. 53A and 53B, which are simplified illustrations of an injection site engagement stage of the reusable automatic injection assembly 100 of FIGS. 1A-15F, 17A-17H and 19A-24C following the RNS removal stage. FIGS. 53A and 53B are respective simplified perspective and sectional illustrations, taken along lines B-B in FIG. 53A.

The reusable automatic injection assembly 100 is seen in FIGS. 53A and 53B in accordance with an alternative embodiment of the present invention, whereas an alternative trigger element 120 and unitary latch element 122 are incorporated into the reusable automatic injection assembly 100.

It is seen that in this injection site engagement stage of the reusable automatic injection assembly 100, all spatial relations between all of the components remain preferably the same as in FIGS. 52A-52E, other than the relations between the trigger element 120 and the unitary latch element 122, which are preferably as follows:

It is seen in FIGS. 53A and 53B that the unitary latch element 122 remains positioned upwardly, in the sense of FIGS. 53A and 53B thus the unitary latch element 122 engages the trigger element 120 (FIGS. 17A-17H). More specifically, it is noted that convex outer-facing surface 1044 of unitary latch element 122 engages concave inner-facing surface 966 of trigger element 120 in this fourth stage of medicament module 200/300 insertion into the reusable automatic injection assembly 100.

It is further seen in FIGS. 53A and 53B that the multifunctional retaining element 150 is still retained from further forward displacement due to engagement between engagement surface 624 of tapered protrusion 620 of multifunctional retaining element 150 and rearward facing surface 1056 of latch element 122.

It is particularly seen in an enlargement B in FIG. 53B that forward engagement surface 624 of outwardly-facing tapered protrusion 620 of each of generally identical fingers 606 and 608 of the multifunctional retaining element 150 engages rearward facing surface 1056 of unitary latch element 122, thereby preventing forward displacement of the multifunctional retaining element 150 relative to the main housing portion 102 and the cover portion 104.

It is also appreciated from sectional enlargement A in FIG. 53A that at this stage user engageable actuation button 108 is not prevented from being pressed at this stage by virtue of disengagement of downward-facing surface 976 of trigger element 120 from rearward-facing resilient finger 890 of multifunctional engagement element 170 due to rearward axial displacement of finger 890.

It is appreciated that rearward-facing resilient finger 890 is supported against inward displacement thereof by multifunctional retaining element 150, such that inwardly facing protrusion 892 of resilient finger 890 engages outwardly-facing curved surface 612 of multifunctional retaining element 150.

Reference is now made to FIGS. 54A, 54B, 54C and 54D, which are simplified illustrations of a user-engageable actuation button press stage of the reusable automatic injection assembly of FIGS. 1A-16H, 18A-18F and 20A-24C following the injection site engagement stage.

Figure 54A:
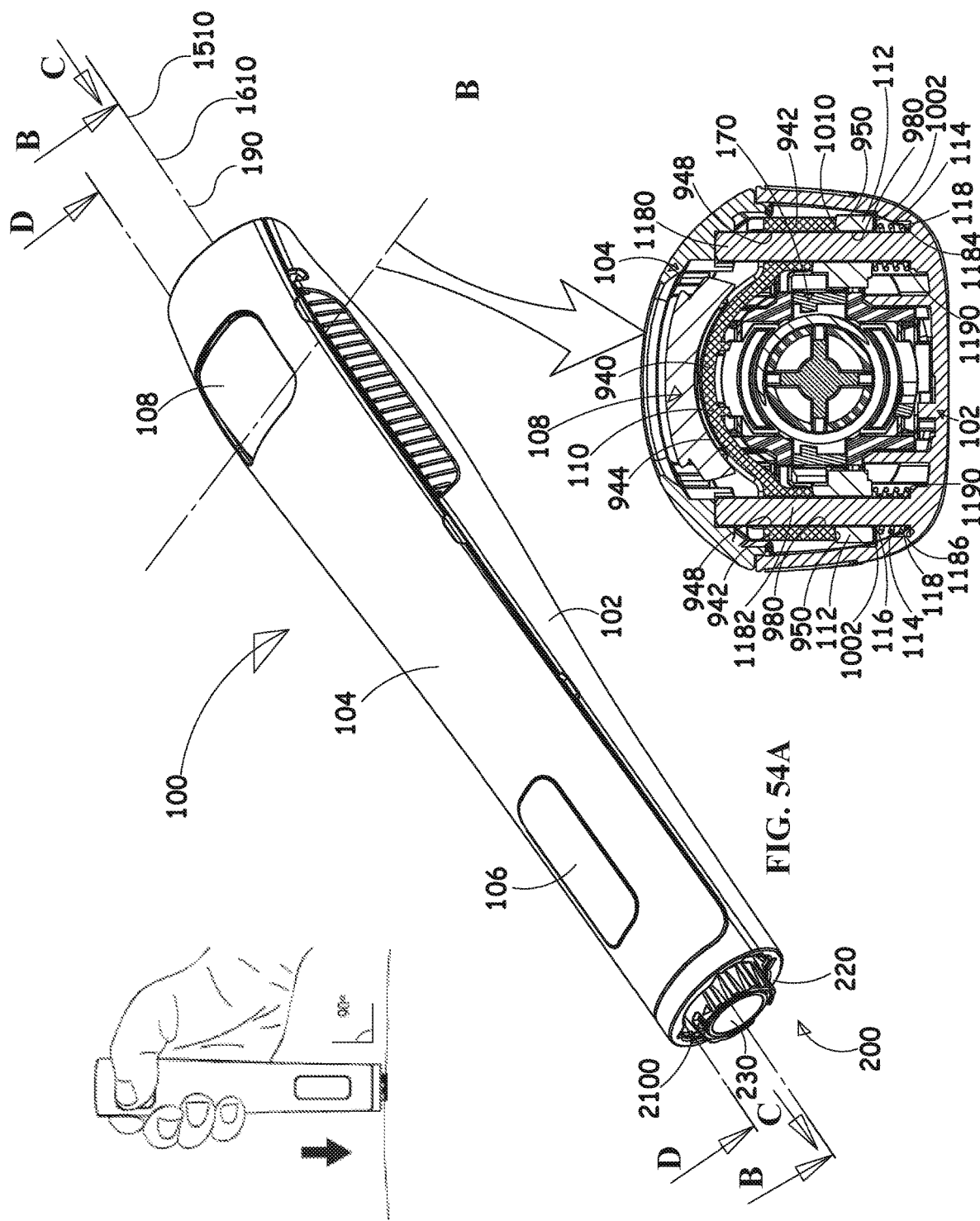
FIGS. 54A, 54B, 54C and 54D are simplified illustrations of a user-engageable actuation button press stage of the reusable automatic injection assembly of FIGS. 1A-16H, 18A-18F and 20A-24C following the injection site engagement stage.
Figure 54B:
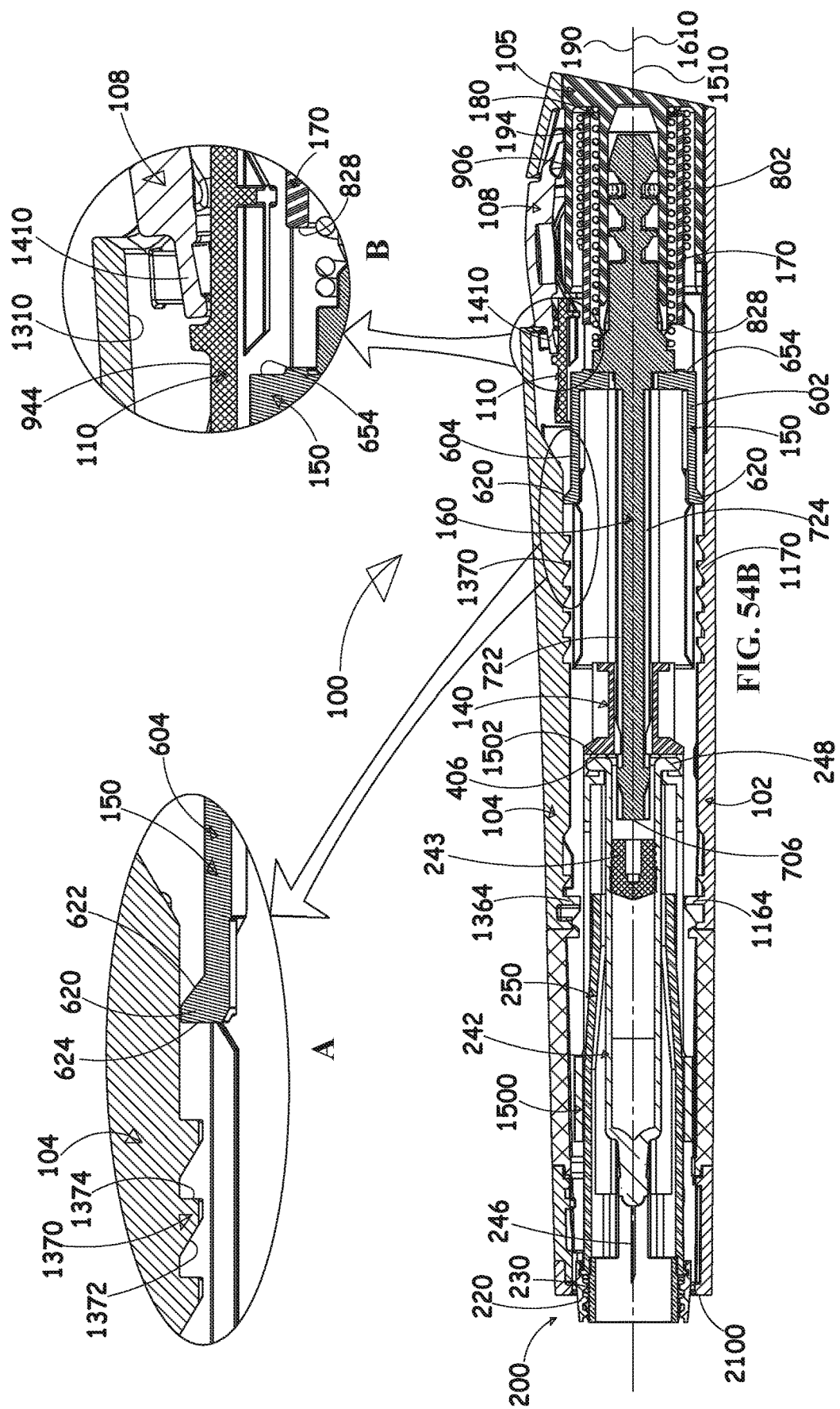
Figure 54C:
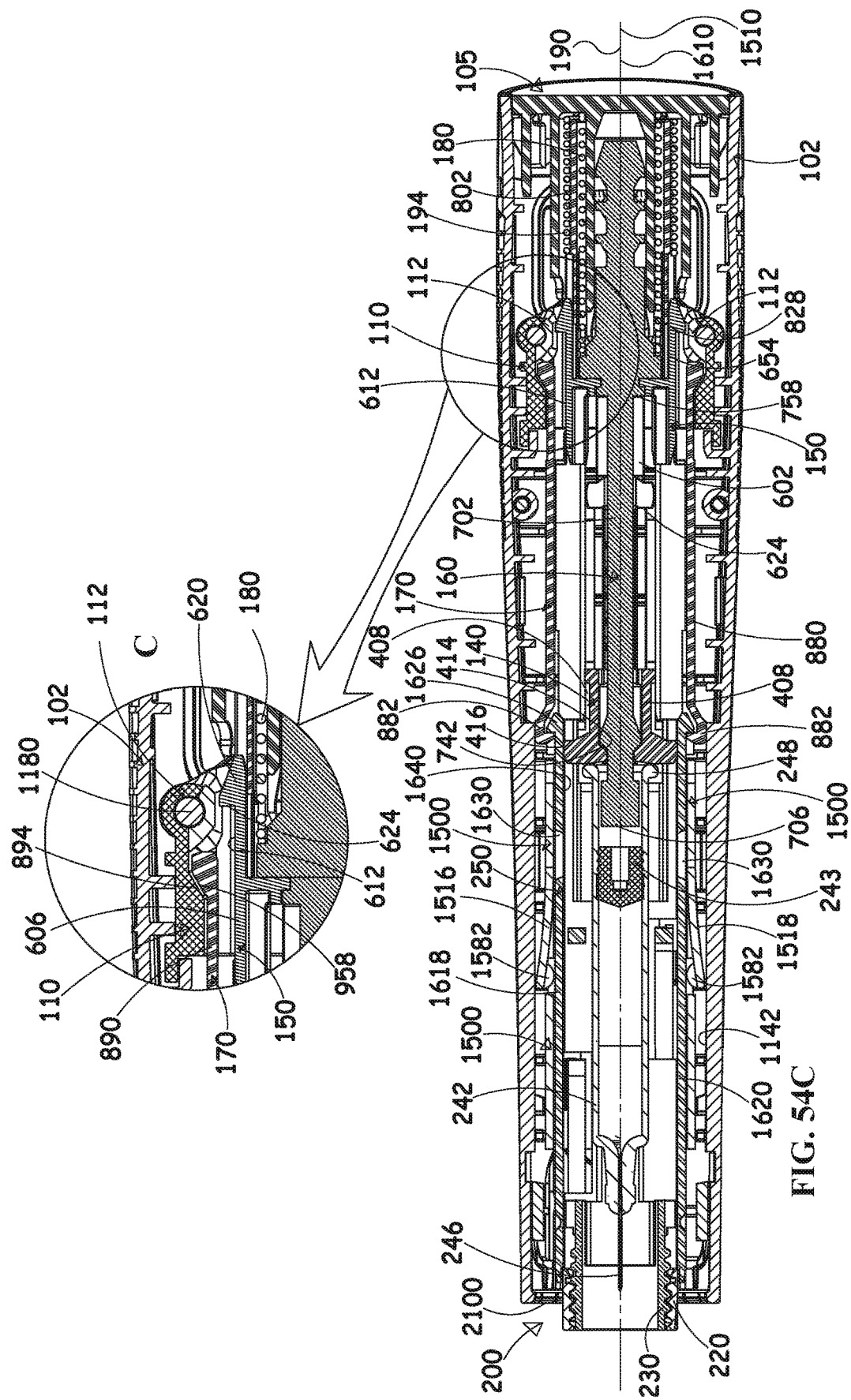

As seen in FIG. 54C, rearwardly-facing tapered surface 414 of control element 140 remains in engagement with tapered planar forward-facing surface 742 of elongate damping driver element 160.

As also seen in FIG. 54C, outwardly-facing surfaces 416 of forwardly-extending engagement fingers 408 of control element 140 still engage corresponding channels 1640 formed in needle shield 250.

As seen in FIG. 54B, the rearwardmost portions of edge 1502 of module housing 1500 still engage forward facing surfaces 406 of control element 140. Module housing 1500 is retained in this axial position since the user is urging the medicament module 200/300 rearwardly along axis 190 by axial engagement thereof with the injection site.

It is appreciated that, as seen in FIG. 54C inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190.

Figure 54D:
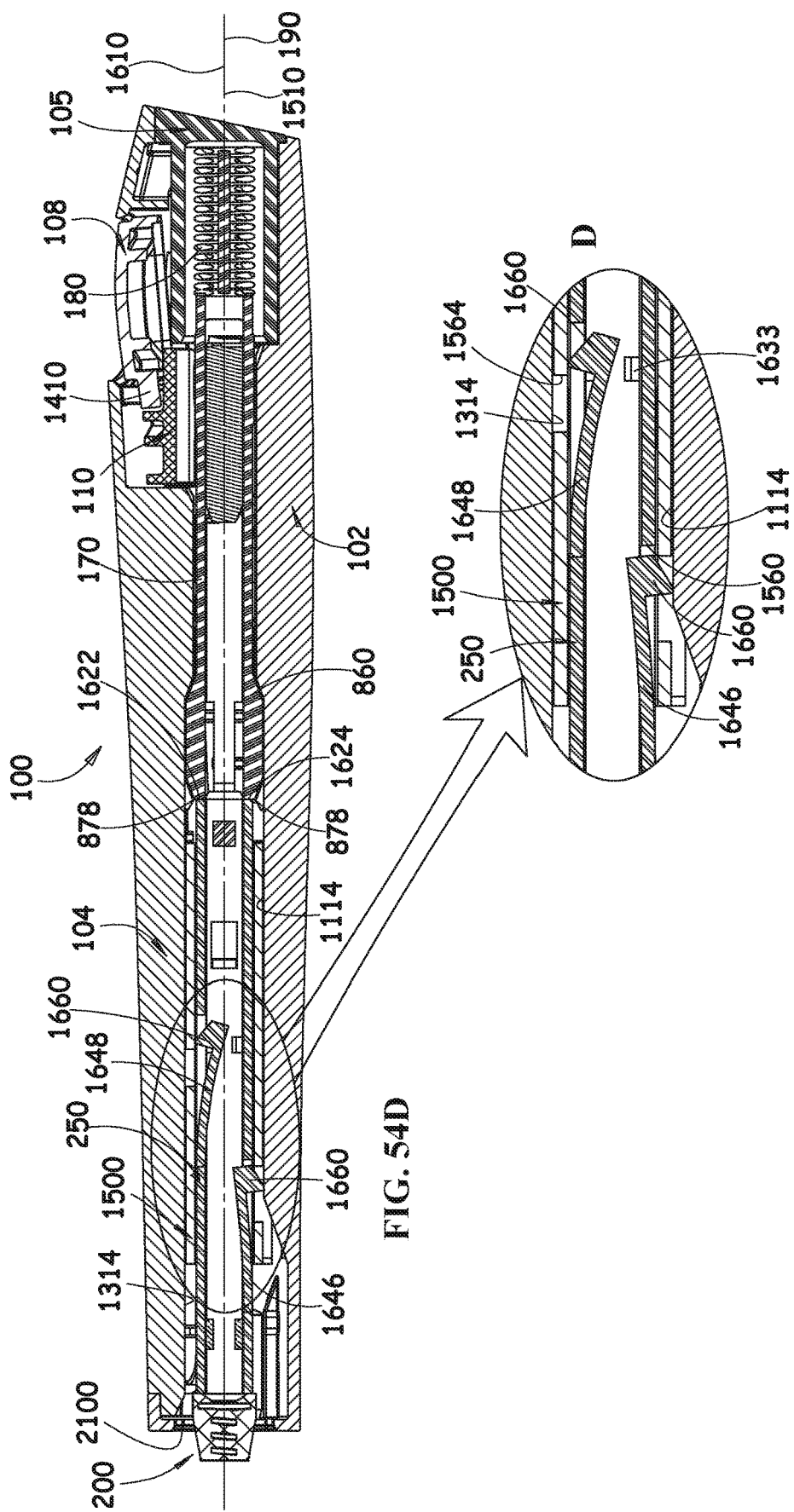

It is also appreciated that, as seen in FIG. 54D and enlargement D thereof that protrusions 1660 of finger portions 1648 and 1658 of needle shield 250 do not engage slots 1560 and 1564 of the module housing 1500 by virtue of engagement with ribs 1114 of the main housing portion 102 and ribs 1314 of the cover portion 104 with protrusions 1660 of finger portions 1648 and 1658, thus permitting relative movement of module housing 1500 relative to needle shield 250. It is further seen in enlargement I in FIG. 52D that finger portions 1646 and 1656 do not fully engage slots 1560 and 1562 of the module housing 1500.

As noted above with respect to FIGS. 23A-23L and as seen in FIG. 54B, multifunctional retaining element 150 is disposed along axis 190 relative to the multifunctional engagement element 170 such that rearwardly-facing surface 654 of multifunctional retaining element 150 still does not engage the forward edge 828 of cylindrical portion 802 of multifunctional engagement element 170.

As seen in enlargement C in FIG. 54C, forward engagement surface 624 of outwardly-facing tapered protrusion 620 of each of generally identical fingers 606 and 608 of the multifunctional retaining element 150 no longer engage radially extending walls 986 of latch elements 112, thereby permitting forward displacement of the multifunctional retaining element 150 relative to the main housing portion 102 and the cover portion 104. This operative orientation results from the following:

The user presses user engageable button 108, which causes inward displacement of trigger element 110, thereby displacing latch elements 112 inwardly along pins 1180 and 1182, against the urging of springs 114.

It is appreciated that inwardly directed side protrusions 1582 and 1584 of module housing 1500 remain disengaged from narrow slots 1632 and 1633, having been deflected outwardly by engagement thereof with respective tapered surfaces 1634 and 1635.

It is a particular feature of the present invention that at this stage, momentarily, outwardly-facing protruding surfaces 894 and 896 of multifunctional engagement element 170 engage tapered rearward facing surfaces 958 of trigger element 110 and elongate outwardly-facing curved surfaces 612 of multifunctional retaining element 150 engage inwardly facing protrusion 892 of multifunctional engagement element 170, thereby momentarily retaining needle shield 250 against forward axial displacement in order to prevent sudden impact of the medicament module 200/300 on the injection site following actuation of the reusable automatic injection assembly 100.

Figure 55A:
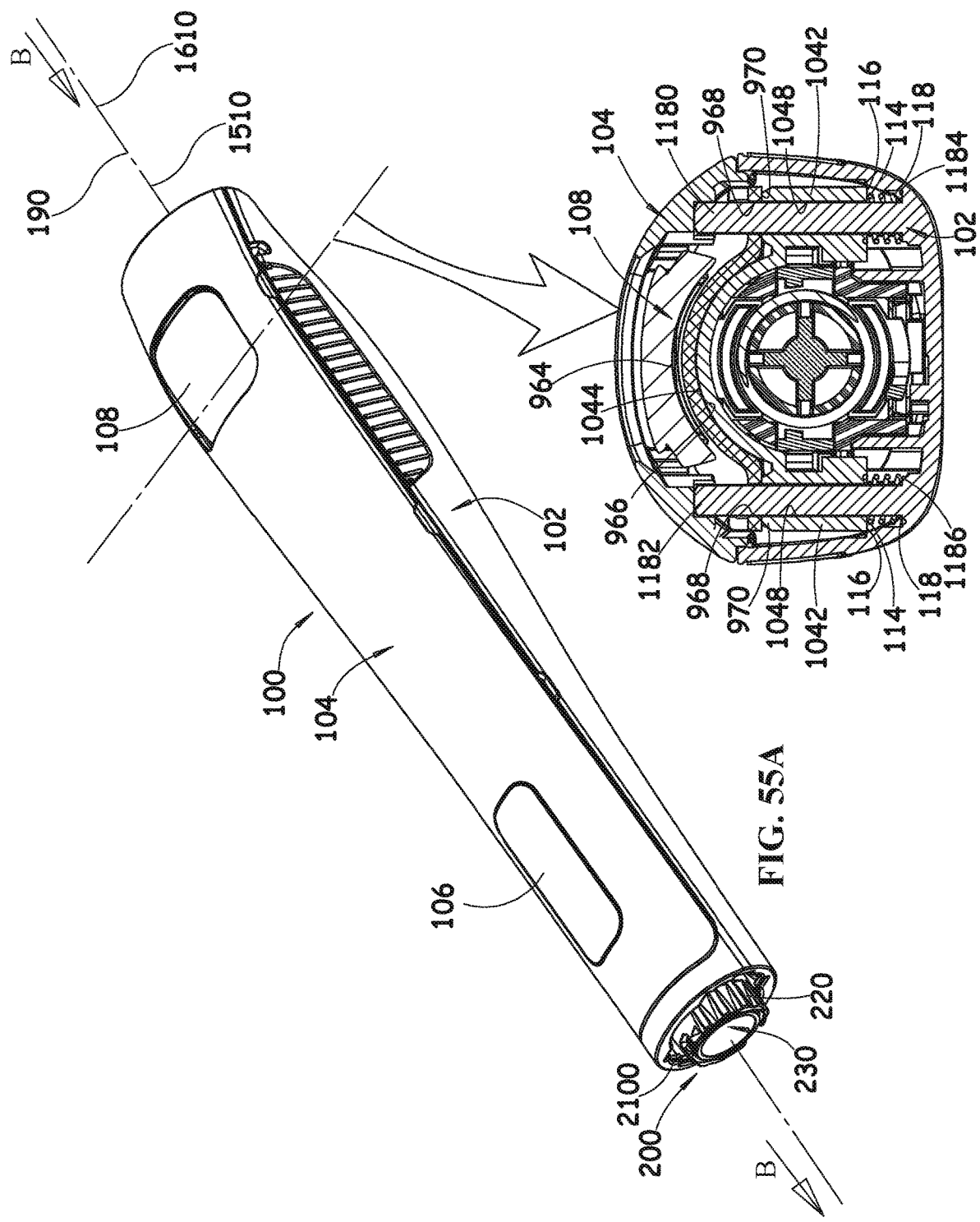
FIGS. 55A and 55B are simplified illustrations of a user-engageable actuation button press stage of the reusable automatic injection assembly of FIGS. 1A-15F, 17A-17H and 19A-24C following the injection site engagement stage.
Figure 55B:
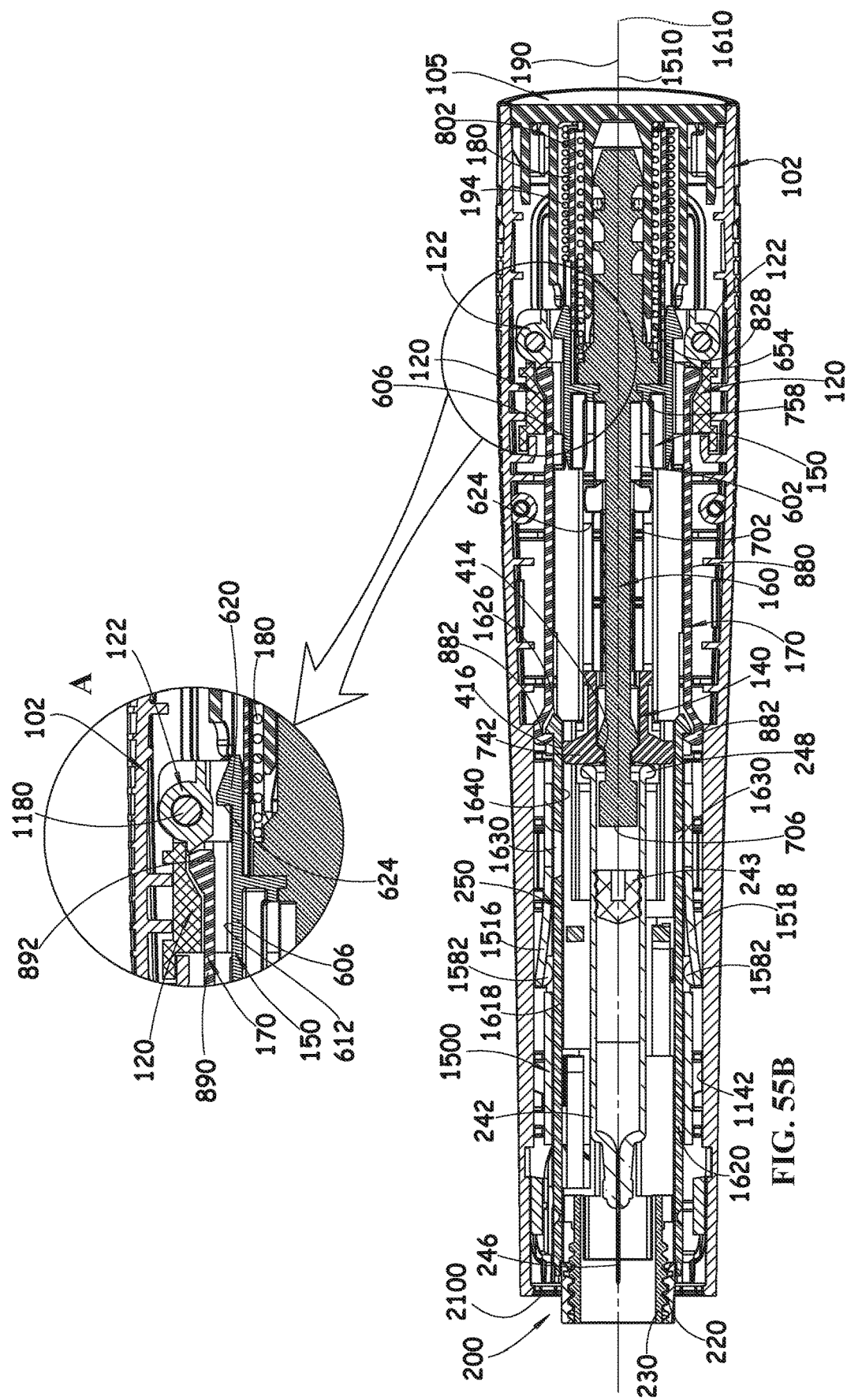

Reference is now made to FIGS. 55A and 55B, which are simplified illustrations of a user-engageable actuation button press stage of the reusable automatic injection assembly of FIGS. 1A-15F, 17A-17H and 19A-24C following the injection site engagement stage. FIGS. 55A and 55B are respective simplified perspective and sectional illustrations taken along lines B-B in FIG. 55A.

The reusable automatic injection assembly 100 is seen in FIGS. 55A and 55B in accordance with an alternative embodiment of the present invention, whereas an alternative trigger element 120 and unitary latch element 122 are incorporated into the reusable automatic injection assembly 100.

It is seen that in this user-engageable actuation button press stage of the reusable automatic injection assembly 100, all spatial relations between all of the components remain preferably the same as in FIGS. 54A-54D, other than the relations between the trigger element 120 and the unitary latch element 122, which are preferably as follows:

It is seen in an enlargement A in FIG. 55B, forward engagement surface 624 of outwardly-facing tapered protrusion 620 of each of generally identical fingers 606 and 608 of the multifunctional retaining element 150 no longer engages rearward facing surface 1056 of unitary latch element 122, thereby permitting forward displacement of the multifunctional retaining element 150 relative to the main housing portion 102 and the cover portion 104. This operative orientation results from the following:

The user presses user engageable button 108, which causes inward displacement of trigger element 120, thereby displacing unitary latch element 122 inwardly along pins 1180 and 1182, against the urging of springs 114.

Figure 56A:
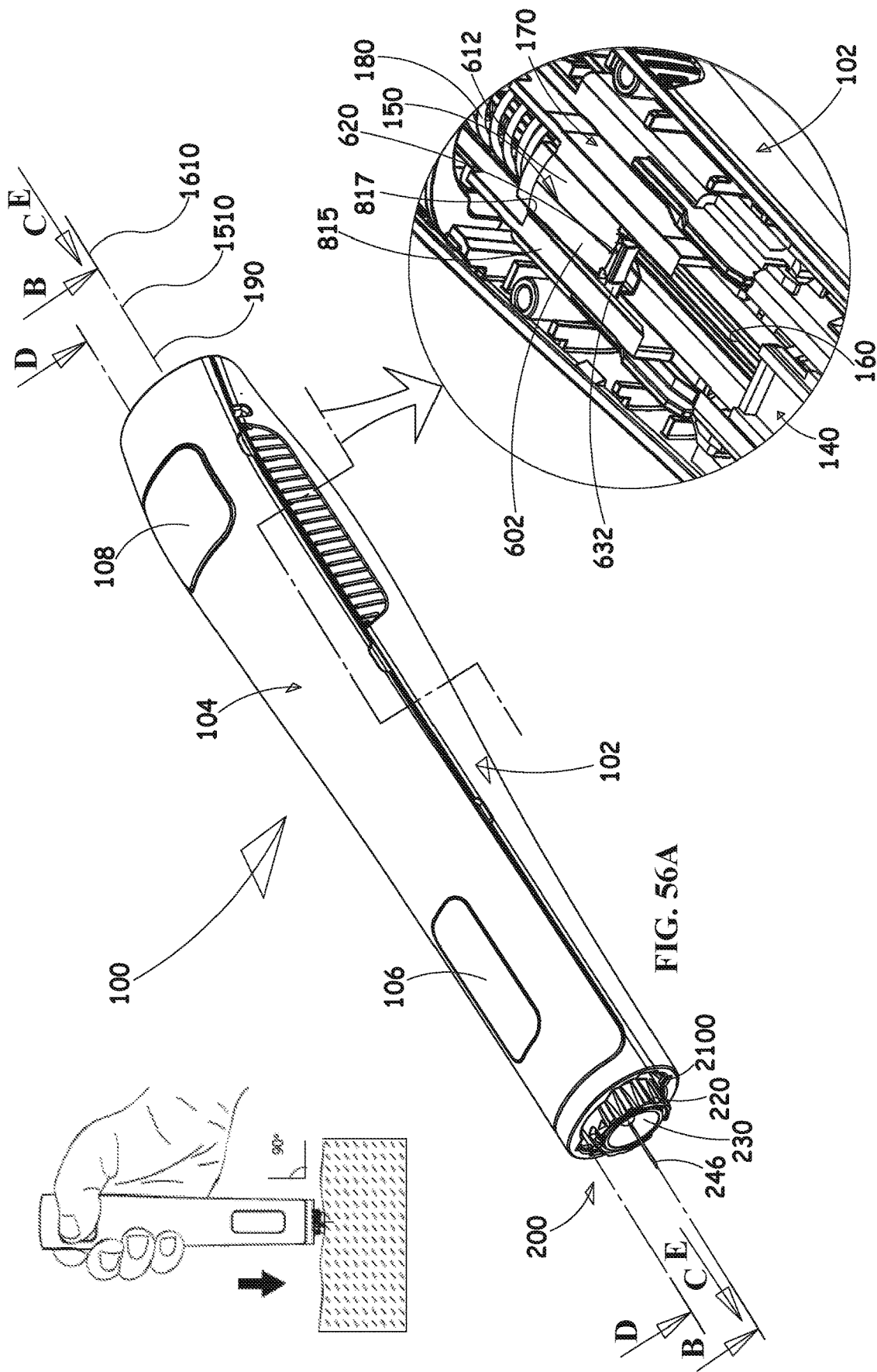
Figure 56B:
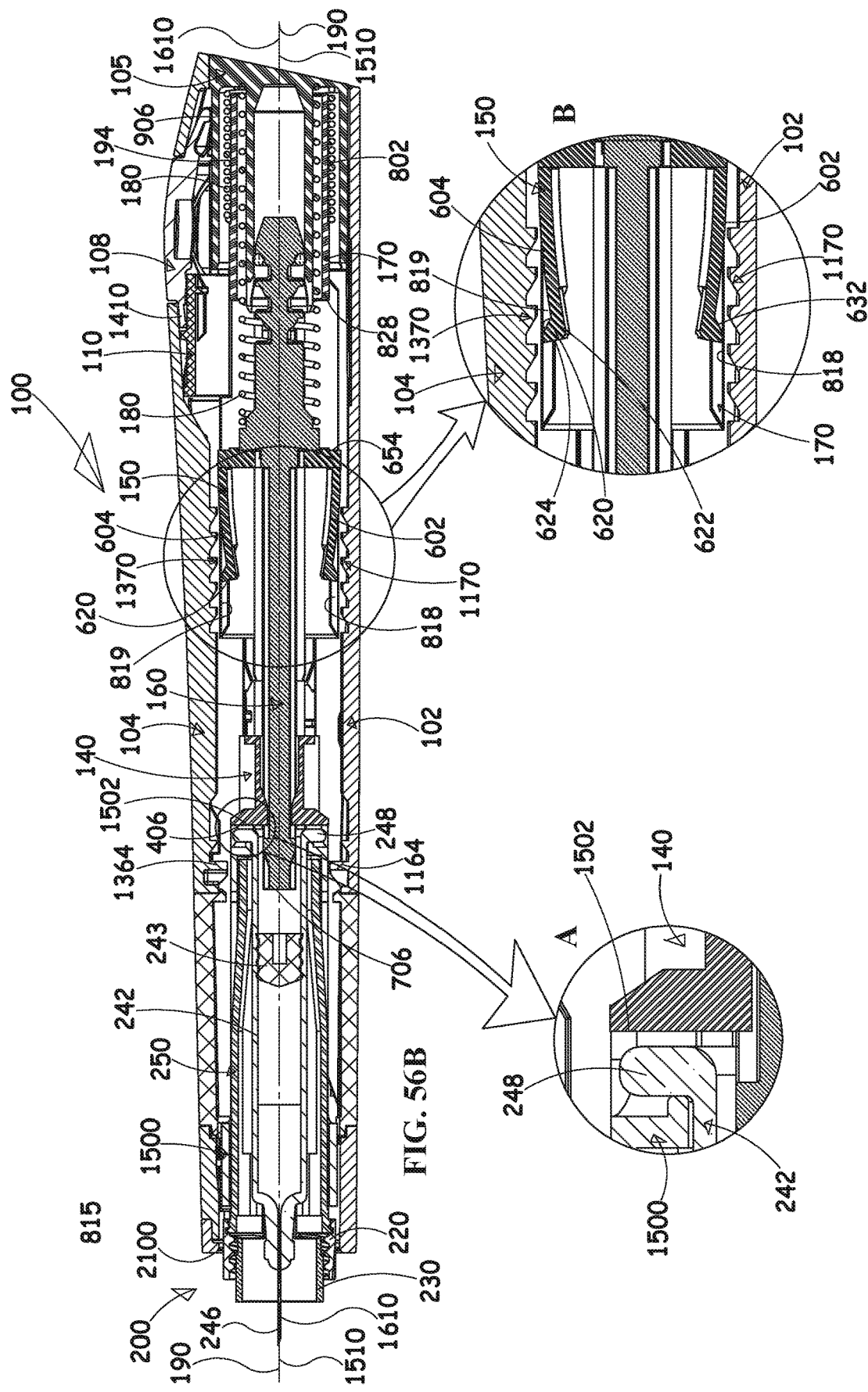
Figure 56C:
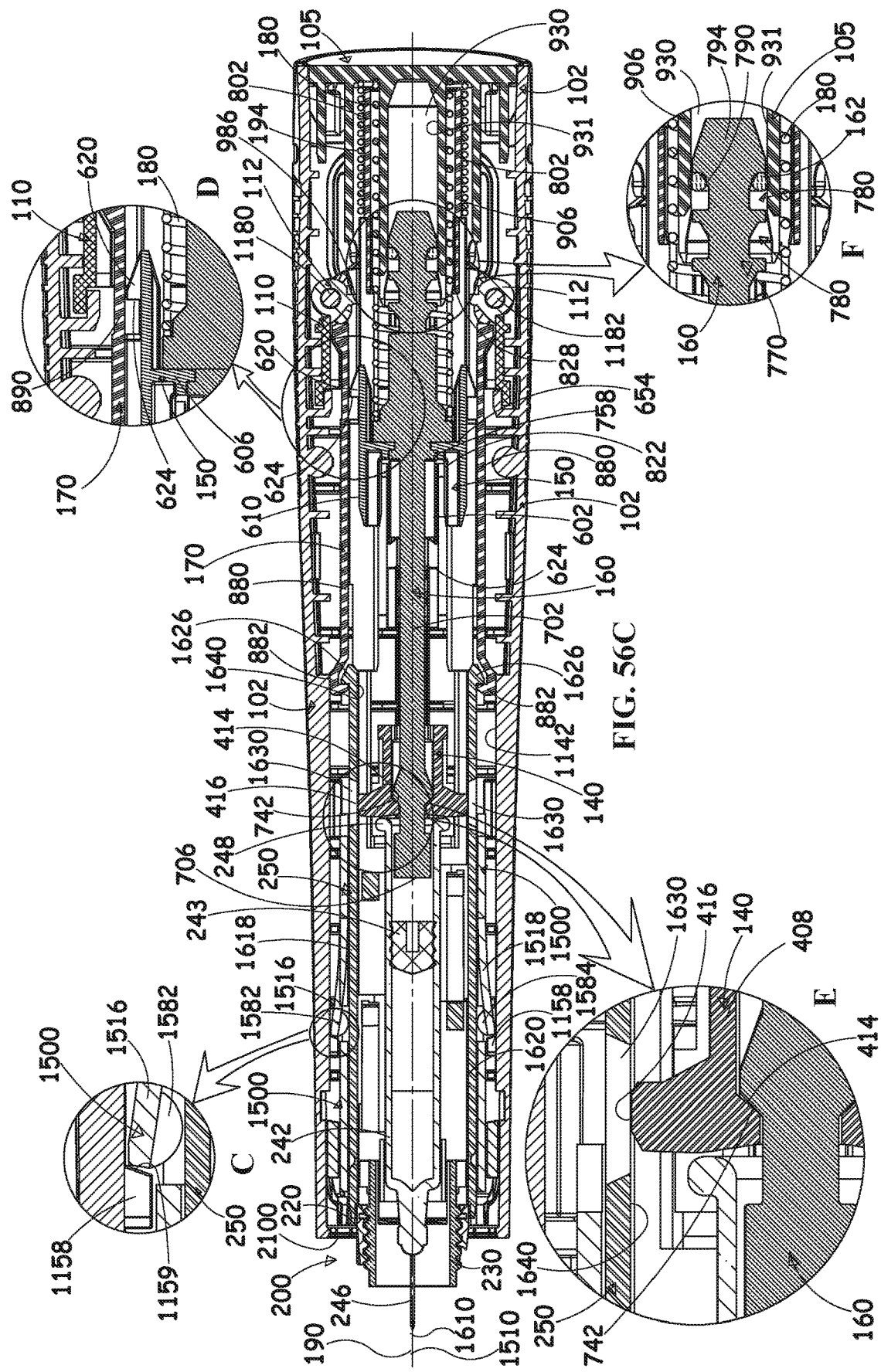

Reference is now made to FIGS. 56A, 56B, 56C, 56D and 56E, which are simplified illustrations of an injection site needle penetration stage of the reusable automatic injection assembly of FIGS. 1A-16H, 18A-18F and 20A-24C following the user-engageable actuation button press stage. FIG. 56A is a simplified perspective illustration, FIGS. 56B-56D are simplified sectional illustrations taken along lines B-B, C-C and D-D in FIG. 56A and FIG. 56E is a simplified partially cut-away illustration of the reusable automatic injection assembly of FIG. 56A.

As seen in enlargement E in FIG. 56C, rearwardly-facing tapered surface 414 of control element 140 remains in engagement with tapered planar forward-facing surface 742 of elongate damping driver element 160.

As also seen in FIG. 56C, outwardly-facing surfaces 416 of forwardly-extending engagement fingers 408 of control element 140 do not engage corresponding channels 1640 formed in needle shield 250, rather fingers 408 are now aligned with rearward slots 1630 of needle shield 250 and are allowed to be outwardly deflected.

As seen in FIG. 56B, the forward facing surfaces 406 of control element 140 engage the rearwardmost portions of edge 1502 of module housing 1500 and flange 248 of syringe 242 and urge it axially forwardly along axis 190 under the force of injection spring 180 thus causing penetration of needle 246 into the injection site.

It is appreciated that, as seen in FIG. 56C inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190.

It is also appreciated that, as seen in enlargement G in FIG. 56D, protrusions 1660 of finger protrusions 1646, 1648, 1656 and 1658 of needle shield 250 are out of engagement with slots 1560, 1562, 1564 and 1566 of the module housing due to forward displacement of the module housing 1500 relative the main housing portion 102 and the cover portion 104.

As noted above with respect to FIGS. 23A-23L and as seen in FIG. 56C, multifunctional retaining element 150 is disposed along axis 190 relative to the multifunctional engagement element 170 such that rearwardly-facing surface 654 of multifunctional retaining element 150 still does not engage the forward edge 828 of cylindrical portion 802 of multifunctional engagement element 170.

As seen in FIG. 56C, forward engagement surface 624 of outwardly-facing tapered protrusion 620 of each of generally identical fingers 606 and 608 of the multifunctional retaining element 150 remain not engaged with radially extending walls 986 of latch elements 112.

As seen in enlargement F in FIG. 56C, a rearward portion of elongate damping driver element 160 including a rearward portion of intermediate elongate portion 770 and the series of axial movement direction dependent damping control friction element seats 780, is partially inserted in inner cylindrical volume 930 of generally circular cylindrical portion 906 of end cover 105, following forward displacement of the elongate damping driver element 160 relative to main housing portion 102 and cover portion 104. In this operative orientation, friction element 162 (FIG. 10A, stage II) abuts a circularly symmetric rearwardly and outwardly tapered axial portion 790 of elongate damping driver element 160, inwardly of inner-facing surface 931 of generally circular cylindrical portion 906 of end cover 105.

It is appreciated from a consideration of enlargement F in FIG. 56C that engagement of friction element 162 with tapered axial portion 790 causes increased friction during forward displacement of the elongate damping driver element 160 thus dampening the forward displacement thereof.

It is further appreciated that during forward motion of the elongate damping drive element 160, a partial vacuum is created between friction element 162 and the end cover 105, which enhances damping of forward axial motion of the elongate damping drive element 160 relative to the main housing portion 102.

It is a particular feature of an embodiment of the present invention that the enhanced friction and partial vacuum are configured for preventing damage to the syringe 242 and additional components of the reusable automatic injection assembly at the end of forward displacement of the elongate damping drive element 160 and additionally reduce noise during actuation of the reusable automatic injection assembly.

It is seen in FIG. 56C that during forward displacement of module housing 1500, fingers 1516 and 1518 of module housing 1500 remain disengaged from narrow slots 1632, 1633 of needle shield 250. Fingers 1516 and 1518 of the module housing 1500 are displaced forwardly up to engagement with tapered surfaces 1159 of protrusions 1158 on main housing portion 102 and corresponding tapered surfaces 1394 of protrusions 1392 on cover portion 104 thereby restricting further forward displacement of the module housing 1500.

It is a particular feature of an embodiment of the present invention that retaining forward displacement of the module housing 1500 by main housing portion 102 and cover portion 104, rather than by needle shield 250, prevents transferring the force of the injection spring 180 to the user. The force of the injection spring 180 is transferred through the elongate damping driver element 160 to the piston 243 of the syringe 242. The flange 248 of the syringe 242 is supported on backward facing edge 1502 of module housing 1500, which is retained from forward displacement by main housing portion 102 and cover portion 104, thus the entire force of injection spring 180 is transferred to module housing 1500.

It is seen in sectional enlargement in FIG. 56A that multifunctional retaining element 150 is displaced forwardly with respect to main housing portion 102 and cover portion 104 under the force of injection spring 180, thus causing engagement of forwardly facing tapered surfaces 632 of generally identical fingers 602, 604 of multifunctional retaining element 150 with rearwardly facing tapered surface 817 of the multifunctional engagement element 170, thus causing inward deflection of fingers 602, 604 and further sliding forward movement of multifunctional retaining element 150 along axial walls 815 of the multifunctional engagement element 170. This sliding forward movement of multifunctional retaining element 150 relative to multifunctional engagement element 170 permits bypassing of the mutually axially spaced ratchet teeth 1170 of the main housing portion 102 and ratchet teeth 1370 of the cover portion 104.

It is seen in FIG. 56E that finger 610 (FIGS. 6A-6I) of multifunctional retaining element 150 as seen at III in FIG. 8 is bent generally inwardly with respect to longitudinal axis 190 by virtue of engagement with rearwardly tapered rearward end 1113 of main housing portion 102 and is now engaged with the inwardly facing surface 1116 of rib 1115 of main housing portion 102.

Figure 57:
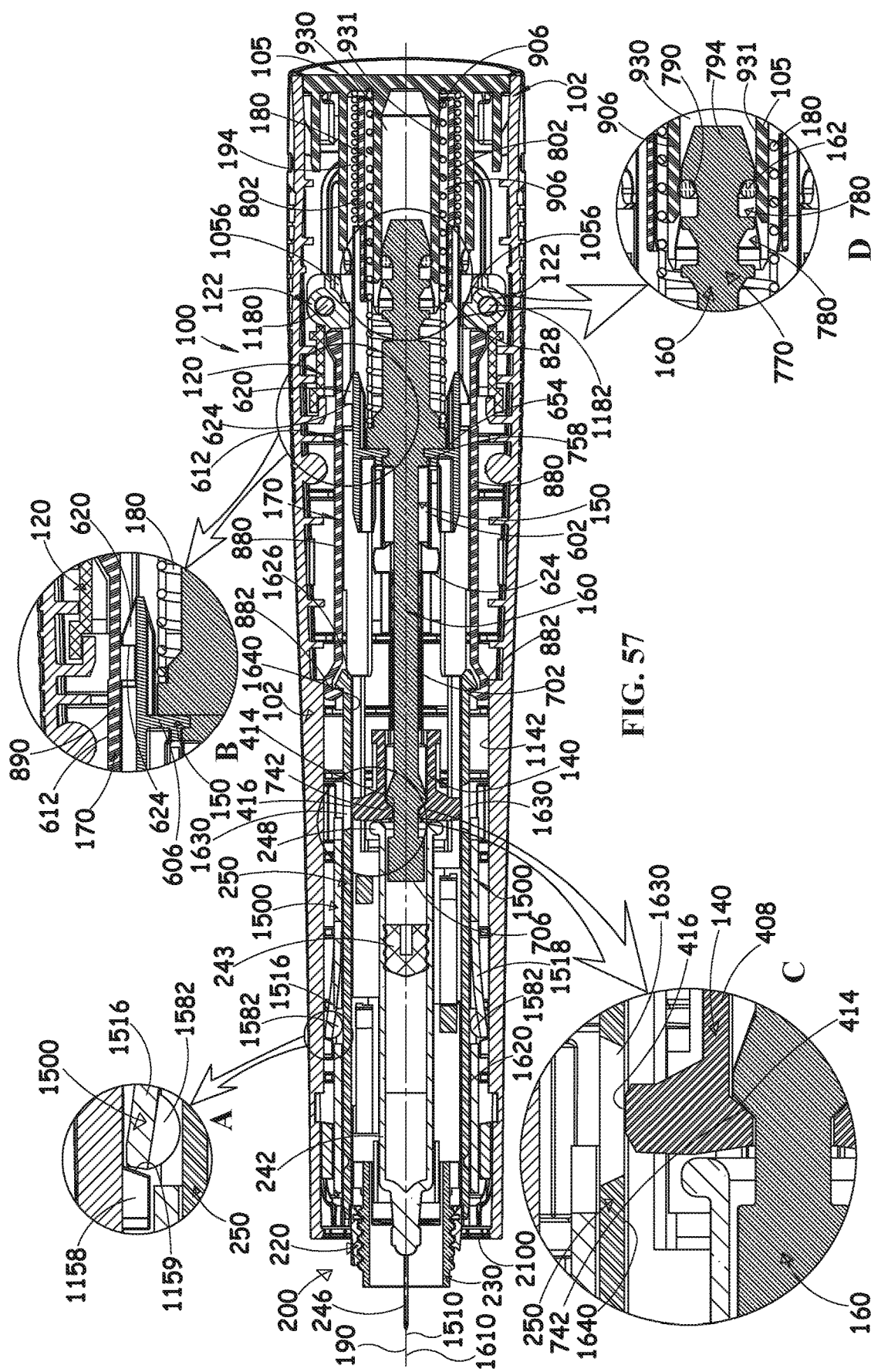
FIG. 57 is a simplified illustration of an injection site needle penetration stage of the reusable automatic injection assembly of FIGS. 1A-15F, 17A-17H and 19A-24C following the user-engageable actuation button press stage.

Reference is now made to FIG. 57, which is a simplified illustration of an injection site needle penetration stage of the reusable automatic injection assembly of FIGS. 1A-15F, 17A-17H and 19A-24C following the user-engageable actuation button press stage. FIG. 57 is a simplified sectional illustrations taken along lines E-E in FIG. 56A.

The reusable automatic injection assembly 100 is seen in FIG. 57 in accordance with an alternative embodiment of the present invention, whereas an alternative trigger element 120 and unitary latch element 122 are incorporated into the reusable automatic injection assembly 100.

It is seen that in this injection site needle penetration stage of the reusable automatic injection assembly 100, all spatial relations between all of the components remain preferably the same as in FIGS. 56A-56E.

It is seen in FIG. 57 that forward engagement surface 624 of outwardly-facing tapered protrusion 620 of each of generally identical fingers 606 and 608 of the multifunctional retaining element 150 remain not engaged with rearward facing surface 1056 of unitary latch element 122, since the multifunctional retaining element 150 is now positioned forwardly to unitary latch element 122, which has been displaced outwardly under the biasing force of springs 114 following pressing of the actuation button 108.

Figure 58A:
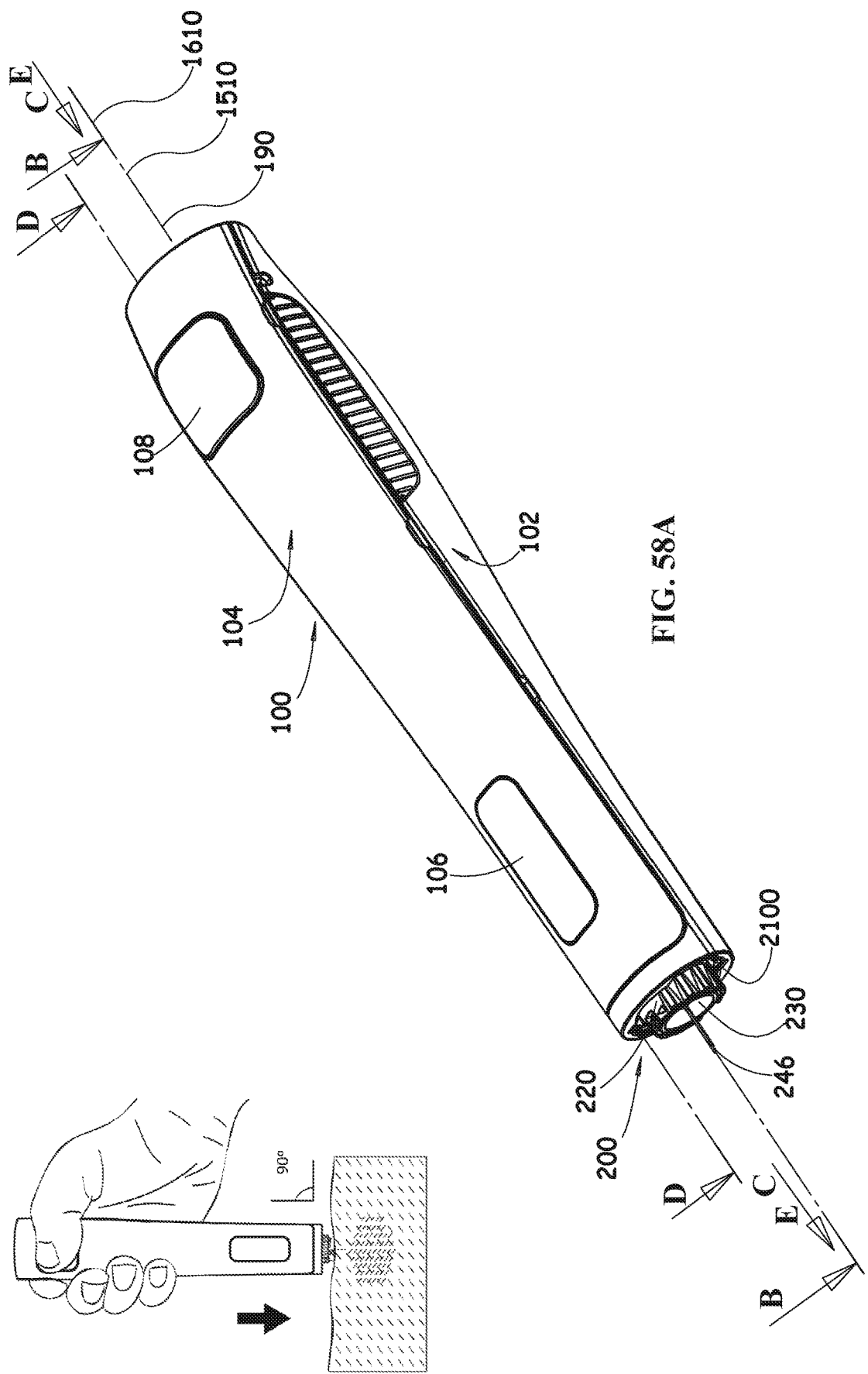
Figure 58B:
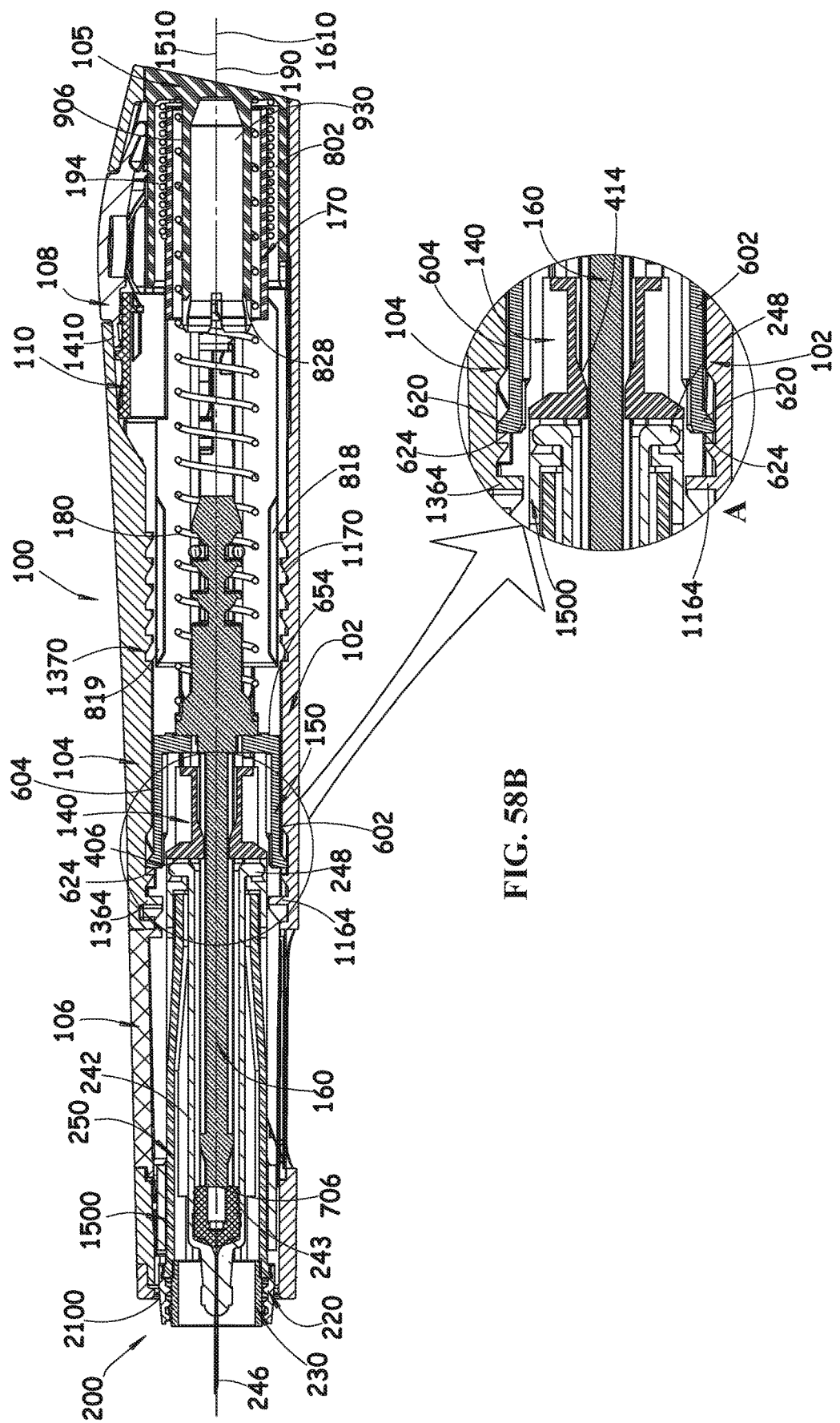
Figure 58C:
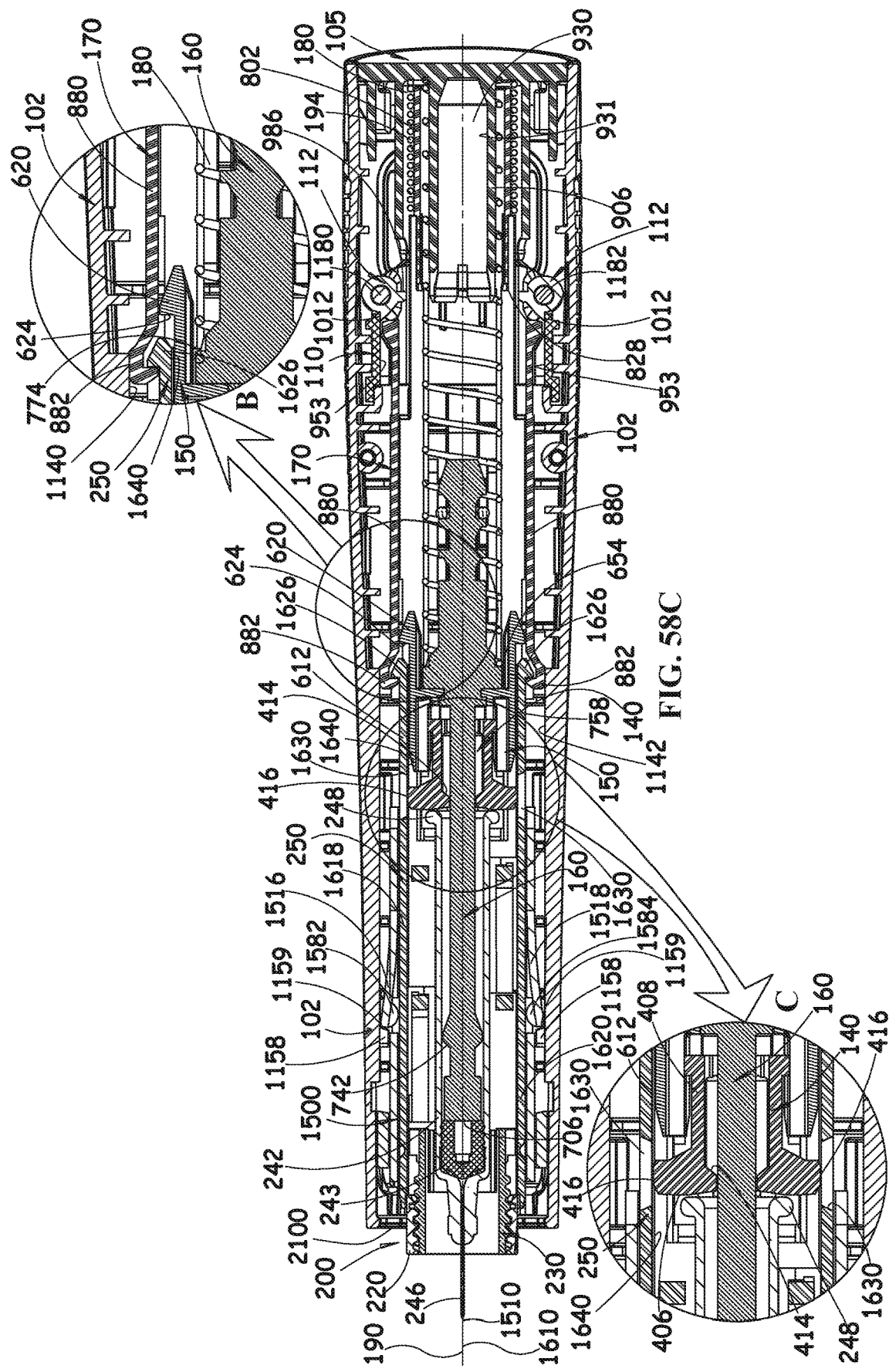

Reference is now made to FIGS. 58A, 58B, 58C, 58D and 58E, which are simplified illustrations of an injection stage of the reusable automatic injection assembly 100 of FIGS. 1A-16H, 18A-18F and 20A-24C following the injection site needle penetration stage. FIG. 58A is a simplified perspective illustration, FIGS. 58B-58D are simplified sectional illustrations taken along lines B-B, C-C and D-D in FIG. 58A and FIG. 58E is a simplified partially cut-away illustration of the reusable automatic injection assembly of FIG. 58A.

In FIGS. 58A-58E the reusable automatic injection assembly 100 is seen at an end of injection operative orientation, wherein the elongate damping driver element 160 has been displaced axially forwardly, engaged the piston 243 thereby ejected the medication contained in the syringe 242 into the body of the patient. Forward advancement of the elongate damping driver element 160 can be seen through transparent window portion 106 in cover portion 104 and window 1162 in main housing portion 102.

Forward axial displacement of the elongate damping driver element 160 relative to module housing 1500 is permitted due to outward deflection of forwardly-extending engagement fingers 408 of control element 140 and insertion thereof into rearward slots 1630 of needle shield 250. This outward deflection of forwardly-extending engagement fingers 408 is urged by engagement of rearwardly facing tapered surface 414 of forwardly-extending engagement fingers 408 with forwardly facing tapered surface 742 of elongate damping driver element 160.

As seen in FIG. 58C, the forward facing surfaces 406 of control element 140 engage the rearwardmost portions of edge 1502 of module housing 1500. Since the module housing 1500 is retained from axial displacement with respect to main housing portion 102 and cover portion 104, control element 140 is retained from axial forward displacement with respect to main housing portion 102 and cover portion 104.

It is appreciated that, as seen in FIG. 58C inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190.

It is also appreciated that, as seen in FIG. 58D, protrusions 1660 of finger protrusions 1646, 1648, 1656 and 1658 of needle shield 250 are out of engagement with slots 1560, 1562, 1564 and 1566 of the module housing due to forward displacement of the module housing 1500 relative the main housing portion 102 and the cover portion 104.

As noted above with respect to FIGS. 23A-23L and as seen in FIG. 58B, multifunctional retaining element 150 is disposed along axis 190 relative to the multifunctional engagement element 170 such that rearwardly-facing surface 654 of multifunctional retaining element 150 has further displaced forwardly with respect to forward edge 828 of cylindrical portion 802 of multifunctional engagement element 170.

It is appreciated that during forward axial displacement of the elongate damping driver element 160 relative to main housing portion 102 and cover portion 104, the rearward portion of intermediate elongate portion 770 and the series of axial movement direction dependent damping control friction element seats 780 gets out of engagement with the inner cylindrical volume 930 of generally circular cylindrical portion 906 of end cover 105. It is a particular feature of an embodiment of the present invention that damping of a forward axial displacement of elongate damping driver element 160 is operative preferably until engagement of the forwardly-facing surface 706 of the elongate damping driver element 160 with piston 243 of syringe 242.

It is a further particular feature of an embodiment of the present invention that at the end of injection, the piston 234 of syringe 242 bears the entire load of the spring 180, which is transferred to the piston 234 through the elongate damping driver element 160, since the elongate damping driver element 160 is not yet positioned in its forwardmost location in this operative orientation. This force transfer pushes the piston 234 forwardly and thus minimizing dead volume within the syringe 242.

It is seen in FIG. 58D that during forward displacement of module housing 1500, fingers 1516 and 1518 of module housing 1500 remain disengaged from narrow slots 1632, 1633 of needle shield 250. Fingers 1516 and 1518 of the module housing 1500 remain in engagement with tapered surfaces 1159 of protrusions 1158 on main housing portion 102 and corresponding tapered surfaces 1394 of protrusions 1392 on cover portion 104 thereby restricting further forward displacement of the module housing 1500.

It is seen in FIG. 58B that multifunctional retaining element 150 has been nearly fully displaced forwardly with respect to module housing 1500 under the force of injection spring 180.

It is seen in FIG. 58E that finger 610 (FIGS. 6A-6I) of multifunctional retaining element 150 as seen at I in FIG. 8 is now at rest and parallel to longitudinal axis 190, in engagement with protrusion 1138 on the main housing portion 102. At the end of injection operative orientation, finger 610 of multifunctional retaining element 150 momentarily disengages from rib 1115 and exerts abrupt impact on protrusion 1138, thereby transitioning from multifunctional retaining element 150 as seen in state III in FIG. 8 and to multifunctional retaining element 150 as seen in state I in FIG. 8, thus causing noise, providing for audible indication of an end of injection for the user. Simultaneously, tactile indication is provided by this exertion of an abrupt impact on protrusion 1138 by finger 610.

Reference is now made to FIG. 59, which is a simplified illustration of an injection stage of the reusable automatic injection assembly of FIGS. 1A-15F, 17A-17H and 19A-24C following the injection site needle penetration stage. FIG. 59 is a simplified sectional illustrations taken along lines E-E in FIG. 58A.

The reusable automatic injection assembly 100 is seen in FIG. 59 in accordance with an alternative embodiment of the present invention, whereas an alternative trigger element 120 and unitary latch element 122 are incorporated into the reusable automatic injection assembly 100.

It is seen that in this injection site needle penetration stage of the reusable automatic injection assembly 100, all spatial relations between all of the components remain preferably the same as in FIGS. 58A-58E, other than the relations between the trigger element 110 and the unitary latch element 122, which preferably remain the same as described above with reference to FIG. 57.

Figure 60A:
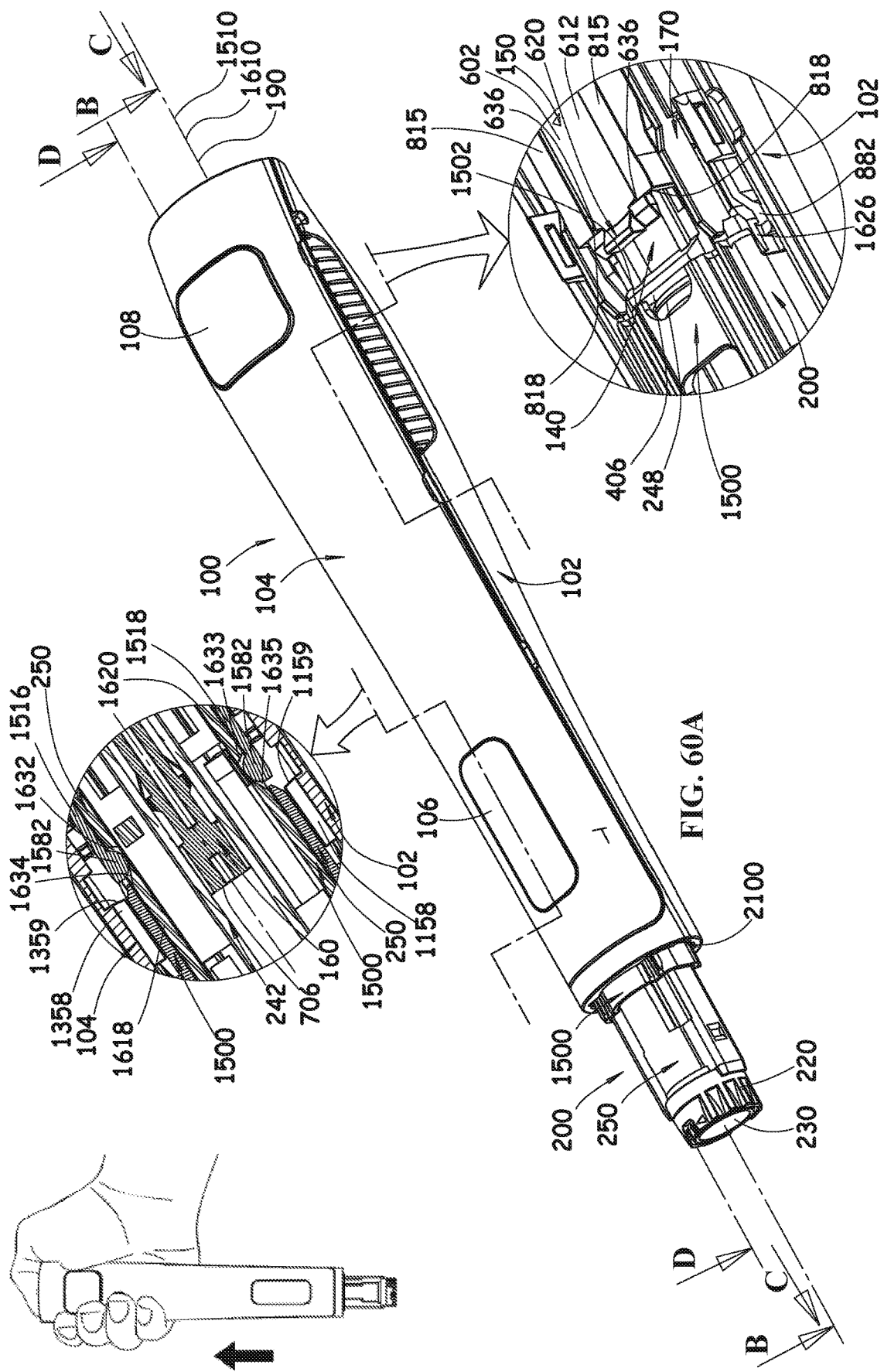
Figure 60D:
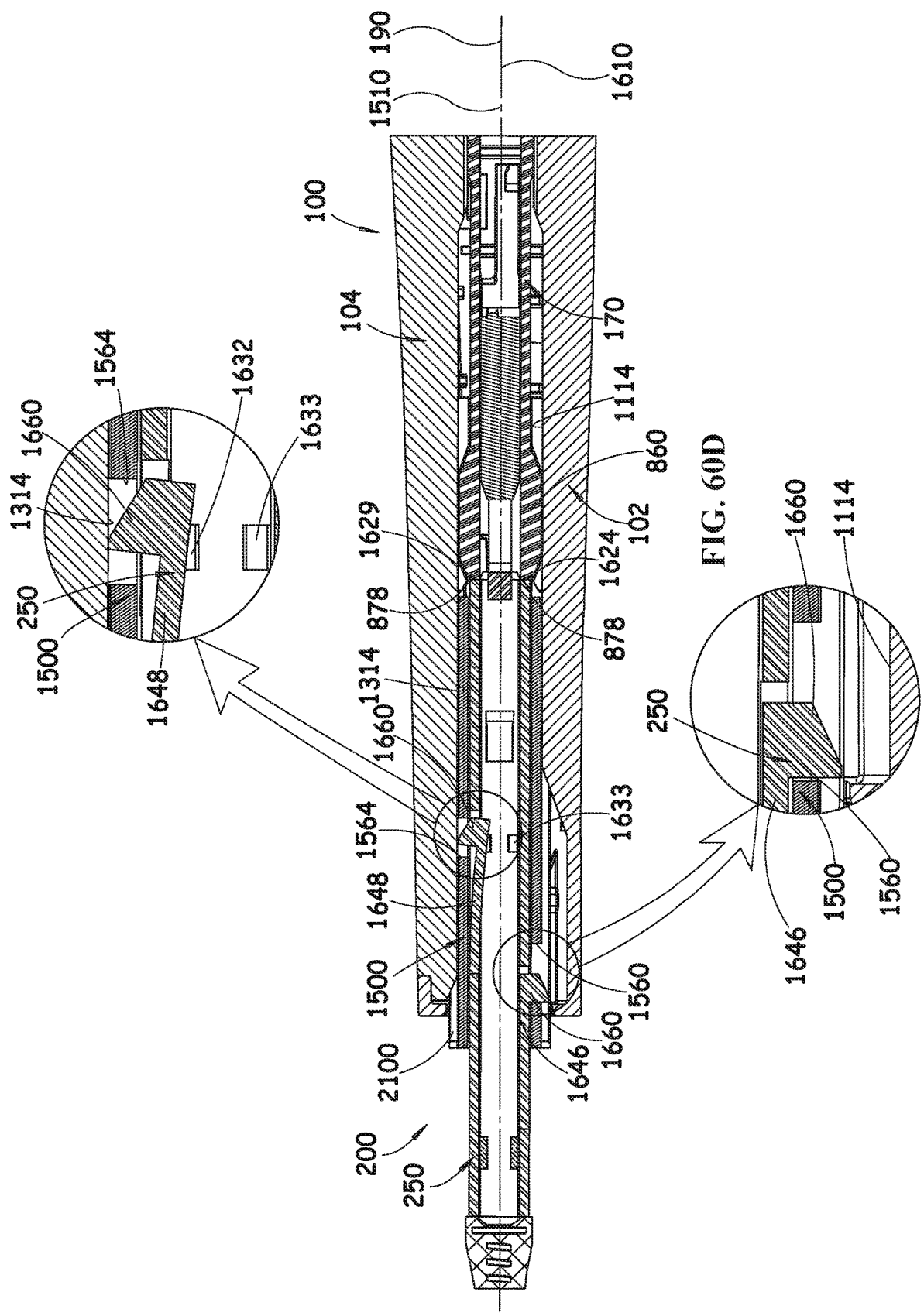

Reference is now made to FIGS. 60A, 60B, 60C and 60D, which are simplified illustrations of an injection site disengagement stage of the reusable automatic injection assembly 100 of FIGS. 1A-16H, 18A-18F and 20A-24C following the injection stage. FIG. 60A is a simplified perspective illustration, FIGS. 60B-60D are sectional simplified illustrations taken along lines B-B, C-C and D-D in FIG. 60A.

In FIGS. 60A-60D the reusable automatic injection assembly 100 is seen after disengagement from injection site by a user, which provides for axial forward displacement of the needle shield 250 relative to module housing 1500, main housing portion 102 and cover portion 104 in order to protect needle 246.

It is appreciated that, as seen in FIG. 60C inwardly-facing hook portions 882 (FIGS. 13A-13H) of multifunctional engagement element 170 remain engaged with generally U-shaped outer facing protrusions 1626 of needle shield 250, thereby attaching needle shield 250 to multifunctional engagement element 170 for axial movement together along axis 190. Hook portions 882 are still retained in engagement with corresponding protrusions 1626 by virtue of engagement of an inwardly-facing side surfaces 1140 and 1142 of the main housing portion 102 with respective outwardly-facing protruding surfaces 884 of hook portions 882.

It is also appreciated that, as seen in FIG. 60D, protrusions 1660 of finger portions 1646 and 1656 of needle shield 250 are engaged with slots 1560 and 1562 of the module housing 1500 due to forward displacement of the needle shield 250 relative to module housing 1500. Protrusions 1660 of finger portions 1648 and 1658 of needle shield 250 are not fully engaged with slots 1564 and 1566 of the module housing

1500. This engagement of finger portions 1646 and 1656 of needle shield 250 with slots 1560 and 1562 of the module housing 1500 provides for limited displacement between the needle shield 250 and module housing 1500, such that rearward axial displacement of needle shield 250 relative to module housing 1500 prevents exposure of needle 246 of syringe 242.

Multifunctional retaining element 150 is restrained from forward axial displacement with respect to main housing portion 102 and cover portion 104 by engagement of engagement surfaces 624 of fingers 602 and 604 of multifunctional retaining element 150 with corresponding inwardly facing protrusions 1164 of main housing portion 102 and 1364 of cover portion 104.

It is particularly seen in sectional enlargement in FIG. 60A that multifunctional engagement element 170 is limited from forward axial displacement by engagement of forwardly facing tapered surfaces 818 of axial walls 815 of multifunctional engagement element 170 with rearwardly facing tapered surface 636 of fingers 602 and 604 of multifunctional retaining element 150, thus preventing further advancement of the multifunctional engagement element 170 until the user pulls the medicament module 200/300 axially forwardly out of the reusable automatic injection assembly 100.

It is further particularly seen in sectional enlargement in FIG. 60A that during forward displacement of needle shield 250, fingers 1516 and 1518 of module housing 1500 engage narrow slots 1632, 1633 of needle shield 250 since the fingers 1516 and 1518 of module housing 1500 are now allowed to return to their at rest operative orientation. Fingers 1516 and 1518 of the module housing 1500 disengage from tapered surfaces 1159 of protrusions 1158 on main housing portion 102 and corresponding tapered surfaces 1394 of protrusions 1392 on cover portion 104 thereby no longer restricting further forward displacement of the module housing 1500.

It is seen in FIG. 60D that multifunctional retaining element 150 has been fully displaced forwardly with respect to main housing portion 102 and cover portion 104 under the force of injection spring 180.

Figure 61A:
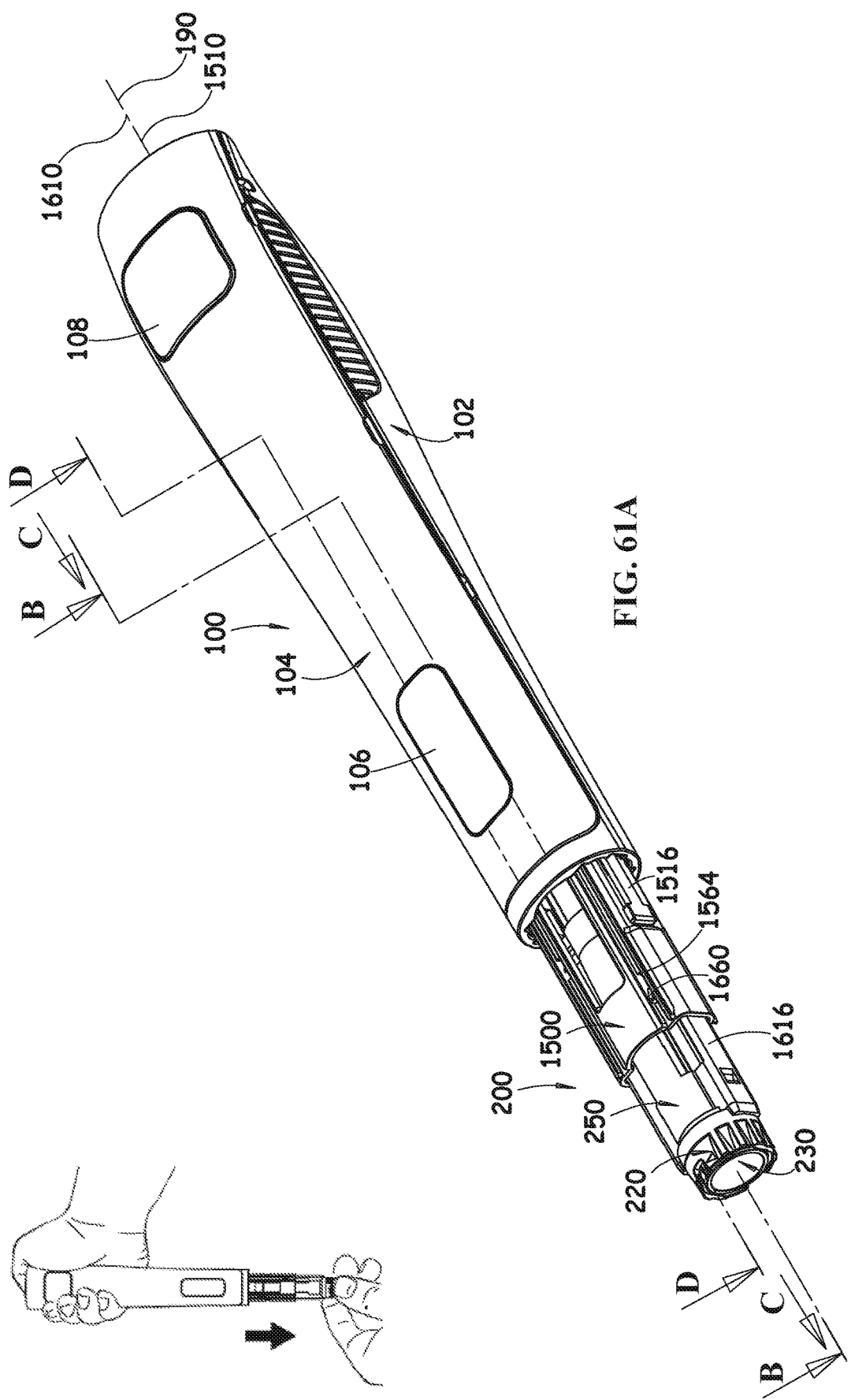
Figures 61B, 61C:
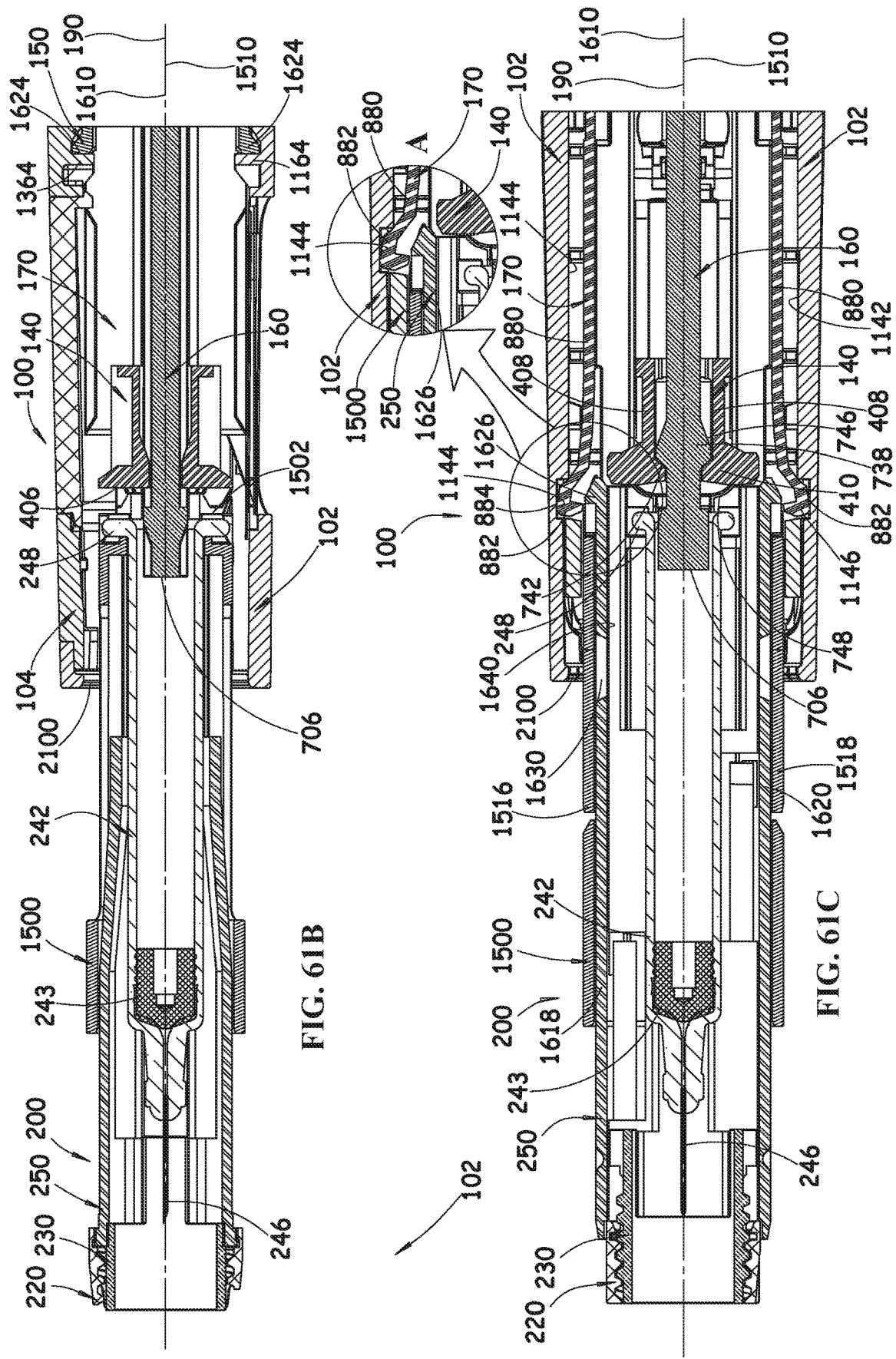

Reference is now made to FIGS. 61A, 61B, 61C, 61D and 61E, which are simplified illustrations of a medication module removal from the reusable automatic injection assembly of FIGS. 1A-23L. FIG. 61A is a simplified perspective illustration, FIGS. 61B-61D are simplified partial sectional illustrations taken along lines B-B, C-C and D-D in FIG. 61A and FIG. 61E is a simplified partially cut-away illustration of the reusable automatic injection assembly of FIG. 61A.

In FIGS. 61A-61D, it is seen that the medicament module 200/300 is axially forwardly pulled by the user in order to remove the medicament module 200/300 from the reusable automatic injection assembly 100 and thereby allow further use of the reusable automatic injection assembly 100 with another medicament module 200/300.

Multifunctional retaining element 150 remains restrained from forward axial displacement with respect to main housing portion 102 and cover portion 104 by engagement of engagement surfaces 624 of fingers 602 and 604 of multifunctional retaining element 150 with corresponding inwardly facing protrusions 1164 of main housing portion 102 and 1364 of cover portion 104.

The user pulls the medicament module 200/300 axially forwardly, thus displacing the needle shield 250 along with the multifunctional engagement element 170, due to engagement of inwardly-facing hook portions 882 (FIGS. 13A-13H) of multifunctional engagement element 170 with the generally U-shaped outer facing protrusions 1626 of needle shield 250. Forward axial displacement of the multifunctional engagement element 170 results in disengagement of forwardly facing tapered surfaces 818 of multifunctional engagement element 170 with rearwardly facing tapered surface 636 of fingers 602 and 604 of multifunctional retaining element 150, thus permitting forward advancement of the multifunctional engagement element 170 along axis 190, as seen in FIG. 61E.

It is particularly seen in enlargement D in FIG. 61E that during forward axial displacement of multifunctional engagement element 170, control element 140 is urged to be displaced forwardly with respect to elongate damping driver element 160. The control element 140 is displaced forwardly due to engagement of planar forward facing surface 819 of the multifunctional engagement element 170 with rearwardly facing surface 405 of control element 140. Once control element 140 reaches forward side protrusion 738 of the elongate damping driver element 160, the forwardly-extending engagement fingers 408 of control element 140 are outwardly deflected, thus allowing the control element to be displaced forwardly, bypass the forward side protrusion 738 and be seated along planar forward side surface portion 748 of the elongate damping driver element 160. This forward displacement is allowed due to engagement of inwardly facing protrusions 410 of forwardly-extending engagement fingers 408 of control element 140 with rearwardly facing tapered surface 746 of elongate damping driver element 160. This forward position of the control element 140 is similar to the position of control element 140 as shown and described with reference to FIGS. 23A-23L, where the reusable auto injection assembly 100 is shown in a storage operative orientation.

It is seen in FIG. 61C that at the end of forward axial displacement of the multifunctional engagement element 170 during medicament module 200/300 removal from the reusable auto injection assembly 100, the outwardly-facing protruding surfaces 884 of hook portions 882 of multifunctional engagement element 170 are not engaged with the inwardly-facing side surfaces 1140 and 1142 of the main housing portion 102 anymore, thus permitting the hook portions 882 to disengage from corresponding protrusions 1626 of the needle shield 250 and lie against mutually facing recesses 1144 and 1146 of the main housing portion 102. This disengagement allows the removal of the medicament module 200/300 out of the reusable auto injection assembly 100.

Following removal of the medicament module 200/300 from the reusable auto injection assembly 100, the reusable auto injection assembly 100 is positioned again in a storage operative orientation shown and described with respect to FIGS. 23A-23L and an additional medicament module 200/300 can be now charged into the reusable auto injection assembly 100.

It is also appreciated that, as seen in enlargements B and C in FIG. 61D, protrusions 1660 of finger portions 1646 and 1656 of needle shield 250 remain engaged with slots 1560 and 1562 of the module housing 1500 due to forward displacement of the needle shield 250 relative to module housing 1500. Protrusions 1660 of finger portions 1648 and 1658 of needle shield 250 are now fully engaged with slots 1564 and 1566 of the module housing 1500. This engagement prevents displacement between the needle shield 250 and module housing 1500.

Figure 62:
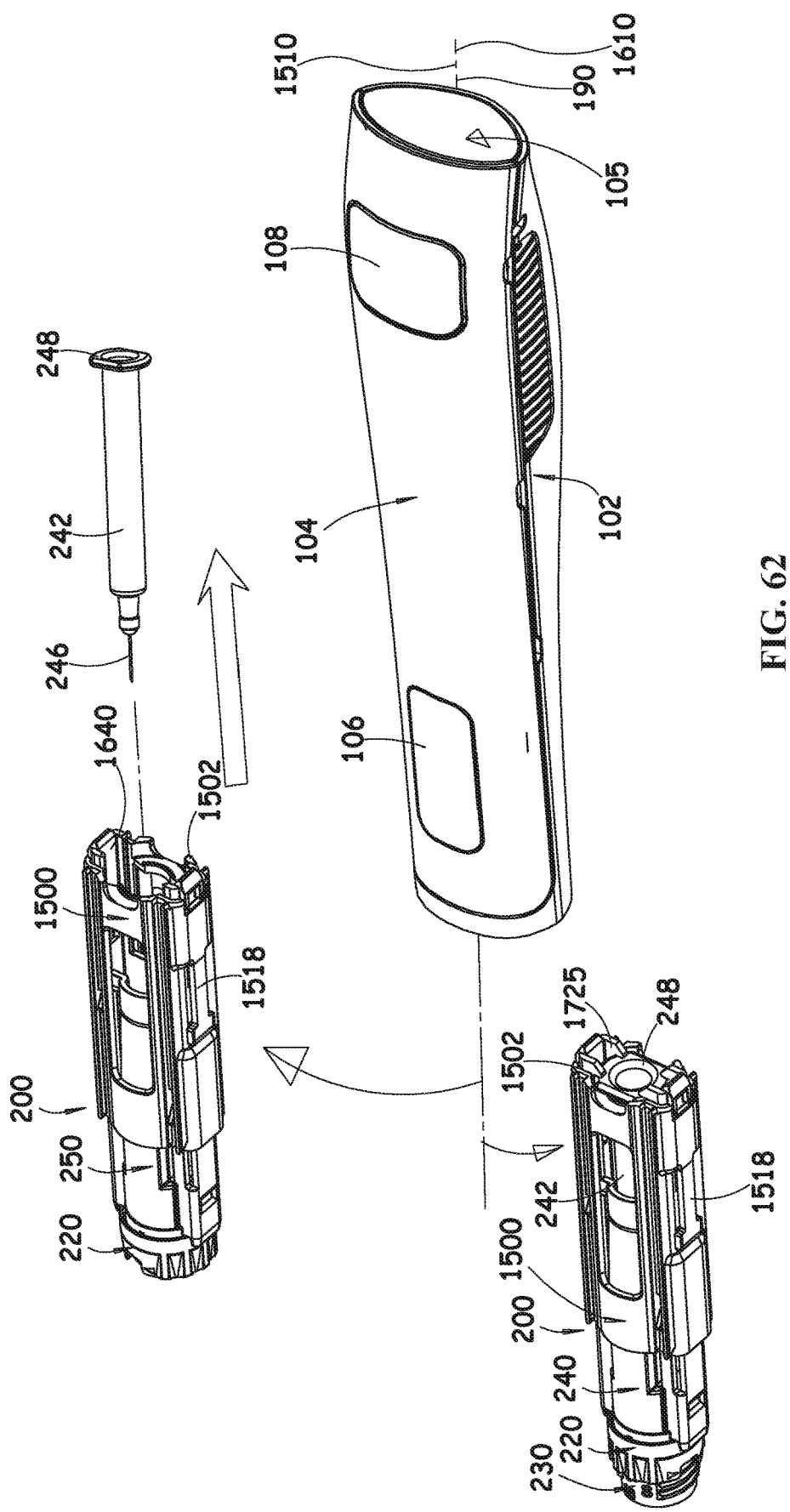
FIG. 62 is a simplified illustration of a medication module following removal from the reusable automatic injection assembly of FIGS. 1A-23L.

Reference is now made to FIG. 62, which is a simplified illustration of medication module 200/300 following removal from the reusable automatic injection assembly 100 of FIGS. 1A-23L.

Two alternatives of medicament modules 200/300 are seen in FIG. 62 to be removed from the reusable automatic injection assembly 100.

In a first alternative, where medicament module 200 of FIGS. 34A-34D is shown, the syringe 242 is removed from the medicament module 200 and is discarded, while the medicament module 200 can be re-used.

In a second alternative, where medicament module 200 of FIGS. 35A-35D is shown, the syringe 242 is retained by protrusion 1725 of needle shield 240, thus the medicament module 200 is discarded along with the syringe 242 at this operative orientation.

It is appreciated that in an alternative embodiment of the present invention, medicament module 300, such as shown in FIGS. 36A-36D, 37A-37D and in FIGS. 51A & 51B can be used in association with the reusable automatic injection assembly 100.

Figure 63A:
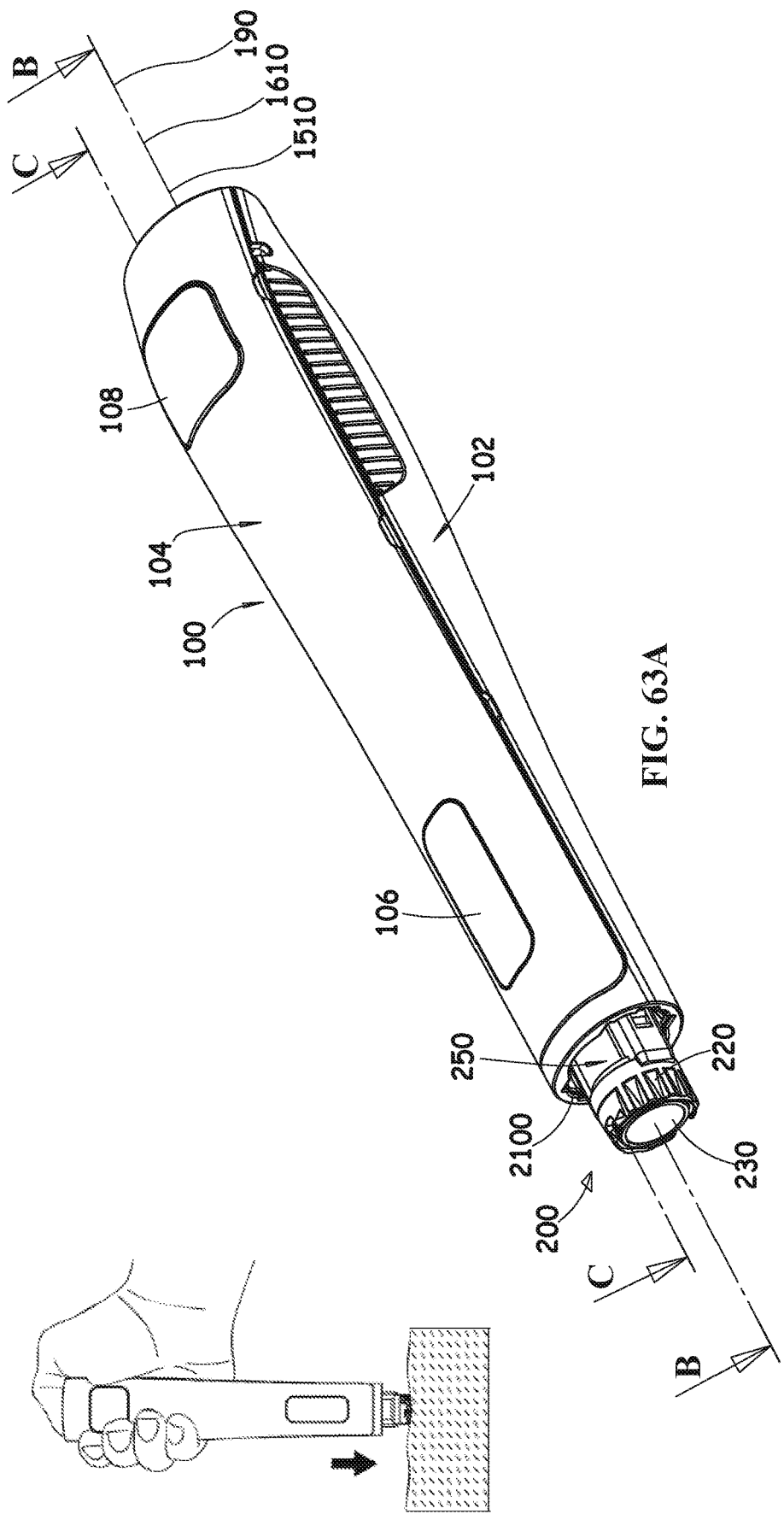

Reference is now made to FIGS. 63A, 63B and 63C, which are simplified illustrations of a first mis-use orientation of the medicament module 200 associated with the reusable automatic injection assembly 100 of FIGS. 1A-23L. FIG. 63A is a simplified perspective illustration, FIGS. 63B and 63C are simplified sectional illustrations, section lines being taken along lines B-B and C-C in FIG. 63A.

An undesirable orientation is seen in FIGS. 63A-63C, in which the injection was completed as seen in FIGS. 60A-60D and the needle shield 250 is displaced forwardly and protects the needle 246, and at this stage the user attempts to press the medicament module 200/300 against an injection site again without charging a new medicament module 200/300 into the reusable automatic injection assembly 100.

It is appreciated that in this first mis-use orientation, it is desirable that the needle 246 remains protected, thus the following structural relationships exist:

It is seen in FIG. 63C that there is no relative displacement between the needle shield 250 and the module housing 1500 once the user pushes the medicament module 200/300 inwardly into the reusable automatic injection assembly 100, due to the engagement of outwardly-facing protrusions 1660 of finger portions 1646 and 1656 within the forward slots 1560 and 1562 of module housing 1500, which retain the needle shield 250 from moving rearwardly relative to module housing 1500.

It is also seen in FIG. 63B that there is no relative displacement between the medicament module 200/300 and the reusable automatic injection assembly 100 due to the following structural relationships:

The piston 243 is positioned at its most forward location at the end of injection, as shown in FIGS. 60A-60D. Once the user pushes the medicament model 200/300 rearwardly, force is transferred from piston 243 to elongate damping driver element 160 and to multifunctional retaining element 150, due to the fact that elongate damping driver element 160 is fixedly connected with multifunctional retaining element 150.

This rearward displacement of medicament module 200/300 positions the multifunctional retaining element 150 such that surfaces inclined surfaces 622 of tapered protrusions 620 of fingers 602 and 604 thereof engage forwardly facing tapered surfaces 1175 and 1375 of the main housing 102 and the cover element 104 respectively.

Following rearward displacement of the medicament module 200/300 by the user, control element 140 is displaced rearwardly due to engagement of forward facing surfaces 406 of control element 140 with edges 1502 of module housing 1500. Following this displacement, the control element 140 is positioned within multifunctional retaining element 150 so that fingers 602 and 604 of multifunctional retaining element 150 are limited from inward deflection by engagement with outwardly facing protrusions 426 of control element 140, thus preventing rearward displacement of the needle shield 250 and exposure of needle 246.

Figure 64A:
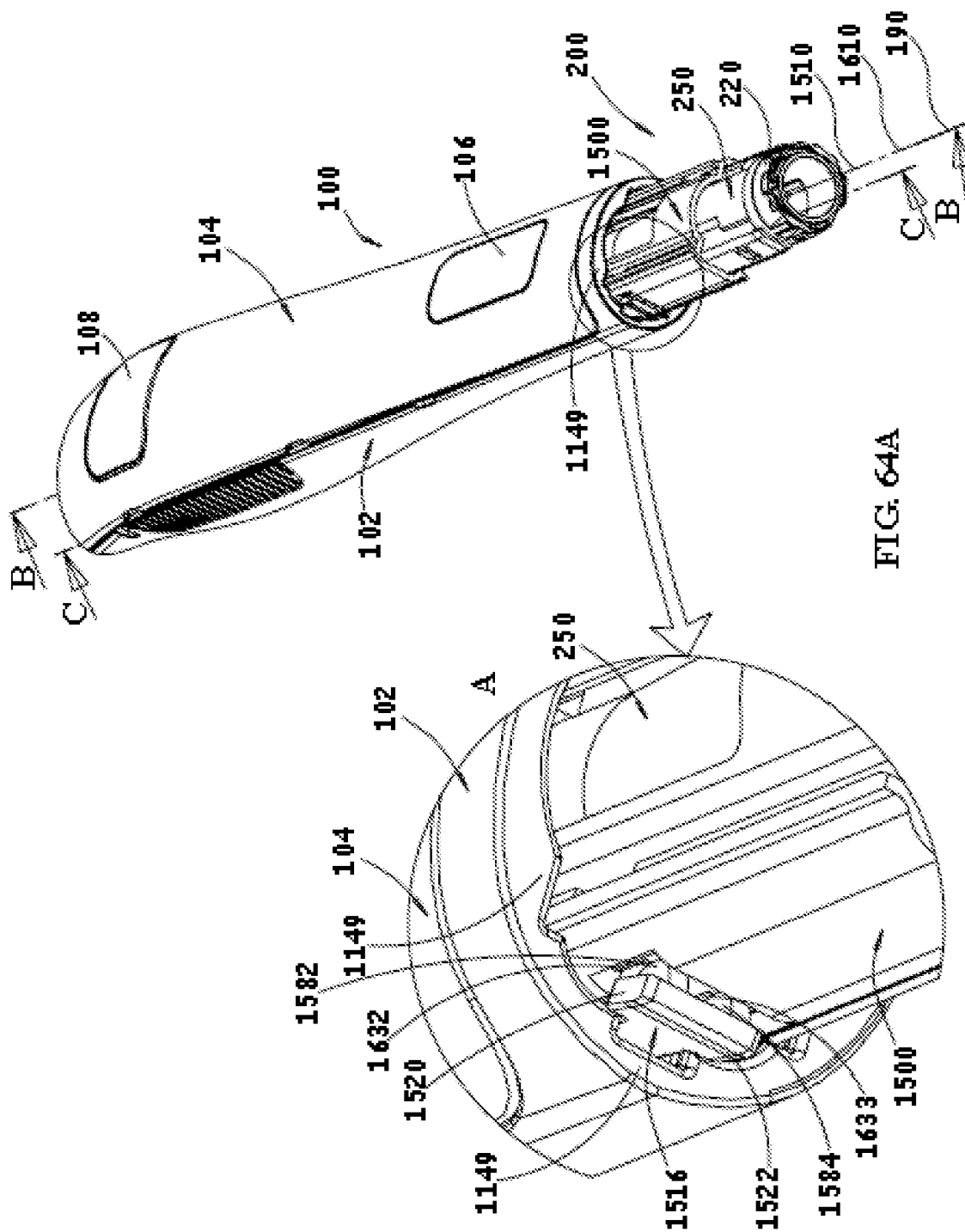

Reference is now made to FIGS. 64A, 64B and 64C, which are simplified illustrations of a second mis-use orientation of the medicament module 200/300 associated with the reusable automatic injection assembly 100 of FIGS. 1A-23L. FIG. 64A is a simplified perspective illustration, FIGS. 64B and 64C are simplified sectional illustrations, section lines being taken along lines B-B and C-C in FIG. 64A.

An undesirable orientation is seen in FIGS. 64A-64C, in which the user attempts to insert a medicament module 200/300 without RNS remover 210 into the reusable automatic injection assembly 100. It is appreciated that in this mis-use orientation, the user may attempt to charge a used medicament module 200/300 into the reusable automatic injection assembly 100 and it is desirable to prevent such charging, thus the following structural relationships exist:

It is seen in enlargement C in FIG. 64B that once the user inserts medicament module 200/300 without RNS remover 210 rearwardly into the reusable automatic injection assembly 100, control element 140, which is retained from rearward displacement by engagement of rearward facing tapered surface 414 with forward-facing surface 742 of elongate damping driver element 160, exerts force on module housing 1500 by means of engagement of forward facing surface 406 of the control element 140 with backward facing edge 1502 of module housing. Control element 140 thereby resists rearward displacement of module housing 1500.

It is further seen in enlargement D in FIG. 64C that protrusions 1660 of finger portions 1648 and 1658 of needle shield 250 disengage slots 1564 and 1566 of the module housing 1500 by virtue of engagement with rib 1114 of the main housing portion 102 and rib 1314 of the cover portion 104 with protrusions 1660 of finger portions 1648 and 1658 due to the fact that there is a resistance for rearward displacement of the module housing 1500.

This disengagement permits limited relative displacement of the module housing 1500 with respect to needle shield 250, due to limited movement of finger portions 1646 and 1656 of needle shield 250 within slots 1560 and 1562 of the module housing 1500. This limited displacement causes inwardly directed side protrusions 1582 and 1584 of fingers 1516 and 1518 of module housing 1500 to be disengaged from narrow slots 1632 and 1633 and thus to deflect outwardly by engagement thereof with respective tapered surfaces 1634 and 1635.

It is clearly seen in FIG. 64A that once the fingers 1516 and 1518 of the module housing 1500 are disengaged from narrow slots 1632 and 1633 of needle shield 250, they are deflected outwardly and thus side-to-side facing protrusions 1520 and 1522 of each of fingers 1516 and 1518 is supported by forwardly-facing generally ringed surface 1149 of the main housing portion 102 and prevent further rearward insertion of the medicament module 200/300 into the reusable automatic injection assembly 100.

It is noted that when the RNS remover 210/310 is in place on the needle shield 250, it prevents this limited displacement of module housing 1500 relative to finger portions 1646 and 1648 of needle shield 250.

It is appreciated that in an alternative embodiment of the present invention, medicament module 300, such as shown in FIGS. 36A-36D, 37A-37D and in FIGS. 51A & 51B can be used in association with the reusable automatic injection assembly 100.

This invention generally relates to a reusable automatic injection device for parenteral administration of substances (e.g., a medication) to a living organism (human or animal). The administration may be delivered into the subcutaneous tissue.

The invention is further related to, but is not limited to a self-administration of patients with chronic diseases such as rheumatoid arthritis (RA), multiple sclerosis (MS), HIV, and growth hormone deficiency.

It is appreciated that in accordance with an embodiment of the present invention the medicament is enclosed in a pre-filled syringe, but it can alternatively be used with other drug enclosures such as vials or ampoules, where a vial adaptor or an ampoule adaptor is used to reconstitute, mix, or pump the drug into the syringe prior to injection. The pre-filled syringe can be either a conventional one chambered pre-filled syringe with a ready-to-inject liquid form drug, or it can be a multiple-chambered pre-filled syringe.

The reusable automatic injection device provides an automate needle insertion through the skin, which therefore overcomes the main obstacle in self-administration, i.e., the needle phobia; the user does not see the needle through all the procedure, i.e., before, during and after injection.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The invention claimed is:

1. A user-powered medicament injector comprising: a reusable, user-powered automatic injection assembly including a user energizable medicament injection subassembly, which comprises at least one mechanical energy storage element; and a medicament module removably insertable into said reusable, user-powered automatic injection assembly and wherein said medicament module comprises: a module housing adapted to receive a syringe having a barrel, a needle engaged to said barrel, and a removeable needle cap adapted to cover said needle; a needle shield configured to be moveable with respect to said module housing; and a needle cap remover associated with said needle shield; and wherein said medicament module is configured for energizing said user energizable medicament injection subassembly by insertion of said medicament module into said reusable, user-powered automatic injection assembly, said at least one mechanical energy storage element for ejecting a medicament from said syringe in an injection operative state of said user-powered medicament injector.

2. A user-powered medicament injector according to claim 1 and wherein said reusable, user-powered automatic injection assembly includes a driving assembly, which is comprised of a control element, a multifunctional retaining element and a damping driver element, which are adapted to operatively engage each other.

3. A user-powered medicament injector according to claim 1 and wherein said at least one mechanical energy storage element comprises at least one resilient element and wherein said insertion of said medicament module into said reusable, user-powered automatic injection assembly comprises relative displacement of said medicament module relative to said reusable, user-powered automatic injection assembly, which causes said mechanical energy storage element to store energy.

4. A user-powered medicament injector according to claim 3 and wherein said reusable, user-powered automatic injection assembly includes a driving assembly, which is comprised of a control element, a multifunctional retaining element and a damping driver element, which are adapted to operatively engage each other.

5. A user-powered medicament injector according to claim 1 and wherein said reusable, user-powered automatic injection assembly includes a driving assembly, which is comprised of a control element, a multifunctional retaining element and a damping driver element, which are adapted to operatively engage each other.

6. A user-powered medicament injector according to claim 5 and wherein at least one sealing element is adapted to be operatively engaged with said damping driver element.

7. A user-powered medicament injector according to claim 6 and wherein said reusable, user-powered automatic injection assembly includes a triggering subassembly comprised of a trigger element, actuation button and at least one spring loaded latch element.

8. A user-powered medicament injector according to claim 5 and wherein said reusable, user-powered automatic injection assembly includes a triggering subassembly comprised of a trigger element, actuation button and at least one spring loaded latch element.

9. A user-powered medicament injector according to claim 8 and wherein said triggering subassembly is adapted to be operatively engaged with said driving assembly such that said actuation button is locked in a pre-injection site engagement operative orientation.

10. A user-powered medicament injector according to claim 9 and wherein said multifunctional retaining element is configured to displace said at least one spring loaded latch element during insertion of said medicament module into said reusable, user-powered automatic injection assembly.

11. A user-powered medicament injector according to claim 8 and wherein said multifunctional retaining element is configured to displace said at least one spring loaded latch element during insertion of said medicament module into said reusable, user-powered automatic injection assembly.

12. A user-powered medicament injector according to claim 11 and wherein said at least one spring loaded latch element is displaced axially.

13. A user-powered medicament injector according to claim 11 and wherein said at least one spring loaded latch element is displaced rotationally.

14. A user-powered medicament injector comprising: a reusable automatic injection assembly including a medicament injection subassembly enclosed in at least one housing element; and a medicament module removably axially insertable into said reusable automatic injection assembly, said medicament module includes a module housing and a needle shield, adapted to be moveable with respect to said module housing; and wherein in an injection operative state said module housing is selectably retained from forward displacement by engagement with said at least one housing element, and wherein said reusable automatic injection assembly further including a multifunctional engagement element operative in a post-injection operative stage to displace said needle shield forwardly, and wherein during removal of said medicament module from said reusable automatic injection assembly, said multifunctional engagement element is displaced forwardly along with said medicament module until further forward displacement of said multifunctional engagement element is restricted by said at least one housing element.

15. A user-powered medicament injector according to claim 14 and wherein said reusable automatic injection assembly comprises at least one mechanical energy storage element.

16. A user-powered medicament injector according to claim 15 and wherein said at least one mechanical energy storage element comprises at least one resilient element and wherein said insertion of said medicament module into said reusable, automatic injection assembly comprises relative displacement of said medicament module relative to said reusable, automatic injection assembly, which causes said mechanical energy storage element to store energy.

17. A user-powered medicament injector according to claim 14 and wherein said reusable automatic injection assembly includes a driving assembly, which is comprised of a control element, a multifunctional retaining element and a damping driver element, which are adapted to operatively engage each other.

18. A user-powered medicament injector according to claim 17 and wherein at least one sealing element is adapted to be operatively engaged with said damping driver element.

19. A user-powered medicament injector according to claim 17 and wherein said reusable automatic injection assembly includes a triggering subassembly comprised of a trigger element, actuation button and at least one spring loaded latch element.

* * * * *